US008697737B2

(12) United States Patent  (10) Patent No.: US 8,697,737 B2
Anand et al.  (45) Date of Patent: Apr. 15, 2014

(54) RAF MODULATORS AND METHODS OF USE

(75) Inventors: Neel Kumar Anand, Burlingame, CA (US); Charles M. Blazey, San Francisco, CA (US); Owen Joseph Bowles, Pacifica, CA (US); Joerg Bussenius, Foster City, CA (US); Simona Costanzo, Los Altos, CA (US); Jeffry Kimo Curtis, San Anselmo, CA (US); Larisa Dubenko, San Francisco, CA (US); Abigail R. Kennedy, Oakland, CA (US); Steven Charles Defina, Burlingame, CA (US); Angie I. Kim, San Mateo, CA (US); Jean-Claire L. Manalo, Daly City, CA (US); Csaba J. Peto, Alameda, CA (US); Kenneth D. Rice, San Rafael, CA (US); Tsze H. Tsang, El Cerrito, CA (US); Anagha Abhijit Joshi, Fremont, CA (US)

(73) Assignee: Exelixis, Inc., South San Francisco, CA (US)

( * ) Notice: Subject to any disclaimer, the term of this patent is extended or adjusted under 35 U.S.C. 154(b) by 201 days.

(21) Appl. No.: 12/903,031

(22) Filed: Oct. 12, 2010

(65) Prior Publication Data

US 2011/0071145 A1  Mar. 24, 2011

Related U.S. Application Data

(62) Division of application No. 11/568,789, filed as application No. PCT/US2005/010187 on Mar. 25, 2005, now Pat. No. 7,846,959.

(60) Provisional application No. 60/569,009, filed on May 7, 2004.

(51) Int. Cl.
*A01N 43/56* (2006.01)
*A61K 31/415* (2006.01)
*C07D 231/56* (2006.01)

(52) U.S. Cl.
USPC ........ 514/405; 514/403; 548/356; 548/360.1; 548/361.1

(58) Field of Classification Search
USPC ............ 514/403, 405; 548/356, 360.1, 361.1
See application file for complete search history.

(56) References Cited

FOREIGN PATENT DOCUMENTS

WO  WO2004015130  2/2004
WO  2004/103974 A1  5/2004

OTHER PUBLICATIONS

Pinedo et al., "Translational Research . . . ", The Oncologist 2000, 5 (suppl1): 1-2 (www.The Oncologist .com).*

McMahon, Gerald, "VEGF Receptor Signaling in Tumor Angiogenesis", The Oncologist 2000; 5(suppl 1): 3-10 (www.The Oncologist.com).*
Cancer Drug Design and Discovery Neidle, Stephen, ed. (Elsevier/Academic Press, 2008) pp. 427-431.*
Aikawa, R. et al., "Oxidative Stress Activates Extracellular Signal-regulated Kinase through Src and Ras in Cultured Cardiac Myocytes of Neonatal Rats", J. Clin. Invest., 1997, 100(7), 1813-1821.
Bendinelli, P. et al., "The MAP kinase cascades are activated during post-ischemic liver reperfusion", FEBS Letters, 1996, vol. 398, 193-197.
Berk, B. C. et al., "Angiotensin II Signal Transduction in Vascular Smooth Muscle: Role of Tyrosine Kinases", Circ. Res., 1997, vol. 80, 607-616.
Chen, X. Q. et al., "14-3-3γ Is Upregulated by In Vitro Ischemia and Binds to Protein Kinase Raf in Primary Cultures of Astrocytes", GLIA, 2003, vol. 42, 315-324.
Danis, R. P. et al., "Intravitreous anti-raf-1 kinase antisense oligonucleotide as an angioinhibitory agent in porcine preretinal neovascularization", Current Eye Research, 2003, 26(1), 45-54.
Fagin et al., "How thyroid tumors start and why it matters: kinase mutants as targets for solid cancer pharmacotherapy", Journal of Endocrinology, 2004, vol. 183, 249-256.
Hecquet, C. et al., "Activiation and Role of MAP Kinase-Dependent Pathyways in Retinal Pigment Epithelial Cells: ERK and RPE Cell Proliferation", Investigative Ophthalmology & Visual Science, 2002, 43(9), 3091-3098.
Indolfi, C. et al., "Inhibition of cellular ras prevents smooth muscle cell proliferation after vascular injury in vivo", Nature Medicine, 1995, 1(6), 541-545.
Kolesnick, R. et al., "Inflammatory bowel disease reveals the kinase activity of KSR1", The Journal of Clinical Investigation, 2004, 114(9), 1233-1237.
Mandiyan, S. et al., "Molecular and Cellular Characterization of Baboon C-Raf as a Target for Antiproliferative Effects of Antisense Oligonucleotides", Antisense & Nucleic Acid Drug Development, 1997, vol. 7, 539-548.
Olah, Z. et al., "Cerebral ischemia induces transient intracellular redistribution and intranuclear translocation of the raf proto-oncogene product in hippocampal pyramidal cells", Experimental Brain Research, 1991, vol. 84, 403-410.

(Continued)

*Primary Examiner* — Paul V. Ward
(74) *Attorney, Agent, or Firm* — McDonnell Boehnen Hulbert & Berghoff LLP

(57) ABSTRACT

The present invention relates to compounds of the Formula I, wherein G, A, X1, X2, X3, Z, E, Y, and X are defined herein. The compounds modulate protein kinase enzymatic activity to modulate cellular activities such as proliferation, differentiation, programmed cell death, migration and chemoinvasion. Compounds of the invention inhibit, regulate and/or modulate kinases, particularly Raf. Methods of using and preparing the compounds, and pharmaceutical compositions thereof, to treat kinase-dependent diseases and conditions are also an aspect of the invention.

(I)

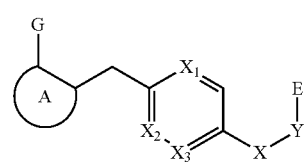

18 Claims, No Drawings

(56) References Cited

OTHER PUBLICATIONS

Pfeifer, A. M. A. et al., "Cooperation of c-raf-1 and c-myc protooncogenes in the neoplastic transformation of simian virus 40 large tumor antigen-immortalized human bronchial epithelial cells", Proc. Natl. Acad. Sci., 1989, vol. 86, 10075-10079.

Riva, C. et al., "Differential c-myc, c-jun, c-raf and p53 Expression in Squamous Cell Carcinoma of the Head and Neck: Implication in Drug and Radioresistance", Oral Oncol. Eur. F. Cancer, 1995, 31B(6), 384-391.

Schmidt, C. A. et al., "Overexpression of the Raf-1 Proto-Oncogene in Human Myeloid Leukemia", Leukemia Research, 1994, 18(6), 409-413.

Sun, Y. et al., "Basic Calcium Phosphate Crystals Induce Matrix Metalloproteinase-1 through the Ras/Mitogen-activated Protein Kinase/c-Fos/AP-1/Metalloproteinase 1 Pathway", The Journal of Biological Chemistry, 2002, 277(2), 1544-1552.

Weissinger, E. M. et al., "Inhibition of the Raf-1 Kinase by Cyclic AMP Agonists Causes Apoptosis of v-abl-Transformed Cells", Molecular and Cellular Biology, 1997, 17(6), 3229-3241.

Westermarck, J. et al., "p38 Mitogen-Activated Protein Kinase-Dependent Activation of Protein Phosphates 1 and 2A Inhibits MEK1 and MEK2 Activity and Collagenase 1 (MMP-1) Gene Expression", Molecular and Cellular Biology, 2001, 21(7), 2373-2383.

Yan, F. et al., "Kinase Suppressor of Ras Determines Survival of Intestinal Epithelial Cells Exposed to Tumor Necrosis Factor", Cancer Research, 2001, vol. 61, 8668-8675.

Zablocka, B. et al., "Opposite reaction of ERK and JNK in ischemia vulnerable and resistant regions of hippocampus: involvement of mitochondria", Molecular Brain Research, 2003, vol. 110, 245-252.

Pande, R. K. et al., "A novel route for the synthesis of ketobenzoic acid derivatives, auxin transport inhibitors", Database CA [Online] Chemical Abstract Service, Columbus, Ohio, US; retrieved from STN Database accession No. 1981-523544 & Revue Roumaine De Chimie, 26(6), 875-8, CODEN:RRCHAX, 1981.

Pinedo et al., "Translational Research: The Role of VEGF in Tumor Angiogenesis", The Oncologist, 2000, 5(suppl1): 1-2 (www.The Oncologist.com).

McMahon, G., "VEGF Receptor Signaling in Tumor Angiogenesis", The Oncologist 2000, 5(suppl1): 3-10 (www.The Oncologist.com).

International Search Report prepared by the PCT ISA/US for associated PCT application PCT/US05/10187 mailed Aug. 25, 2006.

Havens, S. J. et al., "Polyamideimides Containing Carbonyl and Ether Connecting Groups", Part A- Polymer Chemistry, Journal of Polymer Science, 28(9), 2427-2436, 1990.

* cited by examiner

RAF MODULATORS AND METHODS OF USE

REFERENCE TO RELATED APPLICATIONS

This application is a division of U.S. application Ser. No. 11/568,789, filed Sep. 4, 2007 now U.S. Pat. No. 7,846,959, which was the National Stage of International Application No. PCT/US05/10187, filed Mar. 25, 2005, which claims priority to U.S. provisional patent application 60/569,009 filed May 7, 2004. The contents of the prior applications are hereby incorporated in their entirety.

BACKGROUND OF THE INVENTION

1. Field of the Invention

This invention relates to compounds for modulating protein kinase enzymatic activity for modulating cellular activities such as proliferation, differentiation, programmed cell death, migration and chemoinvasion. Even more specifically, the invention relates to compounds that inhibit, regulate and/or modulate kinases, particularly Raf. Kinase receptor signal transduction pathways related to the changes in cellular activities as mentioned above are modulated using compounds of the invention. Methods of using the compounds to treat kinase-dependent diseases and conditions are also an aspect of the invention.

2. Summary of Related Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity are staggering; cell differentiation and proliferation; i.e., virtually all aspects of cell life in one-way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., DN&P 7(6): 334-339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993), which is hereby incorporated by reference.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers. Gleevec is a selective Abl kinase inhibitor.

Modulation (particularly inhibition) of cell proliferation and angiogenesis, two key cellular processes needed for tumor growth and survival (Matter A. Drug Disc Technol 2001 6, 1005-1024), is an attractive goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. As well, cell antiproliferative agents are desirable to slow or stop the growth of tumors.

One particularly attractive target for small-molecule modulation, with respect to antiangiogenic and antiproliferative activity is Raf. The Raf-MEK-ERK signal transduction cascade is a conserved pathway which regulates cell growth, proliferation, differentiation, and apoptosis in response to growth factors, cytokines, and hormones. This pathway operates downstream of Ras which is often upregulated or mutated in human tumors. It has been demonstrated that Raf is a critical effector of Ras function. A large portion of human cancers, including 80% pancreatic, 50% colorectal, and 40% lung cancers, harbor activating Ras mutations. In addition, somatic mutations of the B-Raf gene are associated with 60% of malignant melanomas and also occur with high frequency in colorectal and papillary thyroid tumors. It has been shown that inhibition of the ERK pathway, and in particular inhibition of Raf kinase activity, results in anti-metastatic and anti-angiogenic effects largely due to a reduction of cell-cell contact and motility as well as downregulation of vascular endothelial growth factor (VEGF) expression. Furthermore, expression of dominant negative Raf, MEK, or ERK reduced the transforming ability of mutant Ras as seen in cell culture and in primary and metastatic growth of human tumor xenografts in vivo. Therefore, the Raf-MEK-ERK signal transduction pathway is an appropriate pathway to target for therapeutic intervention.

Accordingly, the identification of small-molecule compounds that specifically inhibit, regulate and/or modulate the signal transduction of kinases, particularly Raf, is desirable as a means to treat or prevent disease states associated with cancer and is an object of this invention.

SUMMARY OF THE INVENTION

The present invention provides compounds for modulating kinase activity and methods of treating diseases mediated by kinase activity, in particular Raf, utilizing the compounds and pharmaceutical compositions thereof. Diseases mediated by kinase activity are from herein referred to as "kinase-dependent diseases or conditions" (see definition in detailed description of invention below). Inhibitors that are selective for a Raf are included in this invention.

In another aspect, the invention provides methods of screening for modulators of kinase activity. The methods comprise combining a composition of the invention, a kinase, and at least one candidate agent and determining the effect of the candidate agent on the kinase activity.

In yet another aspect, the invention also provides pharmaceutical kits comprising one or more containers filled with one or more of the ingredients of pharmaceutical compounds and/or compositions of the present invention, including, one or more kinase enzyme activity modulators as described herein. Such kits can also include, for example, other compounds and/or compositions (e.g., diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In still yet another aspect, the invention also provides a diagnostic agent comprising a compound of the invention and, optionally, pharmaceutically acceptable adjuvants and excipients.

These and other features and advantages of the present invention will be described in more detail below.

DETAILED DESCRIPTION OF THE INVENTION

The compositions of the invention are used to treat diseases associated with abnormal and or unregulated cellular activities. Disease states which can be treated by the methods and compositions provided herein include, but are not limited to, cancer (further discussed below), immunological disorders such as rheumatoid arthritis, graft-host diseases, multiple sclerosis, psoriasis; cardiovascular diseases such as atherosclerosis, myocardioinfarction, ischemia, pulmonary hypertension, stroke and restenosis; other inflammatory and degenerative diseases such as interbowel diseases, osteoarthritus, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally," but proliferation and migration enhancement may be desired. Alternatively, reduction in "normal" cell proliferation and/or migration rate may be desired.

The present invention comprises a compound for modulating kinase activity, particularly Raf, of Formula I,

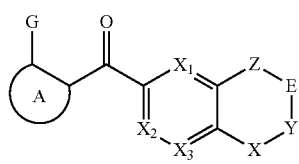

I or a pharmaceutically acceptable salt, hydrate or prodrug thereof, wherein,

A is a three- to seven-membered alicyclic, a five- to six-membered ortho-arylene or a five- to six-membered ortho-heteroarylene containing between one and three heteroatoms, either of the aforementioned optionally substituted with up to four R;

each R is independently selected from —H, halogen, —CN, —$NO_2$, —$OR^3$, —$N(R^3)R^3$, —$S(O)_{0-2}R^3$, —$SO_2N(R^3)R^3$, —$CO_2R^3$, —$C(O)N(R^3)R^3$, —$N(R^3)SO_2R^3$, —$N(R^3)C(O)R^3$, —$N(R^3)CO_2R^3$, —$C(O)R^3$, —$OC(O)R^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

optionally two of R, together with the atoms to which they are attached, form a first ring system fused with A, said first ring system substituted with zero to three of $R^1$;

$X_1$, $X_2$ and $X_3$ are independently selected from —$CR^1$= or —N=;

each $R^1$ is independently selected from —H, halogen, —CN, —$NO_2$, —$OR^3$, —$N(R^3)R^3$, —$S(O)_{0-2}R^3$, —$SO_2N(R^3)R^3$, —$CO_2R^3$, —$C(O)N(R^3)R^3$, —$N(R^3)SO_2R^3$, —$N(R^3)C(O)R^3$, —$N(R^3)CO_2R^3$, —$C(O)R^3$, —$OC(O)R^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

Z and X are each independently selected from —$C(R^2)$=, —N=, —$N(R^2)$—, —$S(O)_{0-2}$—, and —O—;

E and Y are each independently selected from absent, —$C(R^2)(R^2)$—, —C(=O)—, —$C(R^2)$= and —N=, but E and Y are not both absent, and E and Y are not both —N= when both Z and X are —N=;

each $R^2$ is independently selected from $R^3$, —$N(R^3)(R^3)$, —$C(O)N(R^3)R^3$, —$N(R^3)CO_2R^3$, —$N(R^3)C(O)N(R^3)R^3$, and —$N(R^3)C(O)R^3$;

each $R^3$ is independently selected from —H, optionally substituted $C_{1-6}$alkyl, optionally substituted $C_{3-7}$alicyclic, optionally substituted aryl, optionally substituted aryl $C_{1-3}$alkyl, optionally substituted heterocyclyl, and optionally substituted heterocyclyl $C_{1-3}$alkyl;

optionally two of $R^3$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P; and G is selected from —$CO_2R^3$, —$C(O)R^3$, —$C(O)N(R^3)R^3$, —$C(O)(NR^3)$, —$C(O)NR^3[C(R^3)_2]_{0-1}R^3$, —$C(O)NR^3O[C(R^3)_2]_{0-1}R^3$, —$N(R^3)CO_2R^3$, —$N(R^3)C(O)N(R^3)R^3$, —$N(R^3)C(O)R^3$, —$N(R^3)R^3$, —$S(O)_{0-2}R^3$, —$SO_2N(R^3)R^3$, optionally substituted aryl $C_{0-3}$alkyl, and optionally substituted heterocyclyl $C_{0-3}$alkyl;

with the proviso, however, that the compound is not CAS Registry No. 439096-29-4:

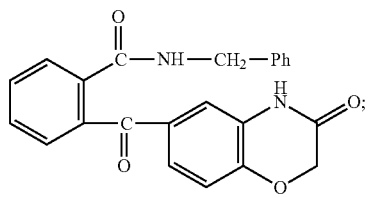 [SMILES: O=C1COc2ccc(C(=O)c3ccccc3C(=O)NCc3ccccc3)cc2N1]

CAS Registry No. 439107-32-1:

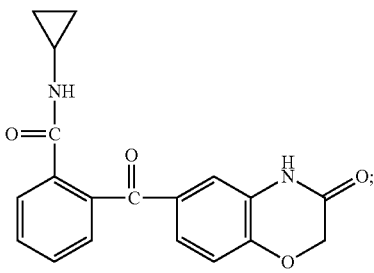 [SMILES: O=C1COc2ccc(C(=O)c3ccccc3C(=O)NC3CC3)cc2N1]

or
CAS Registry No. 439107-34-3:

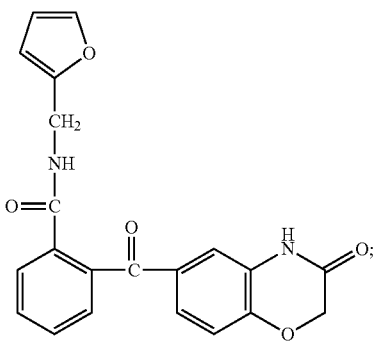 [SMILES: O=C1COc2ccc(C(=O)c3ccccc3C(=O)NCc3ccco3)cc2N1]

hereinafter referred to as embodiment 20.

In one example, the compound is according to Formula I, wherein A is a six-membered ortho-arylene, hereinafter referred to as embodiment 21.

In one example, the compound is according to embodiment 21, wherein A is ortho-phenylene, hereinafter referred to as embodiment 22.

In one example, the compound is according to embodiment 22, wherein G is —C(O)R$^3$, —C(O)N(R$^3$)R$^3$, —C(O)(NR$^3$), —C(O)NR$^3$[C(R$^3$)$_2$]$_{0-1}$R$^3$, —C(O)NR$^3$O[C(R$^3$)$_2$]$_{0-1}$R$^3$, hereinafter referred to as embodiment 23.

In one example, the compound is according to embodiment 23, wherein G is —C(O)N(R$^3$)R$^3$, hereinafter referred to as embodiment 24.

In one example, the compound is according to embodiment 24, wherein G is —C(O)NHR$^3$, hereinafter referred to as embodiment 25.

In one example, the compound is according to embodiment 25, wherein R$^3$ is optionally substituted C$_{1-6}$alkyl, hereinafter referred to as embodiment 26.

In one example, the compound is according to embodiment 25, wherein R$^3$ is optionally substituted aryl, hereinafter referred to as embodiment 27.

In one example, the compound is according to embodiment 25, wherein R$^3$ is optionally substituted aryl C$_{1-3}$alkyl, hereinafter referred to as embodiment 28.

In one example, the compound is according to embodiment 25, wherein R$^3$ is optionally substituted heterocyclyl, hereinafter referred to as embodiment 29.

In one example, the compound is according to embodiment 25, wherein R$^3$ is optionally substituted heterocyclyl C$_{1-3}$alkyl, hereinafter referred to as embodiment 30.

In one example, the compound is according to embodiment 25, wherein X$_1$, X$_2$ and X$_3$ are —CR$^1$=, hereinafter referred to as embodiment 31.

In one example, the compound is according to embodiment 31, wherein E is absent, hereinafter referred to as embodiment 32.

In one example, the compound is according to embodiment 32, wherein Z is —N=; Y is —C(R$^2$)=; and X is selected from —N(R$^2$)—, —S—, and —O—, hereinafter referred to as embodiment 33.

In one example, the compound is according to embodiment 25, wherein it is recognized that the present invention covers tautomeric interconversions of each compound, hereinafter referred to as embodiment 34.

In one example, the compound is according to embodiment 34, wherein it is recognized that the present invention covers tautomeric interconversions of each compound according to the following Formula Ia, wherein R$^3$, A, X$_1$, X$_2$, X$_3$, Z, E, Y and X are as defined above, hereinafter referred to as embodiment 35.

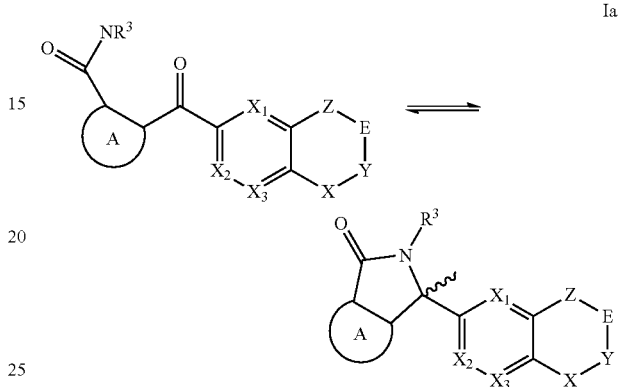

Ia

In one example, the compound is according to Formula I, wherein the compound is a pharmaceutically acceptable salt, hereinafter referred to as embodiment 36.

In one example, the compound is according to Formula I, wherein the compound is a prodrug, hereinafter referred to as embodiment 37.

The present invention also comprises a compound for modulating kinase activity, particularly Raf, of Formula II,

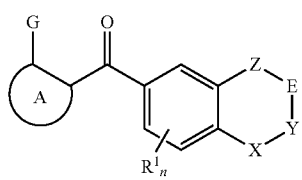

II or a pharmaceutically acceptable salt, hydrate, or prodrug thereof, wherein,

A is either a five- to six-membered ortho-arylene or a five- to six-membered ortho-heteroarylene containing between one and three heteroatoms, either of the aforementioned optionally substituted with up to four R;

each R is independently selected from —H, halogen, —CN, —NO$_2$, —OR$^3$, —N(R$^3$)R$^3$, —S(O)$_{0-2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —C(O)R$^3$, —OC(O)R$^3$, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;

optionally two of R, together with the atoms to which they are attached, form a first ring system fused with A, said first ring system substituted with zero to three of R$^1$;

n is zero to three;

each R$^1$ is independently selected from —H, halogen, —CN, —NO$_2$, —OR$^3$, —N(R$^3$)R$^3$, —S(O)$_{0-2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —C(O)R$^3$, —OC(O)R$^3$, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;

Z and X are each independently selected from —C(R²)═, —N═, —N(R²)—, —S(O)₀₋₂—, and —O—;

E and Y are each independently selected from absent, —C(R²)(R²)—, —C(═O)—, —C(R²)═ and —N═, but E and Y are not both absent, and E and Y are not both —N═ when both Z and X are —N═;

each R² is independently selected from R³, —C(O)N(R³)R³, —N(R³)CO₂R³, —N(R³)C(O)N(R³)R³, and —N(R³)C(O)R³;

each R³ is independently selected from —H, optionally substituted C₁₋₆alkyl, optionally substituted aryl, optionally substituted aryl C₁₋₆alkyl, optionally substituted heterocyclyl, and optionally substituted heterocyclyl C₁₋₃alkyl;

optionally two of R³, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P; and G is selected from —C(O)R³, —C(O)N(R³)R³, —N(R³)CO₂R³, —N(R³)C(O)N(R³)R³, —N(R³)C(O)R³, —N(R³)R³, —S(O)₀₋₂R³, —SO₂N(R³)R³, optionally substituted aryl C₁₋₃alkyl, and optionally substituted heterocyclyl C₁₋₃alkyl;

with the proviso, however, that the compound is not CAS Registry No. 439096-29-4:

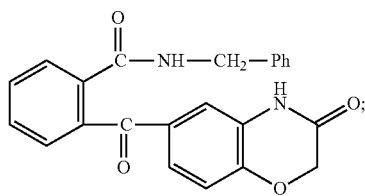 [SMILES: O=C1COc2ccc(C(=O)c3ccccc3C(=O)NCc3ccccc3)cc2N1]

CAS Registry No. 439107-32-1:

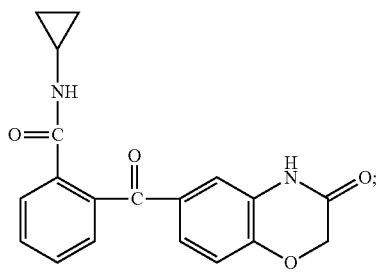 [SMILES: O=C1COc2ccc(C(=O)c3ccccc3C(=O)NC3CC3)cc2N1]

or
CAS Registry No. 439107-34-3:

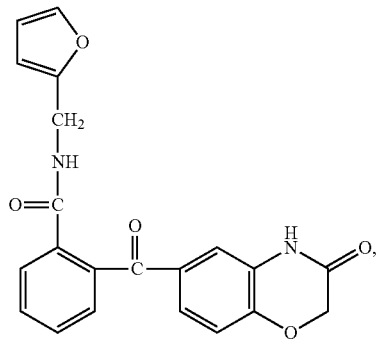 [SMILES: O=C1COc2ccc(C(=O)c3ccccc3C(=O)NCc3ccco3)cc2N1]

hereinafter referred to as embodiment 38.

In one example, the compound is according to Formula II, wherein E is absent, hereinafter referred to as embodiment 39.

In another example, the compound is according to embodiment 39, wherein A is ortho-phenylene, hereinafter referred to as embodiment 40.

In another example, the compound is according to embodiment 40, of Formula III,

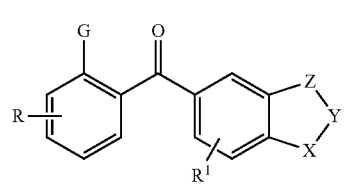

wherein Z, Y, and X are as defined above; G is selected from —C(O)R³, —C(O)N(R³)R³, —N(R³)CO₂R³, —N(R³)C(O)N(R³)R³, —N(R³)C(O)R³, —N(R³)R³, —S(O)₀₋₂R³, —SO₂N(R³)R³, optionally substituted aryl C₁₋₃alkyl, and optionally substituted heterocyclyl C₁₋₃alkyl; R is selected from —H, halogen, —CN, —NO₂, —OR³, —N(R³)R³, —SR³, —CO₂R³, and optionally substituted C₁₋₆alkyl; and R¹ is selected from —H, halogen, —CN, —NO₂, —OR³, —N(R³)R³, —S(O)₀₋₂R³, —SO₂N(R³)R³, —CO₂R³, —C(O)N(R³)R³, —N(R³)SO₂R³, —N(R³)C(O)R³, —N(R³)CO₂R³, —C(O)R³, —OC(O)R³, optionally substituted C₁₋₆alkyl, optionally substituted aryl, optionally substituted aryl C₁₋₆alkyl, optionally substituted heterocyclyl, and optionally substituted heterocyclyl C₁₋₆alkyl, hereinafter referred to as embodiment 41.

In another example, the compound is according to embodiment 41, wherein Z is —N═; Y is —C(R²)═; and X is selected from —N(R²)—, —S—, and —O—, hereinafter referred to as embodiment 42.

In another example, the compound is according to embodiment 42, wherein R and R¹ are —H, hereinafter referred to as embodiment 43.

In another example the compound is according to embodiment 43, of Formula IVa or IVb,

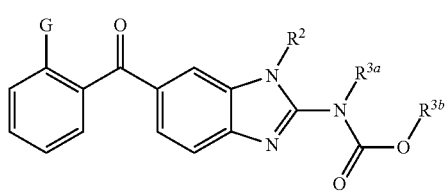

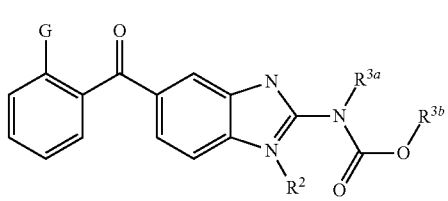

G is selected from —C(O)R³, —C(O)N(R³)R³, —N(R³)CO₂R³, —N(R³)C(O)N(R³)R³, —N(R³)C(O)R³, —N(R³)R³, —SO₂N(R³)R³, optionally substituted aryl C₁₋₃alkyl, and optionally substituted heterocyclyl C₁₋₃alkyl; wherein R³ is as defined above; R² is either —H or optionally substituted C₁₋₆alkyl, it being understood that when R² is —H and all other groups are the same, IVa and IVb represent tautomers of a single molecule; R³ᵃ is either —H or optionally substituted C₁₋₆alkyl; R³ᵇ is selected from optionally substituted $C_{1-6}$alkyl, optionally substituted aryl, optionally substituted aryl $C_{1-3}$alkyl, optionally substituted heterocyclyl, and optionally substituted heterocyclyl $C_{1-3}$alkyl, hereinafter referred to as embodiment 44.

In another example, the compound is according to embodiment 44, wherein $R^{3a}$ is —H, hereinafter referred to as embodiment 45.

In another example, the compound is according to 45, wherein $R^2$ is —H, hereinafter referred to as embodiment 46.

In another example, the compound is according to embodiment 46, wherein G is selected from —C(O)$R^3$, —C(O)N($R^3$)$R^3$, —N($R^3$)CO$_2R^3$, —N($R^3$)C(O)N($R^3$)$R^3$, and —N($R^3$)C(O)$R^3$, hereinafter referred to as embodiment 47.

In another example, the compound is according to embodiment 47, of Formula V,

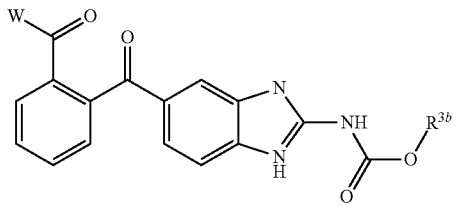

V wherein W is $R^3$ or —N($R^3$)$R^3$; and $R^{3b}$ is selected from optionally substituted $C_{1-6}$alkyl, optionally substituted aryl, and optionally substituted aryl $C_{1-3}$alkyl, hereinafter referred to as embodiment 48.

In another example, the compound is according to embodiment 48, wherein W is —N(H)$R^3$, hereinafter referred to as embodiment 49.

In another example, the compound is according to embodiment 49, wherein $R^3$ is optionally substituted aryl, hereinafter referred to as embodiment 50.

In another example, the compound is according to embodiment 50, wherein $R^{3b}$ is optionally substituted $C_{1-6}$alkyl, hereinafter referred to as embodiment 51.

In another example, the compound is according to embodiment 51, wherein $R^{3b}$ is $C_{1-6}$alkyl, hereinafter referred to as embodiment 52.

In another example, the compound is according to Formula II, wherein the compound is a pharmaceutically acceptable salt, hereinafter referred to as embodiment 53.

In another example, the compound is according to Formula II, wherein the compound is a prodrug, hereinafter referred to as embodiment 54.

The present invention also comprises a compound for modulating kinase activity, particularly Raf, of Formula VI,

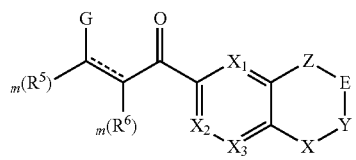

VI or a pharmaceutically acceptable salt, hydrate or prodrug thereof, wherein, each $R^5$ and $R^6$ is independently selected from —H, halogen, —CN, —NO$_2$, —O$R^3$, —N($R^3$)$R^3$, —S(O)$_{0-2}R^3$, —SO$_2$N($R^3$)$R^3$, —CO$_2R^3$, —C(O)N($R^3$)$R^3$, —N($R^3$)SO$_2R^3$, —N($R^3$)C(O)$R^3$, —N($R^3$)CO$_2R^3$, —C(O)$R^3$, —OC(O)$R^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

m is 1 or 2 dependent upon the presence or absence of saturation of the carbon bond between $R^5$ and $R^6$;

$X_1$, $X_2$ and $X_3$ are independently selected from —C$R^1$= or —N=;

each $R^1$ is independently selected from —H, halogen, —CN, —NO$_2$, —O$R^3$, —N($R^3$)$R^3$, —S(O)$_{0-2}R^3$, —SO$_2$N($R^3$)$R^3$, —CO$_2R^3$, —C(O)N($R^3$)$R^3$, —N($R^3$)SO$_2R^3$, —N($R^3$)C(O)$R^3$, —N($R^3$)CO$_2R^3$, —C(O)$R^3$, —OC(O)$R^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

Z and X are each independently selected from —C($R^2$)=, —N=, —N($R^2$)—, —S(O)$_{0-2}$—, and —O—;

E and Y are each independently selected from absent, —C($R^2$)($R^2$)—, —C(=O)—, —C($R^2$)= and —N=, but E and Y are not both absent, and E and Y are not both —N= when both Z and X are —N=;

each $R^2$ is independently selected from $R^3$, —N($R^3$)($R^3$), —C(O)N($R^3$)$R^3$, —N($R^3$)CO$_2R^3$, —N($R^3$)C(O)N($R^3$)$R^3$, and —N($R^3$)C(O)$R^3$;

each $R^3$ is independently selected from —H, optionally substituted $C_{1-6}$alkyl, optionally substituted $C_{3-7}$alicyclic, optionally substituted aryl, optionally substituted aryl $C_{1-3}$alkyl, optionally substituted heterocyclyl, and optionally substituted heterocyclyl $C_{1-3}$alkyl;

optionally two of $R^3$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P; and G is selected from —CO$_2R^3$, —C(O)$R^3$, —C(O)N($R^3$)$R^3$, —C(O)(N$R^3$), —C(O)N$R^3$[C($R^3$)$_2$]$_{0-1}R^3$, —C(O)N$R^3$O[C($R^3$)$_2$]$_{0-1}R^3$, —N($R^3$)CO$_2R^3$, —N($R^3$)C(O)N($R^3$)$R^3$, —N($R^3$)C(O)$R^3$, —N($R^3$)$R^3$, —S(O)$_{0-2}R^3$, —SO$_2$N($R^3$)$R^3$, optionally substituted aryl $C_{0-3}$alkyl, and optionally substituted heterocyclyl $C_{0-3}$alkyl, hereinafter referred to as embodiment 55.

In one example, the compound is according to Formula VI, wherein $R^4$ is —OH, hereinafter referred to as embodiment 56.

In one example, the compound is according to embodiment 56, wherein G is —C(O)$R^3$, —C(O)N($R^3$)$R^3$, —C(O)(N$R^3$), —C(O)N$R^3$[C($R^3$)$_2$]$_{0-1}R^3$, —C(O)N$R^3$O[C($R^3$)$_2$]$_{0-1}R^3$, hereinafter referred to as embodiment 57.

In one example, the compound is according to embodiment 57, wherein G is —C(O)N($R^3$)$R^3$, hereinafter referred to as embodiment 58.

In one example, the compound is according to embodiment 58, wherein G is —C(O)NH$R^3$, hereinafter referred to as embodiment 59.

In one example, the compound is according to Formula VI, wherein $R^3$ is optionally substituted $C_{1-6}$alkyl, hereinafter referred to as embodiment 60.

In one example, the compound is according to Formula VI, wherein $R^3$ is optionally substituted aryl, hereinafter referred to as embodiment 61.

In one example, the compound is according to Formula VI, wherein $R^3$ is optionally substituted aryl $C_{1-3}$alkyl, hereinafter referred to as embodiment 62.

In one example, the compound is according to Formula VI, wherein $R^3$ is optionally substituted heterocyclyl, hereinafter referred to as embodiment 63.

In one example, the compound is according to Formula VI, wherein $R^3$ is optionally substituted heterocyclyl $C_{1-3}$alkyl, hereinafter referred to as embodiment 64.

In one example, the compound is according to Formula VI, wherein $X_1$, $X_2$ and $X_3$ are —$CR^1$=, hereinafter referred to as embodiment 65.

In one example, the compound is according to embodiment 65, wherein E is absent, hereinafter referred to as embodiment 66.

In one example, the compound is according to embodiment 66, wherein Z is —N=; Y is —C($R^2$)=; and X is selected from —N($R^2$)—, —S—, and —O—, hereinafter referred to as embodiment 67.

In one example, the compound is according to embodiment 67, wherein $R^5$ and $R^6$ are optionally substituted $C_{1-6}$alkyl, hereinafter referred to as embodiment 68.

In one example, the compound is according to embodiment 68, wherein m is 1, hereinafter referred to as embodiment 69.

In one example, the compound is according to Formula VI, wherein the compound is a pharmaceutically acceptable salt, hereinafter referred to as embodiment 70.

In one example, the compound is according to Formula VI, wherein the compound is a prodrug, hereinafter referred to as embodiment 71.

The present invention also comprises a compound for modulating kinase activity, particularly Raf, of Formula VII,

VII or a pharmaceutically acceptable salt, hydrate, or prodrug thereof, wherein, A is a three- to seven-membered alicyclic, a five- to six-membered ortho-arylene or a five- to six-membered ortho-heteroarylene containing between one and three heteroatoms, either of the aforementioned optionally substituted with up to four R;

each R is independently selected from —H, halogen, —CN, —$NO_2$, —$OR^3$, —N($R^3$)$R^3$, —S(O)$_{0-2}R^3$, —$SO_2$N($R^3$)$R^3$, —$CO_2R^3$, —C(O)N($R^3$)$R^3$, —N($R^3$)$SO_2R^3$, —N($R^3$)C(O)$R^3$, —N($R^3$)$CO_2R^3$, —C(O)$R^3$, —OC(O)$R^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

optionally two of R, together with the atoms to which they are attached, form a first ring system fused with A, said first ring system substituted with zero to three of $R^1$;

$X_1$, $X_2$ and $X_3$ are independently selected from —$CR^1$= or —N=;

each $R^1$ is independently selected from —H, halogen, —CN, —$NO_2$, —$OR^3$, —N($R^3$)$R^3$, —S(O)$_{0-2}R^3$, —$SO_2$N($R^3$)$R^3$, —$CO_2R^3$, —C(O)N($R^3$)$R^3$, —N($R^3$)$SO_2R^3$, —N($R^3$)C(O)$R^3$, —N($R^3$)$CO_2R^3$, —C(O)$R^3$, —OC(O)$R^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

Z and X are each independently selected from —C($R^2$)=, —N=, —N($R^2$)—, —S(O)$_{0-2}$—, and —O—;

E and Y are each independently selected from absent, —C($R^2$)($R^2$)—, —C(=O)—, —C($R^2$)= and —N=, but E and Y are not both absent, and E and Y are not both —N= when both Z and X are —N=;

each $R^2$ is independently selected from $R^3$, —N($R^3$)($R^3$), —C(O)N($R^3$)$R^3$, —N($R^3$)$CO_2R^3$, —N($R^3$)C(O)N($R^3$)$R^3$, and —N($R^3$)C(O)$R^3$;

each $R^3$ is independently selected from —H, optionally substituted $C_{1-6}$alkyl, optionally substituted $C_{3-7}$alicyclic, optionally substituted aryl, optionally substituted aryl $C_{1-3}$alkyl, optionally substituted heterocyclyl, and optionally substituted heterocyclyl $C_{1-3}$alkyl;

optionally two of $R^3$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P; and $R^4$ is selected from —H, —OH, optionally substituted $C_{1-6}$ alkyl and optionally substituted $C_{1-6}$ alkoxy;

with the proviso, however, that the compound is not CAS Registry No. 439096-29-4:

CAS Registry No. 439107-32-1:

or

CAS Registry No. 439107-34-3:

hereinafter referred to as embodiment 72.

In one example, the compound is according to Formula VII, wherein A is a six-membered ortho-arylene, hereinafter referred to as embodiment 73.

In one example, the compound is according to embodiment 73, wherein A is ortho-phenylene, hereinafter referred to as embodiment 74.

In one example, the compound is according to embodiment 74, wherein $R^4$ is —OH, hereinafter referred to as embodiment 75.

In one example, the compound is according to Formula VII, wherein $R^3$ is optionally substituted $C_{1-6}$alkyl, hereinafter referred to as embodiment 76.

In one example, the compound is according to Formula VII, wherein $R^3$ is optionally substituted aryl, hereinafter referred to as embodiment 77.

In one example, the compound is according to Formula VII, wherein $R^3$ is optionally substituted aryl $C_{1-3}$alkyl, hereinafter referred to as embodiment 78.

In one example, the compound is according to Formula VII, wherein $R^3$ is optionally substituted heterocyclyl, hereinafter referred to as embodiment 79.

In one example, the compound is according to Formula VII, wherein $R^3$ is optionally substituted heterocyclyl $C_{1-3}$alkyl, hereinafter referred to as embodiment 80.

In one example, the compound is according to embodiment 80, wherein $X_1$, $X_2$ and $X_3$ are —CR$^1$=, hereinafter referred to as embodiment 81.

In one example, the compound is according to embodiment 81, wherein E is absent, hereinafter referred to as embodiment 82.

In one example, the compound is according to embodiment 82, wherein Z is —N=; Y is —C(R$^2$)=; and X is selected from —N(R$^2$)—, —S—, and —O—, hereinafter referred to as embodiment 83.

In one example, the compound is according to Formula VII, wherein the compound is a pharmaceutically acceptable salt, hereinafter referred to as embodiment 84.

In one example, the compound is according to Formula VII, wherein the compound is a prodrug, hereinafter referred to as embodiment 85.

The present invention also comprises a compound for modulating kinase activity, particularly Raf, of Formula VIII,

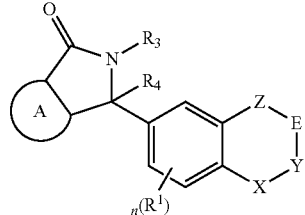

VIII or a pharmaceutically acceptable salt, hydrate, or prodrug thereof, wherein, A is either a five- to six-membered ortho-arylene or a five- to six-membered ortho-heteroarylene containing between one and three heteroatoms, either of the aforementioned optionally substituted with up to four R;

each R is independently selected from —H, halogen, —CN, —NO$_2$, —OR$^3$, —N(R$^3$)R$^3$, —S(O)$_{0-2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —C(O)R$^3$, —OC(O)R$^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

optionally two of R, together with the atoms to which they are attached, form a first ring system fused with A, said first ring system substituted with zero to three of R$^1$;

n is zero to three;

each R$^1$ is independently selected from —H, halogen, —CN, —NO$_2$, —OR$^3$, —N(R$^3$)R$^3$, —S(O)$_{0-2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —C(O)R$^3$, —OC(O)R$^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

Z and X are each independently selected from —C(R$^2$)=, —N=, —N(R$^2$)—, —S(O)$_{0-2}$—, and —O—;

E and Y are each independently selected from absent, —C(R$^2$)(R$^2$)—, —C(=O)—, —C(R$^2$)= and —N=, but E and Y are not both absent, and E and Y are not both —N= when both Z and X are —N=;

each R$^2$ is independently selected from R$^3$, —C(O)N(R$^3$)R$^3$, —N(R$^3$)CO$_2$R$^3$, —N(R$^3$)C(O)N(R$^3$)R$^3$, and —N(R$^3$)C(O)R$^3$;

each R$^3$ is independently selected from —H, optionally substituted $C_{1-6}$alkyl, optionally substituted aryl, optionally substituted aryl $C_{1-3}$alkyl, optionally substituted heterocyclyl, and optionally substituted heterocyclyl $C_{1-3}$alkyl;

optionally two of R$^3$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P; and R$^4$ is selected from —H, —OH, optionally substituted $C_{1-6}$ alkyl and optionally substituted $C_{1-6}$ alkoxy;

with the proviso, however, that the compound is not CAS Registry No. 439096-29-4:

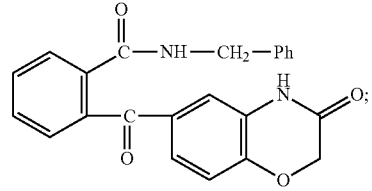 [SMILES: O=C1COc2ccc(C(=O)c3ccccc3C(=O)NCc3ccccc3)cc2N1]

CAS Registry No. 439107-32-1:

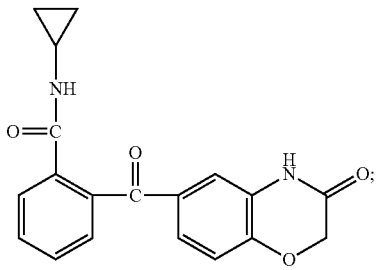 [SMILES: O=C1COc2ccc(C(=O)c3ccccc3C(=O)NC3CC3)cc2N1]

or
CAS Registry No. 439107-34-3:

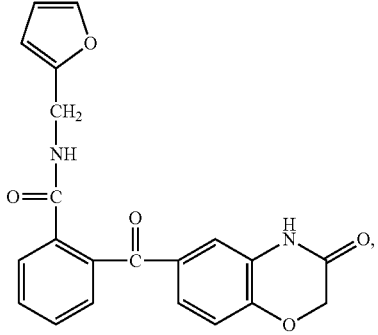 [SMILES: O=C1COc2ccc(C(=O)c3ccccc3C(=O)NCc3ccco3)cc2N1]

hereinafter referred to as embodiment 86.

In one example, the compound is according to Formula VIII, wherein E is absent, hereinafter referred to as embodiment 87.

In another example, the compound is according to embodiment 87, wherein A is ortho-phenylene, hereinafter referred to as embodiment 88.

In another example, the compound is according to embodiment 88, of Formula IX,

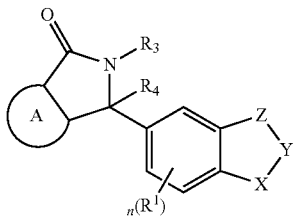

IX wherein A, n, R, $R^1$, $R^2$, $R^3$, $R^4$, Z, Y, and X are as defined above, hereinafter referred to as embodiment 89.

In another example, the compound is according to embodiment 89, wherein Z is —N=; Y is —C($R^2$)=; and X is selected from —N($R^2$)—, —S—, and —O—, hereinafter referred to as embodiment 90.

In another example, the compound is according to embodiment 90, wherein R and $R^1$ are —H, hereinafter referred to as embodiment 91.

In another example the compound is according to embodiment 91, of Formula Xa or Xb,

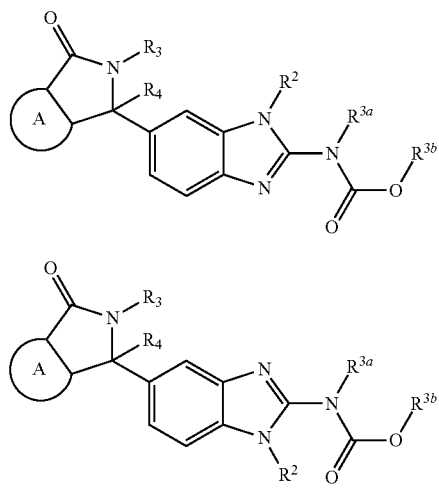

wherein A, $R^3$ and $R^4$ are as defined above; $R^2$ is either —H or optionally substituted $C_{1-6}$alkyl, it being understood that when $R^2$ is —H and all other groups are the same, Xa and Xb represent tautomers of a single molecule; $R^{3a}$ is either —H or optionally substituted $C_{1-6}$alkyl; $R^{3b}$ is selected from optionally substituted $C_{1-6}$alkyl, optionally substituted aryl, optionally substituted aryl $C_{1-3}$alkyl, optionally substituted heterocyclyl, and optionally substituted heterocyclyl $C_{1-3}$alkyl, hereinafter referred to as embodiment 92.

In another example, the compound is according to embodiment 92, wherein $R^{3a}$ is —H, hereinafter referred to as embodiment 93.

In another example, the compound is according to embodiment 93, wherein $R^2$ is —H, hereinafter referred to as embodiment 94.

In another example, the compound is according to embodiment 94, wherein $R^3$ is optionally substituted aryl, hereinafter referred to as embodiment 95.

In another example, the compound is according to embodiment 95, of Formula XI,

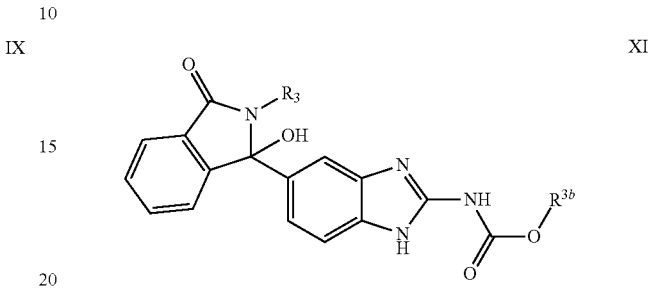

XI wherein $R^3$ is as defined above; and $R^{3b}$ is selected from optionally substituted $C_{1-6}$alkyl, optionally substituted aryl, and optionally substituted aryl $C_{1-3}$alkyl, hereinafter referred to as embodiment 96.

In another example, the compound is according to embodiment 96, wherein $R^3$ is disubstituted aryl, hereinafter referred to as embodiment 97.

In another example, the compound is according to embodiment 97, wherein $R^3$ is aryl disubstituted with alkyl and halogen, hereinafter referred to as embodiment 98.

In another example, the compound is according to Formula VIII, wherein the compound is a pharmaceutically acceptable salt, hereinafter referred to as embodiment 99.

In another example, the compound is according to Formula VIII, wherein the compound is a prodrug, hereinafter referred to as embodiment 100.

The present invention also comprises a compound for modulating kinase activity, particularly Raf, of Formula XII,

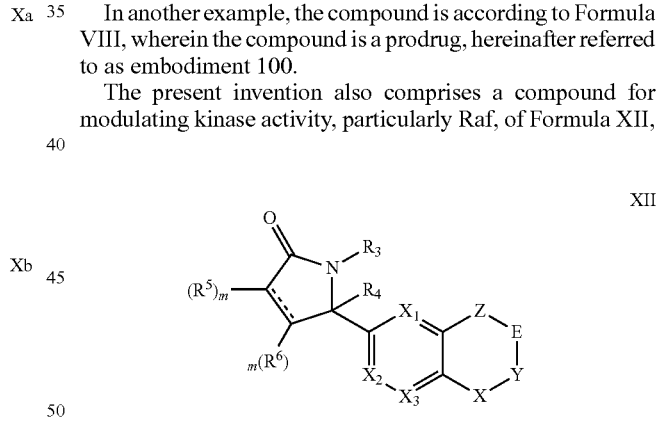

XII or a pharmaceutically acceptable salt, hydrate, or prodrug thereof, wherein, each $R^5$ and $R^6$ is independently selected from —H, halogen, —CN, —$NO_2$, —$OR^3$, —N($R^3$)$R^3$, —S(O)$_{0-2}R^3$, —$SO_2$N($R^3$)$R^3$, —$CO_2R^3$, —C(O)N($R^3$)$R^3$, —N($R^3$)$SO_2R^3$, —N($R^3$)C(O)$R^3$, —N($R^3$)$CO_2R^3$, —C(O)$R^3$, —OC(O)$R^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

m is 1 or 2 dependent upon the presence or absence of saturation of the carbon bond between $R^5$ and $R^6$;

$X_1$, $X_2$ and $X_3$ are independently selected from —$CR^1$= or —N=;

each $R^1$ is independently selected from —H, halogen, —CN, —$NO_2$, —$OR^3$, —N($R^3$)$R^3$, —S(O)$_{0-2}R^3$, —$SO_2$N($R^3$)

$R^3$, —$CO_2R^3$, —$C(O)N(R^3)R^3$, —$N(R^3)SO_2R^3$, —$N(R^3)C(O)R^3$, —$N(R^3)CO_2R^3$, —$C(O)R^3$, —$OC(O)R^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

Z and X are each independently selected from —$C(R^2)$=, —N=, —$N(R^2)$—, —$S(O)_{0-2}$—, and —O—;

E and Y are each independently selected from absent, —$C(R^2)(R^2)$—, —$C(=O)$—, —$C(R^2)$= and —N=, but E and Y are not both absent, and E and Y are not both —N= when both Z and X are —N=;

each $R^2$ is independently selected from $R^3$, —$N(R^3)(R^3)$, —$C(O)N(R^3)R^3$, —$N(R^3)CO_2R^3$, —$N(R^3)C(O)N(R^3)R^3$, and —$N(R^3)C(O)R^3$;

each $R^3$ is independently selected from —H, optionally substituted $C_{1-6}$alkyl, optionally substituted $C_{3-7}$alicyclic, optionally substituted aryl, optionally substituted aryl $C_{1-3}$alkyl, optionally substituted heterocyclyl, and optionally substituted heterocyclyl $C_{1-3}$alkyl;

optionally two of $R^3$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P; and $R^4$ is selected from —H, —OH, optionally substituted $C_{1-6}$ alkyl and optionally substituted $C_{1-6}$ alkoxy, hereinafter referred to as embodiment 101.

In one example, the compound is according to Formula XII, wherein $R^4$ is —OH, hereinafter referred to as embodiment 102.

In one example, the compound is according to embodiment 102, wherein G is —$C(O)R^3$, —$C(O)N(R^3)R^3$, —$C(O)(NR^3)$, —$C(O)NR^3O[C(R^3)_2]_{0-1}R^3$, —$C(O)NR^3O[C(R^3)_2]_{0-1}R^3$, hereinafter referred to as embodiment 103.

In one example, the compound is according to embodiment 103, wherein G is —$C(O)N(R^3)R^3$, hereinafter referred to as embodiment 104.

In one example, the compound is according to embodiment 104, wherein G is —$C(O)NHR^3$, hereinafter referred to as embodiment 105.

In one example, the compound is according to Formula XII, wherein $R^3$ is optionally substituted $C_{1-6}$alkyl, hereinafter referred to as embodiment 106.

In one example, the compound is according to Formula XII, wherein $R^3$ is optionally substituted aryl, hereinafter referred to as embodiment 107.

In one example, the compound is according to Formula XII, wherein $R^3$ is optionally substituted aryl $C_{1-3}$alkyl, hereinafter referred to as embodiment 108.

In one example, the compound is according to Formula XII, wherein $R^3$ is optionally substituted heterocyclyl, hereinafter referred to as embodiment 109.

In one example, the compound is according to Formula XII, wherein $R^3$ is optionally substituted heterocyclyl $C_{1-3}$alkyl, hereinafter referred to as embodiment 110;

In one example, the compound is according to Formula XII, wherein $X_1$, $X_2$ and $X_3$ are —$CR^1$=, hereinafter referred to as embodiment 111.

In one example, the compound is according to embodiment 111, wherein E is absent, hereinafter referred to as embodiment 112.

In one example, the compound is according to embodiment 112, wherein Z is —N=; Y is —$C(R^2)$=; and X is selected from —$N(R^2)$—, —S—, and —O—, hereinafter referred to as embodiment 113.

In one example, the compound is according to embodiment 113, wherein $R^5$ and $R^6$ are optionally substituted $C_{1-6}$alkyl, hereinafter referred to as embodiment 114.

In one example, the compound is according to embodiment 114, wherein m is 1, hereinafter referred to as embodiment 115.

In one example, the compound is according to Formula XII, wherein the compound is a pharmaceutically acceptable salt, hereinafter referred to as embodiment 116.

In one example, the compound is according to Formula XII, wherein the compound is a prodrug, hereinafter referred to as embodiment 117.

The present invention also comprises a compound for modulating kinase activity, particularly Raf, of Formula XIII,

XIII or a pharmaceutically acceptable salt, hydrate, or prodrug thereof, wherein, A is either a five- to six-membered ortho-arylene or a five- to six-membered ortho-heteroarylene containing between one and three heteroatoms, either of the aforementioned optionally substituted with up to four R;

each R is independently selected from —H, halogen, —CN, —$NO_2$, —$OR^3$, —$N(R^3)R^3$, —$S(O)_{0-2}R^3$, —$SO_2N(R^3)R^3$, —$CO_2R^3$, —$C(O)N(R^3)R^3$, —$N(R^3)SO_2R^3$, —$N(R^3)C(O)R^3$, —$N(R^3)CO_2R^3$, —$C(O)R^3$, —$OC(O)R^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

optionally two of R, together with the atoms to which they are attached, form a first ring system fused with A, said first ring system substituted with zero to three of $R^1$;

each $R^1$ is independently selected from —H, halogen, —CN, —$NO_2$, —$OR^3$, —$N(R^3)R^3$, —$S(O)_{0-2}R^3$, —$SO_2N(R^3)R^3$, —$CO_2R^3$, —$C(O)N(R^3)R^3$, —$N(R^3)SO_2R^3$, —$N(R^3)C(O)R^3$, —$N(R^3)CO_2R^3$, —$C(O)R^3$, —$OC(O)R^3$, optionally substituted $C_{1-6}$alkyl, optionally substituted aryl, optionally substituted aryl $C_{1-6}$alkyl, optionally substituted heterocyclyl, and optionally substituted heterocyclyl $C_{1-6}$alkyl;

each $R^3$ is independently selected from —H, optionally substituted $C_{1-6}$alkyl, optionally substituted aryl, optionally substituted aryl $C_{1-3}$alkyl, optionally substituted heterocyclyl, and optionally substituted heterocyclyl $C_{1-3}$alkyl;

optionally two of $R^3$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P; and $R^4$ is selected from —H, —OH, optionally substituted $C_{1-6}$ alkyl and optionally substituted $C_{1-6}$ alkoxy;

with the proviso, however, that the compound is not CAS Registry No. 439096-29-4:

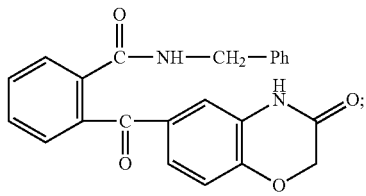

CAS Registry No. 439107-32-1:

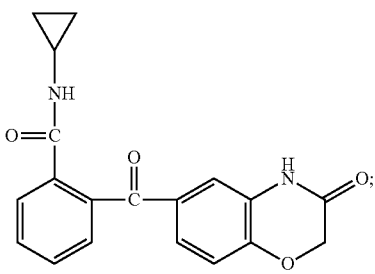 [SMILES: O=C1COc2ccc(C(=O)c3ccccc3C(=O)NC3CC3)cc2N1]

or
CAS Registry No. 439107-34-3:

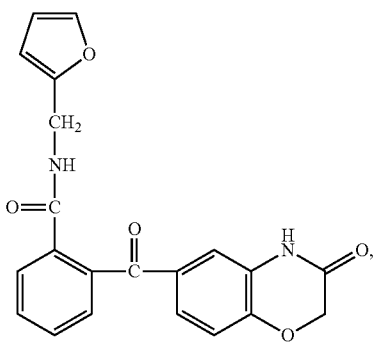 [SMILES: O=C1COc2ccc(C(=O)c3ccccc3C(=O)NCc3ccco3)cc2N1]

hereinafter referred to as embodiment 118.

In another example, the compound is according to Formula XIII, wherein A is ortho-phenylene, hereinafter referred to as embodiment 119.

In another example, the compound is according to embodiment 119, wherein $R^4$ is —OH, hereinafter referred to as embodiment 120.

In another example, the compound is according to embodiment 120, wherein $R^3$ is optionally substituted aryl, hereinafter referred to as embodiment 121.

In another example, the compound is according to embodiment 121, wherein $R^3$ is mono- or di-substituted phenyl, hereinafter referred to as embodiment 122.

In another example, the compound is according to embodiment 120, wherein $R^3$ is optionally substituted aryl $C_{1-3}$alkyl, hereinafter referred to as embodiment 123.

In another example, the compound is according to embodiment 120, wherein $R^3$ is optionally substituted heterocyclyl, hereinafter referred to as embodiment 124.

In another example, the compound is according to 120, wherein $R^3$ is optionally substituted heterocyclyl $C_{1-3}$alkyl, hereinafter referred to as embodiment 125.

In one example, the compound is according to Formula XIII, wherein the compound is a pharmaceutically acceptable salt, hereinafter referred to as embodiment 126.

In one example, the compound is according to Formula XIII, wherein the compound is a prodrug, hereinafter referred to as embodiment 127.

In another example, the compound is according to any one of embodiments 20-127, selected from Tables 1 or 2 below, and hereinafter referred to as embodiment 128.

Another aspect of the invention is a pharmaceutical composition comprising the compound according to any one of embodiments 20-128 and at least one pharmaceutically acceptable carrier or excipient, hereinafter referred to as embodiment 129.

Another aspect of the invention is a metabolite of the compound or the pharmaceutical composition according to any one of embodiments 20-129.

Another aspect of the invention is a method of modulating the in vivo activity of a kinase, the method comprising administering to a subject an effective amount of a composition comprising at least one of the compound according to any of embodiments 20-128 and the pharmaceutical composition according to embodiment 129, and a compound of CAS Registry No. 439096-29-4:

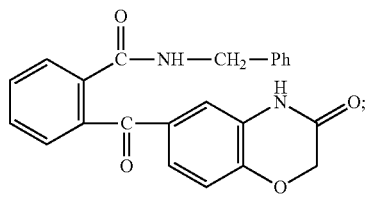 [SMILES: O=C1COc2ccc(C(=O)c3ccccc3C(=O)NCc3ccccc3)cc2N1]

CAS Registry No. 439107-32-1:

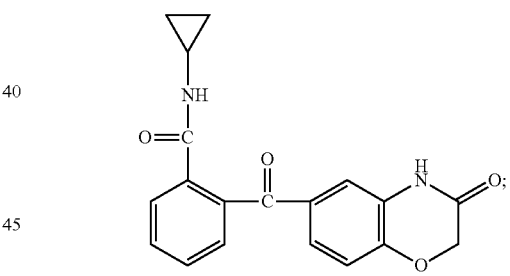

Or CAS Registry No. 439107-34-3:

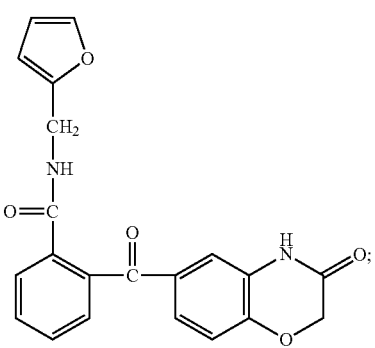 [SMILES: O=C1COc2ccc(C(=O)c3ccccc3C(=O)NCc3ccco3)cc2N1]

and a pharmaceutical composition thereof, hereinafter referred to as embodiment 131.

Another aspect of the invention is the method according to embodiment 131, wherein the kinase is Raf, hereinafter referred to as embodiment 132.

Another aspect of the invention is the method according to embodiment 132, wherein modulating the in vivo activity of Raf comprises inhibition of Raf.

Another aspect of the invention is a method of treating diseases or disorders associated with uncontrolled, abnormal, and/or unwanted cellular activities, the method comprising administering, to a mammal in need thereof, a therapeutically effective amount of a composition comprising at least one of the compound according to any of embodiments 20-128 and the pharmaceutical composition according to embodiment 129, and a compound of CAS Registry No. 439096-29-4:

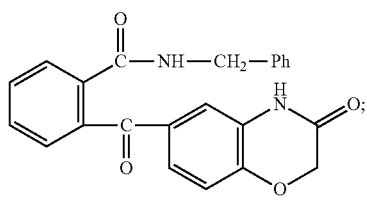 [SMILES: O=C1COc2ccc(C(=O)c3ccccc3C(=O)NCc3ccccc3)cc2N1]

CAS Registry No. 439107-32-1:

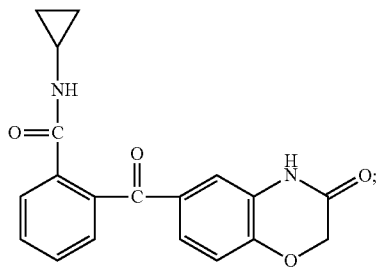 [SMILES: O=C1COc2ccc(C(=O)c3ccccc3C(=O)NC3CC3)cc2N1]

or CAS Registry No. 439107-34-3:

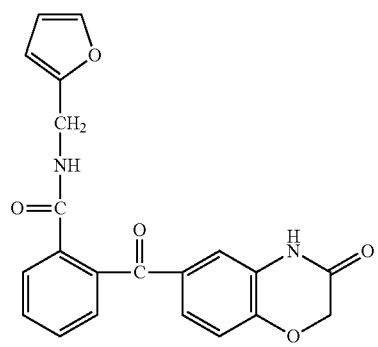 [SMILES: O=C1COc2ccc(C(=O)c3ccccc3C(=O)NCc3ccco3)cc2N1]

and a pharmaceutical composition thereof.

Another aspect of the invention is a method of screening for modulator of a Raf kinase, the method comprising combining either a composition comprising at least one of the compound according to any of embodiments 20-128 and the pharmaceutical composition according to embodiment 129, or a compound of CAS Registry No. 439096-29-4:

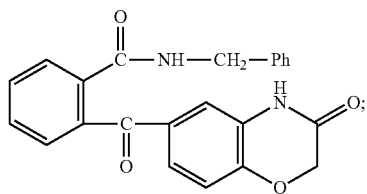 [SMILES: O=C1COc2ccc(C(=O)c3ccccc3C(=O)NCc3ccccc3)cc2N1]

CAS Registry No. 439107-32-1:

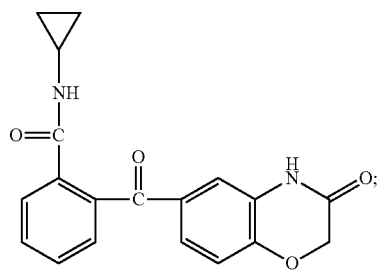 [SMILES: O=C1COc2ccc(C(=O)c3ccccc3C(=O)NC3CC3)cc2N1]

Or CAS Registry No. 439107-34-3:

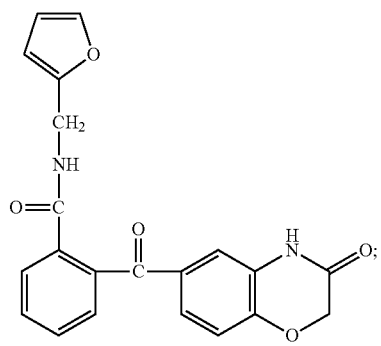 [SMILES: O=C1COc2ccc(C(=O)c3ccccc3C(=O)NCc3ccco3)cc2N1]

and a pharmaceutical composition thereof, and at least one candidate agent and determining the effect of the candidate agent on the activity of said kinase.

Another aspect of the invention is a method of inhibiting proliferative activity in a cell or a plurality of cells, the method comprising administering an effective amount of at least one of the compound according to any of embodiments 20-128 and the pharmaceutical composition according to embodiment 129, or a compound of CAS Registry No. 439096-29-4:

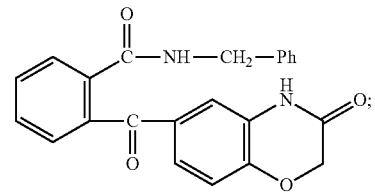

CAS Registry No. 439107-32-1:

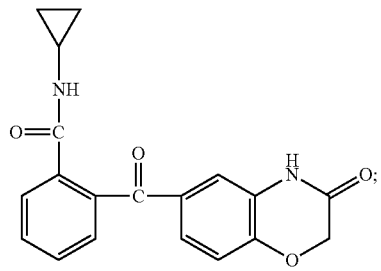 [SMILES: O=C1COc2ccc(C(=O)c3ccccc3C(=O)NC3CC3)cc2N1]

or CAS Registry No. 439107-34-3:

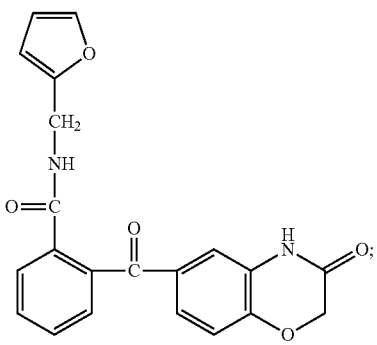 [SMILES: O=C1COc2ccc(C(=O)c3ccccc3C(=O)NCc3ccco3)cc2N1]

and a pharmaceutical composition thereof, to said cell or plurality of cells.

Another aspect of the invention is a method of preparing the compounds according to any of embodiments 20-129.

Definitions

As used in the present specification, the following words and phrases are generally intended to have the meanings as set forth below, except to the extent that the context in which they are used indicates otherwise or they are expressly defined to mean something different.

The symbol "—" means a single bond, "═" means a double bond, "≡" means a triple bond. The symbol "∼∼∼" refers to a group on a double-bond as occupying either position on the terminus of a double bond to which the symbol is attached; that is, the geometry, E- or Z-, of the double bond is ambiguous. When a group is depicted removed from its parent formula, the "∼" symbol will be used at the end of the bond which was theoretically cleaved in order to separate the group from its parent structural formula.

Chemical formulae use descriptors such as "$R^1$" accompanied by a list of formulae or verbage describing the scope of what is meant by the descriptor. A subsequent descriptor such as "$R^{1a}$" is used to describe some subset of the scope of $R^1$, and "$R^{1b}$" is used to describe another subset of the scope of $R^1$, and so on. In such subsequent cases, all other formulae containing simply "$R^1$" are meant to include the entire scope of the descriptor.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

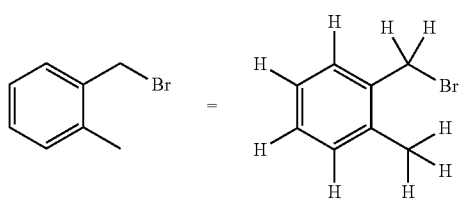

In this application, some ring structures are depicted generically and will be described textually. For example, in the schematic below, if in the structure on the left, ring A is used to describe a "spirocyclyl," then if ring A is cyclopropyl, there are at most four hydrogens on ring A (when "R" can also be —H). In another example, as depicted on the right side of the schematic below, if ring B is used to describe a "phenylene" then there can be at most four hydrogens on ring B (assuming depicted cleaved bonds are not C—H bonds).

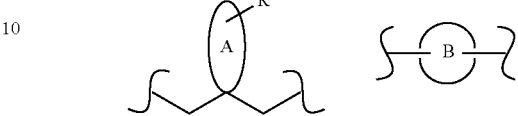

If a group "R" is depicted as "floating" on a ring system, as for example in the formula:

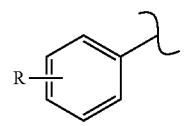

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

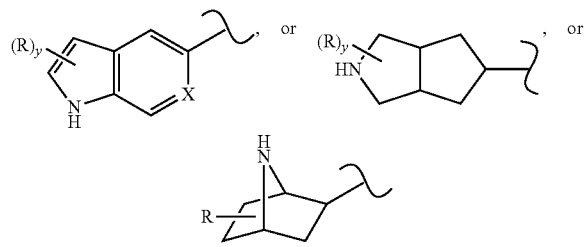

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals ═CH—) from one of the ring atoms, so long as a stable structure is formed. In the example depicted, the "R" group may reside on either the 5-membered or the 6-membered ring of the fused ring system. In the formula depicted above, when y is 2 for example, then the two "R' s" may reside on any two atoms of the ring system, again assuming each replaces a depicted, implied, or expressly defined hydrogen on the ring.

When a group "R" is depicted as existing on a ring system containing saturated carbons, as for example in the formula:

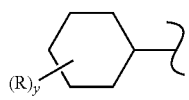

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

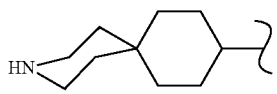

"Alkyl" is intended to include linear, branched, or cyclic hydrocarbon structures and combinations thereof, inclusively. For example, "$C_8$ alkyl" may refer to an n-octyl, isooctyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus, when an alkyl residue having a specific number of carbons is named, all geometric isomers having that number of carbons are intended to be encompassed; thus, for example, either "butyl" or "$C_4$alkyl" is meant to include n-butyl, sec-butyl, isobutyl, t-butyl, isobutenyl and but-2-yne radicals; and for example, "propyl" or "$C_3$alkyl" each include n-propyl, propenyl, and isopropyl. Otherwise, if alkenyl and/or alkynyl descriptors are used in a particular definition of a group, for example "$C_4$alkyl" along "$C_4$alkenyl," then $C_4$alkenyl geometric isomers are not meant to be included in "$C_4$alkyl," but other 4-carbon isomers are, for example $C_4$alkynyl. For example, a more general description, intending to encompass the invention as a whole may describe a particular group as "$C_{1-8}$alkyl" while a preferred species may describe the same group as including, "$C_{1-8}$alkyl," "$C_{1-6}$alkenyl" and "$C_{1-5}$alkynyl."

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—CH$_2$CH$_2$—), propylene (—CH$_2$CH$_2$CH$_2$—), dimethylpropylene (—CH$_2$C(CH$_3$)$_2$CH$_2$—), and cyclohexylpropylene (—CH$_2$CH$_2$CH(C$_6$H$_{13}$)).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above radicals, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —OCH$_2$CH$_2$OCH$_3$, and glycol ethers such as polyethyleneglycol and —O(CH$_2$CH$_2$O)$_x$CH$_3$, where x is an integer of between about two and about twenty, in another example, between about two and about ten, and in a further example between about two and about five. Another exemplary substituted alkoxy group is hydroxyalkoxy or —OCH$_2$(CH$_2$)$_y$OH, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —NH$_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, and furanyl-oxy-sulfonamino.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Arylene" generically refers to any aryl that has at least two non-hydrogen groups attached thereto. For a more specific example, "phenylene" refers to a divalent phenyl ring radical. A phenylene, thus may have more than two groups attached, but is defined by a minimum of two non-hydrogen groups attached thereto. The terms "ortho-arylene," "meta-arylene" or "para-arylene" refer to geometrical isomers of a particular arylene wherein, two groups attached to an aryl as depicted in a formula are situated in an ortho, meta or para geometrical relationship about the aryl, respectively.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. Both the aryl, and the corresponding alkylene, alkylidene, or alkylidyne radical portion of an arylalkyl group may be optionally substituted. "Lower arylalkyl" refers to an arylalkyl where the "alkyl" portion of the group has one to six carbons; this can also be referred to as aryl $C_{1-6}$alkyl.

"Exo-alkenyl" refers to a double bond that emanates from an annular carbon, and is not within the ring system, for example the double bond depicted in the formula below.

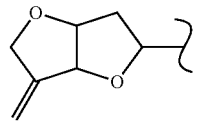

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroarylene" generically refers to any heteroaryl that has at least two groups attached thereto. For a more specific example, "pyridylene" refers to a divalent pyridyl ring radical. A pyridylene, thus may have more than two groups attached, but is defined by a minimum of two non-hydrogen groups attached thereto. For the purposes of this application, the term "ortho-heteroarylene" refers to a geometrical isomer of a particular heteroarylene wherein two groups attached to a heteroaryl as depicted in a formula are situated on contiguous atoms of the heteroaryl.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —S(O)$_{0-2}$—, refers to —S-(sulfide), —S(O)— (sulfoxide), and —SO$_2$-(sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl, and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic Such terms may be described in more than one way, for example, "lower heterocyclylalkyl" and "heterocyclyl $C_{1-6}$alkyl" are equivalent terms.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example in the term "optionally substituted aryl $C_{1-8}$alkyl," optional substitution may occur on both the "$C_{1-8}$alkyl" portion and the "aryl" portion of the molecule; and for example, optionally substituted alkyl includes optionally substituted cycloalkyl groups, which in turn are defined as including optionally substituted alkyl groups, potentially ad infinitum. A list of exemplary optional substitutions is included below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

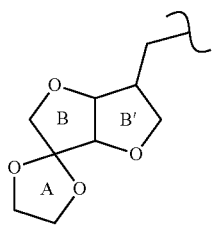

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected from: optionally substituted alkyl (for example, fluoromethyl, hydroxypropyl, nitromethyl, aminoethyl and the like), optionally substituted aryl (for example, 4-hydroxyphenyl, 2,3-difluorophenyl, and the like), optionally substituted arylalkyl (for example, 1-phenyl-ethyl, para-methoxyphenylethyl and the like), optionally substituted heterocyclylalkyl (for example, 1-pyridin-3-yl-ethyl, N-ethylmorphonlino and the like), optionally substituted heterocyclyl (for example, 5-chloro-pyridin-3-yl, 1-methyl-piperidin-4-yl and the like), optionally substituted alkoxy (for example methoxyethoxy, hydroxypropyloxy, methylenedioxy and the like), optionally substituted amino (for example, methylamino, diethylamino, trifluoroacetylamino and the like), optionally substituted amidino, optionally substituted aryloxy (for example, phenoxy, para-chlorophenoxy, meta-aminophenoxy, para-phenoxyphenoxy and the like), optionally substituted arylalkyloxy (for example, benzyloxy, 3-chlorobenzyloxy, meta-phenoxybenzyloxy and the like), carboxy (—$CO_2H$), optionally substituted carboalkoxy (that is, acyloxy or —OC(=O)R), optionally substituted carboxyalkyl (that is, esters or —$CO_2R$), optionally substituted carboxamido, optionally substituted benzyloxycarbonylamino (CBZ-amino), cyano, optionally substituted acyl, halogen, hydroxy, nitro, optionally substituted alkylsulfanyl, optionally substituted alkylsulfinyl, optionally substituted alkylsulfonyl, thiol, oxo, carbamyl, optionally substituted acylamino, optionally substituted hydrazino, optionally substituted hydroxylamino, and optionally substituted sulfonamido.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —$S(O_2)$—H, —$S(O_2)$-(optionally substituted alkyl), —$S(O_2)$-optionally substituted aryl), —$S(O_2)$-(optionally substituted heterocyclyl), —$S(O_2)$-(optionally substituted alkoxy), —$S(O_2)$-optionally substituted aryloxy), and —$S(O_2)$-(optionally substituted heterocyclyloxy).

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Compounds were named using the nomenclature engine published by ACD/Labs of Toronto Canada—ACD/Name Batch 7.00 Release, Product v. 7.10, Build 15 Sep. 2003.

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers.

The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —$OCH_2$—, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—OCH₂—" is meant to mean not only "—OCH₂—" as drawn, but also "—CH₂O—."

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular c-Met, c-Kit, KDR, flt-3, or flt-4-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one of ordinary skill in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one of ordinary skill in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a compound of the invention as the/an active agent, and, in addition, may include at least one other conventional pharmaceutical carrier or excipient, such as medicinal agents, pharmaceutical agents, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example Raf receptor kinase, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, Raf protein may be done in a number of ways. In one example, the candidate agent (the compound of the invention) is labeled, for example, with a fluorescent or radioactive moiety and binding determined directly. For example, thus may be done by attaching all or a portion of the Raf protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, Raf protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to Raf.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to Raf, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to Raf protein for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to Raf and thus is capable of binding to, and potentially modulating, the activity of the Raf. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to Raf with a higher affinity. Thus, if the candidate agent is labeled, the presence of the label on the support, coupled with a lack of competitor binding, may indicate the candidate agent is capable of binding to Raf.

It may be of value to identify the binding site of Raf. This can be done in a variety of ways. In one embodiment, once Raf has been identified as binding to the candidate agent, the Raf is fragmented or modified and the assays repeated to identify the necessary components for binding.

Modulation is tested by screening for candidate agents capable of modulating the activity of Raf comprising the steps of combining a candidate agent with Raf, as above, and determining an alteration in the biological activity of the Raf. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native Raf, but cannot bind to modified Raf.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components can be added in any order that provides for the requisite binding.

One of ordinary skill in the art would understand that certain crystallized, protein-ligand complexes, in particular Raf-ligand complexes, and their corresponding x-ray structure coordinates can be used to reveal new structural information useful for understanding the biological activity of Raf kinase's as described herein. As well, the key structural features of the aforementioned proteins, particularly, the shape of the ligand binding site, are useful in methods for designing or identifying selective modulators of Raf kinase's and in solving the structures of other proteins with similar features. Ligands of such complexes may include compounds of the invention as described herein.

As well, one of ordinary skill in the art would appreciate that such suitable x-ray quality crystals can be used as part of a method of identifying a candidate agent capable of binding to and modulating the activity of Raf kinases. Such methods may be characterized by the following aspects: a) introducing into a suitable computer program, information defining a ligand binding domain of a Raf kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one of ordinary skill in the art would appreciate that such methods may further entail: employing a candidate agent, so-determined to fit spatially into the ligand binding domain, in a biological activity assay for Raf kinase modulation, and determining whether said candidate agent modulates Raf kinase activity in the assay. Such methods may also include administering the candidate agent, determined to modulate Raf kinase activity, to a mammal suffering from a condition treatable by Raf kinase modulation, such as those described above.

Also, one of ordinary skill in the art would appreciate that compounds of the invention can be used in a method of evaluating the ability of a test agent to associate with a molecule or molecular complex comprising a ligand binding domain of a Raf kinase. Such a method may be characterized by the following aspects: a) creating a computer model of a Raf kinase binding pocket using structure coordinates obtained from suitable x-ray quality crystals of the Raf kinase, b) employing computational algorithms to perform a fitting operation between the test agent and the computer model of the binding pocket, and c) analyzing the results of the fitting operation to quantify the association between the test agent and the computer model of the binding pocket.

Abbreviations and their Definitions

The following abbreviations and terms have the indicated meanings throughout:

| Abbreviation | Meaning |
| --- | --- |
| Ac | acetyl |
| ACN | acetonitrile |
| ATP | adenosine triphosphate |
| BNB | 4-bromomethyl-3-nitrobenzoic acid |
| Boc | t-butyloxy carbonyl |
| br | broad |
| Bu | butyl |
| ° C. | degrees Celsius |
| c- | cyclo |
| CBZ | CarboBenZoxy = benzyloxycarbonyl |
| d | doublet |
| dd | doublet of doublet |
| dt | doublet of triplet |
| DBU | Diazabicyclo[5.4.0]undec-7-ere |
| DCM | dichloromethane = methylene chloride = $CH_2Cl_2$ |
| DCE | dichloroethylene |
| DEAD | diethyl azodicarboxylate |
| DIC | diisopropylcarbodiimide |
| DIEA | N,N-diisopropylethyl amine |
| DMAP | 4-N,N-dimethylaminopyridine |
| DMF | N,N-dimethylfonnamide |
| DMSO | dimethyl sulfoxide |
| DVB | 1,4-divinylbenzene |
| EEDQ | 2-ethoxy-1-ethoxycarbonyl-1,2-dihydroquinoline |
| EI | Electron Impact ionization |
| Et | ethyl |
| Fmoc | 9-fluorenylmethoxycarbonyl |
| g | gram(s) |
| GC | gas chromatography |
| h or hr | hour(s) |
| HATU | O-(7-Azabenzotriazol-1-yl)-1,1,3,3-tetramethyluronium hexafluorophosphate |
| HMDS | hexamethyldisilazane |
| HOAc | acetic acid |
| HOBt | hydroxybenzotriazole |
| HPLC | high pressure liquid chromatography |
| L | liter(s) |
| M | molar or molarity |
| m | multiplet |
| Me | methyl |
| mesyl | methanesulfonyl |
| mg | milligram(s) |
| MHz | megahertz (frequency) |
| Min | minute(s) |
| mL | milliliter(s) |
| mM | millimolar |
| mmol | millimole(s) |
| mol | mole(s) |
| MS | mass spectral analysis |

-continued

| Abbreviation | Meaning |
| --- | --- |
| MTBE | methyl t-butyl ether |
| N | normal or normality |
| NBS | N-bromosuccinimide |
| NCS | N-chlorosuccinimide |
| nM | nanomolar |
| NMO | N-methylmorpholine oxide |
| NMR | nuclear magnetic resonance spectroscopy |
| PEG | polyethylene glycol |
| pEY | poly-glutamine, tyrosine |
| Ph | phenyl |
| PhOH | phenol |
| PfP | pentafluorophenol |
| PfPy | pentafluoropyridine |
| PPTS | Pyridinium p-toluenesulfonate |
| Py | pyridine |
| PyBroP | bromo-tris-pyrrolidino-phosphonium hexafluorophosphate |
| q | quartet |
| RT | Room temperature |
| Sat'd | saturated |
| s | singlet |
| s- | secondary |
| t- | tertiary |
| t or tr | triplet |
| TBDMS | t-butyldimethylsilyl |
| TES | triethylsilane |
| TFA | trifluoroacetic acid |
| THF | tetrahydrofuran |
| TMOF | trimethyl orthoformate |
| TMS | trimethylsilyl |
| tosyl | p-toluenesulfonyl |
| Trt | triphenylmethyl |
| μL | microliter(s) |
| μM | Micromole(s) or micromolar |

Synthesis of Compounds

Scheme 1 depicts two general synthetic routes for compounds of the invention and is not intended to be limiting. Specific examples are described subsequently to this general synthetic description. In the generalizations below, specific reaction conditions or details, for example, added reagents, catalysts, solvents, reaction temperature, and the like are not described. The general routes depicted in conjunction with the specific examples provided contain sufficient information to allow one of ordinary skill in the art to synthesize compounds of the invention.

Referring to Scheme 1, a suitable reactive intermediate (1) may be prepared, for example, in situ by metal-halogen exchange, where M is a metal such at lithium or magnesium, followed by condensation with a suitable aldehyde precursor, for example, to give alcohol (2). Oxidation of intermediate (2) may be expected to provide a compound of the invention (6) according to Formula I, or (6) may be an intermediate or precursor requiring derivatization known to one of ordinary skill in the art to obtain a compound of the invention. In an alternative synthetic approach, one may proceed by reaction, for example an electrophilic aromatic substitution, of a suitable precursor such as a cyclic anhydride (3) with select aromatic fragments in a regioselective manner to afford an intermediate (4) where G' is introduced as for example a carboxylic acid, which may then be converted by a range of either single or multi-step synthetic transformations to give intact A-ring substituent G as depicted in intermediate (5). One such example includes the activation of a carboxylate intermediate (4), where G' is —$CO_2H$, with selected peptide coupling agents, followed by reaction with a primary amine to provide (5), where G is C(=O)NHR. Groups X' and Z' may then be elaborated further to afford (6).

Scheme 1

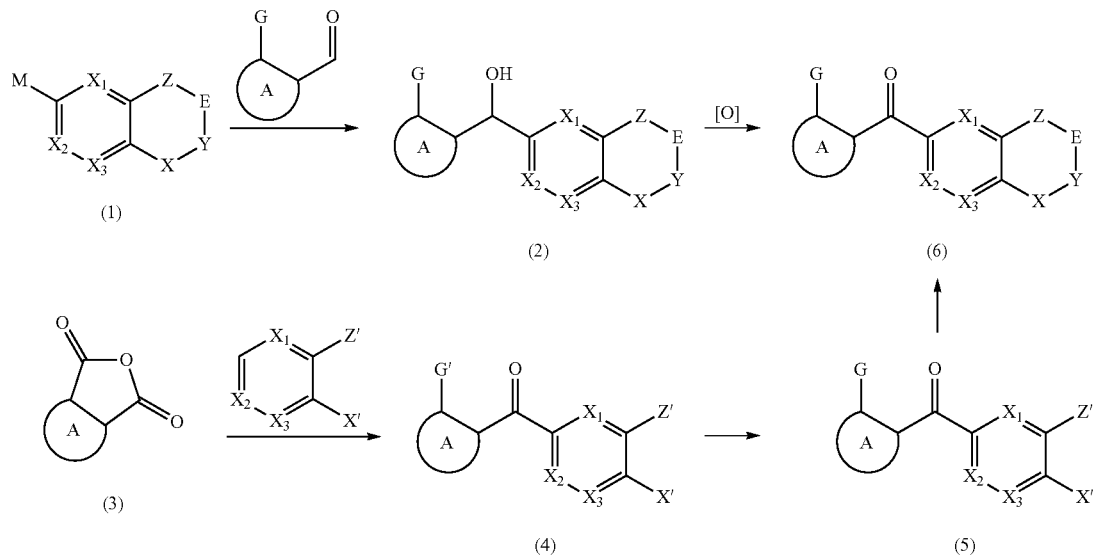

Compounds of the invention may also generally be prepared according to the sequence outlined in Scheme 2. Thus, 2-(4-chloro-3-nitrobenzoyl)benzoic acid (1) on treatment with cyanuric fluoride affords fluorolactone (2) which may be reacted with a range of nucleophilic amines to provide lactam products such as (3). Nucleophilic displacement of the chloride may then be carried out on treatment with ammonia in an appropriate solvent with heating or alternatively by using sodium azide to afford either (4a), X=NH$_2$ or (4b), X=N$_3$, respectively. Reduction of either intermediate to give (5) may be carried out under a range of conditions, the appropriate choice of which depends on the nature of the substrate, including the selection of R. For example, catalytic hydrogenation using palladium on carbon, platinum oxide or Raney nickel may be employed. Alternatively, iron metal or tin (II) chloride may also be used as effective reducing agents. The choice of reagents and reaction conditions applicable to the aforementioned transformations are well known in the art, see: 1) Larock, Comprehensive Organic Transformations, VCH Publishers, Inc. 2) March, Advanced Organic Chemistry, Wiley Interscience. Conversion of the resulting phenylenediamine (5) to benzimidazole (6) can be achieved in one step by treatment with 1,3-bis(methoxycarbonyl)2-methyl-2-thiopseudourea in acetic acid with heating. Alternatively, the conversion to (6) may be carried out by treatment first with methoxycarbonyl isothiocyanate following by heating in the presence of an appropriate carbodimide such as DCC or EDCI (J. C. Hazelton et al., Tetrahedron 1995, 51 (39), 10771-10794).

Scheme 2

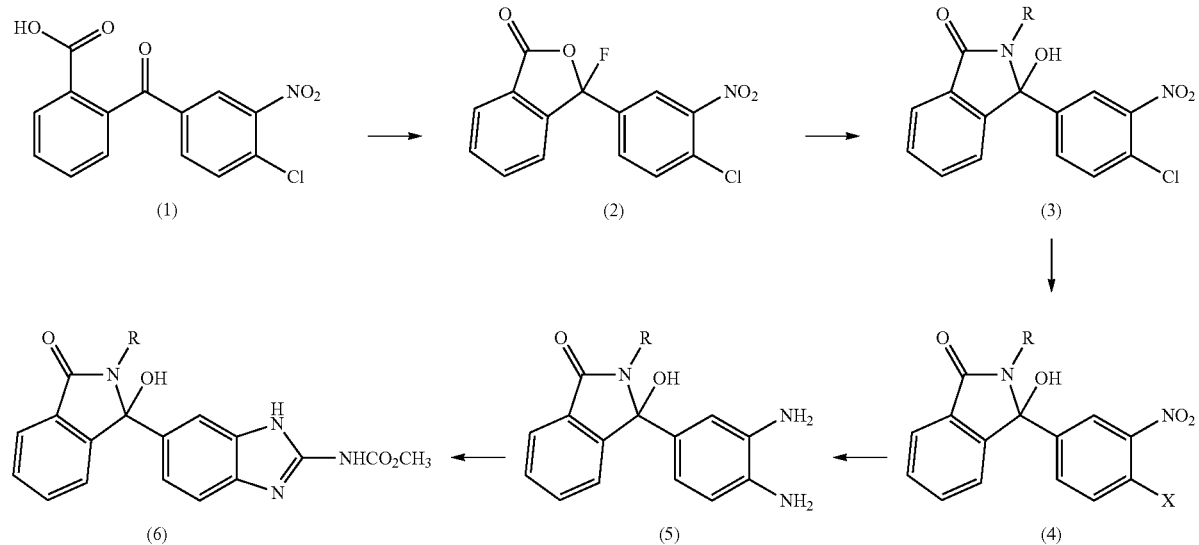

In some cases, it may be desired to introduce a carbamate or amide at the benzimidazole 2-position in which the methoxycarbonyl moiety is replaced by another alkoxycarbonyl or acyl group. In such an instance, the thiopsueudourea reagent of choice may be straightforwardly prepared according to the general method illustrated in Scheme 3. For example, reaction of an alcohol with 4-nitrophenyl chloroformate to give carbonate (7) followed by reaction with 2-methyl-2-thiopseudourea sulfate under basic conditions affords the 1-alkoxycarbonyl-2-methyl-2-thiopsueudourea reagent (8), which will also readily undergo reaction with phenylenediamines to give compounds of the invention. Alternatively, chloroformates, acid chlorides or anhydrides as well as activated esters and the like may also be reacted with 2-methyl-2-thiopseudourea under appropriate conditions to afford monoacylated derivatives such as (8) which are also useful in the synthesis of functionalized 2-aminobenzimidazoles.

Scheme 3

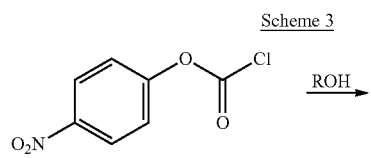

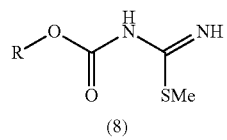

(8)

An alternative general approach to compounds of the invention that may be employed for the rapid parallel synthesis of a range of lactam derivatives is outlined in Scheme 4. Thus, conversion of (1) to the corresponding benzyl ester (9) under standard conditions followed by proceeding as outlined in Scheme 1 affords (10) in 3 steps. Protection of the basic aminobenzimidazole moiety using a suitable protecting group (Greene and Wuts, Protective Groups in Organic Synthesis, Wiley Interscience) and cleavage of the benzyl ester by hydrogenation affords benzoic acid (11). Introduction of the lactam may be carried out under a range of amide bond forming conditions well known in the art. Of particular utility is the conversion of (11) to the fluorolactone (12), which affords lactam products even with relatively weakly nucleophilic amines. Subsequent deprotection of the aminobenzimidazole ring completes this synthetic approach.

Scheme 4

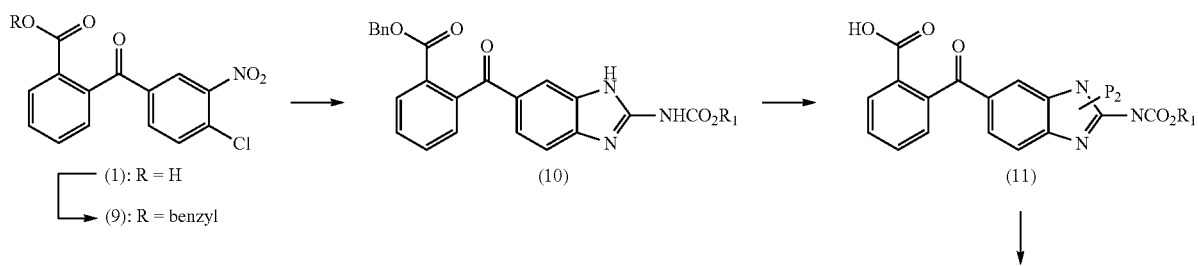

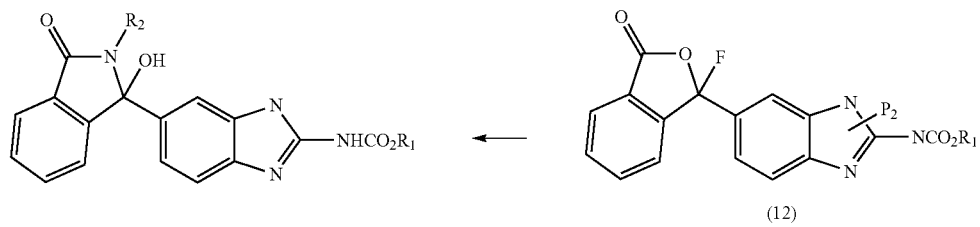

-continued

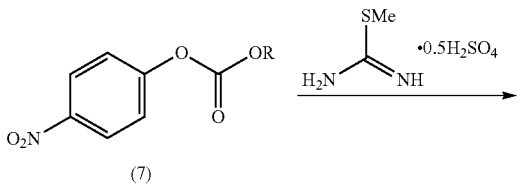

The ring-chain structural tautomerism of 2-benzoylbenzamides is well established in the art and thus it is understood that compounds of the invention such as (6) exist in dynamic equilibrium as a mixture of the chain or benzamide form (6a) and the ring or lactam form (6b), Figure VI. The thermodynamic equilibrium ratio is a function of substrate, temperature, solvent and pH and may be qualitatively determined by using appropriate spectroscopic techniques including NMR and UV or IR spectroscopy.

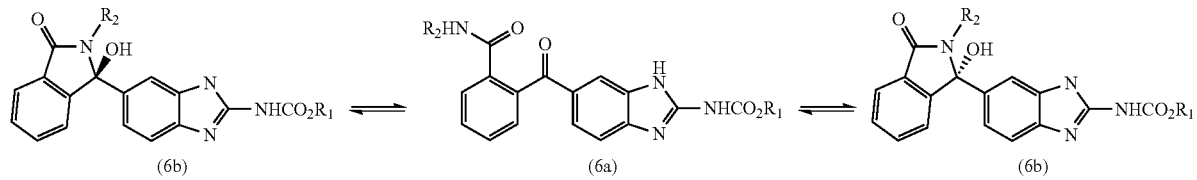

FIG. VI

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety. Generally, each example is set out below with a corresponding multi-step synthesis scheme. Following specific examples are lists of compounds that were made in a similar way.

Example 1

6-{2-[(4-Chlorophenyl)methyl]-1-hydroxy-3-oxo-2,3-dihydro-1H-isoindol-1-yl}-2H-1,4-benzoxazin-3(4H)-one To a solution of 2-[(3-oxo-3,4-dihydro-2H-1,4-benzoxazine-6-yl)carbonylbenzoic acid (50 mg, 0.17 mmol) in N,N-dimethylformamide (1.00 mL) was added N-methylmorpholine (74 uL, 0.67 mmol) followed by addition of HOAt (55 mg, 0.40 mmol) and HATU (130 mg, 0.34 mmol). The mixture was stirred for 30 minutes at room temperature followed by the addition of 4-chloro-benzylamine (49 uL, 0.40 mmol). The reaction mixture was then heated to 60° C. for 2 h. The mixture was cooled to room temperature and the solvent was evaporated. The residue was dissolved in ethyl acetate and the organic layer was washed with brine, 1.0 M aq. hydrochloric acid, brine, saturated aq. sodium-hydrogencarbonate and brine. The organic layer was separated, dried over anhydrous sodium sulfate, filtered and the filtrate concentrated in vacuo. The residue was recrystallized from methanol to afford the title compound (7.3 mg, 15%). MS (EI) for $C_{22}H_{15}ClN_2O_4$: 443 (MNa$^+$).

Using the same or analogous synthetic techniques and/or substituting with alternative reagents, the following compounds of the invention were prepared:

6-(1-hydroxy-2-{[4-(methyloxy)phenyl]methyl}-3-oxo-2,3-dihydro-1H-isoindol-1-yl)-2H-1,4-benzoxazin-3(4H)-one: MS (EI) for $C_{24}H_{20}N_2O_5$: 399 (MH$^+$—H$_2$O).

6-(1-hydroxy-2-{[3-(methyloxy)phenyl]methyl}-3-oxo-2,3-dihydro-1H-isoindol-1-yl)-2H-1,4-benzoxazin-3(4H)-one: MS (EI) for $C_{24}H_{20}N_2O_5$: 399 (MH$^+$—H$_2$O), 417 (MH$^+$).

6-{2-[(4-bromophenyl)methyl]-1-hydroxy-3-oxo-2,3-dihydro-1H-isoindol-1-yl}-2H-1,4-benzoxazin-3(4H)-one: MS (EI) for $C_{23}H_{17}BrN_2O_4$: 467 (MH$^+$).

6-{2-[(3-bromophenyl)methyl]-1-hydroxy-3-oxo-2,3-dihydro-1H-isoindol-1-yl}-2H-1,4-benzoxazin-3(4H)-one: MS (EI) for $C_{23}H_{17}BrN_2O_4$: 467 (MH$^+$).

6-{2-[(3,4-dichlorophenyl)methyl]-1-hydroxy-3-oxo-2,3-dihydro-1H-isoindol-1-yl}-2H-1,4-benzoxazin-3(4H)-one: MS (EI) for $C_{23}H_{16}Cl_2N_2O_4$: 455 (MH$^+$).

6-{2-[(4-fluorophenyl)methyl]-1-hydroxy-3-oxo-2,3-dihydro-1H-isoindol-1-yl}-2H-1,4-benzoxazin-3(4H)-one: MS (EI) for $C_{23}H_{17}FN_2O_4$: 405 (MH$^+$).

6-(2-{[4-chloro-3-(trifluoromethyl)phenyl]methyl}-1-hydroxy-3-oxo-2,3-dihydro-1H-isoindol-1-yl)-2H-1,4-benzoxazin-3(4H)-one: MS (EI) for $C_{24}H_{16}ClF_3N_2O_4$: 489 (MH$^+$).

6-{1-hydroxy-2-[(4-methylphenyl)methyl]-3-oxo-2,3-dihydro-1H-isoindol-1-yl}-2H-1,4-benzoxazin-3(4H)-one: MS (EI) for $C_{24}H_{20}N_2O_4$: 423 (MH$^+$).

6-{2-[(3,4-dimethylphenyl)methyl]-1-hydroxy-3-oxo-2,3-dihydro-1H-isoindol-1-yl}-2H-1,4-benzoxazin-3(4H)-one: MS (EI) for $C_{25}H_{22}N_2O_4$: 416 (MH$^+$).

6-(2-{[4-(dimethylamino)phenyl]methyl}-1-hydroxy-3-oxo-2,3-dihydro-1H-isoindol-1-yl)-2H-1,4-benzoxazin-3(4H)-one: MS (EI) for $C_{25}H_{23}N_3O_4$: 444 (MNa$^+$).

6-[1-hydroxy-3-oxo-2-(3-phenylpropyl)-2,3-dihydro-1H-isoindol-1-yl]-2H-1,4-benzoxazin-3(4H)-one: MS (EI) for $C_{25}H_{22}N_2O_4$: 437 (MNa$^+$).

6-[1-hydroxy-3-oxo-2-(2-phenylethyl)-2,3-dihydro-1H-isoindol-1-yl]-2H-1,4-benzoxazin-3(4H)-one: $^1$H NMR (400 MHz, d$_6$-DMSO): 10.60 (s, 1H), 7.76 (d, 1H), 7.58 (dd, 2H), 7.12-7.36 (m, 6H), 6.85 (m, 3H), 4.54 (s, 2H), 3.52 (m, 1H), 3.16 (m, 1H), 2.82 (m, 1H), 2.62 (m, 1H). MS (EI) for $C_{24}H_{20}N_2O_4$: 401 (MH$^+$), 384 (MH$^+$–H$_2$O).

6-(1-hydroxy-3-oxo-2-phenyl-2,3-dihydro-1H-isoindol-1-yl)-2H-1,4-benzoxazin-3(4H)-one: MS (EI) for $C_{22}H_{16}N_2O_4$: 373 (MH$^+$).

6-[2-(3-chlorophenyl)-1-hydroxy-3-oxo-2,3-dihydro-1H-isoindol-1-yl]-2H-1,4-benzoxazin-3(4H)-one: MS (EI) for $C_{22}H_{15}ClN_2O_4$: 429 (MNa$^+$).

6-[2-(4-chlorophenyl)-1-hydroxy-3-oxo-2,3-dihydro-1H-isoindol-1-yl]-2H-1,4-benzoxazin-3(4H)-one: MS (EI) for $C_{22}H_{15}ClN_2O_4$: 407 (MH$^+$).

6-(2-butyl-1-hydroxy-3-oxo-2,3-dihydro-1H-isoindol-1-yl)-2H-1,4-benzoxazin-3(4H)-one: MS (EI) for $C_{20}H_{20}N_2O_4$: 353 (MH$^+$).

6-[1-hydroxy-2-(1-methylethyl)-3-oxo-2,3-dihydro-1H-isoindol-1-yl]-2H-1,4-benzoxazin-3(4H)-one: MS (EI) for $C_{19}H_{18}N_2O_4$: 361 (MNa$^+$).

6-(1-hydroxy-2-{[2-(methyloxy)phenyl]methyl}-3-oxo-2,3-dihydro-1H-isoindol-1-yl)-2H-1,4-benzoxazin-3(4H)- one: ¹H NMR (400 MHz, d₆-DMSO): 10.53 (s, 1H), 7.75 (d, 1H), 7.53-7.61 (m, 2H), 7.28 (d, 1H), 7.11-7.15 (m, 3H), 6.75-6.88 (m, 5H), 4.52 (s, 2H), 4.51 (d, 1H), 4.09 (d, 1H), 3.71 (s, 3H); MS (EI) for $C_{24}H_{20}N_2O_5$: 439 (MNa⁺).

6-{2-[(3-chlorophenyl)methyl]-1-hydroxy-3-oxo-2,3-dihydro-1H-isoindol-1-yl}-2H-1,4-benzoxazin-3(4H)-one: ¹H NMR (400 MHz, d₆-DMSO): 10.52 (s, 1H), 7.76 (d, 1H), 7.54-7.62 (m, 2H), 7.15-7.30 (m, 6H), 6.78-6.83 (m, 3H), 4.52 (s, 2H), 4.42 (d, 1H), 4.24 (d, 1H); MS (EI) for $C_{23}H_{17}ClN_2O_4$: 421 (MH⁺).

6-{2-[(2-chlorophenyl)methyl]-1-hydroxy-3-oxo-2,3-dihydro-1H-isoindol-1-yl]-2H-1,4-benzoxazin-3(4H)-one: ¹H NMR (400 MHz, d₆-DMSO): 10.52 (s, 1H), 7.78 (d, 1H), 7.55-7.64 (m, 2H), 7.16-7.33 (m, 6H), 6.88 (s, 1H), 6.80 (s, 2H), 4.60 (d, 1H), 4.5 (s, 2H), 4.25 (d, 1H); MS (EI) for $C_{23}H_{17}ClN_2O_4$: 443 (MNa⁺).

6-{2-[(3-fluorophenyl)methyl]-1-hydroxy-3-oxo-2,3-dihydro-1H-isoindol-1-yl]-2H-1,4-benzoxazin-3(4H)-one: ¹H NMR (400 MHz, d₆-DMSO): 10.52 (s, 1H), 7.75 (d, 1H), 7.53-7.62 (m, 2H), 7.22-7.30 (m, 3H), 6.96-7.03 (m, 3H), 6.82-6.84 (m, 3H), 4.52 (s, 2H), 4.45 (d, 1H), 4.22 (d, 1H); MS (EI) for $C_{23}H_{17}FN_2O_4$: 427 (MNa⁺).

6-{2-[(2-bromophenyl)methyl]-1-hydroxy-3-oxo-2,3-dihydro-1H-isoindol-1-yl}-2H-1,4-benzoxazin-3(4H)-one: ¹H NMR (400 MHz, d₆-DMSO): δ 10.53 (s, 1H), 7.5-7.8 (m, 4H), 7.13-7.32 (m, 5H), 6.90 (s, 1H), 6.82 (s, 2H), 4.57 (d, 1H), 4.52 (s, 2H), 4.20 (d, 1H); MS (EI) for $C_{23}H_{17}BrN_2O_4$: 489 (MNa⁺).

6-{2-[(2-fluorophenyl)methyl]-1-hydroxy-3-oxo-2,3-dihydro-1H-isoindol-1-yl}-2H-1,4-benzoxazin-3(4H)-one: ¹H NMR (400 MHz, d₆-DMSO): 10.50 (s, 1H), 7.77 (d, 1H), 7.55-7.62 (m, 2H), 7.27-7.30 (m, 2H), 7.20 (s, 2H), 7.0-7.10 (m, 2H), 6.78-6.83 (m, 3H), 4.54 (d, 1H), 4.50 (s, 2H), 4.27 (d, 1H); MS (EI) for $C_{23}H_{17}FN_2O_4$: 427 (MNa⁺).

6-(1-hydroxy-3-oxo-2-{[2-(trifluoromethyl)phenyl]methyl}-2,3-dihydro-1H-isoindol-1-yl)-2H-1,4-benzoxazin-3(4H)-one: ¹H NMR (400 MHz, d₆-DMSO): 10.51 (s, 1H), 7.80 (d, 1H), 7.57-7.66 (m, 3H), 7.27-7.50 (m, 5H), 6.8-6.86 (m, 3H), 4.72 (d, 1H), 4.50 (s, 2H), 4.35 (d, 1H); MS (EI) for $C_{24}H_{17}F_3N_2O_4$: 477 (MNa⁺).

6-{2-[(5-bromo-2-fluorophenyl)methyl]-1-hydroxy-3-oxo-2,3-dihydro-1H-isoindol-1-yl}-2H-1,4-benzoxazin-3(4H)-one: ¹H NMR (400 MHz, d₆-DMSO): 10.52 (s, 1H), 7.80 (d, 1H), 7.55-7.64 (m, 2H), 7.27-7.40 (m, 4H), 7.02-7.07 (m, 1H), 6.80-6.83 (m, 3H), 4.51 (s, 2H), 4.48 (d, 1H), 4.27 (d, 1H); MS (EI) for $C_{23}H_{16}BrFN_2O_4$: 506 (MNa⁺).

6-{1-hydroxy-2-[(3-nitrophenyl)methyl]-3-oxo-2,3-dihydro-1H-isoindol-1-yl}-2H-1,4-benzoxazin-3(4H)-one: ¹H NMR (400 MHz, d₆-DMSO): 10.50 (s, 1H), 8.0 (d, 1H), 7.93 (s, 1H), 7.78 (d, 1H), 7.47-7.64 (m, 4H), 7.25-7.30 (m, 2H), 6.77 (s, 3H), 4.54 (s, 1H), 4.50 (s, 2H), 4.45 (d, 1H); MS (EI) for $C_{23}H_{17}N_3O_6$: 454 (MNa⁺).

6-(1-hydroxy-3-oxo-2-{[3-(trifluoromethyl)phenyl]methyl}-2,3-dihydro-1H-isoindol-1-yl)-2H-1,4-benzoxazin-3(4H)-one: ¹H NMR (400 MHz, d₆-DMSO): 10.50 (s, 1H), 7.76 (d, 1H), 7.40-7.62 (m, 6H), 7.26-7.30 (m, 2H), 6.77-6.82 (m, 3H), 4.50 (d, 1H), 4.49 (s, 2H), 4.37 (d, 1H); MS (EI) for $C_{24}H_{17}F_3N_2O_4$: 477 (MNa⁺).

6-(2-{[2,3-bis(methyloxy)phenyl]methyl}-1-hydroxy-3-oxo-2,3-dihydro-1H-isoindol-1-yl)-2H-1,4-benzoxazin-3(4H)-one: ¹H NMR (400 MHz, d₆-DMSO): 10.54 (s, 1H), 7.75 (d, 1H), 7.55-7.59 (m, 2H), 7.27 (d, 1H), 7.14 (s, 1H), 6.78-6.90 (m, 6H), 4.57 (d, 1H), 4.52 (s, 2H), 4.15 (d, 1H), 3.75 (s, 3H), 3.66 (s, 3H); MS (EI) for $C_{25}H_{22}N_2O_6$: 469 (MNa⁺).

6-{1-hydroxy-2-[(3-iodophenyl)methyl]-3-oxo-2,3-dihydro-1H-isoindol-1-yl}-2H-1,4-benzoxazin-3(4H)-one: ¹H NMR (400 MHz, d₆-DMSO): 10.50 (s, 1H), 7.75 (d, 1H), 7.48-7.60 (m, 3H), 7.22-7.40 (m, 4H), 6.98-7.02 (m, 1H), 6.78-6.80 (m, 3H), 4.53 (s, 2H), 4.35 (d, 1H), 4.23 (d, 1H); MS (EI) for $C_{23}H_{17}IN_2O_4$: 513 (MH⁺).

6-[1-hydroxy-3-oxo-2-({3-[(trifluoromethyl)oxy]phenyl}methyl)-2,3-dihydro-1H-isoindol-1-yl]-2H-1,4-benzoxazin-3(4H)-one: ¹H NMR (400 MHz, d₆-DMSO): 10.52 (s, 1H), 7.76 (d, 1H), 7.56-7.60 (m, 2H), 7.12-7.34 (m, 6H), 6.85 (s, 1H), 6.79 (s, 2H), 4.50 (s, 2H), 4.47 (d, 1H), 4.29 (d, 1H); MS (EI) for $C_{24}H_{17}F_3N_2O_5$: 493 (MNa⁺).

6-(1-hydroxy-2-{[2-(methylthio)phenyl]methyl}-3-oxo-2,3-dihydro-1H-isoindol-1-yl)-2H-1,4-benzoxazin-3(4H)-one: ¹H NMR (400 MHz, d₆-DMSO): 10.13 (s, 1H), 7.77 (d, 1H), 7.50-7.63 (m, 2H), 7.15-7.31 (m, 5H), 6.82-7.0 (m, 4H), 4.53 (d, 1H), 4.51 (s, 2H), 4.11 (d, 1H), 2.43 (s, 3H); MS (EI) for $C_{24}H_{20}N_2O_4S$: 455 (MNa⁺).

6-[2-(3,4-difluorophenyl)-1-hydroxy-3-oxo-2,3-dihydro-1H-isoindol-1-yl]-2H-1,4-benzoxazin-3(4H)-one: ¹H NMR (400 MHz, d₆-DMSO): 10.53 (s, 1H), 7.82-7.86 (m, 2H), 7.57-7.69 (m, 3H), 7.29-7.45 (m, 3H), 6.83-6.98 (m, 3H), 4.53 (s, 2H); MS (EI) for $C_{22}H_{14}F_2N_2O_4$: 431 (MNa⁺).

6-[2-(3,5-difluorophenyl)-1-hydroxy-3-oxo-2,3-dihydro-1H-isoindol-1-yl]-2H-1,4-benzoxazin-3(4H)-one: ¹H NMR (400 MHz, d₆-DMSO): 10.55 (s, 1H), 7.99 (s, 1H), 7.86 (d, 1H), 7.58-7.69 (m, 2H), 7.46-7.49 (m, 2H), 7.30 (d, 1H), 6.85-7.06 (m, 4H), 4.54 (s, 2H); MS (EI) for $C_{22}H_{14}F_2N_2O_4$: 431 (MNa⁺).

6-{1-hydroxy-2-[3-(methylsulfonyl)phenyl]-3-oxo-2,3-dihydro-1H-isoindol-1-yl}-2H-1,4-benzoxazin-3(4H)-one: ¹H NMR (400 MHz, d₆-DMSO): 10.55 (s, 1H), 8.30 (s, 1H), 7.87-7.92 (m, 3H), 7.58-7.72 (m, 4H), 7.32 (d, 1H), 6.83-7.0 (m, 3H), 4.52 (s, 2H), 3.15 (s, 3H); MS (EI) for $C_{23}H_{18}N_2O_6S$: 473 (MNa⁺).

ethyl 3-[1-hydroxy-3-oxo-1-(3-oxo-3,4-dihydro-2H-1,4-benzoxazin-6-yl)-1,3-dihydro-2H-isoindol-2-yl]benzoate: ¹H NMR (400 MHz, d₆-DMSO): 10.49 (s, 1H), 8.21 (s, 1H), 7.54-7.84 (m, 6H), 7.41-7.45 (m, 1H), 7.27 (d, 1H), 6.80-6.96 (m, 3H), 4.50 (s, 2H), 4.27 (q, 2H), 1.29 (t, 3H); MS (EI) for $C_{25}H_{20}N_2O_6$: 467 (MNa⁺).

3-[1-hydroxy-3-oxo-1-(3-oxo-3,4-dihydro-2H-1,4-benzoxazin-6-yl)-1,3-dihydro-2H-isoindol-2-yl]benzonitrile: ¹H NMR (400 MHz, d₆-DMSO): 10.49 (s, 1H), 8.06 (s, 1H), 7.83-7.90 (m, 3H), 7.50-7.66 (m, 4H), 7.29 (d, 1H), 6.80-6.96 (m, 3H), 4.50 (s, 2H); MS (EI) for $C_{23}H_{15}N_3O_4$: 420 (MNa⁺).

6-[2-(3-amino-5-chlorophenyl)-1-hydroxy-3-oxo-2,3-dihydro-1H-isoindol-1-yl]-2H-1,4-benzoxazin-3(4H)-one trifluoroacetate: ¹H NMR (400 MHz, d₆-DMSO): 10.52 (s, 1H), 7.75 (d, 1H), 7.50-7.63 (m, 3H), 7.21 (d, 2H), 6.75-6.93(m, 6H), 6.36-6.37 (m, 1H), 4.51 (s, 2H); MS (EI) for $C_{22}H_{16}ClN_3O_4$: 444 (MNa⁺).

6-[2-(3,5-dichlorophenyl)-1-hydroxy-3-oxo-2,3-dihydro-1H-isoindol-1-yl]-2H-1,4-benzoxazin-3(4H)-one: ¹H NMR (400 MHz, d₆-DMSO): 7.87 (d, 1H), 7.74 (s, 2H), 7.56-7.67 (m, 2H), 7.33 (d, 1H), 7.20-7.21 (m, 1H), 7.0-7.03 (m, 2H), 6.87 (d, 2H), 6.55-6.56 (m, 1H), 4.53 (s, 2H); MS (EI) for $C_{22}H_{14}Cl_2N_2O_4$: 463 (MNa⁺).

6-{1-hydroxy-2-[3-(1-methylethyl)phenyl]-3-oxo-2,3-dihydro-1H-isoindol-1-yl}-2H-1,4-benzoxazin-3(4H)-one: ¹H NMR (400 MHz, d₆-DMSO): 10.54 (s, 1H), 7.81 (d, 1H), 7.62 (m, 3H), 7.28 (m, 3H), 7.20 (t, 1H), 7.04 (d, 1H), 6.96 (s, 1H), 6.88 (m, 1H), 6.82 (d, 1H), 4.51 (s, 2H), 2.78 (m, 1H), 1.10 (d, 6H); MS (EI) for $C_{25}H_{22}N_2O_4$: 437 (MNa⁺).

6-{2-[5-chloro-2-(methyloxy)phenyl]-1-hydroxy-3-oxo-2,3-dihydro-1H-isoindol-1-yl}-2H-1,4-benzoxazin-3(4H)- one: ¹H NMR (400 MHz, d₆-DMSO): 10.78 (s, 1H), 7.89 (d, 1H), 7.44 (m, 3H), 6.97 (m, 3H), 6.84 (s, 2H), 6.53 (s, 1H), 4.63 (s, 2H), 3.71 (s, 3H); MS (EI) for $C_{23}H_{17}N_2O_5Cl$: 437 (MH⁺).

6-{2-[4-fluoro-3-(trifluoromethyl)phenyl]-1-hydroxy-3-oxo-2,3-dihydro-1H-isoindol-1-yl}-2H-1,4-benzoxazin-3(4H)-one: ¹H NMR (400 MHz, d₆-DMSO): 10.55 (s, 1H), 8.04 (m, 1H), 7.88 (m, 3H), 7.67 (m, 1H), 7.62 (m, 1H), 7.52 (m, 1H), 7.32 (d, 1H), 6.99 (s, 1H), 6.93 (m, 1H), 6.86 (m, 1H), 4.53 (t, 2H); MS (EI) for $C_{23}H_{14}N_2O_5F_4$: 481 (MNa⁺).

6-[2-(3-fluoro-5-iodophenyl)-1-hydroxy-3-oxo-2,3-dihydro-1H-isoindol-1-yl]-2H-1,4-benzoxazin-3(4H)-one: ¹H NMR (400 MHz, d₆-DMSO): 10.53 (s, 1H), 7.99 (s, 1H), 7.90 (s, 1H), 7.85 (d, 1H), 7.67 (m, 1H), 7.59 (m, 1H), 7.52 (m, 1H), 7.44 (m, 1H), 7.29 (d, 1H), 6.95 (m 2H), 6.86 (d, 1H), 4.54 (s, 2H); MS (EI) for $C_{22}H_{14}N_2O_4FI$: 539 (MNa⁺).

6-[2-(3-aminophenyl)-1-hydroxy-3-oxo-2,3-dihydro-1H-isoindol-1-yl]-2H-1,4-benzoxazin-3(4H)-one: ¹H NMR (400 MHz, d₆-DMSO): 10.54 (s, 1H), 7.83 (d, 1H), 7.65 (m, 2H), 7.57 (m, 1H), 7.37 (s, 1H), 7.24 (m, 3H), 6.98 (m, 1H), 6.89 (m, 1H), 6.82 (d, 2H), 4.52 (s, 2H); MS (EI) for $C_{22}H_{17}N_3O_4$: 410 (MNa⁺).

6-(2-biphenyl-3-yl-1-hydroxy-3-oxo-2,3-dihydro-1H-isoindol-1-yl)-2H-1,4-benzoxazin-3(4H)-one: ¹H NMR (400 MHz, d₆-DMSO): 10.55 (s, 1H), 7.82 (m, 2H), 7.71 (s, 1H), 7.63 (m, 1H), 7.56 (m, 1H), 7.50 (m, 3H), 7.44 (m, 3H), 7.36 (m, 2H), 7.28 (d, 1H), 7.01 (d, 1H), 6.93 (dd, 1H), 6.83 (d, 1H), 4.50 (s, 2H); MS (EI) for $C_{28}H_{20}N_2O_4$: 471 (MNa⁺).

6-(2-{3-[(dimethylamino)methyl]phenyl}-1-hydroxy-3-oxo-2,3-dihydro-1H-isoindol-1-yl)-2H-1,4-benzoxazin-3(4H)-one: ¹H NMR (400 MHz, d₆-DMSO): 10.51 (s, 1H), 9.65 (broad s, 1H), 7.77 (m, 2H), 7.63 (m, 4H), 7.41 (m, 1H), 7.28 (m, 2H), 6.94 (s, 1H), 6.78 (m, 2H), 4.49 (s, 2H), 3.24 (d, 2H), 2.60 (dd, 6H); MS (EI) for $C_{25}H_{23}N_3O_4$: 430 (MH⁺).

6-[2-(3-fluorophenyl)-1-hydroxy-3-oxo-2,3-dihydro-1H-isoindol-1-yl]-2H-1,4-benzoxazin-3(4H)-one: ¹H NMR (400 MHz, CD₃OD): 7.87 (d, 1H), 7.65-7.62 (m, 1H), 7.58-7.55 (m, 1H), 7.42-7.38 (m, 2H), 7.32 (d, 1H), 7.29-7.23 (m, 1H), 7.01-6.96 (m, 2H), 6.92-6.87 (m, 1H), 6.84-6.82 (m, 1H), 4.51 (s, 2H); MS (EI) for $C_{22}H_{15}FN_2O_4$: 413 (MH⁺).

6-[1-hydroxy-2-(3-iodophenyl)-3-oxo-2,3-dihydro-1H-isoindol-1-yl]-2H-1,4-benzoxazin-3(4H)-one: ¹H NMR (400 MHz, CD₃OD): 7.95-7.92 (m, 1H), 7.86 (d, 1H), 7.66-7.62 (m, 1H), 7.59-7.55 (m, 1H), 7.53-7.49 (m, 2H), 7.32 (d, 1H), 7.06-7.02 (m, 1H), 6.96-6.94 (m, 2H), 6.85-6.82 (m, 1H), 4.52 (s, 2H); MS (EI) for $C_{22}H_{15}IN_2O_4$: 520 (MH⁺).

6-[2-(3-bromophenyl)-1-hydroxy-3-oxo-2,3-dihydro-1H-isoindol-1-yl]-2H-1,4-benzoxazin-3(4H)-one: ¹H NMR (400 MHz, CD₃OD): 7.87 (d, 1H), 7.78-7.74 (m, 1H), 7.66-7.63 (m, 1H), 7.59-7.55 (m, 1H), 7.52-7.48 (m, 2H), 7.34-7.30 (m, 2H), 7.21-7.16 (m, 1H), 6.98-6.94 (m, 2H), 6.85-6.83 (m, 1H), 4.52 (s, 2H); MS (EI) for $C_{22}H_{15}BrN_2O_4$: 474 (MH⁺).

6-[1-hydroxy-2-(3-nitrophenyl)-3-oxo-2,3-dihydro-1H-isoindol-1-yl]-2H-1,4-benzoxazin-3(4H)-one: ¹H NMR (400 MHz, CD₃OD): 8.67-8.65 (m, 1H), 8.08-7.99 (m, 2H), 7.91 (d, 1H), 7.68-7.49 (m, 4H), 7.35 (d, 1H), 7.03-7.00 (m, 2H), 6.85-6.83 (m, 1H), 4.51 (s, 2H); MS (EI) for $C_{22}H_{15}N_3O_6$: 440 (MH⁺).

6-{1-hydroxy-2-[3-(methyloxy)phenyl]-3-oxo-2,3-dihydro-1H-isoindol-1-yl}-2H-1,4-benzoxazin-3(4H)-one: ¹H NMR (400 MHz, CD₃OD): 7.85 (d, 1H), 7.64-7.61 (m, 1H), 7.57-7.54 (m, 1H), 7.32 (d, 1H), 7.19-7.14 (m, 1H), 7.05-7.03 (m, 2H), 6.97-6.95 (m, 2H), 6.81 (d, 1H), 6.76-6.74 (m, 1H), 4.50 (s, 2H), 3.70 (s, 3H); MS (EI) for $C_{23}H_{18}N_2O_5$: 425 (MH⁺).

6-[1-hydroxy-2-(3-methylphenyl)-3-oxo-2,3-dihydro-1H-isoindol-1-yl]-2H-1,4-benzoxazin-3(4H)-one: ¹H NMR (400 MHz, CD₃OD): 7.84 (d, 1H), 7.62-7.58 (m, 1H), 7.55-7.51 (m, 1H), 7.31 (d, 1H), 7.26 (s, 1H), 7.18-7.10 (m, 2H), 7.00-6.92 (m, 3H), 6.78 (d, 1H), 4.47 (s, 2H), 2.26 (s, 3H); MS (EI) for $C_{23}H_{18}N_2O_4$: 409 (MH⁺).

6-(1-hydroxy-3-oxo-2-{3-[(trifluoromethyl)oxy]phenyl}-2,3-dihydro-1H-isoindol-1-yl)-2H-1,4-benzoxazin-3(4H)-one: ¹H NMR (400 MHz, CD₃OD): 7.87 (d, 1H), 7.65-7.54 (m, 4H), 7.37-7.32 (m, 2H), 7.05 (d, 1H), 6.99-6.95 (m, 2H), 6.82 (d, 1H), 4.50 (s, 2H); MS (EI) for $C_{23}H_{15}F_3N_2O_5$: 479 (MH⁺).

6-{1-hydroxy-3-oxo-2-[3-(trifluoromethyl)phenyl]-2,3-dihydro-1H-isoindol-1-yl}-2H-1,4-benzoxazin-3(4H)-one: ¹H NMR (400 MHz, CD₃OD): 7.96 (s, 1H), 7.88 (d, 1H), 7.82-7.78 (m, 1H), 7.66-7.62 (m, 1H), 7.59-7.55 (m, 1H), 7.48-7.43 (m, 2H), 7.34 (d, 1H), 6.99-6.97 (m, 2H), 6.82 (d, 1H), 4.50 (s, 2H); MS (EI) for $C_{23}H_{15}F_3N_2O_4$: 463 (MH⁺).

3-[1-hydroxy-3-oxo-1-(3-oxo-3,4-dihydro-2H-1,4-benzoxazin-6-yl)-1,3-dihydro-2H-isoindol-2-yl]benzenesulfonamide: ¹H NMR (400 MHz, d₆-DMSO): 10.52 (s, 1H), 8.22 (s, 1H), 7.84-7.82 (m, 2H), 7.65-7.54 (m, 4H), 7.50-7.46 (m, 1H), 7.40 (s, 2H), 7.29 (d, 1H), 6.96 (s, 1H), 6.90-6.88 (m, 1H), 6.83-6.80 (m, 1H), 4.50 (s, 2H); MS (EI) for $C_{22}H_{17}N_3O_6$: 474 (MH⁺).

6-[2-(3-ethylphenyl)-1-hydroxy-3-oxo-2,3-dihydro-1H-isoindol-1-yl]-2H-1,4-benzoxazin-3(4H)-one: ¹H NMR (400 MHz, d₆-DMSO): 7.81 (d, 1H), 7.65-7.55 (m, 3H), 7.34 (s, 1H), 7.27 (d, 2H), 7.21-7.18 (m, 1H), 7.01 (d, 1H), 6.96 (s, 1H), 6.88 (d, 1H), 6.82 (d, 1H), 4.51 (s, 2H), 2.51 (q, 2H), 1.07 (t, 3H); MS (EI) for $C_{24}H_{20}N_2O_4$: 423 (MH⁺).

6-[2-(3-ethynylphenyl)-1-hydroxy-3-oxo-2,3-dihydro-1H-isoindol-1-yl]-2H-1,4-benzoxazin-3(4H)-one: ¹H NMR (400 MHz, CD₃OD): 7.87 (d, 1H), 7.66-7.62 (m, 2H), 7.59-7.55 (m, 1H), 7.50-7.45 (m, 1H), 7.33 (d, 1H), 7.29-7.23 (m, 2H), 6.97-6.94 (m, 2H), 6.83 (d, 1H), 4.52 (s, 2H), 3.49 (s, 1H); MS (EI) for $C_{24}H_{16}N_2O_4$: 419 (MH⁺).

6-[1-hydroxy-2-(3-hydroxyphenyl)-3-oxo-2,3-dihydro-1H-isoindol-1-yl]-2H-1,4-benzoxazin-3(4H)-one: ¹H NMR (400 MHz, CD₃OD): 7.84 (d, 1H), 7.62-7.58 (m, 1H), 7.55-7.51 (m, 1H), 7.31 (d, 1H), 7.09-7.05 (m, 1H), 6.98-6.90 (m, 4H), 6.80 (d, 1H), 6.62 (dd, 1H), 4.49 (s, 2H); MS (EI) for $C_{22}H_{16}N_2O_5$: 411 (MH⁺).

6-{1-hydroxy-3-oxo-2-[3-(phenyloxy)phenyl]-2,3-dihydro-1H-isoindol-1-yl}-2H-1,4-benzoxazin-3(4H)-one: ¹H NMR (400 MHz, d₆-DMSO): 10.52 (s, 1H), 7.81 (d, 1H), 7.69 (s, 1H), 7.65-7.61 (m, 1H), 7.58-7.54 (m, 1H), 7.37-7.24 (m, 6H), 7.15-7.11 (m, 1H), 6.92-6.79 (m, 6H), 4.53 (s, 2H); MS (EI) for $C_{28}H_{20}N_2O_5$: 487 (MH⁺).

6-(1-hydroxy-3-oxo-2-{3-[(phenylmethyl)oxy]phenyl}-2,3-dihydro-1H-isoindol-1-yl)-2H-1,4-benzoxazin-3(4H)-one: ¹H NMR (400 MHz, CD₃OD): 7.84 (d, 1H), 7.61-7.57 (m, 1H), 7.54-7.50 (m, 1H), 7.33-7.23 (m, 6H), 7.15-7.07 (m, 3H), 6.97 (s, 1H), 6.93 (d, 1H), 6.78-6.75 (m, 2H), 4.91 (s, 2H), 4.42 (s, 2H); MS (EI) for $C_{29}H_{22}N_2O_5$: 501 (MH⁺).

3-[1-hydroxy-3-oxo-1-(3-oxo-3,4-dihydro-2H-1,4-benzoxazin-6-yl)-1,3-dihydro-2H-isoindol-2-yl]benzamide: ¹H NMR (400 MHz, d₆-DMSO): 10.49 (s, 1H), 8.09 (s, 1H), 7.87 (s, 1H), 7.81 (d, 1H), 7.67 (s, 1H), 7.63-7.54 (m, 4H), 7.36-7.32 (m, 1H), 7.26 (d, 1H), 6.96 (s, 1H), 6.87-6.85 (m, 1H), 6.80-6.77 (m, 1H), 4.49 (s, 2H); MS (EI) for $C_{23}H_{17}N_3O_5$: 438 (MH⁺).

6-{1-hydroxy-2-[3-(hydroxymethyl)phenyl]-3-oxo-2,3-dihydro-1H-isoindol-1-yl}-2H-1,4-benzoxazin-3(4H)-one: $^1$H NMR (400 MHz, CD$_3$OD): 7.86 (d, 1H), 7.64-7.61 (m, 1H), 7.58-7.54 (m, 1H), 7.47 (s, 1H), 7.35-7.31 (m, 2H), 7.27-7.23 (m, 1H), 7.20-7.18 (m, 1H), 6.96-6.94 (m, 1H), 6.79 (d, 1H), 4.54 (s, 2H), 4.49 (s, 2H); MS (EI) for C$_{23}$H$_{18}$N$_2$O$_5$: 425 (MH$^+$).

6-[2-(2-fluorophenyl)-1-hydroxy-3-oxo-2,3-dihydro-1H-isoindol-1-yl]-2H-1,4-benzoxazin-3(4H)-one: $^1$H NMR (400 MHz, CD$_3$OD): 7.87 (d, 1H), 7.67-7.63 (m, 1H), 7.60-7.56 (m, 1H), 7.36-7.27 (m, 3H), 7.11-7.06 (m, 2H), 6.95 (s, 1H), 6.91 (d, 1H), 6.77 (d, 1H), 4.49 (s, 2H); MS (EI) for C$_{22}$H$_{15}$FN$_2$O$_4$: 413 (MH$^+$).

6-[2-(3-{[2-(dimethylamino)ethyl]oxy}phenyl)-1-hydroxy-3-oxo-2,3-dihydro-1H-isoindol-1-yl]-2H-1,4-benzoxazin-3(4H)-one: $^1$H NMR (400 MHz, CD$_3$OD): 7.86 (d, 1H), 7.65-7.61 (m, 1H), 7.58-7.54 (m, 1H), 7.32 (d, 1H), 7.25-7.16 (m, 3H), 6.97-6.93 (m, 2H), 6.87-6.80 (m, 2H), 4.49 (s, 2H), 4.23 (t, 2H), 3.46 (t, 2H), 2.89 (s, 6H); MS (EI) for C$_{26}$H$_{25}$N$_3$O$_5$: 460 (MH$^+$).

6-[1-hydroxy-2-(2-methylphenyl)-3-oxo-2,3-dihydro-1H-isoindol-1-yl]-2H-1,4-benzoxazin-3(4H)-one: $^1$H NMR (400 MHz, CD$_3$OD): 7.90 (d, 1H), 7.74-7.64 (m, 3H), 7.52-7.48 (m, 1H), 7.29-7.22 (m, 3H), 6.92-6.80 (m, 3H), 6.69-6.64 (m, 2H), 4.50 (s, 2H), 1.63 (s, 3H); MS (EI) for C$_{23}$H$_{18}$N$_2$O$_4$: 409 (MH$^+$).

N-methyl-2-[(3-oxo-3,4-dihydro-2H-1,4-benzoxazin-6-yl)carbonyl]-N-phenylbenzamide: $^1$H NMR (400 MHz, CD$_3$OD): 7.40-7.30 (m, 4H), 7.24-7.17 (m, 4H), 7.13-7.06 (m, 3H), 6.99 (d, 1H), 4.69 (s, 2H), 3.41 (s, 3H); MS (EI) for C$_{23}$H$_{18}$N$_2$O$_4$: 409 (MH$^+$)

1,1-Dimethylethyl 4-{[1-hydroxy-3-oxo-1-(3-oxo-3,4-dihydro-2H-1,4-benzoxazin-6-yl)-1,3-dihydro-2H-isoindol-2-yl]methyl}piperidine-1-carboxylate: $^1$H NMR (400 MHz, CDCl$_3$): 8.68-8.39 (m, 1H), 7.72-7.64 (m, 1H), 7.51-7.38 (m, 2H), 7.26 (d, 1H), 6.95-6.85 (m, 3H), 4.55 (s, 2H), 4.02-3.85 (m, 2H), 3.43-3.32 (m, 1H), 2.84-2.67 (m, 1H), 2.65-2.37 (m, 2H), 1.95-1.72 (m, 1H), 1.64-1.50 (m, 2H), 1.39 (s, 9H), 1.16-0.99 (m, 2H); MS (EI) for C$_{27}$H$_{31}$N$_3$O$_6$: 516 (MNa$^+$).

6-[2-(2-chlorophenyl)-1-hydroxy-3-oxo-2,3-dihydro-1H-isoindol-1-yl]-2H-1,4-benzoxazin-3(4H)-one: $^1$H NMR (400 MHz, d$_6$-DMSO): 10.53 (br s, 0.2H) open, 10.46 (br s, 0.8H) closed, 7.82 (d, 0.8H) closed, 7.74-6.36 (m, 10.2H), 4.57 (s, 0.4H) open, 4.48 (s, 1.6H) closed; MS (EI) for C$_{22}$H$_{15}$ClN$_2$O$_4$: 429 (MNa$^+$).

6-[2-(5-chloro-2-methylphenyl)-1-hydroxy-3-oxo-2,3-dihydro-1H-isoindol-1-yl]-2H-1,4-benzoxazin-3(4H)-one: MS (EI) for C$_{23}$H$_{17}$ClN$_2$O$_4$: 443 (MNa$^+$).

6-[2-(3-chloro-2-methylphenyl)-1-hydroxy-3-oxo-2,3-dihydro-1H-isoindol-1-yl]-2H-1,4-benzoxazin-3(4H)-one: MS (EI) for C$_{23}$H$_{17}$ClN$_2$O$_4$: 443 (MNa$^+$).

6-(1-hydroxy-3-oxo-2-piperidin-4-yl-2,3-dihydro-1H-isoindol-1-yl)-2H-1,4-benzoxazin-3(4H)-one trifluoroacetate: $^1$H NMR (400 MHz, CD$_3$OD): 7.76 (d, 1H), 7.57 (td, 1H), 7.52 (td, 1H), 7.22 (d, 1H), 7.08-7.01 (m, 2H), 6.93 (d, 1H), 4.57 (s, 2H), 3.62-3.52 (m, 1H), 3.48-3.41 (m, 1H), 3.39-3.33 (m, 1H), 3.04 (td, 1H), 2.92-2.66 (m, 3H), 2.04-1.96 (m, 1H), 1.68-1.60 (m, 1H); MS (EI) for C$_{21}$H$_{21}$N$_3$O$_4$: 380 (MH$^+$).

Example 2

Methyl{5-[1-hydroxy-3-oxo-2-(phenylmethyl)-2,3-dihydro-1H-isoindol-1-yl]-1H-benzimidazol-2-yl}carbamate A solution of 2-(4-chloro-3-nitrobenzoyl)benzoic acid (5.0 g, 16.36 mmol) was heated to reflux in 28-30% aq. ammonium hydroxide (100 mL) for 18 h. The solution was cooled to room temperature followed by addition of 6N aq. hydrochloric acid until pH to 7. The precipitated yellow solid was collected by filtration and washed with water then dried in vacuo to provide 2-[(4-amino-3-nitrophenyl)carbonyl]benzoic acid (4.60 g, 98%). MS (EI) for C$_{14}$H$_{10}$N$_2$O$_5$: 288 (MH$^+$).

A solution of 2-[(4-amino-3-nitrophenyl)carbonyl]benzoic acid (4.60 g, 16.00 mmol) in methanol (300 mL) in the presence of catalytic amount of cc. sulfuric acid was heated to reflux for 18 h. The solution was cooled to room temperature and the solvent was evaporated. The yellow precipitate formed was collected by filtration, washed with water and dried in vacuo to provide methyl 2-[(4-amino-3-nitrophenyl)carbonyl]benzoate (4.8 g, quantitative). MS (EI) for C$_{15}$H$_{12}$N$_2$O$_5$: 301 (MH$^+$).

A solution of methyl 2-[(4-amino-3-nitrophenyl)carbonyl]benzoate (420 mg, 1.39 mmol) in a mixture of terahydrofuran-ethyl acetate (1:1, 20 mL) was hydrogenated over 10% Pd—C (10 mg) for 18 h. The catalyst removed by filtration and the filtrate concentrated to give methyl 2-[(3,4-diaminophenyl)carbonyl]benzoate (370 mg, 98%) as a brown powder. MS (EI) for C$_{15}$H$_{14}$N$_2$O$_3$: 293 (MNa$^+$).

To a solution of methyl 2-[(3,4-diaminophenyl)carbonyl]benzoate (134 mg, 0.50 mmol) in a mixture of acetonitrile-benzene (1:1, 5 mL) methyl isothiocyanatidocarbonate (70 mg, 0.60 mmol) was added followed by the addition of DCC (153 mg, 0.75 mmol) and the reaction mixture was heated to reflux for 18 h. After cooling to room temperature the reaction mixture was concentrated. The residue was triturated with diethyl ether (2×, 10 mL) and the pale orange solid was collected by filtration to give methyl 2-[(2-{[(methoxy)carbonyl]amino}-1H-benzimidazol-5-yl)carbonyl]benzoate (125 mg, 71%). MS (EI) for C$_{18}$H$_{15}$N$_3$O$_5$: 354 (MH$^+$).

Methyl 2-[(2-{[(methoxy)carbonyl]amino}-1H-benzimidazol-5-yl)carbonyl]benzoate (125 mg, 0.35 mmol) was dissolved in a mixture of tetrahydrofuran-methanol (3:1, 12 mL) and a 3.0 M aq. solution of lithium hydroxide (0.12 mL) was added. The solution was heated to reflux for 10 min then cooled to room temperature and the solvent was concentrated. An excess of hydrogen chloride (4M in dioxane) was added and the acidic mixture was concentrated to dryness. The resulting crude, 2-[(2-{[(methoxy)carbonyl]amino}-1H-benzimidazol-5-yl)carbonyl]benzoic acid (120 mg), was used without further purification. MS (EI) for C, 17; H, 13; N, 3; O, 5: 340 (MH$^+$).

To a solution of 2-[(2-{[(methoxy)carbonyl]amino}-1H-benzimidazol-5-yl)carbonyl]benzoic acid (120 mg, 0.35 mmol), HOAt (0.5 M in DMF, 1.06 mL, 0.53 mmol), N-methylmorpholine (98 uL, 0.71 mmol) and HATU (175 mg, 0.46 mmol) was added benzylamine (64 uL, 0.60 mmol) and the reaction mixture was stirred at 60° C. for 18 h. The mixture was cooled to room temperature and the solvent was evaporated. The residue was dissolved in a mixture of acetonitrile-chloroform (1:1, 50 mL) and the organic layer was washed with water and brine then dried over anhydrous sodium sulfate, filtered and the filtrate concentrated in vacuo. The residue was purified by reverse phase HPLC to afford methyl{5-[1-hydroxy-3-oxo-2-(phenylmethyl)-2,3-dihydro-1H-isoindol-1-yl]-1H-benzimidazol-2-yl}carbamate trifluoroacetic acid salt (5.7 mg). MS (EI) for C$_{17}$H$_{13}$N$_3$O$_5$: 429 (MH$^+$).

Using the same or analogous synthetic techniques and/or substituting with alternative reagents, the following compounds of the invention were prepared:

methyl{5-[1-hydroxy-3-oxo-2-(phenylmethyl)-2,3-dihydro-1H-isoindol-1-yl]-1H-benzimidazol-2-yl}carbamate): $^1$H NMR (400 MHz, d$_6$-DMSO), closed isomer only: 7.75 (dd, 1H), 7.64 (br s, 1H), 7.58-7.51 (m, 2H), 7.40 (d, 1H), 7.35 (br s, 1H), 7.23 (dd, 1H), 7.16-7.06 (m, 6 H), 4.46 (d, 1H), 4.18 (d, 1H), 3.85 (s, 3H); $^{13}$C NMR (100 MHz, d$_6$-DMSO), closed isomer only: 166.5, 152.6, 149.3, 144.5, 137.8, 135.9, 132.5, 130.0, 129.1, 127.5, 126.2, 122.7, 122.4, 121.9, 112.9, 111.1, 90.5, 53.5, 42.5; MS (EI) for C$_{24}$H$_{20}$N$_4$O$_4$: 429 (MH$^+$).

methyl[6-(1-hydroxy-3-oxo-2-phenyl-2,3-dihydro-1H-isoindol-1-yl)-1H-benzimidazol-2-yl]carbamate. $^1$H NMR (400 MHz, DMSO-d$_6$): 7.85 (dd, 1H), 7.75 (s, 1H), 7.62 (d, 1H), 7.59 (m, 2H), 7.49 (2d, 2H), 7.35 (d, 1H), 7.25 (m, 3H), 7.12 (m, 2H), 3.88 (s, 3H). $^{13}$C NMR (400 MHz, DMSO-d$_6$): 53.01, 92.33, 122.74, 122.96, 125.38, 125.62, 128.21, 129.91, 129.48, 133.15, 136.39, 149.62, 166.19; MS (EI) for C$_{23}$H$_{18}$N$_4$O$_4$: 414 (MH$^+$).

Example 3

3-Hydroxy-3-[2-(methylamino)-1H-benzimidazol-5-yl]-2-(phenylmethyl)-2,3-dihydro-1H-isoindol-1-one A solution of 2-(4-chloro-3-nitrobenzoyl)benzoic acid (38.5 g, 0.126 mol) in ammonium hydroxide (33% wt, 200 mL) was heated to a gentle reflux and stirred for 24 h. An additional ammonium hydroxide (200 mL) was added every 5 h within the 24 h reaction time period. The reaction mixture was cooled to room temperature and was added 6N aqueous hydrochloric acid until pH reached 2. The precipitated yellow solid was collected by filtration and washed with water then dried in vacuo to provide 2-[(4-amino-3-nitrophenyl)carbonyl]benzoic acid (38.8 g, 95%). $^1$H NMR (400 MHz, CD$_3$OD): 8.27 (d, 1H), 8.11 (d, 1H), 7.80 (dd, 1H), 7.72 (td, 1H), 7.65 (td, 1H), 7.39 (d, 1H), 7.01 (d, 1H); MS (EI) for C$_{14}$H$_{10}$N$_2$O$_5$: 309 (MNa$^+$).

To a solution of 2-[(4-amino-3-nitrophenyl)carbonyl]benzoic acid (9.3 g, 32.4 mmol), HOAt (0.5 M in DMF, 97 mL, 48.7 mmol), N-methylmorpholine (14 mL, 129 mmol) and HATU (16 g, 42.0 mmol) was added benzylamine (7.08 mL, 65.0 mmol) and the reaction mixture was stirred at 60° C. for 1 h. The reaction mixture was cooled to room temperature and the solvent was evaporated. The residue was partition between water and ethyl acetate. The organic layer was washed with brine, dried over anhydrous magnesium sulfate, filtered and the filtrate concentrate in vacuo. The resulting crude 3-(4-amino-3-nitrophenyl)-3-hydroxy-2-(phenylmethyl)-2,3-dihydro-1H-isoindol-1-one (10 g, 82%) was used without further purification. MS (EI) for C$_{21}$H$_{17}$N$_3$O$_4$: 398 (MNa$^+$).

A solution of 3-(4-amino-3-nitrophenyl)-3-hydroxy-2-(phenylmethyl)-2,3-dihydro-1H-isoindol-1-one (10 g, 26.6 mmol) in a mixture of terahydrofuran-ethyl acetate (1:1, 20 mL) was hydrogenated over 10% Pd—C (100 mg) at 40 psi for 18 h. The catalyst was removed by filtration and the filtrate concentrated in vacuo. The residue was purified by column chromatography (SiO$_2$, hexanes/ethyl acetate) to afford 3-(3,4-diaminophenyl)-3-hydroxy-2-(phenylmethyl)-2,3-dihydro-1H-isoindol-1-one (9.0 g, 98%) as a brown powder. MS (EI) for C$_{21}$H$_{19}$N$_3$O$_2$: 368 (MNa$^+$).

To a solution of 3-(3,4-diaminophenyl)-3-hydroxy-2-(phenylmethyl)-2,3-dihydro-1H-isoindol-1-one (100 mg, 0.289 mmol) and methyl isothiocyanate (31 mg, 0.434 mmol) in tetrahydrofuran (30 mL) was added 1-[3-dimethylamino)propyl]-3-ethylcarbodiimide hydrochloride (89 mg, 0.462 mmol) at room temperature. The reaction mixture was heated to 65° C. and stirred for 3 h, at which time it was cooled to room temperature and partitioned with water and a mixture of acetonitrile-ethyl acetate (1:9, 200 mL). The organic layer was washed with water and brine then dried over anhydrous magnesium sulfate, filtered and the filtrate concentrated in vacuo. The residue was purified by column chromatography (SiO$_2$, methanol/dichloromethane) to afford 3-hydroxy-3-[2-(methylamino)-1H-benzimidazol-5-yl]-2-(phenylmethyl)-2,3-dihydro-1H-isoindol-1-one (3.3 mg). $^1$H NMR (400 MHz, CD$_3$OD): 7.79 (d, 1H), 7.54-7.48 (m, 2H), 7.29-7.26 (m, 2H), 7.18-7.16 (m, 2H), 7.11-7.01 (m, 4H), 6.86 (dd, 1H), 4.57 (d, 1H), 4.34 (d, 1H), 2.96 (s, 3H); MS (EI) for C$_{23}$H$_{20}$N$_4$O$_2$: 385 (MH$^+$).

Using the same or analogous synthetic techniques and/or substituting with alternative reagents, the following compounds of the invention were prepared:

3-(2-{[3,5-bis(methyloxy)phenyl]amino}-1H-benzimidazol-5-yl)-3-hydroxy-2-phenyl-2,3-dihydro-1H-isoindol-1-one. $^1$H NMR (400 MHz, DMSO-d$_6$): 10.98 (s, 1H), 7.83 (d, 1H), 7.77 (s, 1H), 7.58 (m, 3H), 7.52 (d, 2H), 7.42 (s, 1H), 7.24 (m, 4H), 7.12 (m, 3H), 6.61 (s, 1H), 6.41 (s, 1H), 4.45 (d, 1H), 4.18 (d, 1H), 3.82 (s, 6H); MS (EI) for C$_{29}$H$_{24}$N$_4$O$_4$: 493 (MH$^+$).

3-(2-{[3,5-bis(methyloxy)phenyl]amino}-1H-benzimidazol-5-yl)-3-hydroxy-2-(phenylmethyl)-2,3-dihydro-1H-isoindol-1-one. $^1$H NMR (400 MHz, DMSO-d$_6$): 11.10 (s, 1H), 7.74 (d, 1H), 7.53 (m, 3H), 7.36 (s, 1H), 7.32 (s, 1H), 7.23 (m, 3H), 7.13 (m, 5H), 6.62 (d, 1H), 6.41 (s, 1H), 4.45 (d, 1H), 4.18 (d, 1H), 3.82 (s, 6H); MS (EI) for C$_{30}$H$_{26}$N$_4$O$_4$: 507 (MH$^+$).

Example 4

Methyl{5-[1-(ethyloxy)-3-oxo-2-(phenylmethyl)-2,3-dihydro-1H-isoindol-1-yl]-1H-benzimidazol-2-yl}carbamate A solution of 3-(3,4-diaminophenyl)-3-hydroxy-2-(phenylmethyl)-2,3-dihydro-1H-isoindol-1-one (1.5 g, 4.34 mmol) and 1,3-bis(methoxycarbonyl)-2-methyl-2-thiopseudourea (1.8 g, 8.68 mmol) in anhydrous ethanol (15 mL) was heated to 95° C. and stirred for 18 h, at which time the reaction mixture was cooled to room temperature. The white precipitate was filtered and the powder was triturated in hot ethanol (50 mL). The white powder was collected by filtration to afford methyl{5-[1-(ethyloxy)-3-oxo-2-(phenylmethyl)-2,3-dihydro-1H-isoindol-1-yl]-1H-benzimidazol-2-yl}carbamate (700 mg). $^1$H NMR (400 MHz, d$_6$-DMSO): 7.82-7.81 (m, 1H), 7.58-7.52 (m, 3H), 7.51 (d, 1H), 7.33-7.16 (m, 6H), 6.90 (d, 1H), 4.75 (d, 1H), 4.75 (d, 1H), 3.79 (d, 1H), 2.74-2.67 (m, 2H), 0.65 (t, 3H); $^{13}$C NMR (100 MHz, d$_6$-DMSO): 166.9, 154.5, 147.8, 145.7, 137.6, 132.6, 131.1, 130.7, 130.6, 129.4, 128.3, 127.8, 126.8, 122.9, 122.8, 118.9, 95.3, 57.9, 52.4, 42.5, 14.1; MS (EI) for C$_{26}$H$_{24}$N$_4$O$_4$: 457 (MH$^+$).

Using the same or analogous synthetic techniques and/or substituting with alternative reagents, the following compounds of the invention were prepared:

3-(2-{[3,5-bis(methyloxy)phenyl]amino}-1H-benzimidazol-5-yl)-3-(methyloxy)-2-(phenylmethyl)-2,3-dihydro-1H-isoindol-1-one. MS (EI) for C$_{31}$H$_{28}$N$_4$O$_4$: 521 (MH$^+$).

3-(2-{[3,5-bis(methyloxy)phenyl]amino}-1H-benzimidazol-5-yl)-2-(1-methylethyl)-3-(methyloxy)-2,3-dihydro-1H-isoindol-1-one. MS (EI) for C$_{27}$H$_{28}$N$_4$O$_4$: 473 (MH$^+$).

Example 5

3-(1H-Benzimidazol-5-yl)-3-hydroxy-2-(phenylmethyl)-2,3-dihydro-1H-isoindol-1-one A solution of 3-(3,4-diaminophenyl)-3-hydroxy-2-(phenylmethyl)-2,3-dihydro-1H-isoindol-1-one (27 mg, 0.078 mmol) in formic acid (3.2 µL, 0.086 mmol) was heated to 60° C. for 5 h. The reaction mixture was then heat to 110° C. for an additional 16 h, at which time it was cooled to room temperature. The reaction mixture was dissolved in a mixture of acetonitrile-ethyl acetate (1:9, 50 mL) and the organic layer was washed with saturated aqueous sodium bicarbonate and brine then dried over anhydrous magnesium sulfate, filtered and the filtrate concentrated in vacuo. The residue was purified by reverse phase HPLC to afford 3-(1H-benzimidazol-5-yl)-3-hydroxy-2-(phenylmethyl)-2,3-dihydro-1H-isoindol-1-one trifluoroaceate salt (6.0 mg). $^1$H NMR (400 MHz, CD$_3$OD): 9.24 (s, 1H), 7.93-7.88 (m, 2H), 7.59-7.58 (m, 2H), 7.49 (d, 1H), 7.28-7.27 (m, 1H), 7.26-7.20 (m, 1H), 7.08-7.07 (m, 2H), 6.99-6.98 (m, 3H), 4.63 (d, 1H), 4.45 (d, 1H); MS (EI) for C$_{22}$H$_{17}$N$_3$O$_2$: 356 (MH$^+$).

Example 6

5-[1-Hydroxy-3-oxo-2-(phenylmethyl)-2,3-dihydro-1H-isoindol-1-yl]-N-methyl-1H-benzimidazole-2-carboxamide To a suspension of methylamine hydrochloride (732 mg, 10.8 mmol) and methyl chlorooxoacetate (1 mL, 10.8 mmol) in dioxane (10 mL) was slowly added pyridine (2.0 mL). The reaction mixture was stirred at room temperature for 1.5 h, at which time it was filtered and the filtrate concentrated in vacuo. The residue was dissolved in a mixture of acetonitrile-ethyl acetate (1:9, 150 mL) and the organic layer was washed with water and brine then dried over anhydrous magnesium sulfate, filtered and the filtrate concentrated in vacuo to afford N-methyl-2-oxopropanamide (267 mg, 21%): GCMS for C$_4$H$_7$NO$_3$ 116 (M$^+$).

N-methyl-2-oxopropanamide (267 mg, 2.26 mmol) was taken up in N,N-dimethylformamide (2.00 mL) and was added 3-(3,4-diaminophenyl)-3-hydroxy-2-(phenylmethyl)-2,3-dihydro-1H-isoindol-1-one (45 mg, 0.13 mmol). The reaction mixture was heated to 140° C. and stirred for 16 h, at which time it was cooled to room temperature and concentrated in vacuo. The residue was purified by reverse phase HPLC to afford 5-[1-hydroxy-3-oxo-2-(phenylmethyl)-2,3-dihydro-1H-isoindol-1-yl]-N-methyl-1H-benzimidazole-2-carboxamide trifluoroacetate salt (9.4 mg). $^1$H NMR (400 MHz, CD$_3$OD): 7.91-7.89 (m, 1H), 7.61-7.58 (m, 2H), 7.20-6.96 (m, 9H), 4.48 (d, 1H), 4.36 (d, 1H), 2.73 (s, 3H); MS (EI) for C$_{24}$H$_{20}$N$_4$O$_3$: 412 (M$^+$).

Example 7

3-Hydroxy-3-(2-methyl-1H-benzimidazol-5-yl)-2-(phenylmethyl)-2,3-dihydro-1H-isoindol-1-one A solution of 3-(3,4-diaminophenyl)-3-hydroxy-2-(phenylmethyl)-2,3-dihydro-1H-isoindol-1-one (33 mg, 0.095 mmol) in acetic acid (1 mL) in the presence of catalytic amount of 6N hydrogen chloride was heated to 110° C. and stirred for 2.5 h. The reaction mixture was cooled to room temperature and immediately purified by reverse phase HPLC to afford 3-hydroxy-3-(2-methyl-1H-benzimidazol-5-yl)-2-(phenylmethyl)-2,3-dihydro-1H-isoindol-1-one trifluoroacetate salt (6.3 mg). $^1$H NMR (400 MHz, CD$_3$OD): 7.89-7.87 (m, 1H), 7.81 (br s, 1H), 7.59-7.56 (m, 2H), 7.41 (d, 1H), 7.26-7.24 (m, 1H), 7.18 (dd, 1H), 7.10-7.09 (m, 2H), 7.02-7.00 (m, 3H), 4.59 (d, 1H), 4.46 (d, 1H), 2.82 (s, 3H); MS (EI) for C$_{23}$H$_{19}$N$_3$O$_2$: 370 (MH$^+$).

Example 8

7-[2-(3-Chlorophenyl)-1-hydroxy-3-oxo-2,3-dihydro-1H-isoindol-1-yl]-3,4-dihydroquinoxalin-2(1H)-one A suspension of 2-(4-chloro-3-nitrobenzoyl)benzoic acid (0.31 g 1.00 mmol) and glycine ethyl ester hydrochloride (0.69 g, 5.00 mmol) in a solution of 4M aqueous potassium hydroxide (3.8 mL, 15.0 mmol) was heated to 90° C. for 15 hours. The reaction mixture was cooled to room temperature and it was treated with 2M aqueous hydrochloric acid to adjust the pH to ~5. It was partitioned with ethyl acetate (50 mL) and the organic layer was washed with brine and dried over anhydrous sodium sulfate. Filtration and concentration of the solvent gave 2-({4-[(carboxymethyl)amino]-3-nitrophenyl}carbonyl)benzoic acid (0.26 g, 76% yield) as a white residue. MS (EI) for C$_{16}$H$_{12}$N$_2$O$_7$: 342 (M$^-$).

To a solution of 2-({4-[(carboxymethyl)amino]-3-nitrophenyl}carbonyl)benzoic acid (0.26 g, 0.76 mmol) in N,N-dimethyl formamide (5.0 mL), potassium carbonate (0.52 g, 3.80 mmol) was added, followed by the addition of benzyl bromide (0.22 mL, 1.82 mmol). The reaction mixture was stirred for 15 hours at room temperature. It was poured into ice water and diluted with ethyl acetate (50 mL). The organic layer was separated and it was washed with water, 2M aqueous hydrochloric acid and brine. It was dried over anhydrous sodium sulfate. Evaporating the solvent, followed by purification of the crude product by silica gel flash chromatography (hexane:ethyl acetate 4:1 to 3:2 eluent) resulted in phenylmethyl 2-{[3-nitro-4-({2-oxo-2-[(phenylmethyl)oxy]ethyl}amino)phenyl]carbonyl}benzoate (0.33 g, 82% yield) as an amorphous residue. MS (EI) for C$_{30}$H$_{24}$N$_2$O$_7$: 524 (MH$^+$).

A solution of phenylmethyl 2-{[3-nitro-4-({2-oxo-2-[(phenylmethyl)oxy]ethyl}amino)phenyl]carbonyl}benzoate (0.31 g, 0.59 mmol) in a mixture of tetrahydrofurane-ethyl acetate (1:1, 50 mL) was hydrogenated in the presence of 10% Pd/C (0.15 g) in a Parr shaker at 40 psi, until the consumption of hydrogen ceased. The catalyst was filtered off and the solvent was evaporated. The resulting crude product was converted into its methyl ester in a mixture of benzene-methanol (9:1, 5.0 mL) by the addition of 2.0 M trimethylsilyldiazomethane solution in hexane (0.3 mL, 0.60 mmol). The reaction was quenched by the addition of a few drops of acetic acid and the solvent was evaporated. The resulting crude product was purified by silica gel flash chromatography (hexane:ethyl acetate 4:1 to 1:1 eluent) to give methyl 2-[(3-oxo-1,2,3,4-tetrahydroquinoxalin-6-yl)carbonyl]benzoate (0.12 g, 67% yield). $^1$H NMR (400 MHz, DMSO-d$_6$): 8.06 (s, 1H), 7.83 (dd, 1H), 7.64 (d, 1H), 7.52 (t, 1H), 7.38 (d, 1H), 7.09 (7.03 (d, 1H), 4.41 (s, 2H), 3.77 (s, 3H); MS (EI) for C$_{17}$H$_{14}$N$_2$O$_4$: 311 (MH$^+$).

In a mixture of terahydrofuran-methanol-water (2:1:1, 5.0 mL) methyl 2-[(3-oxo-1,2,3,4-tetrahydroquinoxalin-6-yl)carbonyl]benzoate (0.10 g, 0.32 mol) was treated with 2M aqueous lithium hydroxide (1.60 mL, 3.20 mmol) for 2 hours at room temperature. The pH was adjusted to 2 by the addition of 6M aqueous hydrochloric acid and it was diluted with ethyl acetate (30 mL). The organic layer was separated, it was washed with brine and dried over anhydrous sodium sulfate. While evaporating the solvent, a white precipitate was formed. 2-[(3-oxo-1,2,3,4-tetrahydroquinoxalin-6-yl)carbonyl]benzoic acid (0.10 g, quantitative) and collected via filtration. MS (EI) for C$_{16}$H$_{12}$N$_2$O$_4$: 295 (M$^-$).

To a solution of 2-[(3-oxo-1,2,3,4-tetrahydroquinoxalin-6-yl)carbonyl]benzoic acid (50 mg, 0.16 mmol) in N,N-dimethylformamide (2.0 mL), HOAt (40 mg, 0.28 mmol), HATU (90 mg, 0.23 mmol) and NMM (0.1 mL, 0.80 mmol) was added and the reaction mixture was stirred for 20 minutes at room temperature, followed by the addition of 3-chloroaniline (24 µL, 0.23 mmol). The reaction mixture was stirred for 15 hours at room temperature. The solvent was evaporated and the resulting crude was purified by reverse phase preparative HPLC (CH$_3$CN/H$_2$O with 0.1% TFA). The fractions were collected and the aqueous solution was lyophilized to give 7-[2-(3-chlorophenyl)-1-hydroxy-3-oxo-2,3-dihydro-1H-isoindol-1-yl]-3,4-dihydroquinoxalin-2(1H)-one (36 mg, 39% yield.). $^1$H NMR (400 MHz, DMSO-d$_6$): 12.25 (s, 1H), 10.44 (s, 1H), 8.04 (d, 1H), 7.78 (t, 1H), 7.59 (d, 1H), 7.47 (m, 2H), 7.43 (dd, 1H), 7.33 (m, 3H), 7.08 (m, 3H), 4.22 (s, 2H); MS (EI) for C$_{22}$H$_{16}$ClN$_3$O$_3$: 406 (MH$^+$).

Using the same or analogous synthetic techniques and/or substituting with alternative reagents, the following compounds of the invention were prepared:
7-[1-hydroxy-3-oxo-2-(phenylmethyl)-2,3-dihydro-1H-isoindol-1-yl]-3,4-dihydroquinoxalin-2(1H)-one. MS (EI) for C$_{23}$H$_{19}$N$_3$O$_3$: 386 (MH$^+$).

Example 9

3-Hydroxy-3-(1H-indol-5-yl)-2-(phenylmethyl)-2,3-dihydro-1H-isoindol-1-one

To a suspension of sodium hydride (0.27 g, 6.6 mmol) in tetrahydrofuran (10 mL) at 0° C. was added 5-bromoindole (1.0 g, 5.1 mmol). The reaction was stirred for 30 min at room temperature, then cooled to 0° C. and 2-(trimethylsilyl)ethoxymethyl chloride (1.0 mL, 5.6 mmol) was added. The solution was stirred for 2 h at room temperature. The reaction mixture was poured into saturated aqueous ammonium chloride solution and diluted with ether. The layers were separated and the aqueous layer was extracted (2×100 mL ether). The combined organic layers were washed with brine, dried (magnesium sulfate), filtered and concentrated in vacuo. Column chromatography (silica gel, 20:1 hexanes/ethyl acetate) gave 1.1 g (66%) of 5-bromo-1-({[2-(trimethylsilyl)ethyl]oxy}methyl)-1H-indole. $^1$H NMR (400 MHz, CDCl$_3$): 7.81 (d, 1H), 7.42 (d, 1H), 7.38 (dd, 1H), 7.23 (d, 1H), 6.52 (dd, 1H), 5.51 (s, 2H), 3.60 (m, 2H), 0.93 (m, 2H), 0.00 (s, 9H); MS (EI) for C$_{14}$H$_{20}$NOSiBr: 209 (M–OCH$_2$CH$_2$Si(CH$_3$)$_3$).

To a solution of 5-bromo-1-({[2-(trimethylsilyl)ethyl]oxy}methyl)-1H-indole (0.96 g, 2.9 mmol) in tetrahydrofuran (30 mL) cooled to –78° C. was added n-butyllithium (1.6 M in hexanes, 2.2 mL, 3.5 mmol). After stirring for 15 min at –78° C., 2-cyanobenzaldehyde (0.58 g, 4.4 mmol in 2 mL tetrahydrofuran) was quickly added. After stirring for 30 min at –78° C. and allowing to warm to room temperature, the reaction mixture was quenched with an excess of saturated aqueous ammonium chloride solution, then diluted with ethyl acetate. The layers were separated and the aqueous layer was extracted (2×100 mL ethyl acetate). The combined organic layers were dried (sodium sulfate), filtered and concentrated in vacuo. Column chromatography (silica gel, 1:1 hexanes/ethyl acetate) gave 0.68 g (61%) of 2-{hydroxy[1-({[2-(trimethylsilyl)ethyl]oxy}methyl)-1H-indol-5-yl]methyl} benzonitrile. $^1$H NMR (400 MHz, CDCl$_3$): 7.99 (d, 1H), 7.60 (d, 1H), 7.57 (m, 2H), 7.53 (d, 1H), 7.27 (m, 2H), 7.10 (dd, 1H), 6.56 (m, 2H), 5.52 (s, 2H), 3.50 (m, 2H), 0.51 (m, 2H), 0.00 (s, 9H); MS (EI) for C$_{22}$H$_{26}$N$_2$O$_2$Si: 379 (MH$^+$).

To a solution of oxalyl chloride (0.097 mL, 1.1 mmol) in dichloromethane cooled to –60° C. was added dimethyl sulfoxide (0.16 mL, 2.2 mmol), followed by 2-{hydroxy[1-({[2-(trimethylsilyl)ethyl]oxy}methyl)-1H-indol-5-yl]methyl} benzonitrile (0.21 g, 0.55 mmol in 2 mL dichloromethane). Triethylamine (0.46 mL, 3.3 mmol) was added and the solution was allowed to warm to room temperature and stirred for 30 min. The reaction mixture was quenched with an excess of water, and diluted with dichloromethane and brine. The layers were separated, and the aqueous layer was extracted (2×100 mL dichloromethane), dried (sodium sulfate), filtered and concentrated in vacuo. Column chromatography (silica gel, 4:1 hexanes/ethyl acetate) gave 0.12 g (58%) of 2-{[1-({[2-(trimethylsilyl)ethyl]oxy}methyl)-1H-indol-5-yl]carbonyl}benzonitrile. $^1$H NMR (400 MHz, CDCl$_3$): 8.07 (d, 1H), 7.88 (dd, 2H), 7.70 (m, 3H), 7.60 (d, 1H), 7.30 (d, 1H), 6.65 (m, 1H), 5.56 (s, 2H), 3.53 (m, 2H), 0.95 (m, 2H), 0.00 (s, 9H); $^{13}$C NMR (400 MHz, CDCl$_3$): 194.90 (C=O), 144.16, 140.45, 135.12, 133.07, 131.72, 131.03, 130.81, 129.82, 129.66, 127.08, 125.30, 118.39, 112.98, 111.50, 105.56, 77.05, 67.48, 19.09, 0.00.

A solution of 2-{[1-({[2-(trimethylsilyl)ethyl]oxy}methyl)-1H-indol-5-yl]carbonyl}benzonitrile (0.12 g, 0.32 mmol) was refluxed in 2.0 mL of ethanol and 2.0 mL of aqueous sodium hydroxide solution (20%) for 1 h. The solution was allowed to cool to room temperature and then poured into ice-cold 1M hydrochloric acid solution (pH to 2). The mixture was diluted with ethyl acetate and the layers were separated. The aqueous layer was extracted (2×100 mL ethyl acetate) and the combined organic layers were dried (sodium sulfate), filtered and concentrated in vacuo to give crude 2-{[1-({[2-(trimethylsilyl)ethyl]oxy}methyl)-1H-indol-5-yl]carbonyl}benzoic acid, which was used in the next step without further purification.

Crude 2-{[1-({[2-(trimethylsilyl)ethyl]oxy}methyl)-1H-indol-5-yl]carbonyl}benzoic acid (0.32 mmol) was taken up in N,N-dimethylformamide (1.0 mL), and treated with 4-methylmorpholine (0.14 mL, 1.3 mmol), HOAt (0.065 g, 0.48 mmol), HATU (0.16 g, 0.42 mmol) and benzylamine (0.070 mL, 0.64 mmol) and heated for 12 h at 60° C. The solution was diluted with saturated aqueous sodium bicarbonate solution and ethyl acetate and the layers were separated. The aqueous layer was extracted (2×100 mL ethyl acetate) and the combined organic layers were dried (sodium sulfate), filtered and concentrated in vacuo. Column chromatography (silica gel, 3:1 hexanes/ethyl acetate) gave 0.089 g (58%) of 3-hydroxy-2-(phenylmethyl)-3-[1-({[2-(trimethylsilyl)ethyl]oxy}methyl)-1H-indol-5-yl]-2,3-dihydro-1H-isoindol-1-one. $^1$H NMR (400 MHz, d$_6$-CDCl$_3$): 8.10 (d, 1H), 7.97 (m, 2H), 7.69 (m, 3H), 7.56 (m, 5H), 7.42 (m, 4H), 7.34 (m, 1H), 5.49 (m, 2H), 3.51 (m, 2H), 0.95 (m, 2H), 0.00 (s, 9H).

A solution of 3-hydroxy-2-(phenylmethyl)-3-[1-({[2-(trimethylsilyl)ethyl]oxy}methyl)-1H-indol-5-yl]-2,3-dihydro-1H-isoindol-1-one was taken up in 1M tetrabutylammonium fluoride in tetrahydrofuran (6.0 mL, 6.0 mmol), and ethylenediamine (0.22 mL, 3.6 mmol) was added. The solution was heated to 70° C. for 45 min. The reaction mixture was diluted with ethyl acetate and saturated aqueous sodium bicarbonate solution. The layers were separated and the combined organic layers were dried (sodium sulfate), filtered and concentrated in vacuo. Purification was undertaken via HPLC (reverse-phase, acetonitrile/water with 0.1% trifluoroacetic acid), followed by column chromatography (silica gel, 5% methanol/dichloromethane). The resultant yellow solid was taken up in ethyl acetate and washed with 10% aqueous citric acid solution (3×), dried (sodium sulfate), filtered and concentrated in vacuo. Lyophilization gave 0.0045 g (4%) of 3-hydroxy-3-(1H-indol-5-yl)-2-(phenylmethyl)-2,3-dihydro-1H-isoindol-1-one. $^1$H NMR (400 MHz, d$_6$-DMSO): 8.20 (d, 1H), 7.91 (dt, 2H), 7.84 (dt, 1H), 7.75 (d, 1H), 7.71 (m, 1H), 7.56 (d, 1H), 7.35 (m, 6H), 4.65 (m, 2H); MS (EI) for C$_{23}$H$_{18}$N$_2$O$_2$: 354 (MH$^+$).

Example 10

6-{[2-(1H-Benzimidazol-2-yl)phenyl]carbonyl}-2H-1,4-benzoxazin-3(4H)-one

2-[(3-Oxo-3,4-dihydro-2H-1,4-benzoxazin-6-yl)carbonyl]benzoic acid (100 mg, 0.34 mmol.) was taken into DMF (1 mL) followed by addition of 4-methylmorpholine (75 uL, 0.7 mmol.) and PyBOP (177 mg, 0.34 mmol.) and the resulting solution was stirred for 15 minutes at room temperature. o-Phenylenediamine (37 mg, 0.34 mmol.) was added to the solution thus obtained and the mixture was allowed to stir an additional hour then partitioned with ethyl acetate and water. The organic layer was washed with water (3×), 10% aqueous citric acid (2×), saturated aqueous sodium bicarbonate (1×) and brine then dried over anhydrous sodium sulfate. A portion of the residue obtained on filtration and concentration of the organic solution was purified by silica gel flash chromatography (2:1 ethyl acetate:hexanes to 100% ethyl acetate) gave 6-[2-(2-aminophenyl)-1-hydroxy-3-oxo-2,3-dihydro-1H-isoindol-1-yl]-2H-1,4-benzoxazin-3(4H)-one (4.0 mg, 3% yield). The remainder of the crude residue was taken into acetic acid (5 mL) and heated to reflux for one hour. The solvent was removed in vacuo and the residue partitioned with ethyl acetate and saturated aqueous sodium bicarbonate. The organic layer was dried over anhydrous sodium sulfate and the residue was purified by silica gel flash chromatography (2.5:1 ethyl acetate:hexanes) to give 6-{[2-(1H-benzimidazol-2-yl)phenyl]carbonyl}-2H-1,4-benzoxazin-3(4H)-one (28 mg, 22% yield). 6-[2-(2-Aminophenyl)-1-hydroxy-3-oxo-2,3-dihydro-1H-isoindol-1-yl]-2H-1,4-benzoxazin-3(4H)-one: MS (EI) for $C_{22}H_{17}N_3O_4$: 388 (MH$^+$). 6-{[2-(1H-Benzimidazol-2-yl)phenyl]carbonyl}-2H-1,4-benzoxazin-3(4H)-one: $^1$H NMR (400 MHz, d$_6$-DMSO): 12.84 (br s, 1H), 10.75 (br s, 1H), 8.00 (d, 1H), 7.73 (tr, 1H), 7.59 (tr, 1H), 7.44-7.37 (m, 3H), 7.32 (s, 1H), 7.15-7.06 (m, 3H), 6.87 (d, 1H), 4.58 (s, 2H). MS (EI) for $C_{22}H_{15}N_3O_3$: 370 (MH$^+$).

Example 11

6-{[2-(3-Phenyl-1,2,4-oxadiazol-5-yl)phenyl]carbonyl}-2H-1,4-benzoxazin-3(4H)-one 2-[(3-Oxo-3,4-dihydro-2H-1,4-benzoxazin-6-yl)carbonyl]benzoic acid (100 mg, 0.34 mmol.) was taken into DMF (1 mL) followed by addition of 4-methylmorpholine (75 uL, 0.7 mmol.) and PyBOP (177 mg, 0.34 mmol.) and the resulting solution was stirred for 15 minutes at room temperature. N-Hydroxybenzenecarboximidamide (46 mg, 0.34 mmol.) was added to the solution thus obtained and the mixture was allowed to stir an additional hour then partitioned with ethyl acetate and water. The organic layer was washed with water (3×), 10% aqueous citric acid (2×), saturated aqueous sodium bicarbonate (1×) and brine then dried over anhydrous sodium sulfate. Filtration and concentration afforded a crystalline solid that was suspended in anhydrous 1:1 THF:acetonitrile (1 mL) followed by addition of 1M TBAF in THF (300 uL) and the mixture was allowed to stir at room temperature under a nitrogen atmosphere for 24 hours. The solvent was removed in vacuo and the residue partitioned with ethyl acetate and water. The organic layer was washed twice with additional water and a crystalline solid was obtained from the organic layer. The solid product was collected by filtration and suspended in methanol. The solid was again collected by filtration, washed with additional methanol and dried in vacuo to give 6-{[2-(3-phenyl-1,2,4-oxadiazol-5-yl)phenyl]carbonyl}-2H-1,4-benzoxazin-3(4H)-one (63 mg, 47% yield) as a white crystalline solid. $^1$H NMR (400 MHz, d$_4$-MeOH): 8.26 (d, 1H), 7.91 (d, 2H), 7.83-7.80 (m, 2H), 7.62 (d, 1H), 7.52-7.44 (m, 4H), 7.35 (dd, 1H), 6.96 (d, 1H), 4.61 (s, 2H). MS (EI) for $C_{23}H_{15}N_3O_4$: 398 (MH$^+$).

Example 12

3-Hydroxy-3-(1H-indazol-5-yl)-2-(phenylmethyl)-2,3-dihydro-1H-isoindol-1-one A solution of 5-aminoindazole (5.0 g, 38 mmol) and ice (32 g) in water (16 mL) was further cooled with an ice bath. To this slurry was added concentrated hydrochloric acid (16 mL), followed immediately by sodium nitrite (2.9 g, 41 mmol in 11 mL water). After stirring for 10 min at 0° C., potassium iodide (7.5 g, 45 mmol) was added and the solution was slowly warmed to 40° C. until gas evolution slowed. The reaction mixture was stirred in a 50° C. oil bath for 30 min further, then cooled to room temperature and 3M aqueous sodium hydroxide solution (40 mL) was added, followed by 50% aqueous sodium bicarbonate solution (40 mL). The solution was vacuum filtered and a brown solid was collected, taken up in 100 mL tetrahydrofuran and stirred with 100 mL of dry silica. To this slurry was added hexanes (66 mL), and the mixture was filtered through celite/fritted glass using 40% tetrahydrofuran/hexanes to rinse the silica. Trituration from ethyl acetate gave 1.6 g (18%) of 5-iodo-1H-indazole. $^1$H NMR (400 MHz, CDCl$_3$): 10.55 (broad s, 1H), 8.14 (m, 1H), 8.02 (d, 1H), 7.61 (dd, 1H), 7.31 (m, 1H); MS (EI) for $C_7H_5N_2I$: 245 (MH$^+$).

To a slurry of sodium hydride (0.67 g, 17 mmol) in N,N-dimethylformamide (43 mL) cooled to 0° C. was added 5-iodo-1H-indazole (3.1 g, 13 mmol). After stirring for 15 min, triisopropylsilyl chloride (3.4 mL, 17 mmol) was added dropwise and the solution was allowed to warm to room temperature. The solution was diluted with ethyl acetate and water and the layers were separated. The aqueous layer was extracted (2×100 mL ethyl acetate) and the combined organic layers were dried (sodium sulfate), filtered and concentrated in vacuo. Column chromatography (silica gel, 20:1 hexanes/ethyl acetate) gave 1.8 g (68%) of 5-iodo-1-[tris(1-methylethyl)silyl]-1H-indazole as a yellow solid. $^1$H NMR (400 MHz, CDCl$_3$): 8.14 (d, 1H), 8.11 (d, 1H), 7.55 (dd, 1H), 7.35 (d, 1H), 1.77 (m, 3H), 1.10 (m, 18H).

A solution of 5-iodo-1-[tris(1-methylethyl)silyl]-1H-indazole (1.8 g, 4.6 mmol) in tetrahydrofuran (9.2 mL) was cooled to −78° C., and n-butyllithium was added (1.6M in hexanes, 3.4 mL, 5.5 mmol). After 15 min., 2-cyanobenzaldehyde (0.78 g, 6.0 mmol) in 2.0 mL tetrahydrofuran was added quickly and the solution was allowed to warm to room temperature. The reaction mixture was quenched with an excess of saturated aqueous ammonium chloride solution, then partitioned between water and ethyl acetate. The layers were separated and the aqueous layer was extracted (2×100 mL ethyl acetate). The combined organic layers were dried (sodium sulfate), filtered and concentrated in vacuo. Column chromatography (silica gel, 3:1 hexanes/ethyl acetate) gave 0.17 g (9%) of 2-(hydroxy{1-[tris(1-methylethyl)silyl]-1H-indazol-5-yl}methyl)benzonitrile. $^1$H NMR (400 MHz, CDCl$_3$): 8.20 (s, 1H), 7.95 (m, 1H), 7.69 (s, 1H), 7.51 (m, 3H), 7.23 (m, 1H), 7.09 (m, 1H), 6.50 (s, 1H), 1.77 (m, 3H), 1.06 (m, 18H); MS (EI) for $C_{24}H_{31}N_3OSi$: 250 (M−SiiPr$_3$).

A solution of dimethylsulfoxide (71 μL, 1.0 mmol) in dichloromethane (1.5 mL) was cooled to −60° C. Addition of oxalyl chloride (44 μL, 0.50 mmol) was followed by addition of triethylamine (0.29 mL, 2.1 mmol) and 2-(hydroxy{1-[tris(1-methylethyl)silyl]-1H-indazol-5-yl}methyl)benzonitrile (0.17 g, 0.42 mmol in 2.0 mL of dichloromethane). The solution was allowed to warm to room temperature then diluted with ethyl acetate and saturated aqueous sodium bicarbonate. The layers were separated and the aqueous layer was extracted (2×100 mL ethyl acetate). The combined organic layers were dried (sodium sulfate), filtered and concentrated in vacuo. Column chromatography (silica gel, 5:1 hexanes/ethyl acetate) gave 0.070 g (42%) of 2-({1-[tris(1-methylethyl)silyl]-1H-indazol-5-yl}carbonyl)benzonitrile. $^1$H NMR (400 MHz, CDCl$_3$): 8.32 (d, 1H), 8.13 (m, 1H), 8.01 (dd, 1H), 7.87 (m, 1H), 7.68 (m, 5H), 1.81 (m, 3H), 1.13 (d, 18H); MS (EI) for C$_{24}$H$_{29}$N$_3$OSi: 248 (M−Si(iPr)$_3$).

A solution of 2-({1-[tris(1-methylethyl)silyl]-1H-indazol-5-yl}carbonyl)benzonitrile in ethanol (2.0 mL) and 20% aqueous sodium hydroxide solution (2.0 mL) was refluxed for 30 min. Solid citric acid was added to pH 3-4. The reaction mixture was diluted with ethyl acetate, dried (sodium sulfate), filtered and concentrated in vacuo to give 0.19 g (>100% crude yield) of 2-(1H-indazol-5-ylcarbonyl)benzoic acid. NMR analysis confirmed the concurrent loss of the triisopropylsilyl protecting group during this step. The crude acid was used without further purification for the next step. $^1$H NMR (400 MHz, d$_4$-MeOH): 8.14 (m, 1H), 8.10 (m, 1H), 8.05 (m, 1H), 7.75 (m, 3H), 7.63 (d, 1H), 7.57 (m, 1H).

A solution of crude 2-(1H-indazol-5-ylcarbonyl)benzoic acid (theoretically 0.17 mmol), 4-methylmorpholine (0.076 mL, 0.70 mmol), benzylamine (0.038 mL, 0.35 mmol), HOAt (0.035 g, 0.26 mmol), and HATU (0.086 g, 0.23 mmol) in N,N-dimethylformamide (1.0 mL) was stirred for 3 h at 60° C. The solvent was removed in vacuo and the residue was partitioned between ethyl acetate and brine. The layers were separated and the aqueous layer was extracted (3×100 mL ethyl acetate). The combined organic layers were dried (sodium sulfate), filtered and concentrated in vacuo. Purification via HPLC (reverse-phase, acetonitrile/water with 0.1% trifluoroacetic acid), followed by direct lyophilization of the pure fractions gave 0.023 g (28%) of 3-hydroxy-3-(1H-indazol-5-yl)-2-(phenylmethyl)-2,3-dihydro-1H-isoindol-1-one trifluoroacetate salt. $^1$H NMR (400 MHz, d$_6$-DMSO): 8.23 (s, 1H), 8.16 (d, 1H), 7.84 (m, 4H), 7.67 (m, 2H), 7.33 (m, 7H), 4.55 (m, 2H); MS (EI) for C$_{22}$H$_{17}$N$_3$O$_2$: 356 (MH$^+$).

Using the same or analogous synthetic techniques and/or substituting with alternative reagents, the following compounds of the invention were prepared:

3-hydroxy-3-(1H-indol-6-yl)-2-(phenylmethyl)-2,3-dihydro-1H-isoindol-1-one trifluoroacetate salt: $^1$H NMR (400 MHz, d$_6$-DMSO): 11.10 (broad s, 1H), 8.09 (m, 1H), 7.72 (m, 1H), 7.61 (m, 1H), 7.49 (m, 2H), 7.35 (m, 6H), 7.25 (dd, 1H), 6.42 (s, 1H), 4.32 (m, 2H). MS (EI) for C$_{23}$H$_{18}$N$_2$O$_2$: 355 (MH$^+$).

3-hydroxy-3-(1H-indazol-6-yl)-2-(phenylmethyl)-2,3-dihydro-1H-isoindol-1-one trifluoroacetate salt: $^1$H NMR (400 MHz, d$_6$-DMSO): 8.17 (d, 1H), 8.10 (d, 1H), 7.86 (m, 2H), 7.74 (dt, 1H), 7.49 (m, 3H), 7.30 (m, 5H), 4.42 (m, 2H); MS (EI) for C$_{22}$H$_{17}$N$_3$O$_2$: 356 (MH$^+$).

Example 13

But-3-en-1-yl{5-[1-hydroxy-3-oxo-2-(phenylmethyl)-2,3-dihydro-1H-isoindol-1-yl]-1H-benzimidazol-2-yl}carbamate To a solution of 2-methyl-2-thiopseudourea sulfate (12 g, 278 mmol) and potassium carbonate (12 g, 138 mmol) in toluene (50 ml) and water (50 ml) at 25° C. was added but-3-en-1-yl chloroformate (3.0 g, 134 mmol) then stirred for 2.5 h. The biphasic reaction mixture was separated, and the organic phase was washed with water (2×80 ml), dried over anhydrous sodium sulfate, and filtered. The filtrate was concentrated in vacuo to afford but-3-en-1-yl[imino(methylthio) methyl]carbamate (4.0 g, 96%). MS (EI) for C$_7$H$_{12}$N$_2$O$_2$S: 287 (MH$^+$).

To a solution of but-3-en-1-yl[imino(methylthio)methyl] carbamate (3.0 g, 15.9 mmol) and but-3-en-1-yl chloroformate in N,N-dimethylformamide (25 ml) was added sodium hydride (60% in mineral oil, 0.64 g, 16 mmol), in portions, at 0° C. The reaction mixture was immediately allowed to warm to 25° C. and was stirred for 16 h, at which time the solution was diluted with diethyl ether (200 ml). The organic layer was washed with water (100 ml) and brine (50 ml), dried over anhydrous sodium sulfate, filtered and concentrated in vacuo to afford dibut-3-en-1-yl[(Z)-(methylthio)methylylidene] biscarbamate (1.29 g, 43%). MS (EI) for C$_{12}$H$_{18}$N$_2$O$_4$S: 287 (MH$^+$).

A solution of 3-(3,4-diaminophenyl)-3-hydroxy-2-(phenylmethyl)-2,3-dihydro-1H-isoindol-1-one (250 mg, 0.72 mole) and dibut-3-en-1-yl[(Z)-(methylthio)methylylidene] biscarbamate (289 mg, 0.94 mmol) in acetic acid (10 ml) was heated to 55° C. and stirred for 35 min. The reaction mixture was concentrated in vacuo, and then purified by column chromatography (SiO$_2$, ethyl acetate/hexanes) to give an impure product (0.22 g) as dark gum. The product was further purified by reverse phase HPLC to yield the trifluoroacetic acid salt of But-3-en-1-yl{5-[1-hydroxy-3-oxo-2-(phenylmethyl)-2,3-dihydro-1H-isoindol-1-yl]-1H-benzimidazol-2-yl}carbamate (145 mg, 35%) as a white solid. $^1$H NMR (400 MHz, d$_6$-DMSO): 7.76 (d, 1H), 7.59-7.52 (m, 3H), 7.33 (d, 1H), 7.25 (m, 2H), 7.20-7.20 (m, 4H), 6.99 (d, 1H), 5.85 (m, 1H), 5.17 (m, 1H), 5.10 (m, 1H), 4.48 (d, 1H), 4.28 (t, 2H), 4.15 (d, 1H), 2.44 (m, 2H); MS (EI) for C$_{27}$H$_{24}$N$_4$O$_4$: 469 (MH$^+$).

Using the same or analogous synthetic techniques and/or substituting with alternative reagents, the following compounds of the invention were prepared:

piperidin-4-ylmethyl{5-[1-hydroxy-3-oxo-2-(phenylmethyl)-2,3-dihydro-1H-isoindol-1-yl]-1H-benzimidazol-2-yl}carbamate trifluoroacetic acid salt: $^1$H NMR (400 MHz, d$_6$-DMSO): 8.62-8.49 (br. m, 2H), 8.29-8.12 (br. m, 1H), 7.75 (dd, 1H), 7.62-7.47 (m, 3H), 7.36-7.06 (m, 8H), 7.02-6.90 (d, 1H), 4.50 (d, 1H), 4.18-4.03 (m, 3H), 3.01-2.75 (m, 2H), 2.05-1.77 (m, 5H), 1.48-1.28 (m, 2H).

piperidin-4-yl{5-[1-hydroxy-3-oxo-2-(phenylmethyl)-2,3-dihydro-1H-isoindol-1-yl]-1H-benzimidazol-2-yl}carbamate trifluoroacetic acid salt: $^1$H NMR (400 MHz, d$_6$-DMSO): 8.62-8.42 (br. m, 2H), 7.78-7.73 (dd, 1H), 7.60-7.48 (m, 3H), 7.34-7.05 (m, 7H), 7.00-6.92 (d, 1H), 5.05-4.93 (br. m, 1H), 4.49 (d, 1H), 4.14 (d, 1H), 3.28-3.03 (br. m, 4H), 2.15-2.00 (br. m, 2H), 1.91-1.77 (br. m, 2H).

ethyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, CDCl$_3$): 7.74 (d, 1H), 7.66 (br s, 1H), 7.51-7.43 (m, 3H), 7.31 (d, 1H), 7.22 (d, 1H), 7.18 (br s, 1H), 7.08-7.01 (m, 6H), 4.35 (d, 1H), 4.38 (q, 2H), 4.20 (d, 1H), 1.39 (t, 3H); MS (EI) for C$_{25}$H$_{22}$N$_4$O$_4$: 443 (MH$^+$).

3-(methyloxy)butyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.77 (d, 1H), 7.59 (br s, 1H), 7.55 (dd, 2H), 7.35 (d, 1H), 7.29 (br s, 1H), 7.19-7.09 (m, 6H), 7.02 (d, 1H), 4.48 (d, 1H), 4.31 (t, 2H), 4.16 (d, 1H), 3.41 (m, 1H), 3.23 (s, 3H), 1.81 (m, 2H), 1.11 (d, 3H); MS (EI) for C$_{28}$H$_{28}$N$_4$O$_5$: 501 (MH$^+$).

prop-2-yn-1-yl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.77 (d, 1H), 7.58-7.52 (m, 2H), 7.33 (d, 1H), 7.26 (d, 1H), 7.18-7.10 (m, 6H), 7.00 (d, 1H), 4.90 (s, 2H), 4.48 (d, 1H), 4.16 (d, 1H), 3.68 (t, 1H); MS (EI) for $C_{28}H_{20}N_4O_4$: 453 (MH$^+$).

but-2-yn-1-yl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.76 (d, 1H), 7.59-7.52 (m, 3H), 7.32 (d, 2H), 7.29 (br s, 1H), 7.26 (d, 1H), 7.29-7.10 (m, 6H), 6.99 (d, 1H), 4.85 (q, 2H), 4.48 (d, 1H), 4.16 (d, 1H), 1.86 (t, 3H); MS (EI) for $C_{27}H_{24}N_4O_4$: 466 (MH$^+$).

1-methylethyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.73 (d, 1H), 7.57-7.49 (m, 3H), 7.27-7.11 (m, 7H), 6.85 (d, 1H), 4.96 (m, 1H), 4.51 (d, 1H), 4.10 (d, 1H), 1.28 (d, 6H); MS (EI) for $C_{26}H_{24}N_4O_4$: 457 (MH$^+$).

2-fluoroethyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_3$-MeCN): 7.76 (m, 1H), 7.70 (br s, 1H), 7.55-7.47 (m, 2H), 7.41 (d, 1H), 7.26 (m, 1H), 7.21-7.10 (m, 6H), 6.98 (d, 1H), 4.63 (d, 1H), 4.63 (dt, 2H), 4.53 (dt, 2H), 4.20 (d, 1H); MS (EI) for $C_{25}H_{21}N_4O_4$: 461 (MH$^+$).

propyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.76 (dd, 1H), 7.61 (br s, 1H), 7.56 (m, 1H), 7.37 (d, 1H), 7.37 (br s, 1H), 7.26 (d, 1H), 7.19-7.10 (m, 5H), 7.04 (d, 1H), 4.43 (d, 1H), 4.19 (d, 1H), 4.18 (t, 2H), 1.69 (m, 2H), 0.95 (t, 3H); MS (EI) for $C_{26}H_{24}N_4O_4$: 457 (MH$^+$).

cyclohexyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.76 (d, 1H), 7.59 (br s, 1H), 7.55 (m, 2H), 7.35 (d, 1H), 7.29 (br s, 1H), 7.26 (d, 1H), 7.19-7.10 (m, 4H), 7.02 (d, 1H), 4.77 (m, 1H), 4.48 (d, 2H), 4.16 (d, 2H), 1.92 (m, 2H), 1.73 (m, 2H), 1.56-1.23 (M, 6H); MS (EI) for $C_{29}H_{28}N_4O_4$: 497 (MH$^+$).

tetrahydrofuran-2-ylmethyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.75 (d, 1H), 7.57-7.52 (m, 3H), 7.33 (d, 1H), 7.26 (br s, 1H), 7.24 (d, 1H), 7.17-7.09 (m, 4H), 7.00 (d, 1H), 4.48 (d, 2H), 4.24-4.04 (m, 4H), 3.77 (q, 1H), 3.67 (q, 1H), 1.97 (m, 1H), 1.85 (m, 2H), 1.63 (m, 1H); MS (EI) for $C_{28}H_{26}N_4O_5$: 499 (MH$^+$).

cyclopropylmethyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.75 (d, 1H), 7.58 (br s, 1H), 7.54 (m, 2H), 7.32 (d, 1H), 7.28 (br s, 1H), 7.24 (d, 1H), 7.17-7.09 (m, 4H), 7.01 (d, 1H), 4.47 (d, 1H), 4.16 (d, 1H), 4.07 (d, 2H), 1.21 (m, 1H), 0.58 (m, 2H), 0.38 (m, 2H); MS (EI) for $C_{27}H_{24}N_4O_4$: 469 (MH$^+$).

but-3-en-1-yl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.76 (d, 1H), 7.59-7.52 (m, 3H), 7.33 (d, 1H), 7.25 (m, 2H), 7.20-7.20 (m, 4H), 6.99 (d, 1H), 5.85 (m, 1H), 5.17 (m, 1H), 5.10 (m, 1H), 4.48 (d, 1H), 4.28 (t, 2H), 4.15 (d, 1H), 2.44 (m, 2H); MS (EI) for $C_{27}H_{24}N_4O_4$: 469 (MH$^+$).

2,2,2-trifluoroethyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.76 (d, 1H), 7.55 (m, 2H), 7.47 (br s, 1H), 7.26 (m, 3H), 7.19-7.10 (m, 4H), 6.98 (d, 1H), 4.81 (q, 2H0, 4.47 (d, 1H), 4.17 (d, 1H); MS (EI) for $C_{25}H_{19}F_3N_4O_4$: 497 (MH$^+$).

tetrahydrofuran-3-ylmethyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 11.65 (br s, 1H), 7.74 (d, 1H), 7.57-7.49 (m, 3H), 7.28-7.11 (m, 7H), 6.87 (d, 1H), 4.80-4.71 (m, 2H), 4.50 (d, 1H), 4.64 (q, 1H), 4.16-4.02 (m, 3H), 3.49 (dd, 1H), 2.56 (m, 1H), 1.97 (m, 1H), 1.62 (m, 1H); MS (EI) for $C_{28}H_{26}N_4O_5$: 499 (MH$^+$).

2,3-dihydroxypropyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.76 (d, 1H), 7.58-7.51 (m, 3H), 7.33 (d, 1H), 7.10-7.04 (m, 5H), 6.99 (d, 1H), 4.46 (d, 1H), 4.26-4.10 (m, 3H), 3.76 (m, 1H), 3.42 (dd, 2H); MS (EI) for $C_{26}H_{26}N_4O_6$: 489 (MH$^+$).

N-{5-[2-(3-chloro-2-fluorophenyl)-1-hydroxy-3-oxo-2,3-dihydro-1H-isoindol-1-yl]-1H-benzimidazol-2-yl}-4-piperidin-1-ylbutanamide: $^1$H NMR (400 MHz, CDCl$_3$): 7.78 (dd, 1H), 7.66 (br s, 1H), 7.43 (m, 2H), 7.16-699 (m, 6H), 4.50 (d, 1H), 4.30 (d, 1H), 4.15 (d, 1H), 3.52 (d, 1H), 2.72 (m, 3H), 1.73 (m, 3H), 1.18 (s, 1H); MS (EI) for $C_{30}H_{31}N_5O_4$: 526 (MH$^+$).

1,1-dimethylethyl 4-({[({5-[1-hydroxy-3-oxo-2-(phenylmethyl)-2,3-dihydro-1H-isoindol-1-yl]-1H-benzimidazol-2-yl}amino)carbonyl]oxy}methyl)piperidine-1-carboxylate: $^1$H NMR (400 MHz, d$_6$-DMSO): 7.73 (d, 1H), 7.57-7.43 (m, 3H), 7.27-7.13 (m, 7H), 6.87 (d, 1H), 4.51 (d, 1H), 4.11 (d, 1H), 4.02 (d, 2H), 2.72 (br s, 2H), 1.84 (br s, 2H) 1.67 (d, 1H), 1.39 (s, 9H), 1.12 (m, 2H); MS (EI) for $C_{34}H_{37}N_5O_6$: 612 (MH$^+$).

methyl{5-[1-hydroxy-3-oxo-2-(phenylmethyl)-2,3-dihydro-1H-isoindol-1-yl]-1-methyl-1H-benzimidazol-2-yl}carbamate: $^1$H NMR (400 MHz, CD$_3$OD): 7.87-7.85 (m, 1H), 7.75 (br s, 1H), 7.58-7.54 (m, 2H), 7.39 (d, 1H), 7.27-7.20 (m, 2H), 7.14-7.12 (m, 2H), 7.09-7.05 (m, 3H), 4.50 (d, 2H), 3.94 (s, 3H), 3.75 (s, 3H); MS (EI) for $C_{25}H_{22}N_4O_4$: 443 (MH$^+$).

2-methylpropyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.84-7.82 (m, 1H), 7.61-7.56 (m, 3H), 7.41 (d, 1H), 7.20 (m, 6H), 7.04 (m, 1H), 4.68 (d, 1H), 4.29-4.24 (m, 2H), 3.85 (d, 1H), 3.46-3.39 (m, 1H), 2.74-2.70 (m, 1H), 2.66-2.62 (m, 1H), 1.30-1.27 (m, 3H), 0.70-0.67 (m, 3H); MS (EI) for $C_{27}H_{26}N_4O_4$: 471 (MH$^+$).

but-2-yn-1-yl (5-{1-hydroxy-3-oxo-2-[(1R)-1-phenylethyl]-2,3-dihydro-1H-isoindol-1-yl}-1H-benzimidazol-2-yl)carbamate: $^1$H NMR (400 MHz, d$_6$-DMSO) reported are two closed diastereomers and the open isomer: 10.45 (s, 0.6H), 8.93 (d, 0.3H), 8.76 (d, 0.3H), 7.83-7.76 (m, 1H), 7.74-7.68 (m, 2.9H), 7.63-7.58 (m, 2H), 7.57-7.51 (m, 3.3H), 7.50-7.34 (m, 6.6H), 7.32-7.22 (m, 6.4H), 7.19-7.12 (m, 6.5H), 7.02-6.94 (m, 5.3H), 4.72 (m, 5.3H), 4.52 (q, 0.5H), 4.41 (q, 0.5H), 4.30 (q, 1H), 1.84 (m, 5.2H), 1.74 (d, 3H), 1.46 (d, 2.4H), 1.34 (d, 1.2H); MS (EI) for $C_{28}H_{24}N_4O_4$: 481 (MH$^+$).

phenylmethyl(5-{1-hydroxy-3-oxo-2-[(1R)-1-phenylethyl]-2,3-dihydro-1H-isoindol-1-yl}-1H-benzimidazol-2-yl) carbamate): $^1$H NMR (400 MHz, d$_6$-DMSO) reported are two closed diastereomers and the open isomer: 7.70 (br m, 3H), 7.60-7.39 (m, 26H), 7.23 (t, 3H), 7.16 (br m, 6H), 7.00-6.96 (m, 6H), 5.29-5.26 (m, 4.6H), 4.53 (br m, 0.5H), 4.41 (br m, 0.5H), 1.74 (d, 2.8H), 1.45 (d, 3H), 1.27 (d, 1.7H); MS (EI) for $C_{31}H_{26}N_4O_4$: 519 (MH$^+$).

2,2-dimethyl-3-[(phenylmethyl)oxy]propyl{5-[1-hydroxy-3-oxo-2-(phenylmethyl)-2,3-dihydro-1H-isoindol-1-yl]-1H-benzimidazol-2-yl}carbamate): $^1$H NMR (400 MHz, d$_6$-DMSO): 7.75 (dd, 1H), 7.57-7.50 (m, 3H), 7.34 (d, 1H), 7.30-7.07 (m, 13H), 7.01 (d, 1H), 4.47 (d, 1H), 4.46 (s, 2H), 4.16 (d, 1H), 4.05 (s, 2H), 3.25 (s, 2H), 0.96 (s, 6H); MS (EI) for $C_{35}H_{34}N_4O_5$: 591 (MH$^+$).

2,2-dimethyl-3-(methyloxy)propyl{5-[1-hydroxy-3-oxo-2-(phenylmethyl)-2,3-dihydro-1H-isoindol-1-yl]-1H-benzimidazol-2-yl}carbamate): $^1$H NMR (400 MHz, d$_6$-DMSO): 7.75 (dd, 1H), 7.58-7.51 (m, 3H), 7.36 (d, 1H), 7.32 (br s, 1H), 7.25 (d, 1H), 7.16-7.09 (m, 5H), 7.03 (d, 1H), 4.47 (d, 1H), 4.16 (d, 1H), 4.01 (s, 2H), 3.24 (s, 3H), 3.14 (s, 2H), 0.92 (s, 6H); MS (EI) for $C_{29}H_{30}N_4O_5$: 515 (MH$^+$).

3-hydroxy-2,2-dimethylpropyl{5-[1-hydroxy-3-oxo-2-(phenylmethyl)-2,3-dihydro-1H-isoindol-1-yl]-1H-benzimidazol-2-yl}carbamate): $^1$H NMR (400 MHz, d$_6$-DMSO): 7.76 (d, 1H), 7.69-7.53 (m, 3H), 7.37-7.35 (m, 2H), 7.25 (d, 1H), 7.14-7.11 (m, 5H), 7.04 (d, 1H), 4.46 (d, 1H), 4.17 (d, 1H), 4.00 (s, 2H), 3.23 (s, 2H), 0.88 (s, 6H); MS (EI) for $C_{28}H_{28}N_4O_5$: 501 (MH$^+$).

phenylmethyl{5-[1-hydroxy-3-oxo-2-(phenylmethyl)-2,3-dihydro-1H-isoindol-1-yl]-1H-benzimidazol-2-yl}carbamate: $^1$H NMR (400 MHz, d$_6$-DMSO): 7.74 (dd, 1H), 7.56 (m, 1H), 7.53 (dt, 1H), 7.35-7.46 (m, 6H), 7.31 (d, 1H), 7.24 (m, 2H), 7.08-7.17 (m, 6H), 6.97 (d, 1H), 5.27 (s, 2H), 4.47 (d, 1H), 4.14 (d, 1H); MS (EI) for $C_{30}H_{24}N_4O_4$: 505 (MH$^+$).

2-(methyloxy)ethyl{5-[1-hydroxy-3-oxo-2-(phenylmethyl)-2,3-dihydro-1H-isoindol-1-yl]-1H-benzimidazol-2-yl}carbamate. $^1$H NMR (400 MHz, DMSO-d$_6$): 7.76 (d, 1H), 7.56 (m, 3H), 7.34 (d, 1H), 7.28 (br. s, 1H), 7.26 (d, 1H), 7.15 (m, 5H), 7.00 (d, 1H), 4.48 (d, 1H), 4.35 (m, 2H), 4.15 (d, 1H), 3.61 (m, 2H), 3.29 (s, 3H); MS (EI) for $C_{26}H_{24}N_4O_5$: 473 (MH$^+$).

[(4S)-2,2-dimethyl-1,3-dioxolan-4-yl]methyl{5-[1-hydroxy-3-oxo-2-(phenylmethyl)-2,3-dihydro-1H-isoindol-1-yl]-1H-benzimidazol-2-yl}carbamate acetate: $^1$H NMR (400 MHz, d$_6$-DMSO): 7.76-7.71 (d, 1H), 7.59-7.46 (m, 3H), 7.28-7.10 (m, 7H), 6.90-6.85 (d, 1H), 4.53-4.47 (d, 1H), 4.35-4.22 (m, 2H), 4.16-4.02 (m, 3H), 3.77-3.71 (m, 1H), 1.37-1.32 (s, 3H), 1.30-1.27 (s, 3H); MS (EI) for $C_{29}H_{28}N_4O_6$: 529 (MH$^+$).

Example 14

Methyl{5-[1-hydroxy-2-(3-methylphenyl)-3-oxo-2,3-dihydro-1H-isoindol-1-yl]-1H-benzimidazol-2-yl}carbamate A solution of 2-(4-chloro-3-nitrobenzoyl)benzoic acid (75 g, 0.25 mol) in ammonium hydroxide 28% (250 mL) was heated to 85° C. for four days. Additions of ammonium hydroxide 28% (80 ml) were made three times daily. The solution was partially concentrated in-vacuo, then cooled in an ice bath. To the solution was added 6N hydrochloric acid until the pH became weakly acidic. The solid which formed was collected by vacuum filtration, washed twice with water (250 mL) and dried to afford 2-(4-amino-3-nitrobenzoyl)benzoic acid (72 g, 100%) as a yellow solid. $^1$H NMR (400 MHz, d$_6$-DMSO): 8.09 (br s, 3H), 7.99 (d, 1H), 7.75-7.58 (m, 3H), 7.40 (d, 1H), 7.09 (d, 1H); MS (EI) for $C_{14}H_{10}N_2O_4$: 309 (MNa$^+$)

To a mixture of 2-(4-amino-3-nitrobenzoyl)benzoic acid (50 g, 175 mmol) and potassium carbonate (50 g, 350 mmol) in N,N-dimethylformamide (200 ml), was added benzyl bromide (22.8 ml, 192 mmol). The mixture was stirred at 60° C. for 16 hours, and then partitioned between ethyl acetate (500 mL) and water. The organic portion was washed with 0.2N sodium hydroxide, water, brine, dried over sodium sulfate, filtered and concentrated in-vacuo. The resultant residue was re-crystallized from chloroform and hexanes (1:1) to afford benzyl 2-(4-amino-3-nitrobenzoyl)benzoate (53 g, 81%) as a yellow solid. $^1$H NMR (400 MHz, d$_6$-DMSO): 8.11 (br s, 1H), 8.06-8.01 (m, 2H), 7.79-7.75 (m, 1H), 7.72-7.65 (m, 2H), 7.46 (d, 1H), 7.28-7.19 (m, 5H), 7.02 (d, 1H), 5.12 (s, 2H); MS (EI) for $C_{21}H_{16}N_2O_5$: 377 (MH$^+$)

A 1 L three-neck flask equipped with a mechanical stirrer was charged with a mixture of benzyl 2-(4-amino-3-nitrobenzoyl)benzoate (50 g, 133 mmole), iron powder (74 g, 1.30 mol), and ammonium formate (167 g, 2.60 mol) in tetrahydrofuran (300 mL) and water (200 mL). The mixture was stirred vigorously at 80° C. for 90 minutes, cooled to room temperature and filtered through celite. The celite was washed with ethyl acetate (500 mL), and the filtrate was partitioned. The organic portion was washed with 2N sodium hydroxide (2×100 mL), water, brine, dried over sodium sulfate and concentrated in-vacuo to afford benzyl 2-(3,4-diaminobenzoyl)benzoate (47 g, 1.30 mol) as a brown oil. $^1$H NMR (400 MHz, d$_6$-DMSO): 7.94 (d, 1H), 7.70-7.66 (m, 1H), 7.61-7.58 (m, 1H), 7.37-7.21 (m, 6H), 6.98 (s, 1H), 6.70 (d, 1H), 6.47 (d, 1H), 5.54 (s, 2H), 5.09 (s, 2H), 4.72 (s, 2H); MS (EI) for $C_{21}H_{18}N_2O_3$: 349 (MNa$^+$)

A solution of benzyl 2-(3,4-diaminobenzoyl)benzoate (25 g, 72 mmole) and 1,3-bis(methoxy carbonyl)-2-methyl-2-thiopseudourea (19.3 g, 94 mmole) in acetic acid (100 ml) was heated to 75° C. for 45 minutes. The solution was cooled to room temperature and concentrated in-vacuo. The resultant oil was diluted in ethyl acetate (300 mL) and washed with 1N sodium hydroxide (200 mL), water (2×200 mL), dried over sodium sulfate, filtered and concentrated in-vacuo. The resultant solid was re-crystallized using ethyl ether and ethyl acetate (2:1). The solid was isolated by vacuum filtration and washed ethyl ether to afford [5-(2-benzylcarbanoyl-benzoyl)-1H-benzoimidazol-2-yl]-carbamic acid methyl ester, 21.4 g, 49.8 mmol, (69%) as a yellow solid. $^1$H NMR (400 MHz, d$_6$-DMSO): 8.04 (br s, 1H), 7.77-7.68 (m, 3H), 7.52-7.41 (m, 3H), 7.28-7.10 (m, 5H), 5.05 (s, 2H), 3.76 (s, 3H); MS (EI) for C—$_{24}$H$_{20}$N$_4$O$_4$: 430 (MH$^+$)

A solution of [5-(2-benzylcarbanoyl-benzoyl)-1H-benzoimidazol-2-yl]-carbamic acid methyl ester (21.4 g, 49.8 mmol) in tetrahydrofuran (150 mL) was cooled in an ice bath. To the solution was added di-tert-butyl dicarbonate (33 g, 150 mmol). This was followed by the drop wise addition of a solution of N,N-dimethylaminopyridine (6.1 g, 50 mmole) and Hunig's base (8.7 mL, 50 mmol) in tetrahydrofuran (80 mL). The solution was stirred at 0° C. for 40 minutes, then quenched by pouring over crushed ice and hydrochloric acid 1N (2:1). The mixture was partition and extracted using diethyl ether (200 mL). The organic portion was washed with water, saturated sodium bicarbonate, dried over sodium sulfate, filtered and concentrated in-vacuo. The resultant residue was purified by column chromatography (silica gel, ethyl acetate/hexanes). The isolated product was concentrated in-vacuo to afford, 25 g, 40 mmol (80%) of a colorless oil, which was diluted in ethyl acetate (150 mL). To the solution was added catalytic Palladium on carbon (wet 5%), and the solution was stirred under 1 atmosphere of hydrogen gas at ambient temperature for 18 hr. The solution was filtered through Celite and concentrated in-vacuo to afford 24 g, 39 mmol (95%) of a pale yellow oil, which was diluted in dichloromethane (150 mL) and cooled to 0° C. To the solution was added pyridine (3.6 ml, 39 mmol) followed by the drop wise addition of cyanuric fluoride (6.6 g, 49 mmol). The solution was stirred at ambient temperatures for 3 hr, and then was quenched by adding water (25 mL). The mixture was stirred at ambient temperatures for 30 minutes. The mixture was filtered through celite and washed with dichloromethane (2×50 mL). The filtrate was partitioned and the organic portion was washed with ice-cold 0.5N hydrochloric acid, water and brine, dried over sodium sulfate, and filtered through a silica gel plug column. The product was isolated and concentrated in-vacuo to afford 16.9 g, 31 mmol (62% over 3 steps) of a white solid, to which (1 g, 1.85 mmol) was dissolved in 1,2-dichloroethane (12 mL). To the solution was added N'N-dimethylaniline (470 µl, 3.96 mmol) and m-Toluidine (198 µl, 185 mmol). The solution was stirred at 65° C. for 15 hr. The solution was cooled to room temperature and concentrated in-vacuo. The resultant residue was partitioned between, aqueous 20% citric acid and ethyl acetate. The organic portion was washed with water, saturated sodium bicarbonate, brine, dried over sodium sulfate, filtered and concentrated in-vacuo to afford a purple residue that was purified by column chromatography (silica gel, 50% ethyl acetate in hexanes). The product was isolated to afford 928 mg, 1.48 mmol (80%) of a white solid, which (925 mg, 1.47 mmol) was dissolved in dichloromethane (2 mL). To the solution was added trifluoroacetic acid (1 mL). The solution was stirred at ambient temperature for 30 minutes, and then was partitioned between saturated sodium bicarbonate and dichloromethane. The organic layer was washed with water, brine, dried over sodium sulfate, filtered and concentrated in vacuo. The resultant residue was dissolved in acetonitrile, and 4N HCl in dioxane (325 µl, 1.2 mmol) was added to the solution. A white precipitate formed and was collected by vacuum filtration. The solid was washed with ether, and dried to afford 403 mg, 0.94 mmol (64% over two steps) of methyl{5-[1-hydroxy-2-(3-methylphenyl)-3-oxo-2,3-dihydro-1H-isoindol-1-yl]-1H-benzimidazol-2-yl}carbamate hydrochloride. $^1$H NMR (400 MHz, $d_6$-DMSO): 7.85 (d, 1H), 7.79 (br s, 1H), 7.68 (s, 1H), 7.64-7.56 (m, 2H), 7.44 (d, 1H), 7.38 (s, 1H), 7.26-7.21 (m, 3H), 7.15-7.11 (m, 1H), 6.95 (d, 2H), 3.83 (s, 3H), 2.21 (s, 3H); MS (EI) for $C_{24}H_{20}N_4O_4$: 429 (MH$^+$).

Using the same or analogous synthetic techniques and/or substituting with alternative reagents, the following compounds of the invention were prepared:

methyl(5-{1-hydroxy-2-[3-methyl-5-(trifluoromethyl)phenyl]-3-oxo-2,3-dihydro-1H-isoindol-1-yl}-1H-benzimidazol-2-yl)carbamate $^1$H NMR (400 MHz, $d_6$-DMSO): 7.87-7.76 (m, 4H), 7.62-7.51 (m, 3H), 7.29-7.22 (m, 3H), 7.01-6.99 (d, 1H), 3.76 (s, 0.4H) open, 3.72 (s, 2.6H) close, 2.31 (s, 0.4H) open, 2.28 (s, 2.6H) close; MS (EI) for $C_{25}H_{19}F_3N_4O_4$: 497 (MH$^+$).

methyl{5-[2-(3,4-dichlorophenyl)-1-hydroxy-3-oxo-2,3-dihydro-1H-isoindol-1-yl]-1H-benzimidazol-2-yl}carbamate $^1$H NMR (400 MHz, $d_6$-DMSO): 8.01-8.00 (d, 1H), 7.87 (b, 1H), 7.85 (b, 1H), 7.66-7.52 (m, 5H), 7.30-7.25 (d, d, 2H), 7.01-7.00 (d, 1H), 3.77 (s, 0.3H) open, 3.73 (s, 2.7H) close; MS (EI) for $C_{23}H_{16}Cl_2N_4O_4$: 483 (MH$^+$).

methyl{5-[2-(3-ethylphenyl)-1-hydroxy-3-oxo-2,3-dihydro-1H-isoindol-1-yl]-1H-benzimidazol-2-yl}carbamate $^1$H NMR (400 MHz, $d_6$-DMSO): 7.83-7.81 (d, 2H), 7.61-7.47 (m, 4H), 7.38-7.35 (m, 1H), 7.29-7.23 (m, 3H), 7.16-7.11 (dd, 1H), 6.97-6.94 (m, 2H), 3.76 (s, 0.4H) open, 3.72 (s, 2.6H) close, 2.51-2.45 (q, 2H), 1.06-1.02 (t, 3H); MS (EI) for $C_{25}H_{22}N_4O_4$: 443 (MH$^+$).

methyl{5-[2-(3-ethynylphenyl)-1-hydroxy-3-oxo-2,3-dihydro-1H-isoindol-1-yl]-1H-benzimidazol-2-yl}carbamate $^1$H NMR (400 MHz, $d_6$-DMSO): 7.86-7.84 (d, 1H), 7.75-7.71 (dd, 2H), 7.61-7.51 (m, 4H), 7.31-7.18 (m, 4H), 7.00-6.97 (m, 1H), 4.17 (s 1H), 3.76 (s, 0.1H) open, 3.72 (s, 2.9H) close; MS (EI) for $C_{25}H_{18}N_4O_4$: 439 (MH$^+$).

methyl{5-[2-(4-chloro-3-methylphenyl)-1-hydroxy-3-oxo-2,3-dihydro-1H-isoindol-1-yl]-1H-benzimidazol-2-yl}carbamate $^1$H NMR (400 MHz, $d_6$-DMSO): 7.84-7.82 (d, 1H), 7.68 (s, 1H), 7.61-7.50 (m, 4H), 7.38-7.35 (d, d, 1H), 7.29-7.25 (m, 3H), 6.98-6.96 (d, 1H), 3.77 (s, 0.3H) open, 3.72 (s, 2.7H) close, 2.22 (s, 3H); MS (EI) for $C_{24}H_{19}ClN_4O_4$: 439 (MH$^+$).

methyl{5-[2-(2,3-dimethylphenyl)-1-hydroxy-3-oxo-2,3-dihydro-1H-isoindol-1-yl]-1H-benzimidazol-2-yl}carbamate $^1$H NMR (400 MHz, $d_6$-DMSO): 7.88-7.85 (m, 1H), 7.76-7.05 (m, 8.6H), 6.93-6.91 (d, 0.6H) close, 6.73-6.69 (t, 0.4H) open, 5.95-5.93 (d, 0.4H) open, 3.83 (s, 1.2H) open, 3.81 (s, 1.8H) close, 2.29 (s, 1.2H) open, 2.10 (s, 1.2H) open, 2.04 (s, 1.8H), close, 1.34 (s, 1.8H) close; MS (EI) for $C_{25}H_{22}N_4O_4$: 443 (MH$^+$).

methyl{5-[2-(2,3-dihydro-1H-inden-1-yl)-1-hydroxy-3-oxo-2,3-dihydro-1H-isoindol-1-yl]-1H-benzimidazol-2-yl}carbamate $^1$H NMR (400 MHz, $d_6$-DMSO): 7.76-7.02 (m, 11H), 6.92-6.88 (t, 0.5H), 6.72-6.70 (d, 0.2H), 6.56-6.54 (d, 2H), 3.77-3.73 (m, 3H), 3.04-2.93 (m, 1H), 2.84-2.78 (m, 1H), 2.48-2.22 (m, 1H), 1.78-1.76 (m, 1H); MS (EI) for $C_{26}H_{22}N_4O_4$: 455 (MH$^+$).

methyl(6-{2-[2-fluoro-3-(methyloxy)phenyl]-1-hydroxy-3-oxo-2,3-dihydro-1H-isoindol-1-yl}-1H-benzimidazol-2-yl)carbamate hydrochloride $^1$H NMR (400 MHz, $d_6$-DMSO): 7.88-7.87 (d, 1H), 7.85-7.83 (b, 1H), 7.68-7.61 (m, 3H), 7.46-7.43 (d, 1H), 7.29-7.28 (d, 1H), 7.19-7.17 (d, 1H), 7.09-7.05 (m, 2H), 6.97-6.93 (m, 1H), 3.84 (s, 3H), 3.76 (s, 3H); MS (EI) for $C_{24}H_{19}FN_4O_5$: 463 (MH$^+$).

methyl{6-[2-(2-fluoro-3-methylphenyl)-1-hydroxy-3-oxo-2,3-dihydro-1H-isoindol-1-yl]-1H-benzimidazol-2-yl}carbamate hydrochloride $^1$H NMR (400 MHz, $d_6$-DMSO): 7.88-7.86 (d, 1H), 7.82-7.79 (b, 1H), 7.67-7.60 (m, 3H), 7.44-7.42 (d, 1H), 7.29-7.27 (d, 1H), 7.20-7.14 (m, 3H), 7.03-6.99 (dd, 1H), 3.83 (s, 3H), 2.12 (s, 3H); MS (EI) for $C_{24}H_{19}FN_4O_4$: 447 (MH$^+$).

methyl(6-{2-[(3-bromophenyl)methyl]-1-hydroxy-3-oxo-2,3-dihydro-1H-isoindol-1-yl}-1H-benzimidazol-2-yl)carbamate trifluoroacetate: $^1$H NMR (400 MHz, CDCl$_3$): 7.84-7.86 (m, 1H), 7.51-7.56 (m, 2H), 7.24-7.32 (m, 4H), 7.16-7.18 (m, 3H), 6.95-7.0 (m, 2H), 4.32-4.42 (m, 2H), 3.97 (s, 3H); MS (EI) for $C_{24}H_{19}BrN_4O_4$: 507 (MH$^+$).

methyl(5-{2-[(3-chlorophenyl)methyl]-1-hydroxy-3-oxo-2,3-dihydro-1H-isoindol-1-yl}-1H-benzimidazol-2-yl)carbamate trifluoroacetate: $^1$H NMR (400 MHz, CDCl$_3$): 7.87-7.89 (m, 1H), 7.51-7.55 (m, 2H), 7.31-7.32 (m, 1H), 7.23-7.27 (m, 3H), 7.10-7.13 (m, 2H), 7.04-7.06 (m, 2H), 6.97 (s, 1H), 4.51 (d, 1H), 4.32 (d, 1H), 3.96 (s, 3H); MS (EI) for $C_{24}H_{19}ClN_4O_4$: 507 (MH$^+$).

methyl(5-{2-[(2-fluorophenyl)methyl]-1-hydroxy-3-oxo-2,3-dihydro-1H-isoindol-1-yl}-1H-benzimidazol-2-yl)carbamate trifluoroacetate: $^1$H NMR (400 MHz, CDCl$_3$): 7.74-7.78 (m, 2H), 7.44-7.52 (m, 3H), 7.26-7.30 (m, 2H), 7.20-7.24 (m, 1H), 7.12-7.14 (m, 1H), 6.98-7.03 (m, 1H), 6.84-6.87 (m, 1H), 6.64-6.68 (m, 1H), 4.61 (d, 1H), 4.34 (d, 1H), 3.93 (s, 3H); MS (EI) for $C_{24}H_{19}FN_4O_4$: 447 (MH$^+$).

methyl(5-{2-[(2-chlorophenyl)methyl]-1-hydroxy-3-oxo-2,3-dihydro-1H-isoindol-1-yl}-1H-benzimidazol-2-yl)carbamate trifluoroacetate: $^1$H NMR (400 MHz, CDCl$_3$): 7.81-7.83 (m, 1H), 7.73 (s, 2H), 7.48-7.53 (m, 2H), 7.29 (d, 1H), 7.15-7.25 (m, 3H), 6.96-7.04 (m, 3H), 4.75 (d, 1H), 4.44 (d, 1H), 3.92 (s, 3H); MS (EI) for $C_{24}H_{19}ClN_4O_4$: 463 (MH$^+$).

methyl(5-{2-[(2-bromophenyl)methyl]-1-hydroxy-3-oxo-2,3-dihydro-1H-isoindol-1-yl}-1H-benzimidazol-2-yl)carbamate trifluoroacetate: $^1$H NMR (400 MHz, $d_6$-DMSO): 7.81 (d, 1H), 7.55-7.63 (m, 3H), 7.47-7.49 (m, 1H), 7.30-7.36 (m, 4H), 7.03-7.22 (m, 3H), 4.59 (d, 1H), 4.13 (d, 1H), 3.80 (s, 3H); MS (EI) for $C_{24}H_{19}BrN_4O_4$: 507 (MH$^+$).

methyl(5-{1-hydroxy-2-[(3-methylphenyl)methyl]-3-oxo-2,3-dihydro-1H-isoindol-1-yl}-1H-benzimidazol-2-yl)carbamate trifluoroacetate: $^1$H NMR (400 MHz, CDCl$_3$): 7.75 (d, 1H), 7.65 (s, 1H), 7.44-7.51 (m, 2H), 7.34 (d, 1H), 7.22-7.27 (m, 3H), 6.83-6.92 (m, 4H), 4.43 (d, 1H), 4.18 (d, 1H), 3.94 (s, 3H), 2.11 (s, 3H); MS (EI) for C$_{25}$H$_{22}$N$_4$O$_4$: 442 (MH$^+$).

methyl(5-{1-hydroxy-2-[(4-methylphenyl)methyl]-3-oxo-2,3-dihydro-1H-isoindol-1-yl}-1H-benzimidazol-2-yl)carbamate trifluoroacetate: $^1$H NMR (400 MHz, CDCl$_3$): 7.60 (d, 1H), 7.64 (s, 1H), 7.40-7.52 (m, 3H), 7.22-7.30 (m, 3H), 7.0 (d, 2H), 6.85 (d, 2H), 4.50 (d, 1H), 4.12 (d, 1H), 3.95 (s, 3H), 2.17 (s, 3H); MS (EI) for C$_{25}$H$_{22}$N$_4$O$_4$: 443 (MH$^+$).

methyl(5-{1-hydroxy-2-[(2-methylphenyl)methyl]-3-oxo-2,3-dihydro-1H-isoindol-1-yl}-1H-benzimidazol-2-yl)carbamate trifluoroacetate: $^1$H NMR (400 MHz, CDCl$_3$): 7.60 (d, 1H), 7.64 (s, 1H), 7.40-7.52 (m, 3H), 7.22-7.30 (m, 3H), 7.0 (d, 2H), 6.85 (d, 2H), 4.50 (d, 1H), 4.12 (d, 1H), 3.95 (s, 3H), 2.17 (s, 3H); MS (EI) for C$_{25}$H$_{22}$N$_4$O$_4$: 443 (MH$^+$).

methyl{5-[2-(3,5-dimethylphenyl)-1-hydroxy-3-oxo-2,3-dihydro-1H-isoindol-1-yl]-1H-benzimidazol-2-yl}carbamate trifluoroacetate: $^1$H NMR (400 MHz, d$_6$-DMSO): 7.80 (d, 1H), 7.51-7.62 (m, 4H), 7.30 (d, 1H), 7.21 (d, 1H), 7.06-7.11 (m, 3H), 6.74 (s, 1H), 3.76 (s, 3H), 2.15 (s, 6H); MS (EI) for C$_{25}$H$_{22}$N$_4$O$_4$: 443 (MH$^+$).

methyl{5-[2-(3,5-dichlorophenyl)-1-hydroxy-3-oxo-2,3-dihydro-1H-isoindol-1-yl]-1H-benzimidazol-2-yl}carbamate trifluoroacetate: $^1$H NMR (400 MHz, CDCl$_3$): 7.92 (d, 1H), 7.52-7.64 (m, 4H), 7.26-7.32 (m, 2H), 7.21-7.22 (m, 1H), 7.08 (s, 1H), 6.85 (d, 2H), 3.95 (s, 3H); MS (EI) for C$_{23}$H$_{16}$Cl$_2$N$_4$O$_4$: 483 (MH$^+$).

methyl(5-{2-[1-(2-fluorophenyl)ethyl]-1-hydroxy-3-oxo-2,3-dihydro-1H-isoindol-1-yl}-1H-benzimidazol-2-yl)carbamate: $^1$H NMR (400 MHz, d$_6$-DMSO): 6.94-7.80 (m, 12H), 4.93-5.03 (m, 1H), 3.76 (s, 1.2H), 3.74 (s, 1.1H), 3.71 (s, 0.7H), 1.65 (d, 0.6H), 1.56 (d, 1.2H), 1.29 (d, 1.2H); MS (EI) for C$_{25}$H$_{21}$FN$_4$O$_4$: 461 (MH$^+$).

methyl(5-{1-hydroxy-3-oxo-2-[1-(2-thienyl)ethyl]-2,3-dihydro-1H-isoindol-1-yl}-1H-benzimidazol-2-yl)carbamate: $^1$H NMR (400 MHz, d$_6$-DMSO): 6.29-7.72 (m, 11H), 4.59-4.73 (m, 1H), 3.76 (s, 1H), 3.72 (d, 2H), 1.80 (d, 1.2H), 1.49 (d, 1.2H), 1.36 (d, 0.6H); MS (EI) for C$_{23}$H$_{20}$N$_4$O$_4$S: 449 (MH$^+$).

methyl(5-{2-[1-(3-chlorophenyl)ethyl]-1-hydroxy-3-oxo-2,3-dihydro-1H-isoindol-1-yl}-1H-benzimidazol-2-yl)carbamate: $^1$H NMR (400 MHz, d$_6$-DMSO): 6.80-7.77 (m, 12H), 4.78-4.82 (m, 0.3H), 4.52-4.53 (m, 0.3H), 4.39-4.40 (m, 0.4H), 3.75 (s, 1H), 3.73 (s, 1H), 3.72 (s, 1H), 1.74 (d, 1H), 1.44 (d, 1H), 1.30 (d, 1H); MS (EI) for C$_{25}$H$_{21}$ClN$_4$O$_4$: 477 (MH$^+$).

methyl[5-(1-hydroxy-3-oxo-2-{1-[3-(trifluoromethyl)phenyl]ethyl}-2,3-dihydro-1H-isoindol-1-yl)-1H-benzimidazol-2-yl]carbamate: $^1$H NMR (400 MHz, d$_6$-DMSO): 7.23-7.84 (m, 12H), 4.92-4.93 (m, 0.3H), 4.63-4.64 (m, 0.4H), 4.51-4.53 (m, 0.3H), 3.77 (s, 1H), 3.74 (s, 1H), 3.73 (s, 1H), 1.80 (d, 1H), 1.49 (d, 1H), 1.34 (d, 1H); MS (EI) for C$_{26}$H$_{21}$F$_3$N$_4$O$_4$: 511 (MH$^+$).

methyl(5-{1-hydroxy-3-oxo-2-[(1R)-1-phenylpropyl]-2,3-dihydro-1H-isoindol-1-yl}-1H-benzimidazol-2-yl)carbamate: $^1$H NMR (400 MHz, d$_6$-DMSO): R-isomer: 6.94-7.80 (m, 13H), 4.57-4.63 (m, 1H), 3.76 (s, 2H), 3.74 (s, 0.5H), 3.72 (s, 0.5H), 1.66-1.70 (m, 2H), 0.78 (t, 3H); MS (EI) for C$_{26}$H$_{24}$N$_4$O$_4$: 457 (MH$^+$).

methyl(5-{1-hydroxy-3-oxo-2-[(1S)-1-phenylpropyl]-2,3-dihydro-1H-isoindol-1-yl}-1H-benzimidazol-2-yl)carbamate: $^1$H NMR (400 MHz, d$_6$-DMSO): S-isomer: 6.92-7.77 (m, 13H), 4.55-4.61 (m, 1H), 3.75 (s, 2H), 3.73 (s, 0.5H), 3.71 (s, 0.5H), 1.60-1.67 (m, 2H), 0.78 (t, 3H); MS (EI) for C$_{26}$H$_{24}$N$_4$O$_4$: 457 (MH$^+$).

methyl(5-{2-[1-(3-chloro-2-methylphenyl)ethyl]-1-hydroxy-3-oxo-2,3-dihydro-1H-isoindol-1-yl}-1H-benzimidazol-2-yl)carbamate: $^1$H NMR (400 MHz, d$_6$-DMSO): 6.94-7.84 (m, 11H), 5.00-5.04 (m, 1H), 3.76 (s, 2H), 3.74 (s, 0.5H), 3.72 (s, 0.5H), 2.20 (s, 3H), 1.66 (d, 0.44H), 1.59 (d, 0.40H), 1.26 (d, 2.16H); MS (EI) for C$_{26}$H$_{23}$ClN$_4$O$_4$: 491 (MH$^+$).

methyl(5-{1-hydroxy-2-[1-(4-methyl-2-thienyl)ethyl]-3-oxo-2,3-dihydro-1H-isoindol-1-yl}-1H-benzimidazol-2-yl)carbamate: $^1$H NMR (400 MHz, d$_6$-DMSO): 6.56-7.75 (m, 10H), 4.56-4.66 (m, 1H), 3.77 (s, 1H), 3.73 (d, 2H), 2.10 (d, 2H), 1.92 (d, 1H), 1.78 (d, 1H), 1.47 (d, 1H), 1.33 (d, 1H); MS (EI) for C$_{24}$H$_{22}$N$_4$O$_4$S: 463 (MH$^+$).

methyl(5-{2-[1-(4-bromo-2-thienyl)ethyl]-1-hydroxy-3-oxo-2,3-dihydro-1H-isoindol-1-yl}-1H-benzimidazol-2-yl)carbamate: $^1$H NMR (400 MHz, d$_6$-DMSO): 6.86-7.68 (m, 10H), 4.58-4.70 (m, 1H), 3.75 (s, 0.6H), 3.73 (d, 2.4H), 1.78 (d, 1.2H), 1.47 (d, 1.2H), 1.35 (s, 0.6H); MS (EI) for C$_{23}$H$_{19}$BrN$_4$O$_4$S: 529 (MH$^+$).

methyl(5-{2-[1-(4-chloro-2-thienyl)ethyl]-1-hydroxy-3-oxo-2,3-dihydro-1H-isoindol-1-yl}-1H-benzimidazol-2-yl)carbamate: $^1$H NMR (400 MHz, d$_6$-DMSO): 6.86-7.75 (m, 10H), 4.57-4.69 (m, 1H), 3.77 (s, 1H), 3.73 (d, 2H), 1.78 (d, 1H), 1.47 (d, 1H), 1.36 (d, 1H); MS (EI) for C$_{23}$H$_{19}$ClN$_4$O$_4$S: 483 (MH$^+$).

methyl(5-{2-[1-(3-chloro-2-thienyl)ethyl]-1-hydroxy-3-oxo-2,3-dihydro-1H-isoindol-1-yl}-1H-benzimidazol-2-yl)carbamate hydrochloride: $^1$H NMR (400 MHz, d$_6$-DMSO): 6.83-7.80 (m, 10H), 4.92-5.11 (m, 1H), 3.85 (d, 2H), 3.80 (s, 1H), 1.75 (d, 1H), 1.51 (d, 1H), 1.34 (d, 1H); MS (EI) for C$_{23}$H$_{19}$ClN$_4$O$_4$S: 483 (MH$^+$).

methyl(5-{2-[1-(5-bromo-2-thienyl)ethyl]-1-hydroxy-3-oxo-2,3-dihydro-1H-isoindol-1-yl}-1H-benzimidazol-2-yl)carbamate hydrochloride: $^1$H NMR (400 MHz, d$_6$-DMSO): 6.67-7.79 (m, 10H), 4.59-4.69 (m, 1H), 3.85 (s, 2.2H), 3.80 (s, 0.8H), 1.76 (d, 1H), 1.50 (d, 1H), 1.37 (d, 1H); MS (EI) for C$_{23}$H$_{19}$BrN$_4$O$_4$S: 527 (MH$^+$).

methyl{5-[2-(4,5-dichloro-2-fluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.33-7.95 (m, 9H), 7.10 (s, 1H), 3.81 (s, 2.5H), 3.79 (s, 0.5H); MS (EI) for C$_{23}$H$_{15}$Cl$_2$FN$_4$O$_4$: 501 (MH$^+$).

methyl[5-(1-hydroxy-3-oxo-2-{3-[(1,1,2,2-tetrafluoroethyl)oxy]phenyl}-2,3-dihydro-1H-isoindol-1-yl)-1H-benzimidazol-2-yl]carbamate trifluoroacetate: $^1$H NMR (400 MHz, d$_6$-DMSO): δ 7.27-7.88 (m, 9H), 6.64-7.10 (m, 3H), 6.10 (s, 1H), 3.77 (s, 3H); MS (EI) for C$_{25}$H$_{18}$F$_4$N$_4$O$_5$: 531 (MH$^+$).

methyl{5-[1-hydroxy-3-oxo-2-(3-piperidin-4-ylphenyl)-2,3-dihydro-1H-isoindol-1-yl]-1H-benzimidazol-2-yl}carbamate trifluoroacetate: $^1$H NMR (400 MHz, d$_6$-DMSO): 6.95-8.50 (m, 12H), 3.72 (s, 3H), 1.78-1.80 (m, 6H), 1.66 (s, 4H); MS (EI) for C$_{28}$H$_{27}$N$_5$O$_4$: 498 (MH$^+$).

methyl{5-[2-(3-ethenylphenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.84 (d, 1H), 7.40-7.68 (m, 6H), 7.21-7.28 (m, 4H), 6.99 (d, 1H), 6.56-6.65 (m, 1H), 5.62 (d, 1H), 5.21 (d, 1H), 3.77 (s, 0.5H), 3.72 (s, 2.5H); MS (EI) for C$_{25}$H$_{20}$N$_4$O$_4$: 441 (MH$^+$).

methyl{5-[2-(3-aminophenyl)-1-hydroxy-3-oxo-2,3-dihydro-1H-isoindol-1-yl]-1H-benzimidazol-2-yl}carbamate trifluoroacetate: $^1$H NMR (400 MHz, d$_6$-DMSO): 7.05-7.83 (m, 11H), 6.68 (s, 1H), 3.77 (s, 3H); MS (EI) for C$_{23}$H$_{19}$N$_5$O$_4$: 430 (MH$^+$).

methyl[5-(1-hydroxy-2-{3-[methyl(phenyl)amino]phenyl}-3-oxo-2,3-dihydro-1H-isoindol-1-yl)-1H-benzimidazol-2-yl]carbamate: $^{1}$H NMR (400 MHz, d$_{6}$-DMSO): 7.80 (d, 1H), 7.48-7.61 (m, 5H), 6.57-7.26 (m, 11H), 3.77 (s, 0.3H), 3.73 (s, 2.7H), 3.13 (s, 3H); MS (EI) for C$_{30}$H$_{25}$N$_{5}$O$_{4}$: 520 (MH$^{+}$).

methyl{5-[2-(3-ethynyl-2-fluorophenyl)-1-hydroxy-3-oxo-2,3-dihydro-1H-isoindol-1-yl]-1H-benzimidazol-2-yl}carbamate hydrochloride: $^{1}$H NMR (400 MHz, d$_{6}$-DMSO): 7.02-7.80 (m, 11H), 4.51 (s, 1H), 3.77 (s, 3H); MS (EI) for C$_{25}$H$_{17}$FN$_{4}$O$_{4}$: 457 (MH$^{+}$).

methyl{5-[1-hydroxy-2-(3-morpholin-4-ylphenyl)-3-oxo-2,3-dihydro-1H-isoindol-1-yl]-1H-benzimidazol-2-yl}carbamate: $^{1}$H NMR (400 MHz, d$_{6}$-DMSO): 7.81-7.83 (m, 1H), 7.53-7.60 (m, 4H), 7.23-7.27 (m, 2H), 6.94-7.10 (m, 4H), 6.58-6.71 (m, 1H), 3.77 (s, 0.4H), 3.73 (s, 2.6H), 3.65-3.68 (m, 4H), 2.91-2.93 (m, 4H); MS (EI) for C$_{27}$H$_{25}$N$_{5}$O$_{5}$: 500 (MH$^{+}$).

methyl{5-[1-hydroxy-3-oxo-2-(3-pyrrolidin-1-ylphenyl)-2,3-dihydro-1H-isoindol-1-yl]-1H-benzimidazol-2-yl}carbamate trifluoroacetate: $^{1}$H NMR (400 MHz, d$_{6}$-DMSO): 7.81-7.84 (m, 1H), 7.54-7.62 (m, 4H), 7.37 (d, 1H), 6.97-7.24 (m, 3H), 6.70-6.72 (m, 2H), 6.28-6.30 (m, 1H), 3.80 (s, 3H), 3.05-3.07 (m, 4H), 1.88-1.90 (m, 4H); MS (EI) for C$_{27}$H$_{25}$N$_{5}$O$_{4}$: 484 (MH$^{+}$).

methyl[5-(2-{3-[cyclohexyl(methyl)amino]phenyl}-1-hydroxy-3-oxo-2,3-dihydro-1H-isoindol-1-yl)-1H-benzimidazol-2-yl]carbamate trifluoroacetate: $^{1}$H NMR (400 MHz, d$_{6}$-DMSO): 7.85 (d, 3H), 7.56-7.62 (m, 4H), 7.26-7.34 (m, 3H), 7.00-7.10 (m, 2H), 3.79 (s, 3H), 3.20 (m, 3H), 2.68 (s, 1H), 0.85-1.76 (m, 10H); MS (EI) for C$_{30}$H$_{31}$N$_{5}$O$_{4}$: 526 (MH$^{+}$).

methyl{5-[2-(3-chloro-2,6-difluorophenyl)-1-hydroxy-3-oxo-2,3-dihydro-1H-isoindol-1-yl]-1H-benzimidazol-2-yl}carbamate: $^{1}$H NMR (400 MHz, d$_{6}$-DMSO): 6.56-8.17 (m, 10H), 3.77 (s, 0.5H), 3.73 (s, 2.5H); MS (EI) for C$_{23}$H$_{15}$ClF$_{2}$N$_{4}$O$_{4}$: 485 (MH$^{+}$).

methyl[5-(2-{3-[ethyl(phenyl)amino]phenyl}-1-hydroxy-3-oxo-2,3-dihydro-1H-isoindol-1-yl)-1H-benzimidazol-2-yl]carbamate: $^{1}$H NMR (400 MHz, d$_{6}$-DMSO): 7.82 (d, 1H), 7.56-7.60 (m, 3H), 6.67-7.33 (m, 13H), 3.79 (s, 3H), 3.57-3.59 (q, 2H), 0.96 (t, 3H); MS (EI) for C$_{31}$H$_{27}$N$_{5}$O$_{4}$: 534 (MH$^{+}$).

methyl(5-{1-hydroxy-3-oxo-2-[2-(phenyloxy)phenyl]-2,3-dihydro-1H-isoindol-1-yl}-1H-benzimidazol-2-yl)carbamate hydrochloride: $^{1}$H NMR (400 MHz, d$_{6}$-DMSO): 7.82 (d, 1H), 7.10-7.64 (m, 13H), 6.58-6.66 (m, 3H), 3.76 (s, 3H); MS (EI) for C$_{29}$H$_{22}$N$_{4}$O$_{5}$: 507 (MH$^{+}$).

methyl{5-[2-(2,5-dimethylphenyl)-1-hydroxy-3-oxo-2,3-dihydro-1H-isoindol-1-yl]-1H-benzimidazol-2-yl}carbamate hydrochloride: $^{1}$H NMR (400 MHz, d$_{6}$-DMSO): 6.88-7.94 (m, 11H), 3.83 (s, 2.8H), 3.81 (s, 0.2H), 2.31 (s, 3H), 1.44 (s, 3H); MS (EI) for C$_{25}$H$_{22}$N$_{4}$O$_{4}$: 443 (MH$^{+}$).

methyl{5-[2-(3-ethynyl-2-methylphenyl)-1-hydroxy-3-oxo-2,3-dihydro-1H-isoindol-1-yl]-1H-benzimidazol-2-yl}carbamate hydrochloride: $^{1}$H NMR (400 MHz, d$_{6}$-DMSO): 6.84-7.91 (m, 11H), 3.85 (s, 1H), 3.83 (s, 2H), 2.33 (s, 1H), 1.59 (s, 3H); MS (EI) for C$_{26}$H$_{20}$N$_{4}$O$_{4}$: 453 (MH$^{+}$).

methyl(5-{1-hydroxy-2-[1-(5-methyl-2-thienyl)ethyl]-3-oxo-2,3-dihydro-1H-isoindol-1-yl}-1H-benzimidazol-2-yl)carbamate: $^{1}$H NMR (400 MHz, d$_{6}$-DMSO): 8.95 (d, 0.2H), 7.75-7.16 (m, 7H), 6.95-6.86 (m, 0.8H), 6.79 (d, 0.5H), 6.59-6.51 (m, 1H), 6.33 (d, 0.3H), 6.09 (d, 0.2H), 4.97 (m, 0.2H), 4.63 (q, 0.3H), 4.54 (m, 0.5H), 3.76 (s, 0.6H), 3.74 (s, 1.5H), 3.73 (s, 0.9H), 2.40 (s, 1.5H), 2.35 (s, 0.6H), 2.24 (s, 0.9H), 1.75 (d, 0.9H), 1.46 (d, 1.5H), 1.32 (d, 0.6H); MS (EI) for C$_{24}$H$_{22}$N$_{4}$O$_{4}$S: 463 (MH$^{+}$).

methyl(5-{2-[1-(5-chloro-2-thienyl)ethyl]-1-hydroxy-3-oxo-2,3-dihydro-1H-isoindol-1-yl}-1H-benzimidazol-2-yl)carbamate: $^{1}$H NMR (400 MHz, d$_{6}$-DMSO): 9.06 (d, 0.2H), 7.76-7.20 (m, 8H), 6.95-6.82 (m, 2H), 6.79 (d, 0.5H), 6.66 (d, 0.6H), 6.19 (d, 0.4H), 4.96 (m, 0.2H), 4.66 (q, 0.4H), 4.58 (q, 0.4H), 3.77 (s, 0.6H), 3.74 (s, 1.2H), 3.73 (s, 1.2H), 1.77 (d, 1.2H), 1.47 (d, 1.2H), 1.36 (d, 0.6H); MS (EI) for C$_{23}$H$_{19}$ClN$_{4}$O$_{4}$S: 483 (MH$^{+}$).

methyl{5-[2-(furan-2-ylmethyl)-1-hydroxy-3-oxo-2,3-dihydro-1H-isoindol-1-yl]-1H-benzimidazol-2-yl}carbamate: $^{1}$H NMR (400 MHz, d$_{6}$-DMSO): 7.71 (m, 1H), 7.54-7.40 (m, 3H), 7.35 (d, 1H), 7.22-7.19 (m, 2H), 7.05 (s, 1H), 6.80 (d, 1H), 6.17 (m, 1H), 5.95 (d, 1H), 4.45 (d, 1H), 4.18 (d, 1H), 3.72 (s, 3H); MS (EI) for C$_{22}$H$_{18}$N$_{4}$O$_{5}$: 419 (MH$^{+}$).

methyl{5-[1-hydroxy-3-oxo-2-(3-thienylmethyl)-2,3-dihydro-1H-isoindol-1-yl]-1H-benzimidazol-2-yl}carbamate: $^{1}$H NMR (400 MHz, d$_{6}$-DMSO): 7.73 (m, 1H), 7.57-7.42 (m, 3H), 7.31 (dd, 1H), 7.27-7.23 (m, 2H), 7.12-7.09 (m, 2H), 6.90 (dd, 1H), 6.86 (d, 1H), 4.49 (d, 1H), 4.11 (d, 1H), 3.73 (s, 3H); MS (EI) for C$_{22}$H$_{18}$N$_{4}$O$_{4}$S: 435 (MH$^{+}$), 457 (MNa$^{+}$).

methyl(5-{1-hydroxy-3-oxo-2-[3-(phenylcarbonyl)phenyl]-2,3-dihydro-1H-isoindol-1-yl}-1H-benzimidazol-2-yl)carbamate: $^{1}$H NMR (400 MHz, d$_{6}$-DMSO): 7.97-7.84 (m, 1H), 7.75 (s, 1H), 7.71-7.40 (m, 10H), 7.28 (d, 2H), 7.00 (d, 1H), 3.76 (s, 0.4H), 3.74 (s, 2.6H); MS (EI) for C$_{30}$H$_{22}$N$_{4}$O$_{5}$: 519 (MH$^{+}$), 541 (MNa$^{+}$).

methyl{5-[2-(3-ethyl-4-fluorophenyl)-1-hydroxy-3-oxo-2,3-dihydro-1H-isoindol-1-yl]-1H-benzimidazol-2-yl}carbamate hydrochloride: $^{1}$H NMR (400 MHz, d$_{6}$-DMSO): 7.85 (m, 1H), 7.78 (br s, 1H), 7.65-7.57 (m, 3H), 7.41 (d, 1H), 7.37 (dd, 1H), 7.28-7.23 (m, 2H), 7.17 (d, 1H), 7.04 (t, 1H), 3.82 (s, 3H), 3.70-3.20 (q, 2H), 1.04 (t, 3H); MS (EI) for C$_{25}$H$_{21}$FN$_{4}$O$_{4}$: 461 (MH$^{+}$).

methyl{5-[2-(3-chloro-5-fluorophenyl)-1-hydroxy-3-oxo-2,3-dihydro-1H-isoindol-1-yl]-1H-benzimidazol-2-yl}carbamate hydrochloride: $^{1}$H NMR (400 MHz, d$_{6}$-DMSO): 8.10 (m, 1H), 7.89 (d, 1H), 7.72 (s, 1H), 7.67-7.55 (m, 4H), 7.43-7.38 (m, 1H), 7.29 (d, 1H), 7.22-7.18 (m, 2H), 3.81 (s, 3H); MS (EI) for C$_{23}$H$_{16}$ClFN$_{4}$O$_{4}$: 467 (MH$^{+}$).

methyl{5-[2-(5-bromo-2,4-difluorophenyl)-1-hydroxy-3-oxo-2,3-dihydro-1H-isoindol-1-yl]-1H-benzimidazol-2-yl}carbamate hydrochloride: $^{1}$H NMR (400 MHz, d$_{6}$-DMSO): 7.90 (m, 2H), 7.75-7.63 (m, 3H), 7.56-7.51 (m, 2H), 7.40 (d, 1H), 7.32 (d, 1H), 7.09 (d, 1H), 3.82 (s, 3H); MS (EI) for C$_{23}$H$_{15}$BrF$_{2}$N$_{4}$O$_{4}$: 529, 531 (MH$^{+}$).

methyl{5-[2-(5-chloro-2,4-difluorophenyl)-1-hydroxy-3-oxo-2,3-dihydro-1H-isoindol-1-yl]-1H-benzimidazol-2-yl}carbamate hydrochloride: $^{1}$H NMR (400 MHz, d$_{6}$-DMSO): 7.90 (m, 2H), 7.72-7.55 (m, 5H), 7.39 (d, 1H), 7.34 (d, 1H), 7.07 (d, 1H), 3.81 (s, 3H); MS (EI) for C$_{23}$H$_{15}$ClF$_{2}$N$_{4}$O$_{4}$: 485, 487 (MH$^{+}$).

methyl{5-[2-(3,5-dichloro-4-fluorophenyl)-1-hydroxy-3-oxo-2,3-dihydro-1H-isoindol-1-yl]-1H-benzimidazol-2-yl}carbamate hydrochloride: $^{1}$H NMR (400 MHz, d$_{6}$-DMSO): 8.11 (br s, 1H), 7.90 (d, 1H), 7.86 (d, 2H), 7.70-7.59 (m, 3H), 7.41 (d, 1H), 7.29 (d, 1H), 7.21 (d, 1H), 3.82 (s, 3H); MS (EI) for C$_{23}$H$_{15}$Cl$_{2}$FN$_{4}$O$_{4}$: 501, 503, 505 (MH$^{+}$).

methyl{5-[2-(3-chloro-2-methylphenyl)-1-hydroxy-3-oxo-2,3-dihydro-1H-isoindol-1-yl]-1H-benzimidazol-2-yl}carbamate: $^{1}$H NMR (400 MHz, d$_{6}$-DMSO): 7.90-7.23 (m, 9.4H), 6.90-6.81 (m, 1.3H), 6.08 (d, 0.3H), 3.78 (s, 1H), 3.76 (s, 2H), 2.25 (s, 1H), 1.48 (s, 2H); MS (EI) for $C_{24}H_{19}ClN_4O_4$: 463, 465 (MH$^+$).

methyl{5-[2-(5-chloro-2-methylphenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.88 (d, 1H), 7.78-7.59 (m, 4H), 7.46-7.23 (M, 5H), 7.09 (br s, 1H), 6.84 (br s, 1H), 3.77 (s, 3H), 1.49 (br, s, 3H); MS (EI) for $C_{24}H_{19}ClN_4O_4$: 463, 465 (MH$^+$).

methyl{5-[2-(5-chloro-2,3-difluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.92-7.89 (m, 2H), 7.72-7.62 (m, 3H), 7.51 (br s, 1H), 7.34-7.31 (m, 3H), 7.00 (d, 1H), 3.77 (s, 0.4H), 3.76 (s, 2.6H); MS (EI) for $C_{23}H_{15}ClF_2N_4O_4$: 485, 487 (MH$^+$).

methyl{5-[2-(5-ethynyl-2-methylphenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.891 (d, 1H), 7.76-7.60 (m, 4H), 7.44-7.29 (m, 4H), 7.06 (d, 1H), 6.91 (d, 1H), 4.22 (s, 1H), 3.81 (s, 3H), 1.52 (s, 3H); MS (EI) for $C_{26}H_{20}N_4O_4$: 453 (MH$^+$).

phenylmethyl 2-[(2-{[(methyloxy)carbonyl]amino}-1H-benzimidazol-5-yl)carbonyl]benzoate: $^1$H NMR (400 MHz, d$_6$-DMSO): 8.02 (d, 1H), 7.75 (tr, 1H), 7.68-7.64 (m, 2H), 7.47-7.41 (m, 3H), 7.22-7.11 (m, 5H), 5.03 (s, 2H), 3.74 (s, 3H). MS (EI) for $C_{24}H_{19}N_3O_5$: 430 (MH$^+$).

methyl{5-[1-hydroxy-3-oxo-2-(2-thienylmethyl)-2,3-dihydro-1H-isoindol-1-yl]-1H-benzimidazol-2-yl}carbamate trifluoroacetic acid salt: $^1$H NMR (400 MHz, d$_6$-DMSO): 7.74 (d, 1H), 7.55-7.50 (m, 3H), 7.28 (d, 1H), 7.24-7.20 (m, 3H), 6.93 (br d, 1H), 6.72 (m, 1H), 6.80 (m, 1H), 4.49 (dd AB, 2H), 3.78 (s, 3H). MS (EI) for $C_{22}H_{18}N_4O_4S$: 435 (MH$^+$).

methyl{5-[1-hydroxy-3-oxo-2-(2-phenylethyl)-2,3-dihydro-1H-isoindol-1-yl]-1H-benzimidazol-2-yl}carbamate trifluoroacetic acid salt: $^1$H NMR (400 MHz, d$_6$-DMSO): 7.74 (d, 1H), 7.61 (s, 1H), 7.55-7.51 (m, 2H), 7.43 (d, 1H), 7.26-7.04 (m, 8H), 3.80 (s, 3H), 3.52 (ddd, 1H), 3.11 (ddd, 1H), 2.81 (ddd, 1H), 2.60 (ddd, 1H). MS (EI) for $C_{25}H_{22}N_4O_4$: 443 (MH$^+$).

methyl[5-(1-hydroxy-3-oxo-2,3-dihydro-1H-isoindol-1-yl)-1H-benzimidazol-2-yl]carbamate trifluoroacetic acid salt: $^1$H NMR (400 MHz, d$_6$-DMSO): 9.29 (s, 1H), 7.67 (s, 1H), 7.64 (d, 1H), 7.53-7.43 (m, 3H), 7.31 (d, 1H), 7.25 (d, 1H), 7.00 (br s, 1H), 3.81 (s, 3H). MS (EI) for $C_{17}H_{14}N_4O_4$: 339 (MH$^+$).

methyl{5-[2-(2,3-dihydro-1H-inden-2-yl)-1-hydroxy-3-oxo-2,3-dihydro-1H-isoindol-1-yl]-1H-benzimidazol-2-yl}carbamate trifluoroacetic acid salt: $^1$H NMR (400 MHz, d$_6$-DMSO): 7.73 (s, 1H), 7.72 (s, 1H), 7.55-7.48 (m, 3H), 7.37 (br s, 1H), 7.24-7.17 (m, 3H), 7.11-7.09 (m, 3H), 4.07-3.99 (m, 2H), 3.82 (s, 3H), 3.65-3.57 (m, 2H), 2.98 (dd, 1H). MS (EI) for $C_{26}H_{22}N_4O_4$: 455 (MH$^+$).

methyl{5-[1-hydroxy-3-oxo-2-(pyridin-4-ylmethyl)-2,3-dihydro-1H-isoindol-1-yl]-1H-benzimidazol-2-yl}carbamate trifluoroacetic acid salt: $^1$H NMR (400 MHz, d$_6$-DMSO): 8.67 (d, 2H), 7.82 (d, 1H), 7.72 (d, 2H), 7.65-7.57 (m, 3H), 7.43 (br s, 1H), 7.36 (d, 1H), 7.33 (d, 1H), 7.02 (d, 1H), 4.56 (dd AB, 2H), 3.80 (s, 3H). MS (EI) for $C_{23}H_{19}N_5O_4$: 430 (MH$^+$).

methyl{5-[1-hydroxy-3-oxo-2-(pyridin-3-ylmethyl)-2,3-dihydro-1H-isoindol-1-yl]-1H-benzimidazol-2-yl}carbamate trifluoroacetic acid salt: $^1$H NMR (400 MHz, d$_6$-DMSO): 8.54 (d, 1H), 8.51 (s, 1H), 8.00 (d, 1H), 7.61-7.54 (m, 4H), 7.33 (d, 1H), 7.29 (d, 1H), 6.97 (d, 1H), 4.47 (dd AB, 2H), 3.80 (s, 3H). MS (EI) for $C_{23}H_{19}N_5O_4$: 430 (MH$^+$).

methyl{5-[1-hydroxy-3-oxo-2-(pyridin-2-ylmethyl)-2,3-dihydro-1H-isoindol-1-yl]-1H-benzimidazol-2-yl}carbamate trifluoroacetic acid salt: $^1$H NMR (400 MHz, d$_6$-DMSO): 8.46 (d, 1H), 7.88-7.80 (m, 2H), 7.64-7.56 (m, 3H), 7.46 (d, 1H), 7.40-7.35 (m, 2H), 7.30 (d, 1H), 7.06 (d, 1H), 4.53 (dd AB, 2H), 3.83 (s, 3H). MS (EI) for $C_{23}H_{19}N_5O_4$: 412 (MH$^+$—H$_2$O).

methyl{6-[2-(3,4-dichloro-2-fluorophenyl)-1-hydroxy-3-oxo-2,3-dihydro-1H-isoindol-1-yl]-1H-benzimidazol-2-yl}carbamate acetic acid salt: $^1$H NMR (400 MHz, d$_6$-DMSO): 11.78 (br s, 3H), 7.88 (d, 1H), 7.81 (s, 1H), 7.69-7.60 (m, 2H), 7.51 (dd, 1H), 7.46 (s, 1H), 7.37 (tr, 1H), 7.32 (d, 1H), 7.26 (d, 1H), 6.93 (d, 1H), 3.73 (s, 3H), 1.91 (s, 3H). MS (EI) for $C_{23}H_{15}Cl_2FN_4O_4$: (MH$^+$).

methyl(5-{1-hydroxy-3-oxo-2-[(1R)-1-phenylethyl]-2,3-dihydro-1H-isoindol-1-yl}-1H-benzimidazol-2-yl)carbamate: $^1$H NMR (400 MHz, d6-DMSO) reported are two closed diastereomers and the open isomer: 8.90 (d, 0.8H), 7.79-7.77 (m, 1H), 7.71-7.76 (m, 2.6H), 7.61-7.59 (m, 2.6H), 7.53-7.51 (m, 2.6H), 7.48-7.45 (m, 3.6H), 7.42-7.36 (m, 2.2H), 7.27-7.10 (m, 9.2H), 7.00-6.94 (m, 3.4H), 4.79-4.75 (m, 1H), 4.53-4.50 (m, 0.7H), 4.42-4.39 (m, 0.7H), 3.82 (s, 2.1H), 3.81 (s, 2.1H), 3.78 (s, 3H), 3.47-3.45 (m, 1H), 3.40-3.39 (m, 1H), 1.74 (d, 2.1H), 1.46 (d, 2.1H), 1.28 (d, 3H); MS (EI) for C25H22N4O4: 443 (MH$^+$).

methyl(5-{1-hydroxy-3-oxo-2-[(1S)-1-phenylethyl]-2,3-dihydro-1H-isoindol-1-yl}-1H-benzimidazol-2-yl)carbamate: $^1$H NMR (400 MHz, d$_6$-DMSO) reported are two closed diastereomers and the open isomer: 8.94 (d, 0.6H), 7.82-7.81 (m, 1H), 7.74-7.69 (m, 3.8H), 7.64-7.60 (m, 2.4H), 7.57-7.52 (m, 4.2H), 7.51 (s, 0.9H), 7.48-7.43 (m, 0.3H), 7.42-7.39 (m, 0.8H), 7.30-7.12 (m, 10.7H), 7.02-6.98 (m, 4.9H), 4.81-4.78 (m, 0.6H), 4.55-4.49 (m, 0.7H), 4.44-4.38 (m, 1H), 3.83 (s, 3H), 3.82 (s, 2.3H), 3.79 (s, 2.8H), 1.74 (d, 2.5H), 1.46 (d, 3H), 1.28 (s, 2.1H); MS (EI) for $C_{25}H_{22}N_4O_4$: 443 (MH$^+$).

methyl{5-[2-(5-ethynyl-2,4-difluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.86 (d, 1H), 7.71 (s, 1H), 7.62 (m, 3H), 7.41 (m, 2H), 7.33 (d, 1H), 7.23 (d, 1H), 6.89 (d, 1H), 3.72 (s, 3H); MS (EI) for $C_{25}H_{16}N_4O_4F_2$: 475 (MH$^+$).

methyl{5-[2-(3-ethynyl-2,4-difluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.87 (d, 1H), 7.72 (s, 1H), 7.64 (m, 2H), 7.42 (m, 2H), 7.31 (d, 1H), 7.25 (d, 1H), 7.19 (t, 1H), 6.91 (d, 1H), 3.73 (3H); MS (EI) for $C_{25}H_{16}N_4O_4F_2$: 475 (MH$^+$).

methyl{5-[2-(2-fluoro-3-prop-1-yn-1-ylphenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.86 (d, 1H), 7.66 (s, 1H), 7.62 (m, 2H), 7.45 (broad s, 1H), 7.33 (m, 1H), 7.30 (d, 1H), 7.24 (d, 1H), 7.09 (t, 1H), 6.94 (1H), 3.73 (s, 3H), 2.04 (s, 3H); MS (EI) for $C_{26}H_{19}N_4O_4F$: 471 (MH$^+$).

methyl(5-{1-hydroxy-2-[4-(methyloxy)phenyl]-3-oxo-2,3-dihydro-1H-isoindol-1-yl}-1H-benzimidazol-2-yl)carbamate: $^1$H NMR (400 MHz, d$_6$-DMSO): 7.82 (d, 1H), 7.57 (m, 4H), 7.27 (m, 4H), 7.00 (d, 1H), 6.81 (d, 2H), 3.75 (s, 3H), 3.67 (s, 3H); MS (EI) for $C_{24}H_{20}N_4O_5$: 445 (MH$^+$).

methyl{5-[2-(4-bromophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.86 (m, 2H), 7.58 (m 5H), 7.47 (m, 2H), 7.30 (m, 2H), 7.11 (s, 1H), 3.79 (s, 3H); MS (EI) for $C_{23}H_{17}N_4O_4Br$: 494 (MH$^+$).

methyl{5-[2-(4-chlorophenyl)-1-hydroxy-3-oxo-2,3-dihydro-1H-isoindol-1-yl]-1H-benzimidazol-2-yl}carbamate:

¹H NMR (400 MHz, d₆-DMSO): 7.86 (d, 2H), 7.61 (m, 5H), 7.32 (m, 4H), 7.11 (d, 1H), 3.79 (s, 3H); MS (EI) for $C_{23}H_{17}N_4O_4Cl$: 449 (MH⁺).

methyl{5-[2-(4-fluorophenyl)-1-hydroxy-3-oxo-2,3-dihydro-1H-isoindol-1-yl]-1H-benzimidazol-2-yl}carbamate: ¹H NMR (400 MHz, d₆-DMSO): 7.86 (d, 1H), 7.57 (m, 6H), 7.27 (d, 2H), 7.11 (m, 2H), 6.98 (m, 1H), 3.74 (s, 3H); MS (EI) for $C_{23}H_{17}N_4O_4F$: 434 (MH⁺).

methyl[5-(2-cyclohexyl-1-hydroxy-3-oxo-2,3-dihydro-1H-isoindol-1-yl)-1H-benzimidazol-2-yl]carbamate: ¹H NMR (400 MHz, d₆-DMSO): 7.69 (m, 2H), 7.48 (m, 3H), 7.15 (m, 2H), 3.83 (s, 3H), 3.05 (t, 1H), 2.20 (m, 2H), 1.76-1.49 (m, 2H), 1.27-0.85 (m, 6H); MS (EI) for $C_{23}H_{24}N_4O_4$: 421 (MH⁺).

methyl{5-[2(2,5-difluorophenyl)-1-hydroxy-3-oxo-2,3-dihydro-1H-isoindol-1-yl]-1H-benzimidazol-2-yl}carbamate: ¹H NMR (400 MHz, d₆-DMSO): 11.62 (broad s, 1H), 7.87 (d, 1H), 7.72 (s, 1H), 7.63 (m, 2H), 7.47 (s, 1H), 7.32 (d, 1H), 7.20 (m, 4H), 6.93 (d, 1H), 3.73 (s, 3H); MS (EI) for $C_{23}H_{16}N_4O_4F_2$: 451 (MH⁺).

methyl[5-(1-hydroxy-3-oxo-2-{2-[(trifluoromethyl)oxy]phenyl}-2,3-dihydro-1H-isoindol-1-yl)-1H-benzimidazol-2-yl]carbamate: ¹H NMR (400 MHz, d₆-DMSO): 8.02 (s, 1H), 7.89 (d, 1H), 7.71 (d, 2H), 7.62 (m, 4H), 7.42 (m, 2H), 7.29 (d, 1H), 7.23 (d, 1H), 7.10 (d, 1H), 3.83 (s, 3H); MS (EI) for $C_{24}H_{17}N_4O_5F_3$: 499 (MH⁺).

methyl{5-[2(2,3-difluorophenyl)-1-hydroxy-3-oxo-2,3-dihydro-1H-isoindol-1-yl]-1H-benzimidazol-2-yl}carbamate: ¹H NMR (400 MHz, d₆-DMSO): 7.87 (d, 1H), 7.74 (s, 1H), 7.63 (m, 2H), 7.45 (s, 1H), 7.38-7.14 (m, 5H), 6.93 (d, 1H), 3.72 (s, 3H); MS (EI) for $C_{23}H_{16}N_4O_4F_2$: 451 (MH⁺).

methyl{5-[2-(2,6-difluorophenyl)-1-hydroxy-3-oxo-2,3-dihydro-1H-isoindol-1-yl]-1H-benzimidazol-2-yl}carbamate: ¹H NMR (400 MHz, d₆-DMSO): 7.84 (d, 1H), 7.66 (m, 2H), 7.51 (s, 1H), 7.44-7.07 (m, 5H), 6.88-6.79 (m, 2H), 3.75 (s, 0.6H) open, 3.70 (s, 2.4H) closed; MS (EI) for $C_{23}H_{16}N_4O_4F_2$: 451 (MH⁺).

methyl{5-[2-(3-chloro-4-fluorophenyl)-1-hydroxy-3-oxo-2,3-dihydro-1H-isoindol-1-yl]-1H-benzimidazol-2-yl}carbamate: ¹H NMR (400 MHz, d₆-DMSO): 11.58 (broad s, 1H), 7.79 (d, 2H), 7.58 (m, 4H), 7.29 (m, 3H), 6.97 (s, 1H), 3.72 (s, 3H); MS (EI) for $C_{23}H_{16}N_4O_4FCl$: 466 (MH⁺).

methyl{5-[1-hydroxy-2-(3-iodophenyl)-3-oxo-2,3-dihydro-1H-isoindol-1-yl]-1H-benzimidazol-2-yl}carbamate: ¹H NMR (400 MHz, d₆-DMSO): 8.06 (s, 1H), 7.84 (d, 1H), 7.73 (s, 1H), 7.52-7.63 (m, 5H), 7.46 (d, 1H), 7.27 (d, 2H), 7.03 (m, 2H), 3.73 (s, 3H); MS (EI) for $C_{23}H_{17}N_4O_4I$: 541 (MH⁺).

methyl(5-{1-hydroxy-2-[3-(1-methylethyl)phenyl]-3-oxo-2,3-dihydro-1H-isoindol-1-yl}-1H-benzimidazol-2-yl)carbamate: ¹H NMR (400 MHz, d₆-DMSO): 7.81 (d, 1H), 7.67-7.56 (m, 4H), 7.35 (d, 2H), 7.27 (d, 2H), 7.17-7.10 (m, 2H), 6.99 (d, 1H), 3.79 (s, 3H), 2.74 (m, 1H), 1.10 (d, 0.72H) open, 1.05 (d, 5.28H) closed; MS (EI) for $C_{26}H_{24}N_4O_4$: 457 (MH⁺).

methyl{5-[2-(3-chloro-2-fluorophenyl)-1-hydroxy-3-oxo-2,3-dihydro-1H-isoindol-1-yl]-1H-benzimidazol-2-yl}carbamate: ¹H NMR (400 MHz, d₆-DMSO): 7.88 (t, 2H), 7.67-7.61 (m, 2H), 7.56 (s, 1H), 7.48 (m, 1H), 7.36 (m, 2H), 7.28 (d, 1H), 7.17 (t, 1H), 7.09 (d, 1H), 3.80 (s, 3H); MS (EI) for $C_{23}H_{16}N_4O_4ClF$: 467 (MH⁺).

methyl{5-[2-(2-fluoro-3-iodophenyl)-1-hydroxy-3-oxo-2,3-dihydro-1H-isoindol-1-yl]-1H-benzimidazol-2-yl}carbamate: ¹H NMR (400 MHz, d₆-DMSO): 7.87 (d, 1H), 7.60-7.75 (m, 4H), 7.47 (s, 1H), 7.28 (dd, 3H), 6.94 (t, 2H), 3.74 (s, 3H); MS (EI) for $C_{23}H_{16}N_4O_4FI$: 558 (MH⁺).

methyl{6-[2-(5-ethynyl-2-fluorophenyl)-1-hydroxy-3-oxo-2,3-dihydro-1H-isoindol-1-yl]-1H-benzimidazol-2-yl}carbamate: ¹H NMR (400 MHz, d₆-DMSO): 7.91 (d, 1H), 7.83 (m, 1H), 7.74 (m, 1H), 7.64 (m, 1H), 7.37 (d, 2H), 7.03 (dd, 3H), 6.69 (d, 2H), 4.21 (s, 1H), 3.73 (s, 3H); MS (EI) for $C_{25}H_{17}N_4O_4F$: 457 (MH⁺).

methyl{5-[2-(3-cyanophenyl)-1-hydroxy-3-oxo-2,3-dihydro-1H-isoindol-1-yl]-1H-benzimidazol-2-yl}carbamate: ¹H NMR (400 MHz, d₆-DMSO): 8.10 (s, 1H), 8.03 (s, 1H), 7.92 (dd, 2H), 7.61 (m, 4H), 7.50 (m, 1H), 7.37 (d, 1H), 7.30 (d, 1H), 7.17 (d, 1H), 3.79 (s, 3H); MS (EI) for $C_{24}H_{17}N_5O_4$: 440 (MH⁺).

methyl[5-(2-{3-[(dimethylamino)methyl]phenyl}-1-hydroxy-3-oxo-2,3-dihydro-1H-isoindol-1-yl)-1H-benzimidazol-2-yl]carbamate: ¹H NMR (400 MHz, d₆-DMSO): 7.86 (d, 1H), 7.79 (s, 1H), 7.68-7.54 (m, 5H), 7.38 (t, 1H), 7.31-7.21 (m, 3H), 6.97 (d, 1H), 4.18 (s, 2H), 3.74 (s, 3H), 2.50 (t, 6H); MS (EI) for $C_{26}H_{25}N_5O_4$: 472 (MH⁺).

methyl{5-[2-(3-ethynyl-5-methylphenyl)-1-hydroxy-3-oxo-2,3-dihydro-1H-isoindol-1-yl]-1H-benzimidazol-2-yl}carbamate: ¹H NMR (400 MHz, d₆-DMSO): 7.96 (s, 1H), 7.85 (d, 1H), 7.71 (s, 1H), 7.68 (s, 1H), 7.48-7.63 (m, 4H), 7.23-7.29 (m, 2H), 6.96 (dd, 1H), 3.77 (s, 0.6H) open, 3.72 (s, 2.4H) closed, 2.28 (s, 3H); MS (EI) for $C_{26}H_{20}N_4O_4$: 453 (MH⁺).

methyl{5-[2-(cyclopropylmethyl)-1-hydroxy-3-oxo-2,3-dihydro-1H-isoindol-1-yl]-1H-benzimidazol-2-yl}carbamate. ¹H NMR (400 MHz, CD₃OD): 7.86 (s, 1H); 7.82-7.80 (m, 1H), 7.56-7.52 (m, 2H), 7.28 (s, 1H), 7.27-7.25 (m, 1H), 3.93 (s, 1H), 3.13-2.98 (m, 2H), 0.96-0.91 (m, 1H), 0.35-0.21 (m, 3H), 0.034-0.01 (m, 1H); MS (EI) for $C_{21}H_{20}N_4O_4$: 393 (MH⁺).

methyl{5-[2-(2,2-dimethylpropyl)-1-hydroxy-3-oxo-2,3-dihydro-1H-isoindol-1-yl]-1H-benzimidazol-2-yl}carbamate. ¹H NMR (400 MHz, CD₃OD): 7.82-7.80 (m, 2H), 7.57-7.50 (m, 3H), 7.27-7.25 (m, 1H), 7.1 (br. s, 1H), 3.93 (s, 3H), 3.46 (d, J=14 Hz, 1H), 2.54 (d, J=14.4, 1H), 0.92 (s, 7H), 0.78 (s, 2H); MS (EI) for $C_{22}H_{24}N_4O_4$: 409 (MH⁺).

methyl{5-[2-(cyclohexylmethyl)-1-hydroxy-3-oxo-2,3-dihydro-1H-isoindol-1-yl]-1H-benzimidazol-2-yl}carbamate. ¹H NMR (400 MHz, CD₃OD): 7.85 (t, J=6 Hz, 2H), 7.59-7.55 (m, 3H), 7.27 (dd, $J_1$=17.6 Hz, $J_2$=6 Hz, 2H), 3.99 (s, 3H), 2.87 (q, J=7.2 Hz, 5H), 1.71-1.57 (m, 6H), 1.17-1.07 (m, 3H), 0.96-0.91 (m, 2H); MS (EI) for $C_{24}H_{26}N_4O_4$: 435 (MH⁺).

methyl{5-[1-hydroxy-2-(2-methylpropyl)-3-oxo-2,3-dihydro-1H-isoindol-1-yl]-1H-benzimidazol-2-yl}carbamate. ¹H NMR (400 MHz, CD₃OD): 7.86-7.83 (m, 2H), 7.59-7.54 (m, 3H), 7.25 (dd, $J_1$=18.8 Hz, $J_2$=6.8 Hz, 2H), 3.99 (s, 3H), 2.84 (q, J=7.2 Hz, 5H), 1.90 (t, J=7.2 Hz, 1H), 0.88-0.82 (m, 6H); MS (EI) for $C_{21}H_{22}N_4O_4$: 395 (MH⁺).

methyl{5-[2-(cyclopentylmethyl)-1-hydroxy-3-oxo-2,3-dihydro-1H-isoindol-1-yl]-1H-benzimidazol-2-yl}carbamate. ¹H NMR (400 MHz, CD₃OD): 7.82-7.79 (m, 2H), 7.55-7.49 (m, 3H), 7.26-7.24 (m, 1H), 7.20 (d, J=7.6 Hz, 1H), 3.94 (s, 3H), 3.46 (q, J=7.2 Hz, 1H), 2.96 (q, J=7.6 Hz, 1H), 2.14 (t, J=7.2 Hz, 1H), 1.61 (br. s, 4H), 1.45 (br. s, 2H), 1.26-1.19 (m, 2H); MS (EI) for $C_{23}H_{24}N_4O_4$: 421 (MH⁺).

methyl(2S)-cyclohexyl[1-hydroxy-1-(2-{[(methyloxy)carbonyl]amino}-1H-benzimidazol-5-yl)-3-oxo-1,3-dihydro-2H-isoindol-2-yl]ethanoate. ¹H NMR (400 MHz, CD₃OD): 7.85 (s, 1H), 7.78-7.76 (m, 1H), 7.69-7.65 (m, 3H), 7.54-7.50 (m, 2H), 4.17 (d, J=6.8 Hz, 1H), 3.90 (s, 3H), 3.65 (s, 3H), 1.69-1.45 (m, 6H), 1.23-0.94 (m, 3H), 0.81-0.76 (m, 2H); MS (EI) for $C_{26}H_{28}N_4O_6$: 493 (MH$^+$).

methyl(5-{1-hydroxy-2-[3-(1-methylethyl)phenyl]-3-oxo-2,3-dihydro-1H-isoindol-1-yl}-1H-benzimidazol-2-yl)carbamate. $^1$H NMR (400 MHz, CD$_3$OD): 7.91 (d, J=8 Hz, 1H), 7.76 (s, 1H), 7.65-7.61 (m, 2H), 7.45 (d, J=8.8 Hz, 1H), 7.33 (d, J=6.8 Hz, 1H), 7.34-7.26 (m, 1H), 7.22 (s, 1H), 7.19-7.14 (m, 2H), 7.03 (d, J=7.2 Hz, 1H), 3.92 (s, 3H), 2.77 (sep. J=6.8 Hz, 1H), 1.1 (t, J=6.4 Hz, 6H); MS (EI) for $C_{26}H_{24}N_4O_4$: 457 (MH$^+$).

methyl{5-[2-(cyclobutylmethyl)-1-hydroxy-3-oxo-2,3-dihydro-1H-isoindol-1-yl]-1H-benzimidazol-2-yl}carbamate. $^1$H NMR (400 MHz, CD$_3$OD): 7.79-7.77 (m, 2H), 7.53-7.48 (m, 3H), 7.22-7.20 (m, 2H), 3.90 (s, 3H), 3.55-3.50 (m, 1H), 3.12-3.05 (m, 1H), 2.53-2.44 (m, 1H), 1.93-1.79 (m, 2H), 1.73 (s, 2H), 1.56 (s, 2H); MS (EI) for $C_{22}H_{22}N_4O_4$: 407 (MH$^+$).

methyl{5-[1-hydroxy-3-oxo-2-(tetrahydrofuran-2-ylmethyl)-2,3-dihydro-1H-isoindol-1-yl]-1H-benzimidazol-2-yl}carbamate. $^1$HNMR (400 MHz, CD$_3$OD): 7.84-7.81 (m, 2H), 7.57-7.52 (M, 3H), 7.26 (d, J=6.8 Hz, 2H), 4.08 (t, J=6.8 Hz, 1H), 3.95 (s, 3H), 3.92-3.61 (m, 3H), 3.05-2.99 (m, 1H), 1.92-1.83 (m, 3H), 1.63 (s, 1H); MS (EI) for $C_{22}H_{22}N_4O_5$: 405 (MH$^+$).

methyl{5-[2-(5-bromo-2-methylphenyl)-1-hydroxy-3-oxo-2,3-dihydro-1H-isoindol-1-yl]-1H-benzimidazol-2-yl}carbamate. $^1$H NMR (400 MHz, DMSO-d$_6$): 7.89 (d, J=7.2 Hz, 1H), 7.79-7.69 (m, 4H), 7.40 (d, J=8.8 Hz, 3H), 7.05 (s, 1H), 6.98 (d, J=6.4 Hz, 1H), 3.83 (s, 3H), 1.49 (s, 3H); MS (EI) for $C_{24}H_{19}BrN_4O_4$: 509 (MH$^+$).

methyl(5-{2-[5-chloro-2-(methyloxy)phenyl]-1-hydroxy-3-oxo-2,3-dihydro-1H-isoindol-1-yl}-1H-benzimidazol-2-yl)carbamate. $^1$H NMR (400 MHz, DMSO-d$_6$): 7.84 (d, J=7.2 Hz, 1H), 7.66-7.60 (m, 3H), 7.41-7.39 (m, 2H), 7.16 (d, J=8 Hz, 1H), 6.93 (d, J=8.0 Hz, 1H), 3.84 (s, 3H), 3.40 (s, 3H); MS (EI) for $C_{24}H_{19}ClN_4O_5$: 479 (MH$^+$).

methyl(5-{2-[3-(1,1-dimethylethyl)phenyl]-1-hydroxy-3-oxo-2,3-dihydro-1H-isoindol-1-yl}-1H-benzimidazol-2-yl)carbamate. $^1$H NMR (400 MHz, CD$_3$OD): 7.91 (dd, $J_1$=7.6 Hz, $J_2$=2.0 Hz, 1H), 7.77 (s, 1H), 7.46 (d, J=8.4 Hz, 1H), 7.34-7.33 (m, 2H), 7.29 (dd, $J_1$=8.4 Hz, $J_2$=1.6 Hz, 1H), 7.20-7.16 (m, 3H), 3.92 (s, 3H); MS (EI) for $C_{27}H_{26}N_4O_4$: 471 (MH$^+$).

methyl(5-{1-hydroxy-2-[5-methyl-2-(methyloxy)phenyl]-3-oxo-2,3-dihydro-1H-isoindol-1-yl}-1H-benzimidazol-2-yl)carbamate. $^1$H NMR (400 MHz, DMSO-d$_6$): 11.59 (s, 1H), 7.88 (m, 1H) open, 7.74 (d, 1H) closed, 7.66 (m, 1H), 7.57 (m, 2H), 7.48 (m, 1H), 7.43 (s, 1H) closed, 7.42 (s, 1H) open, 7.26 (s, 1H) closed, 7.24 (s, 1H) open, 7.16 (m, 1H), 6.99 (m, 1H), 6.88 (s, 1H), 6.77 (d, 1H), 3.76 (s, 3H) open, 3.71 (s, 3H) closed, 3.40 (s, 3H) open, 3.35 (s, 3H) closed, 2.16 (s, 3H) closed, 2.09 (s, 3H) open; MS (EI) for $C_{25}H_{22}N_4O_5$: 459 (MH$^+$).

methyl{5-[1-hydroxy-2-(3-methylphenyl)-3-oxo-2,3-dihydro-1H-isoindol-1-yl]-1H-benzimidazol-2-yl}carbamate hydrochloride. $^1$H NMR (400 MHz, d$_6$-DMSO): 7.85 (d, 1H), 7.79 (br s, 1H), 7.68 (s, 1H), 7.64-7.56 (m, 2H), 7.44 (d, 1H), 7.38 (s, 1H), 7.26-7.21 (m,3H), 7.15-7.11 (m, 1H), 6.95 (d, 2H), 3.83 (s, 3H), 2.21 (s, 3H); MS (EI) for $C_{24}H_{20}N_4O_4$: 429 (MH$^+$).

methyl[5-(1-hydroxy-2-{[2-(methyloxy)phenyl]methyl}-3-oxo-2,3-dihydro-1H-isoindol-1-yl)-1H-benzimidazol-2-yl]carbamate trifluoroacetate: $^1$H NMR (400 MHz, CDCl$_3$): 7.76 (1H), 7.68 (br s, 1H), 7.49-7.40 (m, 3H), 7.35-7.28 (m, 2H), 7.23 (d, 1H), 7.08-7.05 (m, 1H), 6.76-6.72 (m, 1H), 6.61 (d, 1H), 4.64 (d, 1H), 4.29 (d, 1H), 3.90 (s, 3H), 3.66 (s, 3H); MS (EI) for $C_{25}H_{22}N_4O_5$: 459 (MH$^+$).

methyl[5-(1-hydroxy-2-{[3-(methyloxy)phenyl]methyl}-3-oxo-2,3-dihydro-1H-isoindol-1-yl)-1H-benzimidazol-2-yl]carbamate trifluoroacetate: $^1$H NMR (400 MHz, CDCl$_3$): 7.74 (1H), 7.67 (br s, 1H), 7.50-7.43 (m, 2H), 7.43 (d, 1H), 7.24-7.20 (m, 2H), 6.93-6.90 (m, 1H), 6.65-6.60 (m, 2H), 6.53 (d, 1H), 4.47 (d, 1H), 4.17 (d, 1H), 3.93 (s, 3H), 3.61 (s, 3H); MS (EI) for $C_{25}H_{22}N_4O_5$: 459 (MH$^+$).

methyl[5-(1-hydroxy-2-{[4-(methyloxy)phenyl]methyl}-3-oxo-2,3-dihydro-1H-isoindol-1-yl)-1H-benzimidazol-2-yl]carbamate trifluoroacetate: $^1$H NMR (400 MHz, CDCl$_3$): 7.75-7.70 (m, 2H), 7.51-7.44 (m, 2H), 7.39 (d, 1H), 7.24-7.20 (m, 2H), 7.00 (d, 2H), 6.51 (d, 2H), 4.47 (d, 1H), 4.17 (d, 1H), 3.92 (s, 3H), 3.62 (s, 3H); MS (EI) for $C_{25}H_{22}N_4O_5$: 459 (MH$^+$).

methyl{5-[2-(3-bromophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.91 (s, 1H), 7.85 (d, 1H), 7.75 (s, 1H), 7.63-7.52 (m, 4H), 7.63-7.52 (m, 4H), 6.99 (s, 1H), 3.72 (s, 3H); MS (EI) for $C_{23}H_{17}N_4O_4$: 494 (MH$^+$).

methyl{5-[2-(3-chlorophenyl)-1-hydroxy-3-oxo-2,3-dihydro-1H-isoindol-1-yl]-1H-benzimidazol-2-yl}carbamate trifluoroacetate: $^1$H NMR (400 MHz, d$_6$-DMSO): 7.92 (br s, 1H), 7.87 (d, 1H), 7.77 (s, 1H), 7.64-7.55 (m, 4H), 7.38 (d, 1H), 7.31-7.27 (m, 2H), 7.18 (d, 1H), 3.80 (s, 3H); MS (EI) for $C_{23}H_{17}ClN_4O_4$: 449 (MH$^+$).

methyl{5-[2-(3-fluorophenyl)-1-hydroxy-3-oxo-2,3-dihydro-1H-isoindol-1-yl]-1H-benzimidazol-2-yl}carbamate trifluoroacetate: $^1$H NMR (400 MHz, d$_6$-DMSO): 7.92 (br s, 1H), 7.87 (d, 1H), 7.65-7.57 (m, 3H), 7.53-7.47 (m, 2H), 7.38 (d, 1H), 7.33-7.27 (m, 2H), 7.18 (d, 1H), 6.98 (t, 1H), 3.80 (s, 3H); MS (EI) for $C_{23}H_{17}FN_4O_4$: 433 (MH$^+$).

methyl(5-{1-hydroxy-2-[3-(methyloxy)phenyl]-3-oxo-2,3-dihydro-1H-isoindol-1-yl}-1H-benzimidazol-2-yl)carbamate trifluoroacetate: $^1$H NMR (400 MHz, d$_6$-DMSO): 7.82 (d, 1H), 7.73 (br s, 1H), 7.60-7.53 (m, 2H), 7.34 (d, 1H), 7.23 (d, 1H), 7.16-7.11 (m, 4H), 6.70-6.66 (m, 1H), 3.78 (s, 3H), 3.62 (s, 3H); MS (EI) for $C_{24}H_{20}N_4O_5$: 445 (MH$^+$).

methyl{5-[2-(2-fluorophenyl)-1-hydroxy-3-oxo-2,3-dihydro-1H-isoindol-1-yl]-1H-benzimidazol-2-yl}carbamate trifluoroacetate: $^1$H NMR (400 MHz, d$_6$-DMSO): 7.84 (d, 1H), 7.72 (br s, 1H), 7.63-7.58 (m, 2H), 7.51 (s, 1H), 7.15-7.10 (m, 2H), 7.15-7.10 (m, 2H), 7.03 (d, 1H), 3.77 (s, 3H); MS (EI) for $C_{23}H_{17}FN_4O_4$: 433 (MH$^+$).

methyl{5-[2-(2-chlorophenyl)-1-hydroxy-3-oxo-2,3-dihydro-1H-isoindol-1-yl]-1H-benzimidazol-2-yl}carbamate trifluoroacetate: $^1$H NMR (400 MHz, d$_6$-DMSO): 7.85 (d, 1H), 7.75-7.62 (m, 3H), 7.56-7.51 (m, 1H), 7.43-7.20 (m, 5H), 6.99 (d, 1H), 3.77 (s, 3H); MS (EI) for $C_{23}H_{17}ClN_4O_4$: 449 (MH$^+$).

methyl{5-[1-hydroxy-2-(2-methylphenyl)-3-oxo-2,3-dihydro-1H-isoindol-1-yl]-1H-benzimidazol-2-yl}carbamate trifluoroacetate: $^1$H NMR (400 MHz, d$_6$-DMSO): 7.85 (d, 1H), 7.75-7.62 (m, 3H), 7.56-7.51 (m, 1H), 7.43-7.20 (m, 5H), 6.99 (d, 1H), 3.77 (s, 3H), 1.49 (s, 3H); MS (EI) for $C_{23}H_{17}ClN_4O_4$: 449 (MH$^+$).

methyl(5-{1-hydroxy-2-[2-(methyloxy)phenyl]-3-oxo-2,3-dihydro-1H-isoindol-1-yl}-1H-benzimidazol-2-yl)carbamate trifluoroacetate: $^1$H NMR (400 MHz, d$_6$-DMSO): 7.80 (d, 1H), 7.63-7.55 (m, 2H), 7.51 (s, 1H), 7.46-7.42 (m, 1H), 7.31-7.17 (m, 4H), 7.10 (d, 2H), 6.88-6.83 (m, 2H), 3.79 (s, 3H), 3.40 (s, 3H); MS (EI) for $C_{24}H_{20}N_4O_5$: 445 (MH$^+$).

methyl{5-[1-hydroxy-2-(4-methylphenyl)-3-oxo-2,3-dihydro-1H-isoindol-1-yl]-1H-benzimidazol-2-yl}carbamate trifluoroacetate: $^1$H NMR (400 MHz, d$_6$-DMSO): 7.80 (d, 1H), 7.61 (br s, 1H), 7.58-7.53 (m, 3H), 7.33-7.22 (m, 3H), 7.05-7.00 (m, 3H), 3.76 (s, 3H), 1.23 (s, 3H); MS (EI) for $C_{24}H_{20}N_4O_4$: 449 (MH$^+$).

methyl(5-{1-hydroxy-3-oxo-2-[3-(trifluoromethyl)phenyl]-2,3-dihydro-1H-isoindol-1-yl}-1H-benzimidazol-2-yl) carbamate trifluoroacetate: $^1$H NMR (400 MHz, d$_6$-DMSO): 8.08 (s, 1H), 7.94 (s, 1H), 7.87-7.82 (m, 2H), 7.64-7.55 (m, 3H), 7.50-7.42 (m, 2H), 7.34 (d, 1H), 7.27 (d, 1H), 7.14 (d, 1H), 3.78 (s, 3H); MS (EI) for $C_{24}H_{17}F_3N_4O_4$: 483 (MH$^+$).

methyl{5-[2-(3,5-difluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.93 (s, 1H), 7.86 (s, 1H), 7.70-7.43 (m, 7H), 7.31-7.26 (m, 2H), 7.04-6.89 (m, 2H), 3.73 (s, 3H); MS (EI) for $C_{23}H_{16}F_2N_4O_4$: 451 (MH$^+$).

methyl{5-[2-(3-{[2-(dimethylamino)ethyl]oxy}phenyl)-1-hydroxy-3-oxo-2,3-dihydro-1H-isoindol-1-yl]-1H-benzimidazol-2-yl}carbamate trifluoroacetate: $^1$H NMR (400 MHz, d$_6$-DMSO): 7.81 (d, 1H), 7.72 (s, 1H), 7.61-7.53 (m, 3H), 7.30-7.28 (m, 2H), 7.25 (d, 1H), 7.18-7.14 (m, 2H), 7.05 (d, 1H), 6.77-6.74 (m, 1H), 4.18 (t, 2H), 3.76 (s, 3H), 3.45 (t, 2H), 2.81 (s, 6H); MS (EI) for $C_{27}H_{27}N_5O_5$: 502 (MH$^+$).

methyl{5-[1-hydroxy-3-oxo-2-(1,3-thiazol-2-ylmethyl)-2,3-dihydro-1H-isoindol-1-yl]-1H-benzimidazol-2-yl}carbamate trifluoroacetate: $^1$H NMR (400 MHz, d$_6$-DMSO): 7.79 (d, 1H), 7.60-7.53 (m, 4H), 7.49 (s, 1H), 7.32 (d, 1H), 7.25 (d, 1H), 6.97 (d, 1H), 4.78 (d, 1H), 4.50 (d, 1H), 3.80 (s, 3H); MS (EI) for $C_{21}H_{17}N_5O_4S$: 418 (MH$^+$).

methyl{5-[2-(3,4-difluorophenyl)-1-hydroxy-3-oxo-2,3-dihydro-1H-isoindol-1-yl]-1H-benzimidazol-2-yl}carbamate trifluoroacetate: $^1$H NMR (400 MHz, CDCl$_3$): 7.79 (br s, 1H), 7.58 (d, 1H), 7.54-7.49 (m, 1H), 7.42-7.36 (m, 3H), 7.24-7.18 (m, 3H), 6.88-6.81 (m, 1H), 3.88 (s, 3H); MS (EI) for $C_{23}H_{16}F_2N_4O_4$: 451 (MH$^+$).

methyl(5-{2-[1-(3,5-difluorophenyl)ethyl]-1-hydroxy-3-oxo-2,3-dihydro-1H-isoindol-1-yl}-1H-benzimidazol-2-yl)carbamate: $^1$H NMR (400 MHz, d$_6$-DMSO): 8.92 (d, 0.33H), 7.81-7.79 (m, 0.33H), 7.70-7.49 (m, 4H), 7.41-7.13 (m, 4H), 7.05-6.80 (m, 3H), 6.61-6.55 (1H), 4.82 (q, 0.33H), 4.56 (q, 0.33H), 4.40 (q, 0.33H), 3.77-3.69 (m, 3H), 1.73 (d, 1H), 1.43 (d, 1H), 1.30 (d, 1H); MS (EI) for $C_{25}H_{20}F_2N_4O_4$: 479 (MH$^+$).

methyl(5-{2-[1-(3-fluorophenyl)ethyl]-1-hydroxy-3-oxo-2,3-dihydro-1H-isoindol-1-yl}-1H-benzimidazol-2-yl)carbamate: $^1$H NMR (400 MHz, d$_6$-DMSO): 8.89 (d, 0.33H), 7.79-7.77 (m, 0.33H), 7.68-7.57 (m, 3H), 7.54-7.48 (m, 1H), 7.32-7.18 (m, 3H), 7.14-6.92 (m, 3H), 6.85-6.71 (m, 1H), 4.82 (q, 0.33H), 4.55 (q, 0.33H), 4.41 (q, 0.33H), 3.75-3.71 (m, 3H), 1.74 (d, 1H), 1.44 (d, 1H), 1.29 (d, 1H); MS (EI) for $C_{25}H_{21}FN_4O_4$: 461 (MH$^+$).

methyl(5-{2-[1-(5-chloro-2-methylphenyl)ethyl]-1-hydroxy-3-oxo-2,3-dihydro-1H-isoindol-1-yl}-1H-benzimidazol-2-yl)carbamate: $^1$H NMR (400 MHz, d$_6$-DMSO): 8.92 (d, 0.5H), 8.01-7.97 (m, 0.5H), 7.78-7.75 (m, 1H), 7.64-7.50 (m, 2H), 7.43-7.27 (m, 4H), 7.15-7.06 (m, 2H), 6.98-6.91 (m, 1H), 4.98 (q, 0.5H), 4.82 (q, 0.25H), 4.51 (q, 0.25H), 3.76-3.72 (m, 3H), 2.19 (s, 1H), 2.14 (s, 2H), 1.66 (d, 0.5H), 1.55 (d, 0.5H), 1.24 (d, 2H); MS (EI) for $C_{26}H_{23}ClN_4O_4$: 461 (MH$^+$).

methyl{5-[1-hydroxy-2-(3-{[2-(methyloxy)ethyl]oxy}phenyl)-3-oxo-2,3-dihydro-1H-isoindol-1-yl]-1H-benzimidazol-2-yl}carbamate: $^1$H NMR (400 MHz, d$_6$-DMSO): 7.82 (d, 1H), 7.62-7.49 (m, 4H), 7.27-7.23 (m, 2H), 7.18-7.11 (m, 3H), 6.99 (d, 1H), 6.69-6.67 (m, 1H), 3.93 (t, 2H), 3.73 (s, 3H), 3.56 (t, 2H), 3.25 (s, 3H); MS (EI) for $C_{26}H_{24}N_4O_6$: 489 (MH$^+$).

methyl{5-[2-(3-bromo-4-fluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.94 (d, 1H), 7.85 (d, 1H), 7.75 (s, 1H), 7.64-7.51 (m, 4H), 7.32-7.25 (m, 3H), 6.98 (d, 1H), 3.73 (s, 3H); MS (EI) for $C_{23}H_{16}BrFN_4O_4$: 512 (MH$^+$).

methyl(5-{2-[3-(aminocarbonyl)phenyl]-1-hydroxy-3-oxo-2,3-dihydro-1H-isoindol-1-yl}-1H-benzimidazol-2-yl) carbamate: $^1$H NMR (400 MHz, d$_6$-DMSO): 8.17 (s, 1H), 7.88 (s, 1H), 7.84 (d, 1H), 7.67 (s, 1H), 7.62-7.50 (m, 5H), 7.33-7.21 (m, 4H), 6.96 (d, 1H), 3.72 (s, 3H), 2.54 (s, 2H); MS (EI) for $C_{24}H_{19}N_5O_5$: 458 (MH$^+$).

methyl(5-{1-hydroxy-2-[3-(methylsulfonyl)phenyl]-3-oxo-2,3-dihydro-1H-isoindol-1-yl}-1H-benzimidazol-2-yl) carbamate: $^1$H NMR (400 MHz, d$_6$-DMSO): 8.37 (s, 1H), 7.90-7.85 (m, 3H), 7.69-7.50 (m, 5H), 7.30 (d, 1H), 7.25 (d, 1H), 7.00 (d, 1H), 3.72 (s, 3H), 3.08 (s, 3H); MS (EI) for $C_{24}H_{20}N_4O_6S$: 493 (MH$^+$).

methyl(5-{1-hydroxy-3-oxo-2-[3-(phenyloxy)phenyl]-2,3-dihydro-1H-isoindol-1-yl}-1H-benzimidazol-2-yl)carbamate: $^1$H NMR (400 MHz, d$_6$-DMSO): 7.79 (d, 1H), 7.61-7.50 (m, 3H), 7.45 (br s, 1H), 7.39 (d, 1H), 7.28-7.20 (m, 6H), 7.08-7.03 (m, 1H), 6.90 (d, 1H), 6.77 (d, 1H), 6.71 (d, 1H), 3.72 (s, 3H); MS (EI) for $C_{29}H_{22}N_4O_5$: 507 (MH$^+$).

methyl[5-(1-hydroxy-3-oxo-2-{3-[(phenylmethyl)oxy]phenyl}-2,3-dihydro-1H-isoindol-1-yl)-1H-benzimidazol-2-yl]carbamate trifluoroacetate: $^1$H NMR (400 MHz, d$_6$-DMSO): 7.84 (d, 1H), 7.75 (s, 1H), 7.63-7.55 (m, 3H), 7.38-7.35 (m, 6H), 7.27-7.25 (m, 2H), 7.16-7.12 (m, 3H), 6.79-6.76 (m, 1H), 4.95 (s, 2H), 3.79 (s, 3H); MS (EI) for $C_{30}H_{24}N_4O_5$: 521 (MH$^+$).

methyl[5-(2-biphenyl-3-yl-1-hydroxy-3-oxo-2,3-dihydro-1H-isoindol-1-yl)-1H-benzimidazol-2-yl]carbamate: $^1$H NMR (400 MHz, d$_6$-DMSO): 7.83 (d, 1H), 7.78 (s, 1H), 7.66-7.47 (m, 5H), 7.44-7.24 (m, 8H), 7.01 (d, 1H), 6.54 (s, 1H), 3.71 (s, 3H); MS (EI) for $C_{29}H_{22}N_4O_4$: 491 (MH$^+$).

methyl{5-[2-(4-fluoro-3-methylphenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.80 (d, 1H), 7.60-7.52 (m, 3H), 7.46 (br s, 1H), 7.39 (d, 1H), 7.02-6.99 (m, 6H), 6.92 (d, 1H), 3.71 (s, 3H), 2.11 (s, 3H); MS (EI) for $C_{24}H_{19}FN_4O_4$: 447 (MH$^+$).

methyl{5-[2-(5-bromo-2-fluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.92-7.87 (m, 2H), 7.72-7.58 (m, 4H), 7.55-7.50 (m, 1H), 7.41 (d, 1H), 7.32 (d, 1H), 7.22-7.18 (m, 1H), 7.12 (d, 1H), 3.82 (s, 3H); MS (EI) for $C_{23}H_{16}BrFN_4O_4$: 512 (MH$^+$).

methyl{5-[2-[3-(acetylamino)phenyl]-1-hydroxy-3-oxo-2,3-dihydro-1H-isoindol-1-yl}-1H-benzimidazol-2-yl)carbamate: $^1$H NMR (400 MHz, d$_6$-DMSO): 9.88 (s, 1H), 7.88-7.78 (m, 2H), 7.63-7.40 (m, 5H), 7.25-7.05 (m, 4H), 6.92 (d, 1H), 3.73 (s, 3H), 1.98 (s, 3H); MS (EI) for $C_{25}H_{21}N_5O_5$: 472 (MH$^+$).

methyl(5-{1-hydroxy-3-oxo-2-[3-(phenylmethyl)phenyl]-2,3-dihydro-1H-isoindol-1-yl}-1H-benzimidazol-2-yl)carbamate hydrochloride: $^1$H NMR (400 MHz, d$_6$-DMSO): 7.81 (d, 1H), 7.68 (br s, 1H), 7.60-7.53 (m, 3H), 7.33-7.29 (m, 3H), 7.23 (d, 1H), 7.17-7.06 (m, 5H), 6.97-6.94 (m, 2H), 3.79 (s, 3H), 3.77 (s, 2H); MS (EI) for $C_{30}H_{24}N_4O_4$: 505 (MH$^+$).

methyl(5-{2-[3-(aminosulfonyl)phenyl]-1-hydroxy-3-oxo-2,3-dihydro-1H-isoindol-1-yl}-1H-benzimidazol-2-yl)

carbamate: $^1$H NMR (400 MHz, d$_6$-DMSO): 8.34 (s, 1H), 7.86 (d, 1H), 7.79 (s, 1H), 7.70-7.39 (m, 9H), 7.29-7.23 (m, 2H), 6.99 (d, 1H), 3.72 (s, 3H); MS (EI) for C$_{23}$H$_{19}$N$_5$O$_6$S: 494 (MH$^+$).

methyl{5-[2-(3-acetylphenyl)-1-hydroxy-3-oxo-2,3-dihydro-1H-isoindol-1-yl]-1H-benzimidazol-2-yl}carbamate: $^1$H NMR (400 MHz, d$_6$-DMSO): 8.22 (s, 1H), 7.86 (d, 1H), 7.79 (d, 1H), 7.73-7.69 (m, 2H), 7.64-7.48 (m, 3H), 7.42-7.38 (m, 1H), 7.29 (d, 1H), 7.26 (d, 1H), 6.99 (d, 1H), 3.73 (s, 3H), 2.46 (s, 3H); MS (EI) for C$_{25}$H$_{20}$N$_4$O$_5$: 457 (MH$^+$).

methyl(5-{1-hydroxy-3-oxo-2-[3-(phenylamino)phenyl]-2,3-dihydro-1H-isoindol-1-yl}-1H-benzimidazol-2-yl)carbamate: $^1$H NMR (400 MHz, d$_6$-DMSO): 8.14 (s, 1H), 7.81 (d, 1H), 7.62-7.52 (m, 4H), 7.30-7.22 (m, 3H), 7.15-6.95 (m, 5H), 6.80-6.72 (m, 4H), 3.73 (s, 3H); MS (EI) for C$_{29}$H$_{23}$N$_5$O$_4$: 506 (MH$^+$).

methyl(5-{2-[3-(dimethylamino)phenyl]-1-hydroxy-3-oxo-2,3-dihydro-1H-isoindol-1-yl}-1H-benzimidazol-2-yl)carbamate trifluoroacetate: $^1$H NMR (400 MHz, d$_6$-DMSO): 7.89 (d, 1H), 7.72 (s, 1H), 7.68-7.59 (m, 2H), 7.48 (d, 1H), 7.28-7.25 (m, 2H), 7.18-7.14 (m, 1H), 7.08 (s, 1H), 6.92 (d, 1H), 6.74 (d, 1H), 3.84 (s, 3H), 2.84 (s, 6H); MS (EI) for C$_{25}$H$_{23}$N$_5$O$_4$: 458 (MH$^+$).

methyl[5-({2-[(2-phenylhydrazino)carbonyl]phenyl}carbonyl)-1H-benzimidazol-2-yl]carbamate trifluoroacetate: $^1$H NMR (400 MHz, d$_6$-DMSO): 8.56 (d, 1H), 8.35-8.31 (m, 1H), 8.15-8.11 (m, 1H), 7.75 (d, 1H), 7.65-7.60 (m, 3H), 7.46 (d, 1H), 7.41-7.35 (m, 3H), 7.26 (d, 1H), 3.78 (s, 3H); MS (EI) for C$_{23}$H$_{19}$N$_5$O$_4$: 430 (MH$^+$).

methyl{5-[(2-{[(phenyloxy)amino]carbonyl}phenyl)carbonyl]-1H-benzimidazol-2-yl}carbamate trifluoroacetate: $^1$H NMR (400 MHz, d$_6$-DMSO): 7.87 (d, 1H), 7.83 (br s, 1H), 7.74-7.70 (m, 1H), 7.66-7.62 (m, 1H), 7.57 (s, 1H), 7.45-7.40 (m, 2H), 7.30-7.25 (m, 2H), 7.14-7.10 (m, 3H), 7.04-7.00 (m, 1H), 3.80 (s, 3H); MS (EI) for C$_{23}$H$_{18}$N$_4$O$_5$: 431 (MH$^+$).

methyl{5-[1-hydroxy-3-oxo-2-(pyrrolidin-2-ylmethyl)-2,3-dihydro-1H-isoindol-1-yl]-1H-benzimidazol-2-yl}carbamate trifluoroacetate: $^1$H NMR (400 MHz, d$_6$-DMSO): 8.88 (br s, 1H), 8.34 (br s, 1H), 7.78 (d, 1H), 7.62-7.53 (m, 3H), 7.44-7.36 (m, 2H), 7.28 (d, 1H), 7.12-6.99 (m, 1H), 3.79 (s, 3H), 3.73-3.70 (m, 1H), 3.62-3.50 (m, 1H), 3.24-3.11 (m, 2H), 1.99-1.85 (m, 2H), 1.80-1.75 (m, 1H), 1.70-1.60 (m, 1H); MS (EI) for C$_{22}$H$_{23}$N$_5$O$_4$: 422 (MH$^+$).

methyl{5-[1-hydroxy-3-oxo-2-(pyrrolidin-3-ylmethyl)-2,3-dihydro-1H-isoindol-1-yl]-1H-benzimidazol-2-yl}carbamate trifluoroacetate: $^1$H NMR (400 MHz, d$_6$-DMSO): 8.68 (br s, 2H), 7.76 (d, 1H), 7.59-7.51 (m, 3H), 7.41 (d, 1H), 7.27-7.23 (m, 2H), 6.99 (d, 1H), 3.79 (s, 3H), 3.58-3.48 (m, 1H), 3.22-3.17 (m, 1H), 3.08-3.00 (m, 1H), 2.96-2.82 (m, 2H), 1.97-1.85 (m, 1H), 1.68-1.51 (m, 1H); MS (EI) for C$_{22}$H$_{23}$N$_5$O$_4$: 422 (MH$^+$).

methyl{5-[2-(5-chloro-3-ethynyl-2-methylphenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.91 (d, 1H), 7.85-7.65 (m, 4H), 7.52-7.48 (m, 1H), 7.45-7.34 (m, 3H), 6.97 (d, 1H), 4.50 (s, 1H), 3.82 (s, 3H), 1.57 (s, 3H); MS (EI) for C$_{26}$H$_{19}$ClN$_4$O$_4$: 486 (MH$^+$).

methyl{5-[2-(5-chloro-3-iodo-2-methylphenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.91-7.87 (m, 2H), 7.80-7.63 (m, 4H), 7.46-7.41 (m, 1H), 7.34-7.28 (m, 1H), 6.87 (d, 1H), 3.78 (s, 3H), 1.55 (s, 3H); MS (EI) for C$_{24}$H$_{18}$ClIN$_4$O$_4$: 589 (MH$^+$).

methyl{5-[2-(3-ethyl-2-fluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.87 (d, 1H), 7.78 (br s, 1H), 7.68-7.58 (m, 3H), 7.41 (d, 1H), 7.30 (d, 1H), 7.21-7.04 (m, 3H), 7.07-7.02 (m, 1H), 3.83 (s, 3H), 2.50 (q, 2H), 1.02 (t, 3H); MS (EI) for C$_{25}$H$_{21}$FN$_4$O$_4$: 461 (MH$^+$).

methyl{5-[2-(3-ethenyl-2-fluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.90-7.87 (m, 2H), 7.71-7.60 (m, 3H), 7.58-7.54 (m, 1H), 7.43 (d, 1H), 7.30-7.25 (m, 2H), 7.20-7.10 (m, 2H), 6.71 (dd, 1H), 5.86 (d, 1H), 5.39 (d, 1H), 3.83 (s, 3H); MS (EI) for C$_{25}$H$_{19}$FN$_4$O$_4$: 459 (MH$^+$).

methyl{5-[2-(2-fluoro-5-methylphenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.87 (d, 1H), 7.83 (s, 1H), 7.68-7.60 (m, 3H), 7.44 (d, 1H), 7.30 (d, 1H), 7.24 (d, 1H), 7.16 (d, 1H), 7.12-7.08 (m, 1H), 7.04-6.99 (m, 1H), 3.84 (s, 3H), 2.22 (s, 3H); MS (EI) for C$_{24}$H$_{19}$FN$_4$O$_4$: 447 (MH$^+$).

methyl(5-{2-[2-fluoro-5-(methyloxy)phenyl]-1-hydroxy-3-oxo-2,3-dihydro-1H-isoindol-1-yl}-1H-benzimidazol-2-yl)carbamate hydrochloride: $^1$H NMR (400 MHz, d$_6$-DMSO): 7.88-7.67 (m, 2H), 7.69-7.61 (m, 3H), 7.44 (d, 1H), 7.30 (d, 1H), 7.16 (d, 1H), 7.11-7.06 (m, 1H), 6.95-6.93 (m, 1H), 6.88-6.84 (m, 1H), 3.84 (s, 3H), 3.64 (s, 3H); MS (EI) for C$_{24}$H$_{19}$FN$_4$O$_5$: 463 (MH$^+$).

Methyl(6-{2-[(3-fluorophenyl)methyl]-1-hydroxy-3-oxo-2,3-dihydro-1H-isoindol-1-yl}-1H-benzimidazol-2-yl)carbamate trifluoroacetate: $^1$H NMR (400 MHz, CDCl$_3$): 7.84-7.70 (m, 2H), 7.55-7.46 (m, 2H), 7.39-7.30 (m, 2H), 7.26-7.11 (m, 2H), 7.07-7.00 (m, 1H), 6.91 (d, 1H), 6.83-6.73 (m, 2H), 4.55 (d, 1H), 4.22 (d, 1H), 3.95 (s, 3H); MS (EI) for C$_{24}$H$_{19}$FN$_4$O$_4$: 447 (MH$^+$).

Methyl(6-{2-[(4-fluorophenyl)methyl]-1-hydroxy-3-oxo-2,3-dihydro-1H-isoindol-1-yl}-1H-benzimidazol-2-yl)carbamate trifluoroacetate: $^1$H NMR (400 MHz, CDCl$_3$): 7.86-7.70 (m, 2H), 7.55-7.47 (m, 2H), 7.41-7.34 (m, 2H), 7.25-7.11 (m, 4H), 6.78 (t, 2H), 4.57 (d, 1H), 4.20 (d, 1H), 3.96 (s, 3H); MS (EI) for C$_{24}$H$_{19}$FN$_4$O$_4$: 447 (MH$^+$).

Methyl{5-{1-hydroxy-2-[(3-iodophenyl)methyl]-3-oxo-2,3-dihydro-1H-isoindol-1-yl}-1H-benzimidazol-2-yl)carbamate trifluoroacetate: $^1$H NMR (400 MHz, CDCl$_3$): 7.86-7.60 (m, 2H), 7.56-7.49 (m, 2H), 7.35 (d, 1H), 7.32-7.20 (m, 3H), 7.12-7.05 (m, 2H), 6.83 (t, 1H), 4.38 (d, 1H), 4.29 (d, 1H), 3.97 (s, 3H); MS (EI) for C$_{24}$H$_{19}$IN$_4$O$_4$: 555 (MH$^+$).

Methyl{6-[2-(3-amino-5-chlorophenyl)-1-hydroxy-3-oxo-2,3-dihydro-1H-isoindol-1-yl]-1H-benzimidazol-2-yl}carbamate trifluoroacetate: $^1$H NMR (400 MHz, d$_6$-DMSO): 7.83 (d, 1H), 7.77 (br s, 1H), 7.64-7.53 (m, 3H), 7.39 (d, 1H), 7.23 (d, 1H), 7.14 (d, 1H), 6.84 (t, 1H), 6.79 (t, 1H), 6.35 (t, 1H), 6.29-6.27 (m, 1H), 6.22-6.19 (m, 1H), 3.81 (s, 3H); MS (EI) for C$_{23}$H$_{18}$ClN$_5$O$_4$: 464 (MH$^+$).

Methyl{5-[2-(3-ethynyl-4-fluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.96 (br s, 1H), 7.88 (d, 1H), 7.74-7.68 (m, 2H), 7.67-7.53 (m, 3H), 7.45 (d, 1H), 7.31-7.14 (m, 3H), 4.54 (s, 1H), 3.84 (s, 3H); MS (EI) for C$_{25}$H$_{17}$FN$_4$O$_4$: 457 (MH$^+$).

Methyl[5-(1-hydroxy-3-oxo-2-pyridin-3-yl-2,3-dihydro-1H-isoindol-1-yl)-1H-benzimidazol-2-yl]carbamate: $^1$H NMR (400 MHz, d$_6$-DMSO): 8.73 (d, 1H), 8.30 (dd, 1H), 7.95-7.85 (m, 2H), 7.77 (s, 1H), 7.72-7.48 (m, 3H), 7.35-7.28 (m, 2H), 7.26 (d, 1H), 6.99 (d, 1H), 3.72 (s, 3H); MS (EI) for C$_{22}$H$_{17}$N$_5$O$_4$: 416 (MH$^+$), 438 (MNa$^+$).

Methyl{5-[2-(3-bromo-2-fluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.93 (br s, 1H), 7.91-7.87 (m, 1H), 7.71-7.57 (m, 4H), 7.45-7.35 (m, 2H), 7.30 (d, 1H), 7.16-7.09 (m, 2H), 3.82 (s, 3H); MS (EI) for C$_{23}$H$_{16}$BrFN$_4$O$_4$: 511 (MH$^+$), 533 (MNa$^+$).

Methyl{5-[2-(3-chloro-2,4-difluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.98 (br s, 1H), 7.93-7.89 (m, 1H), 7.73-7.62 (m, 2H), 7.60 (br s, 1H), 7.47-7.30 (m, 4H), 7.14 (d, 1H), 3.83 (s, 3H); MS (EI) for C$_{23}$H$_{15}$ClF$_2$N$_4$O$_4$: 485 (MH$^+$), 507 (MNa$^+$).

Methyl{5-[2-(5-chloro-2-fluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.97 (br s, 1H), 7.91-7.88 (m, 1H), 7.72-7.62 (m, 3H), 7.51 (dd, 1H), 7.45 (d, 1H), 7.44-7.38 (m, 1H), 7.33 (d, 1H), 7.26 (t, 1H), 7.15 (d, 1H), 3.83 (s, 3H); MS (EI) for C$_{23}$H$_{16}$ClFN$_4$O$_4$: 467 (MH$^+$).

Methyl{5-[1-hydroxy-3-oxo-2-(phenylsulfonyl)-2,3-dihydro-1H-isoindol-1-yl]-1H-benzimidazol-2-yl}carbamate trifluoroacetate: $^1$H NMR (400 MHz, d$_6$-DMSO): 7.92-7.17 (m, 13H), 3.82 (s, 3H); MS (EI) for C$_{23}$H$_{18}$N$_4$O$_6$S: 479 (MH$^+$).

Methyl{5-[2-(3-bromo-2,5-difluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 8.04 (br s, 1H), 7.91 (d, 1H), 7.77-7.58 (m, 4H), 7.45 (d, 1H), 7.35-7.24 (m, 2H), 7.16 (d, 1H), 3.83 (s, 3H); MS (EI) for C$_{23}$H$_{15}$BrF$_2$N$_4$O$_4$: 529 (MH$^+$).

Methyl(5-{1-hydroxy-2-[2-methyl-5-(methyloxy)phenyl]-3-oxo-2,3-dihydro-1H-isoindol-1-yl}-1H-benzimidazol-2-yl)carbamate hydrochloride: $^1$H NMR (400 MHz, d$_6$-DMSO): 7.88 (d, 1H), 7.80-6.70 (m, 10H), 3.85 (s, 3H), 3.72 (s, 2H), 3.24 (s, 1H), 2.16 (s, 1H), 1.43 (s, 2H); MS (EI) for C$_{25}$H$_{22}$N$_4$O$_5$: 459 (MH$^+$).

Example 15

3-[2-Amino-1-(1,1-dimethylethyl)-1H-benzimidazol-5-yl]-3-hydroxy-2-(phenylmethyl)-2,3-dihydro-1H-isoindol-1-one To a solution of 2-({4-[(1,1-dimethylethyl)amino]-3-nitrophenyl}carbonyl)benzoic acid (1.5 g, 4.38 mmol), HOAt (0.5 M in DMF, 13.14 mL, 6.57 mmol), N-methylmorpholine (1.93 mL, 17.5 mmol) and HATU (2.16 g, 5.69 mmol) was added benzylamine (718 uL, 6.57 mmol) and the reaction mixture was stirred at 60° C. for 16 h. The mixture was cooled to room temperature and the solvent was evaporated. The pale yellow precipitate was filtered off and rinsed with a mixture of acetonitrile-ethyl acetate (1:5, 200 mL). The filtrate was washed with water and brine then dried over anhydrous magnesium sulfate, filtered and concentrated in vacuo. The resulting crude 3-{4-[(1,1-dimethylethyl)amino]-3-nitrophenyl}-3-hydroxy-2-(phenylmethyl)-2,3-dihydro-1H-isoindol-1-one (1.8 g, 95%), was used without further purification. MS (EI) for C$_{25}$H$_{25}$N$_3$O$_4$: 454 (MNa$^+$).

A solution of 3-{4-[(1,1-dimethylethyl)amino]-3-nitrophenyl}-3-hydroxy-2-(phenylmethyl)-2,3-dihydro-1H-isoindol-1-one (1.8 mg, 4.17 mmol) in a mixture of terahydrofuran-ethyl acetate (1:1, 20 mL) was hydrogenated over 10% Pd—C (50 mg) at 40 psi for 18 h. The catalyst removed by filtration and the filtrate concentrated in vacuo. The residue was purified by column chromatography (SiO$_2$, hexanes/ethyl acetate) to afford 3-{3-amino-4-[(1,1-dimethylethyl)amino]phenyl}-3-hydroxy-2-(phenylmethyl)-2,3-dihydro-1H-isoindol-1-one (950 mg, 57%). MS (EI) for C$_{25}$H$_{27}$N$_3$O$_2$: 402 (MH$^+$).

A solution of 3-{3-amino-4-[(1,1-dimethylethyl)amino]phenyl}-3-hydroxy-2-(phenylmethyl)-2,3-dihydro-1H-isoindol-1-one (347 mg, 0.862 mmol) and cyanogen bromide (100 mg, 0.948 mmol) in anhydrous ethanol (10 mL) was heated to reflux for 6 h, at which time it was cooled to room temperature and concentrated in vacuo. The residue was taken up in ethyl acetate (200 mL) and washed with saturated aqueous sodium bicarbonate and brine then dried over anhydrous magnesium sulfate, filtered and the filtrate concentrated in vacuo. The residue was purified by reverse phase HPLC to afford 3-[2-amino-1-(1,1-dimethylethyl)-1H-benzimidazol-5-yl]-3-hydroxy-2-(phenylmethyl)-2,3-dihydro-1H-isoindol-1-one (2.7 mg). $^1$H NMR (400 MHz, d$_6$-DMSO): 7.76 (d, 1H), 7.61 (d, 1H), 7.56-7.53 (m, 2H), 7.32 (br s, 1H), 7.30 (d, 1H), 7.09-7.07 (m, 5H), 6.92 (d, 1H), 4.41 (d, 1H), 4.22 (d, 1H), 1.73 (s, 9H); MS (EI) for C$_{26}$H$_{26}$N$_4$O$_2$: 427 (MH$^+$).

Example 16

3-(2-Amino-1H-benzimidazol-5-yl)-3-hydroxy-2-(phenylmethyl)-2,3-dihydro-1H-isoindol-1-one A solution of 3-(3,4-diaminophenyl)-3-hydroxy-2-(phenylmethyl)-2,3-dihydro-1H-isoindol-1-one (613 mg, 1.77 mmol) and cyanogen bromide (188 mg, 1.77 mmol) in anhydrous ethanol (10 mL) was heated to 60° C. for 16 h. The reaction mixture was cooled and partitioned between ethyl acetate (200 mL) and saturated aqueous sodium bicarbonate. The organic layer was washed with water and brine then dried over anhydrous magnesium sulfate, filtered and the filtrate concentrated in vacuo. The residue was purified by reverse phase HPLC. To the combined fractions were added 6N aqueous hydrochloric acid (10 mL) and heated for 10 mins, at which time saturated aqueous sodium bicarbonate was added until pH reached 7. To the aqueous layer was added ethyl acetate (300 mL) and then separated. The organic layer was washed with brine and dried over magnesium sulfate, filtered and the filtrate concentrated in vacuo to afford 3-(2-amino-1H-benzimidazol-5-yl)-3-hydroxy-2-(phenylmethyl)-2,3-dihydro-1H-isoindol-1-one (10.3 mg). $^1$H NMR (400 MHz, d$_6$-DMSO): 7.76 (d, 1H), 7.59-7.52 (m, 2H), 7.26-7.18 (m, 3H), 7.12-7.09 (m, 5H), 7.03-7.01 (m, 1H), 4.43 (d, 1H), 4.21 (d, 1H), 3.48-3.39 (m, 1H); MS (EI) for C$_{22}$H$_{18}$N$_4$O$_2$: 371 (MH$^+$).

Example 17

Methyl{6-[1-hydroxy-3-oxo-2-(phenylmethyl)-2,3-dihydro-1H-isoindol-1-yl]-1-methyl-1H-benzimidazol-2-yl}carbamate Methyl 2-[(4-amino-3-nitrophenyl)carbonyl]benzoate (0.74 g, 2.47 mmol) was dissolved in acetic acid (9 mL) at 45° C. and tin (II) chloride dihydrate (2.22 g, 9.84 mmol) was added. The mixture was stirred at 75° C. for 7 h and then was concentrated in vacuo. The residue was transferred to an Erlenmeyer flask using a little ethyl acetate and diluted with ether (20 mL). The mixture was stirred while cooling in an ice-water bath and sodium hydroxide (50% solution in water) (6 mL) was added dropwise. The solid which formed was removed by filtration and was washed with hot ethyl acetate. The combined filtrate was concentrated in vacuo and the residue was partitioned between ethyl acetate and water. The organic portion was washed with brine, dried over sodium sulfate, filtered and concentrated in vacuo to afford methyl 2-[(3,4-diaminophenyl)carbonyl]benzoate as a yellow solid (0.245 g, 0.907 mmol, 37% yield). $^1$H NMR (400 MHz, d$_6$-DMSO): 7.87 (dd, 1H), 7.65 (td, 1H), 7.57 (td, 1H), 7.32 (dd, 1H), 6.93 (d, 1H), 6.66 (dd, 1H), 6.44 (d, 1H), 5.49 (s, 2H), 4.69 (s, 2H), 3.57 (s, 3H); MS (EI) for C$_{15}$H$_{14}$N$_2$O$_3$: 293 (MNa$^+$).

Methyl 2-[(3,4-diaminophenyl)carbonyl]benzoate (0.215 g, 0.796 mmol) was dissolved in N,N-dimethylformamide (3 mL) and di-tert-butyl dicarbonate (0.208 g, 0.954 mmol) was added. The mixture was stirred at room temperature for 15 h. The mixture was partitioned between ethyl acetate and lithium chloride (5% aqueous solution). The organic portion was washed with saturated sodium bicarbonate solution, brine, dried over sodium sulfate, filtered and concentrated in vacuo to afford an orange oil which was purified by column chromatography (ethyl acetate-hexanes 1:1) to afford methyl 2-{[4-amino-3-({[(1,1-dimethylethyl)oxy]carbonyl}amino)phenyl]carbonyl}benzoate as a yellow foam (0.245 g, 0.662 mmol, 76% yield). $^1$H NMR (400 MHz, d$_6$-DMSO): 8.33 (br s, 1H), 7.90 (dd, 1H), 7.71-7.56 (m, 3H), 7.34 (dd, 1H), 7.10-7.02 (m, 1H), 6.63 (d, 1H), 5.88 (s, 2H), 3.60 (s, 3H), 1.43 (s, 9H); MS (EI) for C$_{20}$H$_{22}$N$_2$O$_5$: 393 (MNa$^+$).

Methyl 2-{[4-amino-3-({[(1,1-dimethylethyl)oxy]carbonyl}amino)phenyl]carbonyl}benzoate (0.217 g, 0.586 mmol) was dissolved in tetrahydrofuran (3 mL) and cooled in an ice bath. Sodium hydride (60 wt. % dispersion in oil; 0.024 g, 0.600 mmol) was added followed by dropwise addition of iodomethane (0.037 mL, 0.594 mmol). The mixture was stirred for 1.1 h and then iodomethane (0.100 mL, 1.61 mmol) was added dropwise. The mixture was stirred for a further 1 h and then sodium hydride (60 wt. % dispersion in oil; 0.019 g, 0.475 mmol) was added and the mixture was stirred for a further 0.25 h. The mixture was quenched with 1 N hydrochloric acid. The aqueous portion was extracted with ethyl acetate (2×). The combined organic portion was washed with saturated sodium bicarbonate solution. The ethyl acetate portion was dried over sodium sulfate, filtered and concentrated in vacuo to afford a mixture of 4:1 mono-N-methylated: di-N-methylated material (0.115 g). The aqueous portion was acidified with 1 N hydrochloric acid and extracted with ethyl acetate (2×). The organic portion was washed with water, brine, dried over sodium sulfate, filtered and concentrated in vacuo to afford 2-({4-amino-3-[{[(1,1-dimethylethyl)oxy]carbonyl}(methyl)amino]phenyl}carbonyl)benzoic acid as an orange oil which was dissolved in methanol (0.5 mL) and toluene (4.5 mL), cooled in an ice-bath and treated with (trimethylsilyl)diazomethane (2.0M solution in hexanes; 0.200 mL, 0.400 mmol). The mixture was stirred for 0.1 h and then was quenched with 0.5 N hydrochloric acid and partitioned with ethyl acetate. The organic portion was washed with saturated sodium bicarbonate solution, brine, dried over sodium sulfate, filtered and concentrated in vacuo to afford a yellow foam (0.120 g). This yellow foam was combined with the 4:1 mixture of mono- and di-methylated material isolated above (0.115 g) and was purified by column chromatography (ethyl acetate-hexanes 1:1) to afford methyl 2-({4-amino-3-[{[(1,1-dimethylethyl)oxy]carbonyl}(methyl)amino]phenyl}carbonyl)benzoate as a yellow foam (0.167 g, 0.435 mmol, 74% yield). $^1$H NMR (400 MHz, CDCl$_3$): 8.02 (dd, 1H), 7.65-7.30 (m, 5H), 6.69 (d, 1H), 4.24 (s, 2H), 3.65 (s, 3H), 3.13 (s, 3H), 1.56 (s, 9H); MS (EI) for C$_{21}$H$_{24}$N$_2$O$_5$: 407 (MNa$^+$).

Methyl 2-({4-amino-3-[{[(1,1-dimethylethyl)oxy]carbonyl}(methyl)amino]phenyl}carbonyl)benzoate (0.167 g, 0.435 mmol) was dissolved in dichloromethane (1 mL) and treated with trifluoroacetic acid (0.7 mL) for 1.5 h. The mixture was brought to pH ~8 by addition of saturated sodium bicarbonate solution.

The aqueous portion was partitioned with ethyl acetate. The organic portion was washed with brine, dried over sodium sulfate, filtered and concentrated in vacuo to afford an orange foam which was dissolved in N,N-dimethylformamide (1 mL) and treated with methyl isothiocyanatidocarbamate (0.120 mL, 1.026 mmol). After 1 h, 1-(3-dimethylaminopropyl)-3-ethylcarbodiimide hydrochloride (0.120 g, 0.625 mmol) was added and the mixture was stirred at 65° C. for 0.5 h. The mixture was partitioned between ethyl acetate and lithium chloride (5% aqueous solution). The organic portion was washed with 0.5 N hydrochloric acid, saturated sodium bicarbonate solution, brine, dried over sodium sulfate, filtered and concentrated in vacuo to afford a yellow oil which was purified by column chromatography (ethyl acetate-hexanes 4:1) to afford methyl 2-[(1-methyl-2-{[(methyloxy)carbonyl]amino}-1H-benzimidazol-6-yl)carbonyl]benzoate as a colorless film (0.049 g, 0.134 mmol, 31% yield). $^1$H NMR (400 MHz, CDCl$_3$): 11.4 (s, 1H), 8.06 (dd, 1H), 7.81 (d, 1H), 7.65 (td, 1H), 7.57 (td, 1H), 7.42 (dd, 1H), 7.39 (dd, 1H), 7.19 (d, 1H), 3.78 (s, 3H), 3.67 (s, 3H), 3.61 (s, 3H); MS (EI) for C$_{19}$H$_{17}$N$_3$O$_5$: 368 (MH$^+$).

Methyl 2-[(1-methyl-2-{[(methyloxy)carbonyl]amino}-1H-benzimidazol-6-yl)carbonyl]benzoate (0.049 g, 0.134 mmol) was dissolved in tetrahydrofuran/methanol (1:1, 1 mL) and 4 N potassium hydroxide (0.250 mL, 1.00 mmol) was added. The mixture was stirred for 0.5 h and then methanol (0.5 mL) and 4 N potassium hydroxide (0.250 mL, 1.00 mmol) was added. The mixture was stirred for 1.1 h and then was concentrated in vacuo. The residue was partitioned between ether and water. The aqueous portion was acidified to pH 1-2 using 1 N hydrochloric acid and then was extracted with ethyl acetate (2×). The organic portion was dried over sodium sulfate, filtered and concentrated in vacuo to afford a colorless solid (0.027 g, 0.076 mmol) which was dissolved in N,N-dimethylformamide (0.6 mL). Benzotriazole-1-yl-oxy-trispyrrolidinophosphonium hexafluorophosphate (PyBOP) (0.050 g, 0.096 mmol) and then N-methylmorpholine (0.015 mL, 0.137 mmol) were added and the mixture was stirred for 0.25 h. Benzylamine (0.011 mL, 0.101 mmol) was added and the mixture was stirred for 15.5 h. The mixture was partitioned between ethyl acetate and lithium chloride (5% aqueous solution). The organic portion was washed with 1 N hydrochloric acid, saturated sodium bicarbonate solution, brine, dried over sodium sulfate, filtered and concentrated in vacuo to afford a yellow oil which was purified by column chromatography (ethyl acetate-hexanes 7:3) to afford a colorless oil which was further purified by reverse phase preparative HPLC eluting with aqueous acetonitrile buffered with 0.1% trifluoroacetic acid. The fractions which contained the required product were concentrated in vacuo to afford methyl{6-[1-hydroxy-3-oxo-2-(phenylmethyl)-2,3-dihydro-1H-isoindol-1-yl]-1-methyl-1H-benzimidazol-2-yl}carbamate trifluoroacetate as a colorless oil (0.014 g, 0.025 mmol, 19% yield). $^1$H NMR (400 MHz, d$_6$-DMSO): 7.76-7.73 (m, 1H), 7.56-7.49 (m, 3H), 7.38-7.31 (m, 2H), 7.28-7.24 (m, 1H), 7.18-7.14 (m, 2H), 7.13-7.00 (m, 4H), 4.46 (d, 1H), 4.29 (d, 1H), 3.74 (s, 3H), 3.56 (s, 3H); MS (EI) for C$_{25}$H$_{22}$N$_4$O$_4$: 443 (MH$^+$).

Example 18

N-{5-[1-Hydroxy-3-oxo-2-(phenylmethyl)-2,3-dihydro-1H-isoindol-1-yl]-1H-benzimidazol-2-yl}morpholine-4-carboxamide A solution of 2-methyl-2-thiopseudourea hemisulfate (1.0 g, 3.6 mmol), 4-morpholinecarbonyl chloride (0.50 mL, 4.3 mmol), triethylamine (1.5 mL, 11 mmol) and N,N-dimethylformamide was stirred for 12 h at room temperature and was concentrated in vacuo. The residue was partitioned between ethyl acetate/10% methanol) and brine/saturated sodium bicarbonate solution. The layers were separated and the aqueous layer was extracted (2×100 mL ethyl acetate/10% methanol). The combined organic layers were dried (sodium sulfate), filtered and concentrated in vacuo to give 0.78 g (>100%) of crude methyl N-(morpholin-4-ylcarbonyl)imidothiocarbamate as a white solid, which was used without further purification in the next step. $^1$H NMR (400 MHz, d$_4$-MeOH): 4.89 (s, 3H), 3.65 (m, 4H), 3.27 (m, 4H); MS (EI) for C$_7$H$_{13}$N$_3$O$_2$S: 204 (MH$^+$).

A solution of 3-(3,4-diaminophenyl)-3-hydroxy-2-(phenylmethyl)-2,3-dihydro-1H-isoindol-1-one (0.10 g, 0.28 mmol) and methyl N-(morpholin-4-ylcarbonyl)imidothiocarbamate (0.11 g, 0.56 mmol) in glacial acetic acid was heated at 85° C. for 1.5 h. The reaction mixture was diluted with saturated aqueous sodium bicarbonate solution and extracted (2×100 mL ethyl acetate). The combined organic layers were dried (sodium sulfate), filtered and concentrated in vacuo. Column chromatography (silica gel, 1:1 dichloromethane/acetone) was followed by preparative HPLC (reverse-phase, acetonitrile/water with 0.1% trifluoroacetic acid). The pure fractions were neutralized with sodium bicarbonate, extracted with ethyl acetate and the combined organic layers were washed with brine and dried over anhydrous sodium sulfate. Filtration and concentration gave 0.0094 g (7%) of N-{6-[1-hydroxy-3-oxo-2-(phenylmethyl)-2,3-dihydro-1H-isoindol-1-yl]-1H-benzimidazol-2-yl}morpholine-4-carboxamide. $^1$H NMR (400 MHz, d$_6$-DMSO): 7.73 (dd, 1H), 7.55 (m, 2H), 7.33 (broad s, 1H), 7.27 (d, 1H), 7.07-7.20 (m, 7H), 6.88 (t, 1H), 6.56 (s, 1H), 4.49 (d, 1H), 4.15 (d, 1H), 3.55 (m, 8H); MS (EI) for C$_{27}$H$_{25}$N$_5$O$_4$: 484 (MH$^+$).

Using the same or analogous synthetic techniques and/or substituting with alternative reagents, the following compounds of the invention were prepared:

N-ethyl-N'-{5-[1-hydroxy-3-oxo-2-(phenylmethyl)-2,3-dihydro-1H-isoindol-1-yl]-1H-benzimidazol-2-yl}urea: $^1$H NMR (400 MHz, d$_6$-DMSO): 11.46 (broad s, 1H), 9.86 (broad s, 1H), 7.73 (dd, 1H), 7.53 (m, 2H), 7.10-7.27 (m, 10H), 6.86 (broad s, 1H), 4.52 (d, 1H), 4.09 (d, 1H), 3.19 (m, 2H), 1.10 (t, 3H); MS (EI) for C$_{25}$H$_{23}$N$_5$O$_3$: 442 (MH$^+$).

N-ethyl-N'-(5-{1-hydroxy-3-oxo-2-[(1R)-1-phenylethyl]-2,3-dihydro-1H-isoindol-1-yl}-1H-benzimidazol-2-yl) urea: $^1$H NMR (400 MHz, d$_6$-DMSO): 11.70 (m, 1H), 10.00 (m, 2H), 8.90 (m, 2H), 7.78 (m, 2H), 7.66 (m, 1H), 7.60 (m, 2H), 7.52 (m, 3H), 7.39 (m, 2H), 7.19 (m, 14H), 7.02 (m, 4H), 6.56 (s, 2H), 4.35 (m, 2H), 4.55 (m, 1H), 4.40 (m, 1H), 3.19 (m, 8), 1.75 (d, 2H), 1.44 (d, 2H), 1.29 (d, 4H), 1.10 (t, 14H); MS (EI) for C$_{26}$H$_{25}$N$_5$O$_3$: 456 (MH$^+$).

N'-{5-[1-hydroxy-3-oxo-2-(phenylmethyl)-2,3-dihydro-1H-isoindol-1-yl]-1H-benzimidazol-2-yl}-N,N-dimethylurea trifluoroacetate (salt): $^1$H NMR (400 MHz, d$_6$-DMSO): 7.78 (d, 1H), 7.62 (broad s, 1H), 7.57 (m, 2H), 7.38 (d, 1H), 7.32 (s, 1H), 7.26 (d, 1H), 7.05-7.18 (m, 7H), 4.47 (d, 1H), 4.20 (d, 1H), 3.02 (s, 6H); MS (EI) for C$_{25}$H$_{23}$N$_5$O$_3$: 442 (MH$^+$).

N-{5-[1-hydroxy-3-oxo-2-(phenylmethyl)-2,3-dihydro-1H-isoindol-1-yl]-1H-benzimidazol-2-yl}-N'-(phenylmethyl) urea trifluoroacetate (salt): $^1$H NMR (400 MHz, d$_6$-DMSO): 8.02 (broad s, 1H), 7.77 (dd, 1H), 7.60 (s, 1H), 7.56 (dt, 2H), 7.36 (m, 5H), 7.27 (m, 5H), 7.14 (m, 5H), 7.02 (d, 1H), 4.48 (d, 1H), 4.41 (d, 2H), 4.17 (d, 1H). MS (EI) for C$_{30}$H$_{25}$N$_5$O$_3$: 504 (MH$^+$).

N-{5-[1-hydroxy-3-oxo-2-(phenylmethyl)-2,3-dihydro-1H-isoindol-1-yl]-1H-benzimidazol-2-yl}-N'-methylurea trifluoroacetate (salt): $^1$H NMR (400 MHz, d$_6$-DMSO): 7.78 (dd, 1H), 7.61 (broad s, 1H), 7.57 (m, 2H), 7.45 (d, 1H), 7.38 (d, 1H), 7.34 (broad s, 1H), 7.26 (dd, 1H), 7.06-7.19 (m, 6H), 4.48 (d, 1H), 4.15 (d, 1H), 2.76 (3H). MS (EI) for C$_{24}$H$_{21}$N$_5$O$_3$: 428 (MH$^+$).

N-{5-[1-hydroxy-3-oxo-2-(phenylmethyl)-2,3-dihydro-1H-isoindol-1-yl]-1H-benzimidazol-2-yl}piperidine-1-carboxamide: $^1$H NMR (400 MHz, d$_6$-DMSO): 7.74 (d, 1H), 7.54 (m, 2H), 7.39 (broad s, 1H), 7.27 (d, 1H), 7.15 (m, 6H), 6.86 (d, 1H), 6.55 (broad s, 1H), 4.49 (d, 1H), 4.14 (d, 1H), 3.52 (s, 4H), 1.52 (m, 6H). MS (EI) for C$_{28}$H$_{27}$N$_5$O$_3$: 483 (MH$^+$).

N-ethyl-N'-{6-[2-(4-fluorophenyl)-1-hydroxy-3-oxo-2,3-dihydro-1H-isoindol-1-yl]-1H-benzimidazol-2-yl}urea: $^1$H NMR (400 MHz, d$_6$-DMSO): 7.89 (d, 2H), 7.62-7.75 (m, 4H), 7.48 (m, 3H), 7.14-7.34 (m, 4H), 3.25 (q, 2H), 1.13 (t, 3H); MS (EI) for C$_{24}$H$_{20}$N$_5$O$_3$F: 446 (MH$^+$).

Example 19

3-(4-Methylpiperazin-1-yl)propyl{6-[1-hydroxy-3-oxo-2-(phenylmethyl)-2,3-dihydro-1H-isoindol-1-yl]-1H-benzimidazol-2-yl}carbamate To a solution of 2-methyl-2-thiopseudourea sulfate (5.56 g, 20.0 mmol) in water (50 mL) sodium bicarbonate (6.73 g, 80.0 mmol) was added and the reaction mixture was cooled to 0° C. A solution of 3-chloropropyl chloroformate (2.41 mL, 20.0 mmol) in 1,4-dioxane (20 mL) was added dropwise and it was stirred for 15 hour at room temperature. The reaction mixture was diluted with ethyl acetate (250 mL) and the organic layer was separated. It was washed with water and brine, dried over anhydrous sodium sulfate and the solvent was evaporated. The resulting crude product was purified by silica gel flash chromatography (hexane:ethyl acetate 7:3 to 1:1 eluent) to give 3-chloropropyl[imino(methylthio)methyl]carbamate (2.70 g, 64% yield) as a white solid. $^1$H NMR (400 MHz, DMSO-d$_6$): 8.58 (br.s, 1H), 4.06 (t, 2H), 3.67 (t, 1H), 2.32 (s, 3H), 2.02 m, 2H); MS (EI) for C$_6$H$_{11}$ClN$_2$O$_2$S: 211 (MH$^+$).

A solution of (3,4-diaminophenyl)-3-hydroxy-2-(phenylmethyl)-2,3-dihydro-1H-isoindol-1-one) (0.42 g, 1.21 mmol) and 3-chloropropyl[imino(methylthio)methyl]carbamate (0.27 g, 1.31 mmol) in glacial acetic acid (5.0 mL) was heated to 80° C. for 20 minutes. The reaction mixture was poured into ice water and the pH was adjusted to 9 by the addition of 2M aqueous sodium hydroxide. The precipitated product was extracted with ethyl acetate (100 mL) and the organic layer was washed with brine and dried over anhydrous sodium sulfate, followed by the evaporation of the solvent. The resulting crude product was purified by silica gel flash chromatography (chloroform-acetonitrile 95:5 to 9:1 eluent) to give 3-chloropropyl {6-[1-hydroxy-3-oxo-2-(phenylmethyl)-2,3-dihydro-1H-isoindol-1-yl]-1H-benzimidazol-2-yl}acetate (0.64 g, 71% yield). MS (EI) for C$_{26}$H$_{23}$ClN$_4$O$_4$: 491 (MH$^+$).

A solution of 3-chloropropyl{6-[1-hydroxy-3-oxo-2-(phenylmethyl)-2,3-dihydro-1H-isoindol-1-yl]-1H-benzimidazol-2-yl}acetate (0.25 g, 0.51 mmol) and 1-methyl-piperazine (0.46 mL, 5.10 mmol) in acetonitrile (5.0 mL) was heated to 80° C. for 2 hours. The reaction mixture was cooled to room temperature and the solvent was evaporated. The resulting crude product was purified by reverse phase preparative HPLC (CH$_3$CN/25 mM aqueous ammonium acetate). The fractions were collected, and the solvent was concentrated. The aqueous residue was partitioned with ethyl acetate. The organic layer was washed with saturated aqueous sodium bicarbonate and brine, and dried over anhydrous sodium sulfate. Filtration and concentration gave a pale yellow residue, which was freeze-dried from a mixture of acetonitrile-water (1:1, 3.0 mL) to give 3-(4-methylpiperazin-1-yl)propyl{6-[1-hydroxy-3-oxo-2-(phenylmethyl)-2,3-dihydro-1H-isoindol-1-yl]-1H-benzimidazol-2-yl}acetate (0.12 g, 43%). $^1$H NMR (400 MHz, DMSO-d$_6$): 11.50 (br.s, 1H), 7.70 (d, 1H), 7.49 (m, 3H), 7.23 (t, 1H), 7.15 (m, 6H), 6.84 (d, 1H), 4.49 (d, 1H), 4.16 (t, 4H), 4.10 (d, 1H), 3.34 (s, 6H), 2.36 (m, 3H), 2.18 (s, 3H) open, 2.16 (s, 3H) closed, 1.78 (m, 1H); MS (EI) for C$_{31}$H$_{34}$N$_6$O$_4$: 555 (MH$^+$).

Using the same or analogous synthetic techniques and/or substituting with alternative reagents, the following compounds of the invention were prepared:

3-piperidin-1-ylpropyl{6-[2-(4-fluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.84 (m, 1H), 7.61 (m, 3H), 7.48 (m, 2H), 7.27 (m, 2H), 7.11 (m, 2H), 6.95 (m, 1H), 6.55 (m, 1H), 6.32 (m, 1H), 4.17 (m, 2H), 3.98 (m, 1H), 2.34 (m, 4H), 1.81 (m, 1H), 1.49 (m, 6H); MS (EI) for C$_{30}$H$_{30}$N$_5$O$_4$F: 544 (MH$^+$).

3-(4-methylpiperazin-1-yl)propyl{6-[2-(4-fluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.84 (d, 1H), 7.60 (m, 3H), 7.48 (m, 2H), 7.27 (d, 1H), 7.23 (d, 1H), 7.16 (m, 2H), 6.94 (d, 1H), 6.56 (s, 1H), 6.32 (s, 1H), 4.16 (t, 2H), 2.15-2.46 (m, 12H), 1.77 (m, 2H); MS (EI) for C$_{30}$H$_{31}$N$_6$O$_4$F: 559 (MH$^+$).

3-piperidin-1-ylpropyl{6-[2-(3-chloro-2-fluorophenyl)-1-hydroxy-3-oxo-2,3-dihydro-1H-isoindol-1-yl]-1H-benzimidazol-2-yl}carbamate. $^1$H NMR (400 MHz, DMSO-d$_6$): 7.96 (s, 1H), 7.88 (d, 1H), 7.66 (m, 2H), 7.52 (m, 1H), 7.39 (t, 1H), 7.35 (s, 1H), 7.28 (m, 2H), 7.21 (t, 1H), 7.07 (d, 1H), 4.07 (t, 2H), 3.42 (t, 2H), 3.26 (t, 4H), 1.90 (m, 2H), 1.48 (m, 2H), 1.37 (m, 4H); MS (EI) for C$_{30}$H$_{29}$ClFN$_5$O$_4$: 578 (MH$^+$).

Example 20

N-{5-[1-Hydroxy-3-oxo-2-(phenylmethyl)-2,3-dihydro-1H-isoindol-1-yl]-1H-benzimidazol-2-yl}-4-piperidin-1-ylbutanamide To a solution of ethyl 3-bromobutanoate (6.0 ml, 42 mmol) in N,N-dimethylformamide (20 ml) was added piperidine (8.0 ml, 80 mmol) at 0° C. The reaction mixture was allowed to warm to 25° C. and stirred for 16 h, at which time it was diluted with ethyl acetate (200 ml). The organic layer was washed with 2.0 N aqueous sodium hydroxide (4:1 v/v) and brine, dried over anhydrous sodium sulfate, filtered and concentrated in vacuo to give ethyl 4-piperin-1-ylbutanoate (6.8 g) as a brown oil. MS (EI) for C$_{11}$H$_{21}$NO$_2$: 200 (MH$^+$).

To a solution of ethyl 4-piperin-1-ylbutanoate (6.8 g, 39 mmol) in ethanol (30 ml) was added a solution of potassium hydroxide (11 g, 0.20 mol) in water (40 ml) at 25° C. and stirred for 2 h. The reaction mixture was concentrated in vacuo then dried under high vacuum for 2 d. The sodium salt of the acid was taken up as a slurry in chloroform (100 ml). To the slurry was added catalytic N,N-dimethylformamide (0.2 ml) followed by a dropwise addition of oxalyl chloride (15 ml, 170 mmol) at 25° C. and stirred for 18 h. The reaction mixture was concentrated in vacuo to afford the crude 4-piperin-1-ylbutanoyl chloride hydrochloride. To a suspension of the 4-piperin-1-ylbutanoyl chloride hydrochloride (ca. 40 mmol) and 2-methyl-2-thiopseudourea sulfate (5.6 g, 20 mmol) in acetonitrile (100 ml) was added dropwise triethylamine (20 ml, 0.27 mol) while cooling in an ice bath. The reaction mixture was then allowed to warm to 25° C. over a period of 1 h. The reaction mixture was filtered through Celite and the solids washed with acetonitrile (100 ml). The filtrate were concentrated in vacuo to afford a crude 3-piperidin-1-ylpropyl[imino(methylthio)methyl]carbamate (10.6 g) as a brown oil. MS (EI) for C$_{11}$H$_{21}$N$_3$OS: 244 (MH$^+$).

A solution of 3-(3,4-diaminophenyl)-3-hydroxy-2-(phenylmethyl)-2,3-dihydro-1H-isoindol-1-one (75 mg, 0.21 mmol) and 3-piperidin-1-ylpropyl[imino(methylthio)methyl]carbamate (200 mg, 0.5 mmol) in tent-butanol (15 ml) was heated to 85° C. and stirred for 1.5 h. The reaction mixture was concentrated in vacuo and the resulting crude product was purified by reverse phase HPLC to afford N-{5-[1-hydroxy-3-oxo-2-(phenylmethyl)-2,3-dihydro-1H-isoindol-1-yl]-1H-benzimidazol-2-yl}-4-piperidin-1-ylbutanamide trifluoroacetic acid salt (40 mg, 36%) as a white solid. $^1$H NMR (400 MHz, d$_6$-DMSO): 7.76 (d, 1H), 7.59 (br s, 1H), 7.54 (m, 2H), 7.36 (d, 1H), 7.23 (d, 1H), 7.12-7.07 (m, 6H), 6.99 (d, 1H), 4.47 (d, 1H), 4.18 (d, 1H), 3.40 (d, 2H), 3.03 (m, 2H), 2.83 (t, 2H), 2.56 (t, 2H), 1.97 (m, 2H), 1.81 (d, 2H), 1.68-1.58 (m, 3H), 1.37 (m, 1H); MS (EI) for C$_{31}$H$_{33}$N$_5$O$_3$: 524 (MH$^+$).

Using the same or analogous synthetic techniques and/or substituting with alternative reagents, the following compounds of the invention were prepared:

3,3,3-trifluoro-2-hydroxy-N-{5-[1-hydroxy-3-oxo-2-(phenylmethyl)-2,3-dihydro-1H-isoindol-1-yl]-1H-benzimidazol-2-yl}-2-(trifluoromethyl)propanamide): $^1$H NMR (400 MHz, d$_6$-DMSO): 7.75 (dd, 1H), 7.54-7.50 (m, 3H), 7.24-7.22 (m, 2H), 7.13-7.10 (m, 5H), 6.95 (d, 1H), 4.44 (d, 1H), 4.20 (d, 1H); MS (EI) for C$_{26}$H$_{18}$F$_6$N$_4$O$_4$: 565 (MH$^+$).

4,4,4-trifluoro-3-hydroxy-N-{5-[1-hydroxy-3-oxo-2-(phenylmethyl)-2,3-dihydro-1H-isoindol-1-yl]-1H-benzimidazol-2-yl}-3-(trifluoromethyl)butanamide): $^1$H NMR (400 MHz, d$_6$-DMSO): 7.74 (dd, 1H), 7.56-7.49 (m, 3H), 7.30 (d, 1H), 7.23 (d, 1H), 7.16-7.09 (m, 5H), 6.95 (d, 1H), 4.46 (d, 1H), 4.16 (d, 1H), 3.06 (s, 2H); MS (EI) for C$_{27}$H$_{20}$F$_6$N$_4$O$_4$: 579 (MH$^+$).

N-{5-[1-hydroxy-3-oxo-2-(phenylmethyl)-2,3-dihydro-1H-isoindol-1-yl]-1H-benzimidazol-2-yl}-3-piperidin-1-ylpropanamide: $^1$H NMR (400 MHz, d$_6$-DMSO): 7.73 (dd, 1H), 7.56-7.49 (m, 3H), 7.28-7.24 (m, 2H), 7.19-7.10 (m, 5H), 6.85 (d, 1H), 4.50 (d, 1H), 4.09 (d, 1H), 5.58 (dd, 4H), 2.37 (br m, 4H), 1.86 (s, 2H), 1.49-1.46 (m, 4H), 1.36 (br m, 2H); MS (EI) for C$_{30}$H$_{31}$N$_5$O$_3$: 510 (MH$^+$).

N-{5-[1-hydroxy-3-oxo-2-(phenylmethyl)-2,3-dihydro-1H-isoindol-1-yl]-1H-benzimidazol-2-yl}-4-[(phenylmethyl)oxy]butanamide: $^1$H NMR (400 MHz, d$_6$-DMSO): 7.76 (d, 1H), 7.63 (br s, 1H), 7.59-7.51 (m, 3H), 7.36 (d, 1H), 7.30-7.10 (m, 11H), 6.99 (d, 1H), 4.49 (d, 1H), 4.45 (s, 2H), 4.15 (d, 1H), 3.50 (t, 2H), 2.58 (t, 2H), 1.92 (m, 2H); MS (EI) for C$_{33}$H$_{30}$N$_4$O$_4$: 547 (MH$^+$).

N-{5-[1-hydroxy-3-oxo-2-(phenylmethyl)-2,3-dihydro-1H-isoindol-1-yl]-1H-benzimidazol-2-yl}-4-piperidin-1-ylbutanamide: $^1$H NMR (400 MHz, d$_6$-DMSO): 7.76 (d, 1H), 7.59 (br s, 1H), 7.54 (m, 2H), 7.36 (d, 1H), 7.23 (d, 1H), 7.12-7.07 (m, 6H), 6.99 (d, 1H), 4.47 (d, 1H), 4.18 (d, 1H), 3.40 (d, 2H), 3.03 (m, 2H), 2.83 (t, 2H), 2.56 (t, 2H), 1.97 9m, 2H), 1.81 (d, 2H), 1.68-1.58 (m, 3H), 1.37 (m, 1H); MS (EI) for C$_{31}$H$_{33}$N$_5$O$_3$: 524 (MH$^+$).

N-{5-[1-hydroxy-3-oxo-2-(phenylmethyl)-2,3-dihydro-1H-isoindol-1-yl]-1H-benzimidazol-2-yl}-4-(4-methylpiperazin-1-yl)butanamide: $^1$H NMR (400 MHz, d$_6$-DMSO): 7.76 (d, 1 H), 7.59 (br s, 1H), 7.55 (m, 3H), 7.37 (d, 1H) 7.23 (d, 1H), 7.14-7.07 (m, 5H), 6.99 (d, 1H), 4.48 (d, 1H), 4.16 (d, 1H), 3.02 (t, 3H), 2.81 (s, 3H), 2.56 (t, 2H), 1.94 (m, 2H); MS (EI) for $C_{31}H_{34}N_6O_3$: 539 (MH$^+$).

N-{5-[1-hydroxy-3-oxo-2-(phenylmethyl)-2,3-dihydro-1H-isoindol-1-yl]-1H-benzimidazol-2-yl}-4-pyrrolidin-1-ylbutanamide: $^1$H NMR (400 MHz, d$_6$-DMSO): 11.83 (br s, 1H), 9.53 (br s, 1H), 7.75 (d, 1H), 7.57 (br s, 1H), 7.54 (m, 2H), 7.32 (d, 1H), 7.26 (d, 1H), 7.22-7.11 (m, 5H), 6.92 (d, 1H), 4.50 (d, 1H), 4.11 (d, 1H), 3.17 (m, 2H), 3.01 (br s, 2H), 2.55 (t, 2H), 2.05-1.93 (m, 4H), 1.90-1.81 (m, 4H); MS (EI) for $C_{30}H_{31}N_5O_3$: 510 (MH$^+$).

4-(diethylamino)-N-{5-[1-hydroxy-3-oxo-2-(phenylmethyl)-2,3-dihydro-1H-isoindol-1-yl]-1H-benzimidazol-2-yl}butanamide: $^1$H NMR (400 MHz, d$_6$-DMSO): 9.21 (br s, 1H), 7.76 (d, 1H), 7.59 (br s, 1H), 7.55 (m, 2H), 7.35 (d, 1H), 7.22-7.11 (m, 5H), 6.96 (d, 1H) 4.51 (d, 1H), 4.11 (d, 1H), 3.19-1.91 (m, 2H), 2.60 (t, 2H), 1.98-1.91 (m, 2H), 1.21 (t, 6H); MS (EI) for $C_{30}H_{33}N_5O_3$: 512 (MH$^+$).

N-{5-[2-(4-fluorophenyl)-1-hydroxy-3-oxo-2,3-dihydro-1H-isoindol-1-yl]-1H-benzimidazol-2-yl}-4-piperidin-1-ylbutanamide: $^1$H NMR (400 MHz, d$_6$-DMSO): 7.84 (d, 1H), 7.63-7.55 (m, 3H), 7.42-7.30 (m, 3H), 7.24 (d, 2H), 7.11-7.04 (m, 2H), 3.39 (d, 2H), 3.01 (t, 2H), 2.81 (t, 2H), 2.54 (t, 2H), 1.94 (m, 2H), 1.80 (d, 2H), 1.68-1.54 (m, 3H), 1.37 (m, 1H); MS (EI) for $C_{30}H_{30}FN_5O_3$: 527 (MH$^+$).

N-{5-[2-(3-chloro-2-fluorophenyl)-1-hydroxy-3-oxo-2,3-dihydro-1H-isoindol-1-yl]-1H-benzimidazol-2-yl}-4-piperidin-1-ylbutanamide: $^1$H NMR (400 MHz, d$_6$-DMSO): 12.02 (br s, 1H), 11.52 (br s, 1H), 7.87 (d, 1H), 7.72 (s, 1H), 7.67-7.57 (m, 2H), 7.48 (t, 1H), 7.40-7.23 (m, 3H), 7.16 (t, 1H), 6.90 (d, 1H), 3.35 (t, 6H), 2.41 (t, 1H), 2.31-2.24 (m, 4H), 1.74 (m, 2H), 1.45 (m, 3H), 1.32 (m, 1H); MS (EI) for $C_{30}H_{29}CFN_5O_3$: 562 (MH$^+$).

N-{6-[1-hydroxy-3-oxo-2-(phenylmethyl)-2,3-dihydro-1H-isoindol-1-yl]-1H-benzimidazol-2-yl}-2-methylpropanamide: $^1$H NMR (400 MHz, d$_6$-DMSO): 12.01 (s, 1H), 11.46 (d, 1H), 7.71 (d, 1H), 7.64-7.40 (m, 3H), 7.34-7.10 (m, 8H), 6.83 (m, 1H), 4.50 (d, 2H), 2.72 (m, 1H), 1.13 (d, 6H); MS (EI) for $C_{26}H_{24}N_4O_3$: 441 (MH$^+$).

N-{6-[1-hydroxy-3-oxo-2-(phenylmethyl)-2,3-dihydro-1H-isoindol-1-yl]-1H-benzimidazol-2-yl}pent-4-ynamide: $^1$H NMR (400 MHz, d$_6$-DMSO): 7.79 (m, 2H), 7.53-7.46 (m, 2H), 7.34 (d, 1H), 7.26-7.17 (m, 2H), 7.10 (m, 2H), 7.05 (m, 3H), 4.52 (d, 1H) 4.24 (d, 1H), 2.91 (t, 2H), 2.64 (tt, 2H), 2.01 (t, 1H); MS (EI) for $C_{27}H_{22}N_4O_3$: 451 (MH$^+$).

2,2-difluoro-N-{6-[1-hydroxy-3-oxo-2-(phenylmethyl)-2,3-dihydro-1H-isoindol-1-yl]-1H-benzimidazol-2-yl}cyclopropanecarboxamide: MS (EI) for $C_{26}H_{20}N_4O_3F_3$: 475 (MH$^+$).

N-{6-[1-hydroxy-3-oxo-2-(phenylmethyl)-2,3-dihydro-1H-isoindol-1-yl]-1H-benzimidazol-2-yl}-2,2-dimethyl-3-piperidin-1-ylpropanamide: $^1$H NMR (400 MHz, d$_6$-CDCl$_3$): 7.81 (m, 1H), 7.46 (m, 3H), 7.16-7.26 (m, 4H), 7.15-7.25 (m, 2H), 7.03 (d, 2H), 4.76 (d, 1H), 4.54 (dd, 2H), 3.53 (d, 4H), 2.05 (s, 3H), 1.64 (d, 3H), 1.39 (d, 3H), 1.28 (s, 1H), 1.23 (d, 2H), 1.21 (s, 1H); MS (EI) for $C_{32}H_{35}N_5O_3$: 538 (MH$^+$).

N-{5-[1-hydroxy-3-oxo-2-(phenylmethyl)-2,3-dihydro-1H-isoindol-1-yl]-1H-benzimidazol-2-yl}propanamide trifluoroacetate: $^1$H NMR (400 MHz, d$_6$-DMSO): 12.0-11.9 (s, 1H), 11.5-11.4 (s, 1H), 7.74-7.69 (d, 1H), 7.57-7.45 (m, 2H), 7.31-7.05 (m, 7H), 6.83-6.78 (d, 1H), 4.55-4.45 (s, 1H), 4.14-4.04 (d, 1H), 2.84-2.76 (m, 1H), 2.46-2.38 (m, 1H), 1.32-1.26 (m, 1.5H), 1.12-1.06 (m, 1.5H); MS (EI) for $C_{25}H_{22}N_4O_3$: 427 (MH$^+$).

Example 21

Methyl(6-{1-methyl-3-oxo-2-[3-(trifluoromethyl)phenyl]-2,3-dihydro-1H-isoindol-1-yl}-1H-benzimidazol-2-yl)carbamate To a mixture of methyltriphenylphosphonium bromide (15.6 g, 44 mmol) in tetrahydrofuran (100 mL) at 0° C. was added a solution of sodium hexamethyldisilazide (22 mL, 2.0M solution in THF, 44 mmol), and the resulting mixture was stirred for one hour at 0° C. Methyl 2-[(4-chloro-3-nitrophenyl)carbonyl]benzoate (7.0 g, 22 mmol) in tetrahydrofuran (50 mL) was then added drop wise to the yellow reaction mixture and stirred at 0° C. for 30 minutes and at room temperature for four hours. The brown reaction mixture was diluted with hexanes, filtered through silica gel, and the filtrate was washed with water (100 mL), brine solution (100 mL), dried over sodium sulfate, filtered, concentrated, and purified by flash chromatography (silica gel, eluting with 5-10% ethyl acetate-hexane) to give methyl 2-[1-(4-chloro-3-nitrophenyl)ethenyl]benzoate (0.95 g, 3 mmol, 14% yield). $^1$H NMR (400 MHz, CDCl$_3$): 7.95-7.93 (dd, 1H), 7.73-7.72 (d, 1H), 7.61-7.57 (dt, 1H), 7.50-7.46 (dt, 1H), 7.46-7.43 (d, 1H), 7.39-7.34 (m, 2H), 5.77 (s, 1H), 5.37 (s, 1H), 3.63 (s, 3H); MS (EI) for $C_{16}H_{12}ClNO_4$: 318 (MH$^+$).

Methyl 2-[1-(4-chloro-3-nitrophenyl)ethenyl]benzoate (0.95 g, 3.0 mmol) was suspended in methanol (45 mL) and 2N sodium hydroxide (100 mL), and stirred at 65° C. for two hours. The reaction mixture was concentrated and acidified to pH of 4, and then extracted with ethyl acetate (3×50 mL). The combined extract was washed with water (100 mL), brine solution (100 mL), dried over sodium sulfate, filtered and concentrated to give 2-[1-(4-chloro-3-nitrophenyl)ethenyl]benzoic acid (0.81 g, 2.7 mmol, 90% yield). $^1$H NMR (400 MHz, CDCl$_3$): 7.92-7.91 (d, 1H), 7.85-7.83 (dd 1H), 7.70-7.67 (d, 1H), 7.66-7.62 (dt, 1H), 7.54-7.50 (dt, 1H), 7.38-7.35 (m, 2H), 5.93 (s, 1H), 5.37 (s, 1H); MS (EI) for $C_{15}H_{10}ClNO_4$: 302 (M$^-$).

Benzotriazol-1-yl-oxy-tris(pyrrolidino)phosphonium-hexafluorophosphate (1.21 g, 2.6 mmol) was added to a mixture of 2-[1-(4-chloro-3-nitrophenyl)ethenyl]benzoic acid (0.78 g, 2.6 mmol) and diiosopropylethylamine (1.12 mL, 6.4 mmol) in DMF (2 mL) and stirred for 10 minutes followed by 3-aminobenzotrifluoroide (0.38 mL, 3.1 mol). The resulting mixture was stirred at room temperature for 18 hours, diluted with ethyl acetate (50 mL), washed with 30 mL each of 20% aqueous citric acid, saturated sodium bicarbonate, water then brine solution, dried over sodium sulfate, filtered and concentrated. The residue was purified by flash chromatography (silica gel, eluting with 5-15% ethyl acetate-hexane) to give 2-[1-(4-chloro-3-nitrophenyl)ethenyl]-N-[3-(trifluoromethyl)phenyl]benzamide (0.82 g, 1.8 mmol, 69% yield). $^1$H NMR (400 MHz, CDCl$_3$): 7.69-7.35 (m, 11H), 5.82 (s, 1H), 5.62 (s, 1H); MS (EI) for $C_{22}H_{14}ClF_3N_2O_3$: 447 (MH$^+$).

A mixture of 2-[1-(4-chloro-3-nitrophenyl)ethenyl]-N-[3-(trifluoromethyl)phenyl]benzamide (0.72 g, 1.6 mmol), sodium azide (3.1 g, 4.8 mmol) and N,N-dimethylformamide (2 mL) was stirred 60° C. for 18 hours. The reaction mixture was diluted with ethyl acetate (50 mL), washed with water (3×30 mL), brine (30 mL), dried over sodium sulfate, filtered and concentrated to give an oily residue. This residue was dissolved in tetrahydrofuran, cooled to 0° C. then sodium borohydride (0.11 g, 2.7 mmol) was added and stirring was continued for 30 minutes at room temperature. The reaction mixture was quenched with methanol (2 mL), concentrated then diluted with ethyl acetate (50 mL). The organic solution was washed with water (30 mL) then brine solution (30 mL)

then dried over sodium sulfate, filtered and concentrated. The residue was purified by flash chromatography (silica gel, eluting with 15-50% ethyl acetate-hexane) to give 2-[1-(4-amino-3-nitrophenyl)ethenyl]-N-[3-(trifluoromethyl)phenyl]benzamide (0.35 g, 0.8 mmol, 50% yield). MS (EI) for $C_{22}H_{16}F_3N_3O_3$: 428 (MH$^+$).

A mixture of 2-[1-(4-amino-3-nitrophenyl)ethenyl]-N-[3-(trifluoromethyl)phenyl]benzamide (0.35 g, 0.80 mmol) and iron powder (0.91 g, 164 mmol) in acetic acid (5 mL) was vigorously stirred at 50° C. for 2 hours. The reaction mixture was concentrated. Ice (ca. 30 g) and 50% sodium hydroxide solution was added until the pH was maintained basic. This mixture was extracted with ethyl acetate (3×20 mL), and the combined extract was washed with water (30 mL) then brine solution (30 mL) then dried over sodium sulfate, filtered and concentrated to give an oily residue. The residue was dissolved in acetic acid (5 mL) containing 1,3-bis(methoxycarbonyl)-2-methyl-2-thiopseudourea (0.17 g, 0.80 mmol) and stirred at 70° C. for 20 minutes. The reaction mixture was concentrated. Ice (ca. 20 g) and solid sodium bicarbonate was added until the pH was maintained basic. This mixture was extracted with ethyl acetate (3×20 mL), and the combined extract was washed with water (30 mL) then brine solution (30 mL), dried over sodium sulfate, filtered and concentrated to give an oily residue. The crude product was dissolved in ethyl acetate (30 mL), 10% palladium-charcoal (200 mg) was added and the resulting mixture was hydrogenated at 45 psi in a Parr Apparatus for 18 hours to consume any olefinic impurities which interfere with the subsequent purification process. The mixture was filtered, concentrated and the crude product was purified by preparative reverse phase HPLC (0.1% trifluoroacetic acid in acetonitrile-water eluent). The fractions containing pure product were concentrated then basified with sodium bicarbonate and extracted with ethyl acetate (150 mL). The extract was concentrated to give 82 mg of a white solid which was dissolved in acetonitrile (2 mL). To this solution was added hydrogen chloride in dioxane (43 uL, 4M, 1.6 mmol) and water (15 mL). The solution was lyophillized to give methyl(6-{1-methyl-3-oxo-2-[3-(trifluoromethyl)phenyl]-2,3-dihydro-1H-isoindol-1-yl}-1H-benzimidazol-2-yl)carbamate hydrochloride (88 mg, 0.17 mmol, 21% yield) $^1$H NMR (400 MHz, d$_6$-DMSO): 7.91-7.89 (d, 1H), 7.67-7.49 (m, 7H), 7.39-7.37 (d, 1H), 7.25-7.21 (m, 2H), 3.83 (s, 3H), 2.02 (s, 3H); MS (EI) for $C_{25}H_{19}F_3N_4O_3$: 481 (MH$^+$).

Using the same or analogous synthetic techniques and/or substituting with alternative reagents, the following compounds of the invention were prepared:
methyl{6-[2-(3-bromophenyl)-1-methyl-3-oxo-2,3-dihydro-1H-isoindol-1-yl]-1H-benzimidazol-2-yl}carbamate hydrochloride $^1$H NMR (400 MHz, d$_6$-DMSO): 7.89, 7.87 (d, 1H), 7.65-7.61 (dd, 1H), 7.57-7.54 (dd, 1H), 7.50-7.43 (m, 4H), 7.35-7.33 (d, 1H), 7.26-7.22 (dd, 1H), 7.14-7.10 (m, 1H), 6.93-6.91 (d, 1H), 3.81 (s, 3H), 1.99 (s, 3H); MS (EI) for $C_{24}H_{19}BrN_4O_3$: 491 (MH$^+$).

Example 22

N-{6-[2-(3-Chloro-2-fluorophenyl)-1-hydroxy-3-oxo-2,3-dihydro-1H-isoindol-1-yl]-1H-benzimidazol-2-yl}-2,2-difluorocyclopropanecarboxamide To a solution of 2-(4-chloro-3-nitrobenzoyl)benzoic acid (6.76 g, 22.00 mmol) in anhydrous dichloromethane (35 ml) at 0° C. pyridine (1.80 ml, 22.00 mmol) was added, followed by the dropwise addition of cyanuric fluoride (2.0 ml, 24.20 mmol) in dichloromethane (4.0 mL). The reaction mixture was stirred for 100 minutes at. 0° C. Water (35 mL) was added to the reaction mixture and it was stirred for 10 min at 0° C. The resulting slurry was filtered through a pad of Celite and it was washed with dichloromethane. The filtrate was partitioned with water and the dichloromethane layer was washed with water and it was dried over anhydrous sodium sulfate. Filtration and concentration provided 3-(4-chloro-3-nitrophenyl)-3-fluoro-2-benzofuran-1(3H)-one, (6.10 g, 90% yield) as a crystalline solid, which was used without further purification. $^1$H NMR (400 MHz, DMSO-d$_6$): 8.34 (d, J=2 Hz, 1H), 8.20 (dd, J$_1$=8 Hz, J$_2$=0.8 Hz, 1H), 8.01-7.94 (m, 3H), 7.86 (td, J$_1$=8 Hz, J$_2$=1.2 Hz, 1H), 7.72 (d, J=7.6 Hz, 1H); MS (EI) for $C_{14}H_7ClFNO_4$: 306 (M$^-$).

To a solution of 3-(4-chloro-3-nitrophenyl)-3-fluoro-2-benzofuran-1(3H)-one (6.10 g, 20.00 mmol) in 1,2-dichloroethane (40 mL) 2-fluoro-3-chloro aniline (3.50 g, 24.00 mmol) was added, followed by addition of N,N-dimethylaniline (3.90 mL, 32.00 mmol). The reaction mixture was stirred for 20 hours, at 70° C. The solvent was evaporated the and residue was dissolved in ethyl acetate (150 mL). It was washed with 20% citric acid (2×30 mL), water (50 mL), brine (50 mL), and dried over anhydrous sodium sulfate. Filtration and concentration provided a semisolid product, which was triturated with hexane (60 mL). The crystalline product was collected by filtration; it was dried in vacuo, to give 2-(3-chloro-2-fluorophenyl)-3-(4-chloro-3-nitrophenyl)-3-hydroxy-2,3-dihydro-1H-isoindol-1-one (7.23 g, 84% yield). $^1$H NMR (400 MHz, CD$_3$OD): 7.95 (d, J=1.2 Hz, 1H), 7.94 (s, 1H), 7.76-7.66 (m, 2H), 7.56 (d, J=8.8 Hz, 1H), 7.49-7.46 (m, 2H), 7.42 (d, J=1.2 Hz, 1H), 7.32 (td, J$_1$=6.8 Hz, J$_2$=1.6 Hz, 1H), 7.16 (td, J$_1$=8 Hz, J$_2$=1.2 Hz, 1H); MS (EI) for $C_{20}H_{11}Cl_2FN_2O_4$: 433 (M$^-$).

To a solution of 2-(3-chloro-2-fluorophenyl)-3-(4-chloro-3-nitrophenyl)-3-hydroxy-2,3-dihydro-1H-isoindol-1-one ((7.22 g, 17.00 mmol) in N,N-dimethylformamide (20 ml) sodium azide (1.80 g, 28.00 mmol) was added and the reaction mixture was stirred at 40° C. for 20 hours. It was cooled to room temperature, and poured into ice water. A light yellow product was precipitated and collected by filtration. It was washed with water and dried in vacuo to give 3-(4-azido-3-nitrophenyl)-2-(3-chloro-2-fluorophenyl)-3-hydroxy-2,3-dihydro-1H-isoindol-1-one (7.0 g, 95% yield). $^1$H NMR (400 MHz, CD$_3$OD): 7.97-7.93 (m, 2H), 7.74-7.65 (m, 2H), 7.51 (dd, J$_1$=8.4 Hz, J$_2$=2 Hz, 1H), 7.45-7.39 (m, 2H), 7.34 (td, J$_1$=8 Hz, J$_2$=1.2 Hz, 1H), 7.15 (td, J$_1$=8.4 Hz, J$_2$=1.6 Hz); MS (EI) for $C_{20}H_{11}ClFN_5O_4$: 438 (M$^-$).

To a solution of 3-(4-azido-3-nitrophenyl)-2-(3-chloro-2-fluorophenyl)-3-hydroxy-2,3-dihydro-1H-isoindol-1-one (7.0 g, 16.00 mmol) in a mixture tetrahydrofurane-water (1:1, 15.0 ml) ammonium formate (5.0 g, 79.30 mmol), was added followed by the addition of iron (4.0 g, 71.60 mmol). The reaction mixture was heated to reflux and stirred for 320 minutes. It was cooled to room temperature and diluted with ethyl acetate (70 mL). The resulting slurry was filtered through a pad of Celite and washed with ethyl acetate (3×30 mL). It was partitioned with water and the organic layer was washed with water (30 mL), brine (30 mL) and dried over anhydrous sodium sulfate. Filtration and concentration resulted in a yellow oily product. It was crystallized from diethyl ether by the addition of hexane. The product was collected by filtration, dried in vacuo, to provide 2-(3-chloro-2-fluorophenyl)-3-(3,4-diaminophenyl)-3-hydroxy-2,3-dihydro-1H-isoindol-1-one (3.42 g, 56% yield). $^1$H NMR (400 MHz, CD$_3$OD): 7.85 (d, J=7.6 Hz, 1H), 7.65-7.58 (m, 2H), 7.41-7.34 (m, 2H), 7.17 (t, J=6.4 Hz, 1H), 7.05 (t, J=8 Hz, 1H), 6.69 (s, 1H), 6.57 (s, 2H); MS (EI) for $C_{20}H_{15}ClFN_3O_2$: 382 (M$^-$).

To a solution of 2,2-difluorocyclopropanecarboxylic acid (0.5 g, 4.10 mmol) in dichloromethane (25 mL) pyridine (0.36 mL, 4.51 mmol) was added and the reaction mixture was cooled to 0° C. A solution of cyanuric fluoride (0.34 mL, 4.10 mmol) in dichloromethane (5.0 mL) was added dropwise and the mixture was stirred for 2 hours. Water (5.0 mL) was added and the stirring was continued for an additional 10 minutes. It was diluted with dichloromethane (100 mL) and the slurry was filtered through a pad of Celite. The filtrate was washed with water and brine, dried over anhydrous sulfate and the solvent was evaporated to result in 2,2-difluorocyclopropanecarbonyl fluoride (0.50 g, quantitative), which was used without further purification. To a suspension of 2-methyl-2-thiopseudourea sulfate (0.28 g, 2.65 mmol) in dichloromethane (5.0 mL) and pyridine (0.21 mL, 2.65 mmol) at 0° C. a solution of 2,2-difluorocyclopropanecarbonyl fluoride in dichloromethane (3.0 mL) was added and the reaction mixture was stirred for 15 hours at room temperature. Ethyl acetate (100 mL) was added into the mixture and it was washed with 1M aqueous hydrochloric acid and brine. The solvent was dried over anhydrous sodium sulfate and it was evaporated. The crude product was purified by silica gel flash chromatography (hexane:ethyl acetate 7:3 to 1:1 eluent) to give methyl N,N-bis[(2,2-difluorocyclopropyl)carbonyl]imidothiocarbamate (0.72 g, 59% yield). MS (EI) for $C_{10}H_{10}F_4N_2O_2S$: 299 (MH$^+$).

A solution of 2-(3-chloro-2-fluorophenyl)-3-(3,4-diaminophenyl)-3-hydroxy-2,3-dihydro-1H-isoindol-1-one (0.25 g, 0.65 mmol) and methyl N,N'-bis[(2,2-difluorocyclopropyl)carbonyl]imidothiocarbamate (0.21 g, 0.72 mmol) in n-butanol (2.0 mL) was heated to 80° C. for 5 hours. The reaction mixture was cooled to room temperature and the solvent was evaporated. The resulting crude product was purified by reverse phase preparative HPLC (acetonitrile/25 mM aqueous ammonium acetate eluent). The fractions were collected, and the solvent was concentrated. The residue was partitioned with ethyl acetate. The organic layer was washed with saturated aqueous sodium bicarbonate and brine, dried over anhydrous sodium sulfate. Filtration and concentration resulted in a pale yellow oily residue, which was freeze-dried from a mixture of acetonitrile-water (5.0 mL) to give N-{6-[2-(3-chloro-2-fluorophenyl)-1-hydroxy-3-oxo-2,3-dihydro-1H-isoindol-1-yl]-1H-benzimidazol-2-yl}-2,2-difluorocyclopropanecarboxamide (48 mg, 38% yield). $^1$H NMR (400 MHz, DMSO-d$_6$): 12.18 (s, 1H), 7.88 (m, 1H), 7.75 (s, 1H), 7.63 (m, 2H), 7.48 (m, 1H), 7.30 (m, 3H), 7.16 (m, 1H), 6.93 (m, 1H), 2.92 (m, 1H), 2.09 (m, 2H); MS (EI) for $C_{25}H_{16}ClF_3N_4O_3$: 513 (MH$^+$).

Using the same or analogous synthetic techniques and/or substituting with alternative reagents, the following compounds of the invention were prepared:

N-(5-{1-hydroxy-3-oxo-2-[3-(phenyloxy)phenyl]-2,3-dihydro-1H-isoindol-1-yl}-1H-benzimidazol-2-yl)-4-piperidin-1-ylbutanamide hydrochloride: $^1$H NMR (400 MHz, d$_6$-DMSO): 10.03 (s, 1H), 7.84 (d, 1H), 7.78 (br s, 1H), 7.64-7.55 (m, 3H), 7.41 (d, 1H), 7.32-7.25 (m, 4H), 7.20 (s, 1H), 7.11-7.07 (m, 2H), 6.81-6.75 (m, 3H), 3.44-3.35 (m, 4H), 3.08-3.01 (m, 2H), 2.92-2.79 (m, 2H), 2.66-2.60 (m, 2H), 2.11-2.19 (m, 2H), 1.83-1.65 (m, 4H); MS (EI) for $C_{36}H_{35}N_5O_5$: 602 (MH$^+$).

cyclobutyl{6-[2-(3-chloro-2-fluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.96-7.94 (b, 1H), 7.91-7.89 (d, 1H), 7.71-7.60 (m, 2H), 7.54-7.50 (m, 1H), 7.44-7.42 (m, 1H), 7.39-7.35 (t, 1H), 7.32-7.30 (m, 1H), 7.22-7.13 (m, 2H), 5.08-5.01 (m, 1H), 2.40-2.30 (m, 2H), 2.18-2.08 (m, 2H), 1.85-1.76 (m, 1H), 1.70-1.61 (m, 1H); MS (EI) for $C_{26}H_{20}ClFN_4O_4$: 517 (MH$^+$).

2,2-difluoroethyl{6-[2-(3-chloro-2-fluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 7.94-7.92 (b, 1H), 7.88-7.87 (d, 1H), 7.67-7.60 (m, 2H), 7.58-7.56 (b, 1H), 7.50-7.44 (dd, 1H), 7.41-7.39 (d, 1H), 7.37-7.33 (d, 1H), 7.30-7.28 (d, 1H), 7.19-7.15 (dd, 1H), 7.12-7.10 (d, 1H), 6.48-6.19 (tt, 1H), 4.55-4.47 (dt, 2H); MS (EI) for $C_{24}H_{16}ClF_3N_4O_4$: 517 (MH$^+$).

but-2-yn-1-yl{5-[2-(4-fluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 11.70 (broad s, 1H), 7.84 (dd, 1H), 7.58 (m, 3H), 7.47 (m, 2H), 7.28 (d, 1H), 7.24 (d, 1H), 7.13 (m, 2H), 6.95 (dd, 1H), 4.77 (m, 2H), 1.85 (3H); MS (EI) for $C_{26}H_{19}N_4O_4F$: 471 (MH$^+$).

(1-methylpiperidin-2-yl)methyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.87 (d, 1H), 7.66 (7.64 (m, 2H), 7.49 (t, 1H), 7.43 (broad s, 1H), 7.33 (m, 2H), 7.23 (d, 1H), 7.17 (t, 1H), 6.92 (d, 1H), 4.19 (m, 2H), 2.76 (d, 1H), 2.23 (s, 3H), 2.06 (m, 2H), 1.70 (m, 2H), 1.20-1.51 (m, 4H); MS (EI) for $C_{29}H_{27}N_5O_4ClF$: 564 (MH$^+$).

[(2S)-1-methylpyrrolidin-2-yl]methyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.87 (d, 1H), 7.64 (m, 2H), 7.49 (t, 1H), 7.45 (broad s, 1H), 7.31 (m, 2H), 7.24 (d, 1H), 7.17 (t, 1H), 6.91 (d, 1H), 4.09 (d, 2H), 2.93 (m, 1H), 2.45 (m, 1H), 2.32 (s, 3H), 2.16 (q, 1H), 1.56-1.67 (m, 4H); MS (EI) for $C_{28}H_{25}N_5O_4ClF$: 550 (MH$^+$).

octahydro-2H-quinolizin-1-ylmethyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.87 (d, 1H), 7.73 (broad s, 1H), 7.64 (m, 2H), 7.49 (t, 1H), 7.43 (broad s, 1H), 7.32 (m, 2H), 7.23 (d, 1H), 7.17 (t, 1H), 6.91 (d, 1H), 4.32 (m, 2H), 2.73 (d, 2H), 1.19-1.91 (m, 13H); MS (EI) for $C_{32}H_{31}N_5O_4ClF$: 604 (MH$^+$).

1-methylethyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.87 (d, 1H), 7.73 (s, 1H), 7.65 (m, 2H), 7.49 (m, 2H), 7.31 (m, 2H), 7.24 (d, 1H), 7.18 (dt, 1H), 6.91 (dd, 1H), 6.57 (s, open), 4.95 (m, 1H), 1.27 (d, 6H); MS (EI) for $C_{25}H_{20}N_4O_4ClF$: 495 (MH$^+$).

cyclopropylmethyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.86 (d, 1H), 7.73 (s, 1H), 7.63 (m, 2H), 7.39 (m, 2H), 7.31 (m, 2H), 7.24 (d, 1H), 7.17 (t, 1H), 6.91 (d, 1H), 6.56 (s, open), 3.99 (d, 2H), 1.15 (m, 1H), 0.54 (m, 2H), 0.32 (m, 2H)); MS (EI) for $C_{26}H_{20}N_4O_4ClF$: 507 (MH$^+$).

tetrahydrofuran-2-ylmethyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.87 (d, 1H), 7.73 (s, 1H), 7.63 (m, 2H), 7.48 (m, 2H), 7.33 (m, 2H), 7.24 (d, 1H), 7.17 (dt, 1H), 6.91 (d, 1H), 6.56 (s, open), 4.10 (m, 2H), 3.76 (m, 1H), 3.65 (m, 1H), 1.79-1.99 (m, 3H), 1.61 (m, 1H); MS (EI) for $C_{27}H_{22}N_4O_5ClF$: 537 (MH$^+$).

(1-methylpiperidin-4-yl)methyl{5-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, d$_6$-DMSO): 7.88 (d, 1H), 7.68 (dd, 1H), 7.63 (dd, 1H), 7.55 (s, 1H), 7.48 (dd, 1H), 7.39 (d, 1H), 7.35 (dd, 1H), 7.28 (d, 1H), 7.17 (dd, 1H), 7.09 (d, 1H), 4.09 (d, 2H), 3.41 (d, 2H), 2.91 (t, 2H), 2.74 (s, 3H), 1.40 (q, 2H); MS (EI) for $C_{29}H_{27}ClFN_5O_4$: 564 (MH$^+$).

2-(1-methylpiperidin-4-yl)ethyl{5-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.88 (d, 1H), 7.84 (s, 1H), 7.67 (dd, 1H), 7.62 (dd, 1H), 7.55 (s, 1H), 7.50 (dd, 1H), 7.37-7.30 (m, 3H), 7.17 (dd, 1H), 7.03 (d, 1H), 4.35 (t, 2H), 3.41 (d, 2H), 2.87 (t, 1H), 1.89 (d, 2H), 1.64 (m, 4H), 1.37 (m, 2H); MS (EI) for $C_{30}H_{29}ClFN_5O_4$: 577 (MH$^+$).

2,2,3,3-tetrafluorocyclobutyl{5-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, CDCl$_3$): 7.85 (d, 1H), 7.72 (s, 1H), 7.55-749 (m, 2H), 7.37 (d, 1H), 7.24-7.18 (m, 3H), 7.08 (dd, 1H), 6.89 (dd, 1H), 5.20 (m, 1H), 2.98 (m, 1H), 2.79 (m, 1H); MS (EI) for $C_{26}H_{16}ClF_5N_4O_4$: 579 (MH$^+$)

1-acetyl-N-{5-[2-(3-chloro-2-fluorophenyl)-1-hydroxy-3-oxo-2,3-dihydro-1H-isoindol-1-yl]-1H-benzimidazol-2-yl}piperidine-4-carboxamide: $^1$H NMR (400 MHz, $d_6$-DMSO): 7.89 (d, 1H), 7.86 (s, 1H), 7.67 (dd, 1H), 7.63 (dd, 1H), 7.57 (s, 1H), 7.50 (dd, 1H), 7.38 (d, 1H), 7.33 (dd, 1H), 7.30 (d, 1H), 7.17 (dd, 1H), 7.05 (d, 1H), 3.08 (m, 1H), 2.75 (m, 1H), 2.62 (m, 1H), 1.87 (t, 2H), 1.59 (q, 2H), 1.44 (q, 2H); MS (EI) for $C_{29}H_{25}ClFN_5O_4$: 562 (MH$^+$).

N-{5-[2-(3-chloro-2-fluorophenyl)-1-hydroxy-3-oxo-2,3-dihydro-1H-isoindol-1-yl]-1H-benzimidazol-2-yl}cyclobutanecarboxamide: $^1$H NMR (400 MHz, CDCl$_3$): 8.23 (s, 1H), 7.96 (d, 1H), 7.63-7.52 (m, 4H), 7.34 (d, 1H), 7.13 (d, 1H), 7.08 (dd, 1H), 6.95 (m, 1H), 6.89 (m, 1H), 3.35 (m, 1H), 2.37 (m, 2H), 1.97 (m, 2H), 0.86 (m, 2H); MS (EI) for $C_{26}H_{20}ClFN_4O_3$: 491 (MH$^+$).

N-{5-[2-(3-chloro-2-fluorophenyl)-1-hydroxy-3-oxo-2,3-dihydro-1H-isoindol-1-yl]-1H-benzimidazol-2-yl}cyclopropanecarboxamide: $^1$H NMR (400 MHz, $d_6$-DMSO): 12.34 (s, 1H), 7.89 (d, 1H), 7.84 (s, 1H), 7.67 (dd, 1H), 7.62 (dd, 1H), 7.56 (s, 1H), 7.50 (dd, 1H), 7.38-7.30 (m, 3H), 7.18 (dd, 1H), 7.03 (d, 1H), 1.96 (m, 1H), 0.95 (m, 4H); MS (EI) for $C_{25}H_{18}ClFN_4O_4$: 477 (MH$^+$).

2-(methyloxy)ethyl{5-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.87 (d, 1H), 7.67 (dd, 1H), 7.62 (dd, 1H), 7.57 (s, 1H), 7.46 (dd, 1H), 7.40 (d, 1H), 7.31 (dd, 1H), 7.27 (d, 1H), 7.15 (dd, 1H), 7.09 (d, 1H), 4.31 (m, 2H), 3.57 (m, 2H), 3.24 (s, 3H); MS (EI) for $C_{25}H_{20}ClFN_4O_5$: 511 (MH$^+$).

N-{5-[2-(3-chloro-2-fluorophenyl)-1-hydroxy-3-oxo-2,3-dihydro-1H-isoindol-1-yl]-1H-benzimidazol-2-yl}-2-(2-thienyl)acetamide: $^1$H NMR (400 MHz, $d_6$-DMSO): 7.86 (d, 1H), 7.66 (dd, 1H), 7.62 (dd, 1H), 7.62 (dd, 1H), 7.55 (s, 1H), 7.46 (dd, 1H), 7.38 (m, 1H), 7.32-7.26 (m, 2H), 7.14 (dd, 1H), 7.04 6.96 (m, 3H), 4.02 (s, 2H); MS (EI) for $C_{27}H_{18}ClFN_4O_3S$: 533 (MH$^+$).

N-{5-[2-(3-chloro-2-fluorophenyl)-1-hydroxy-3-oxo-2,3-dihydro-1H-isoindol-1-yl]-1H-benzimidazol-2-yl}-N,N-diethylpentanediamide: $^1$H NMR (400 MHz, CDCl$_3$): 7.97 (d, 1H), 7.84 (s, 1H), 7.67 (m, 4H), 7.46 (d, 1H), 7.30 (m, 1H), 6.79 (dd, 1H), 6.91 (dd, 1H), 3.34 (m, 4H), 2.71 (t, 2H), 2.08 (m, 2H), 1.21 (t, 3H), 1.09 (t, 3H); MS (EI) for $C_{30}H_{29}ClFN_5O_4$: 578 (MH$^+$).

N-{6-[2-(4-fluorophenyl)-1-hydroxy-3-oxo-2,3-dihydro-1H-isoindol-1-yl]-1H-benzimidazol-2-yl}butanamide: MS (EI) for $C_{25}H_{21}N_4O_3F$: 445 (MH$^+$).

N-{6-[2-(4-fluorophenyl)-1-hydroxy-3-oxo-2,3-dihydro-1H-isoindol-1-yl]-1H-benzimidazol-2-yl}propanamide: $^1$H NMR (400 MHz, $d_6$-DMSO): 11.53 (broad s, 1H), 7.84 (d, 1H), 7.63-7.55 (m, 3H), 7.48 (m, 2H), 7.28 (d, 2H), 7.10 (t, 2H), 6.96 (d, 1H), 2.43 (q, 2H), 1.09 (t, 3H); MS (EI) for $C_{24}H_{19}N_4O_3F$: 431 (MH$^+$).

N-{6-[2-(4-fluorophenyl)-1-hydroxy-3-oxo-2,3-dihydro-1H-isoindol-1-yl]-1H-benzimidazol-2-yl}peny-4-ynamide: $^1$H NMR (400 MHz, $d_6$-DMSO): 12.04 (broad s, 1H), 11.60 (s, 1H), 7.85 (d, 1H), 7.45-7.63 (m, 5H), 7.28 (d, 2H), 7.11 (t, 2H), 6.95 (d, 1H), 2.82 (s, 1H), 2.63 (t, 2H); MS (EI) for $C_{26}H_{19}N_4O_3F$: 455 (MH$^+$).

(1-methylpiperidin-3-yl)methyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.87 (d, 1H), 7.74 (s, 1H), 7.64 (m, 2H), 7.48 (m, 2H), 7.32 (q, 2H), 7.24 (d, 1H), 7.17 (t, 1H), 6.92 (d, 1H), 4.06 (q, 1H), 3.99 (q, 1H), 2.73 (d, 1H), 2.62 (d, 1H), 2.50 (m, 3H), 2.15 (s, 4H), 1.91 (s, 1H), 1.76 (m, 2H), 1.46 (m, 1H), 0.99 (m, 1H); MS (EI) for $C_{29}H_{27}N_5O_4FCl$: 565 (MH$^+$).

8-azabicyclo[3.2.1]oct-3-ylmethyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.87 (d, 1H), 7.64 (m, 2H), 7.46 (m, 2H), 7.32 (m, 2H), 7.24 (d, 1H), 7.16 (t, 1H), 6.92 (d, 1H), 4.16 (d, 2H), 3.47 (s, 2H), 2.05 (m, 1H), 1.92 (m, 2H), 1.83 (s, 3H), 1.77 (m, 1H), 1.67 (d, 1H), 1.42 (d, 1H); MS (EI) for $C_{30}H_{27}N_5O_4FCl$: 577 (MH$^+$).

4-(diethylamino)but-2-yn-1-yl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.87 (d, 1H), 7.75 (s, 1H), 7.62 (m, 2H), 7.49 (t, 1H), 7.44 (s, 1H), 7.31 (m, 2H), 7.24 (d, 1H), 7.17 (t, 1H), 6.93 (d, 1H), 4.83 (s, 2H), 3.40 (s, 4H), 2.43 (q, 3H), 1.90 (s, 1H), 0.94 (t, 5H); MS (EI) for $C_{30}H_{27}N_5O_4FCl$: 576 (MH$^+$).

2-(2-oxopyrrolidin-1-yl)ethyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.90 (t, 1H), 7.64-7.77 (m, 3H), 7.51 (m, 2H), 7.19-7.35 (m, 3H), 6.96 (t, 1H), 4.27 (q, 2H), 3.46 (m, 5H), 2.22 (q, 1H), 1.92 (m, 2H); MS (EI) for $C_{28}H_{23}N_5O_5FCl$: 565 (MH$^+$).

2-(2,5-dioxopyrrolidin-1-yl)ethyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.86 (d, 1H), 7.56-7.68 (m, 2H), 7.47 (m, 2H), 7.31 (d, 2H), 7.24 (d, 1H), 7.17 (t, 1H), 6.93 (d, 1H), 4.25 (t, 2H), 3.68 (t, 2H), 2.61 (s, 3H), 1.88 (s, 1H); MS (EI) for $C_{28}H_{21}N_5O_6FCl$: 577 (MH$^+$).

cyclobutylmethyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.85 (d, 1H), 7.71 (s, 1H), 7.59-7.66 (m, 2H), 7.46 (m, 2H), 7.29 (m, 2H), 7.22 (d, 1H), 7.15 (t, 1H), 6.89 (d, 1H), 4.11 (d, 2H), 3.40 (d, 1H), 3.30 (d, 1H), 2.60 (m, 1H), 1.73-1.89 (m, 4H); MS (EI) for $C_{27}H_{22}N_4O_4FCl$: 521 (MH$^+$).

2,2,2-trifluoroethyl{6-[2-(3-chloro-2-fluorophenyl)-1-hydroxy-3-oxo-2,3-dihydro-1H-isoindol-1-yl]-1H-benzimidazol-2-yl}carbamate: MS (EI) for $C_{24}H_{15}N_4O_4F_4Cl$: 534 (MH$^+$).

ethyl{6-[2-(3-chloro-2-fluorophenyl)-1-hydroxy-3-oxo-2,3-dihydro-1H-isoindol-1-yl]-1H-benzimidazol-2-yl}carbamate. $^1$H NMR (400 MHz, DMSO-$d_6$): 11.62 (s, 1H), 7.86 (d, 1H), 7.73 (s, 1H), 7.64 (m, 2H), 7.44 (m, 2H), 7.33 (t, 1H), 7.30 (d, 1H), 7.23 (d, 1H), 7.16 (t, 1H), 6.91 (d, 1H), 4.20 (dd, 2H), 1.25 (t, 1H); MS (EI) for $C_{24}H_{18}ClFN_4O_4$: 481 (MH$^+$).

2-fluoroethyl{6-[2-(3-chloro-2-fluorophenyl)-1-hydroxy-3-oxo-2,3-dihydro-1H-isoindol-1-yl]-1H-benzimidazol-2-yl}carbamate. $^1$H NMR (400 MHz, DMSO-d$_6$): 11.72 (s, 1H), 7.86 (d, 1H), 7.75 (s, 1H), 7.63 (m, 2H), 7.49 (m, 1H), 7.45 (s, 1H), 7.33 (t, 1H), 7.30 (d, 1H), 7.24 (d, 1H), 7.17 (t, 1H), 6.92 (d, 1H), 4.73 (dd, 1H), 4.61 (dd, 1H), 4.43 (dd, 1H), 4.36 (dd, 1H); MS (EI) for C$_{24}$H$_{17}$ClF$_2$N$_4$O$_4$: 481 (MH$^+$).

Example 23

Methyl(5-{[2-({[(phenylmethyl)oxy]carbonyl}amino)phenyl]carbonyl}-1H-benzimidazol-2-yl)carbamate A solution of [5-(2-benzylcarbanoyl-benzoyl)-1H-benzoimidazol-2-yl]-carbamic acid methyl ester (21.4 g, 49.8 mmol) in tetrahydrofuran (150 mL) was cooled in an ice bath. To the solution was added di-tert-butyl dicarbonate (33 g, 150 mmol). This was followed by the drop wise addition of a solution of N,N-dimethylaminopyridine (6.1 g, 50 mmole) and Hunig's base (8.7 mL, 50 mmol) in tetrahydrofuran (80 mL). The solution was stirred at 0° C. for 40 minutes, then quenched by pouring over crushed ice and hydrochloric acid 1N (2:1). The mixture was partition and extracted using diethyl ether (200 mL). The organic portion was washed with water, saturated sodium bicarbonate, dried over sodium sulfate, filtered and concentrated in-vacuo. The resultant residue was purified by column chromatography (silica gel, ethyl acetate/hexanes). The isolated product was concentrated in-vacuo to afford, 25 g, 40 mmol (80%) of a colorless oil, which was diluted in ethyl acetate (150 mL). To the solution was added catalytic Palladium on carbon (wet 5%), and the solution was stirred under 1 atmosphere of hydrogen gas at ambient temperature for 18 hr. The solution was filtered through Celite and concentrated in-vacuo to afford 24 g, 39 mmol (95%) of a pale yellow oil, which was diluted in dichloromethane (150 mL) and cooled to 0° C. To the solution was added pyridine (3.6 ml, 39 mmol) followed by the drop wise addition of cyanuric fluoride (6.6 g, 49 mmol). The solution was stirred at ambient temperatures for 3 hr, and then was quenched by adding water (25 mL). The mixture was stirred at ambient temperatures for 30 minutes. The mixture was filtered through celite and washed with dichloromethane (2×50 mL). The filtrate was partitioned and the organic portion was washed with ice-cold 0.5N hydrochloric acid, water and brine, dried over sodium sulfate, and filtered through a silica gel plug column. The product was isolated and concentrated in-vacuo to afford 16.9 g, 31 mmol (62% over 3 steps) of a white solid, of which (500 mg, 0.92 mmol) was dissolved in dichloromethane (10 mL). Sodium azide (600 mg, 9.23 mmol) was added to the solution, which was then stirred at ambient temperature for 15 hrs. The mixture was partitioned between water and ethyl acetate. The aqueous portion was extracted twice with ethyl acetate. The combined organic portions were washed with brine, dried over sodium sulfate, filtered and concentrated in-vacuo to afford, 520 mg, 0.92 mmol (100%) of a white solid, to which (120 mg, 0.212 mmol) was dissolved in toluene (3 mL). Benzyl alcohol (190 μl, 1.85 mmol), was added to the solution, and the solution was stirred at 105° C. for 4 hours. The solution was cooled to room temperature and partitioned between water and ethyl acetate. The organic portion was washed with brine, dried over sodium sulfate, filtered and concentrated in-vacuo to afford a yellow oil which was purified by column chromatography (silica gel, 20-40% ethyl acetate in hexanes). The product was isolated and concentrated in-vacuo to afford 300 mg, 0.46 mmol (50%) of a colorless solid, to which (40 mg, 0.06 mmol) was then dissolved in dichloromethane (1 mL). To the solution was added trifluoroacetic acid (100 μl) and the solution was stirred at room temperature for 30 minutes, then partition between saturated sodium bicarbonate and dichloromethane. The organic portion was washed with brine, dried over sodium sulfate, filtered and concentrated in-vacuo to afford a white solid, which was recrystallized from ethyl acetate/hexanes. The solid was collected by vacuum filtration to afford 6 mg, 0.01 mmol (22%) of methyl(5-{[2-({[(phenylmethyl)oxy]carbonyl}amino)phenyl]carbonyl}-1H-benzimidazol-2-yl)carbamate as a white solid. $^1$H NMR (400 MHz, d$_6$-DMSO): 9.67 (s, 1H), 7.79 (br s, 1H), 7.65-7.62 (m, 1H), 7.58-7.54 (m, 1H), 7.50-7.43 (m, 3H), 7.30-7.26 (m, 4H), 7.20-7.17 (m, 2H), 4.97 (s, 2H), 3.77 (s, 3H); MS (EI) for C$_{24}$H$_{20}$N$_4$O$_5$: 445 (MH$^+$).

Example 24

Methyl{5-[(2-{[(phenylamino)carbonyl]amino}phenyl)carbonyl]-1H-benzimidazol-2-yl}carbamate A solution of [5-(2-benzylcarbanoyl-benzoyl)-1H-benzoimidazol-2-yl]-carbamic acid methyl ester (21.4 g, 49.8 mmol) in tetrahydrofuran (150 mL) was cooled in an ice bath. To the solution was added di-tert-butyl dicarbonate (33 g, 150 mmol). This was followed by the drop wise addition of a solution of N,N-dimethylaminopyridine (6.1 g, 50 mmole) and Hunig's base (8.7 mL, 50 mmol) in tetrahydrofuran (80 mL). The solution was stirred at 0° C. for 40 minutes, then quenched by pouring over crushed ice and hydrochloric acid 1N (2:1). The mixture was partition and extracted using diethyl ether (200 mL). The organic portion was washed with water, saturated sodium bicarbonate, dried over sodium sulfate, filtered and concentrated in-vacuo. The resultant residue was purified by column chromatography (silica gel, ethyl acetate/hexanes). The isolated product was concentrated in-vacuo to afford, 25 g, 40 mmol (80%) of a colorless oil, which was diluted in ethyl acetate (150 mL). To the solution was added catalytic Palladium on carbon (wet 5%), and the solution was stirred under 1 atmosphere of hydrogen gas at ambient temperature for 18 hr. The solution was filtered through Celite and concentrated in-vacuo to afford 24 g, 39 mmol (95%) of a pale yellow oil, which was diluted in dichloromethane (150 mL) and cooled to 0° C. To the solution was added pyridine (3.6 ml, 39 mmol) followed by the drop wise addition of cyanuric fluoride (6.6 g, 49 mmol). The solution was stirred at ambient temperatures for 3 hr, and then was quenched by adding water (25 mL). The mixture was stirred at ambient temperatures for 30 minutes. The mixture was filtered through celite and washed with dichloromethane (2×50 mL). The filtrate was partitioned and the organic portion was washed with ice-cold 0.5N hydrochloric acid, water and brine, dried over sodium sulfate, and filtered through a silica gel plug column. The product was isolated and concentrated in-vacuo to afford 16.9 g, 31 mmol (62% over 3 steps) of a white solid, of which (500 mg, 0.92 mmol) was dissolved in dichloromethane (10 mL). Sodium azide (600 mg, 9.23 mmol) was added to the solution, which was then stirred at ambient temperature for 15 hrs. The mixture was partitioned between water and ethyl acetate. The aqueous portion was extracted twice with ethyl acetate. The combined organic portions were washed with brine, dried over sodium sulfate, filtered and concentrated in-vacuo to afford, 520 mg, 0.92 mmol (100%) of a white solid, to which (120 mg, 0.212 mmol) was dissolved in toluene (3 mL). Aniline (30 μl, 0.32 mmol) was added to solution, which was then stirred at 105° C. for 4 hours. The solution was then cooled to room temperature and partitioned between water and ethyl acetate. The organic portion was washed with 20% aqueous citric acid, brine, sodium bicarbonate, brine, dried over sodium sulfate, filtered and concentrated in-vacuo to afford a yellow residue which was purified by column chromatography (silica gel, 35% ethyl acetate in hexanes). The product was isolated and concentrated in-vacuo to afford 50 mg, 0.07 mmol of a yellow solid, which was immediately dissolved in dichloromethane (2 mL). To the solution was added trifluoroacetic acid (100 µl) and the solution was stirred at ambient temperature for 20 minutes, then concentrated in-vacuo to afford a yellow solid which was purified by reverse phase HPLC (acetonitrile/water, 0.1% TFA eluent) to give methyl{5-[(2-{[(phenylamino)carbonyl]amino}phenyl)carbonyl]-1H-benzimidazol-2-yl}carbamate trifluoroacetate. $^1$H NMR (400 MHz, d$_6$-DMSO): 10.11 (s, 1H), 7.57-7.37 (m, 4H), 7.25-7.20 (m, 2H), 7.15-7.02 (m, 3H), 7.02 (d, 3H), 6.83-6.80 (m, 1H), 6.76-6.75 (m, 1H), 3.83 (s, 3H); MS (EI) for $C_{23}H_{19}N_5O_4$: 430 (MH$^+$).

Example 25

Methyl{5-[2-(3-ethynyl-2-fluorophenyl)-3-oxo-2,3-dihydro-1H-isoindol-1-yl]-1H-benzimidazol-2-yl}carbamate A solution of 2-[(4-amino-3-nitrophenyl)carbonyl]benzoic acid (10 g, 35 mmol) in DMF (50 mL) was treated with cesium carbonate (23 g, 70 mmol) followed by iodomethane (2.2 mL, 35 mmol). The mixture was stirred at rt for 1 h, after which time 50 mL of water was added. A yellow precipitate formed. The solid was collected by filtration, rinsed with water, and dried in vacuo. Desired methyl 2-[(4-amino-3-nitrophenyl)carbonyl]benzoate was obtained as a yellow solid (8.36 g, 27.8 mmol, 80% yield). $^1$H NMR (400 MHz, d$_6$-DMSO): 8.12 (br s, 2H), 8.10 (d, 1H), 7.78-7.75 (m, 2H), 7.70 (m, 1H), 7.48 (dd, 1H), 7.10 (d, 1H), 3.64 (s, 3H); MS (EI) for $C_{15}H_{12}N_2O_5$: 323 (MNa$^+$).

To a solution of 2-[(4-amino-3-nitrophenyl)carbonyl]benzoate (8.36 g, 27.8 mmol) in THF (100 mL) and methanol (30 mL) at 0° C. was added sodium borohydride (3.0 g, 79 mmol). The mixture was stirred for 40 min, and then unreacted hydride was quenched with 10% aqueous citric acid. The organic solvents were removed in vacuo. An orange solid precipitated from the resulting aqueous mixture. This solid was collected by filtration, rinsed with water, triturated with ether, and dried in vacuo. Desired 3-(4-amino-3-nitrophenyl)-2-benzofuran-1(3H)-one was obtained as a bright orange solid (5.23 g, 19.4 mmol, 69% yield). $^1$H NMR (400 MHz, d$_6$-DMSO): 8.03 (d, 1H), 7.90 (d, 1H), 7.76 (t, 1H), 7.65-7.60 (m, 3H), 7.45 (d, 1H), 7.11 (dd, 1H), 6.99 (d, 1H), 6.66 (s, 1H); MS (EI) for $C_{14}H_{10}N_2O_4$: 303 (MNa$^+$).

To a solution of 3-(4-amino-3-nitrophenyl)-2-benzofuran-1(3H)-one (1.0 g, 3.7 mmol) in NMP (6 mL) was added 3-ethynyl-2-fluoroaniline hydrochloride (1.9 g, 11.1 mmol). The mixture was heated to 150° C. for 2.25 h, and then the temperature was raised to 170° C. for a further 45 min. After cooling to rt, water and brine were added, and the resulting aqueous mixture was extracted twice with ethyl acetate. The organic extracts were dried over magnesium sulfate, filtered, and pre-absorbed on silica gel. The residue was run through a column, eluting with 60% hexanes and 40% ethyl acetate. The product-containing fractions were combined and concentrated. The resulting brown sticky film was not pure. This material was dissolved in acetic acid, and to this solution was added tin(II) chloride dihydrate (4.2 g, 18.5 mmol). The mixture was then heated to 80° C. for 1.5 h. After cooling to rt, the acetic acid was removed in vacuo. The residue was transferred to a 500-mL erlenmeyer flask in a minimal amount of ethyl acetate. The resulting suspension was then diluted with approximately 200 mL of ether, and then the flask was placed into an ice bath. To the vigorously stirring mixture was added 50% aqueous sodium hydroxide (20 mL), and a pale yellow solid formed. Celite and sodium sulfate were added to adsorb the precipitate and dry the mixture. The solids were removed by filtration and rinsed twice with hot ethyl acetate. The organic filtrates were combined and concentrated. The crude residue was dissolved in acetic acid (10 mL) and treated with 1,3-bis(methoxycarbonyl)-2-methyl-2-thiopseudourea (565 mg, 2.7 mmol) at 80° C. for 25 min. After cooling to rt, the acetic acid was removed in vacuo. The residue was purified by HPLC. The product containing fractions were combined, and sufficient saturated sodium bicarbonate was added to make the pH >7. The organic solvents were removed in vacuo, and the resulting aqueous mixture was extracted with ethyl acetate. The organic extracts were dried over magnesium sulfate, filtered, and concentrated. The residue was taken up in a minimal amount of ethyl acetate and 1 equiv of hydrochloric acid was added (4 N in dioxane). A white precipitate formed, and it was collected by filtration. The material was dried in vacuo yielding methyl{5-[2-(3-ethynyl-2-fluorophenyl)-3-oxo-2,3-dihydro-1H-isoindol-1-yl]-1H-benzimidazol-2-yl}carbamate hydrochloride (202 mg, 0.46 mmol) as a white solid. $^1$H NMR (400 MHz, DMSO-d$_6$): 7.90 (d, 1H), 7.66-7.57 (m, 3H), 7.67-7.54 (m, 3H), 7.41 (m, 1H), 7.31-7.26 (m, 3H), 7.21 (t, 1H), 6.88 (d, 1H), 6.50 (s, 1H), 4.56 (s, 1H), 3.73 (s, 3H); MS (EI) for $C_{25}H_{17}FN_4O_3$: 441 (MH$^+$).

Using the same or analogous synthetic techniques and/or substituting with alternative reagents, the following compounds of the invention were prepared:
methyl{5-[2-(3-bromophenyl)-3-oxo-2,3-dihydro-1H-isoindol-1-yl]-1H-benzimidazol-2-yl}carbamate: $^1$H NMR (400 MHz, d$_6$-DMSO): δ 8.07 (m, 1H), 7.88 (d, 1H), 7.67-7.54 (m, 3H), 7.33-7.26 (m, 5H), 7.01 (br d, 1H), 6.71 (s, 1H), 3.73 (s, 3H); MS (EI) for $C_{23}H_{17}BrN_4O_3$: 477, 479 (MH$^+$).

Example 26

2-(Diethylamino)ethyl{5-[2-(3-chloro-2-fluorophenyl)-1-hydroxy-3-oxo-2,3-dihydro-1H-isoindol-1-yl]-1H-benzimidazol-2-yl}carbamate To a solution of 4-nitrophenyl chloroformate (1.90 g, 9.42 mmol) in diethyl ether (10 mL) at 0° C. was added a dilute solution of N,N-diethylethanolamine (1.20 mL, 8.97 mmol) in diethyl ether (5 mL). The reaction mixture was immediately allowed to warm to room temperature and stirred for 12 h. The white precipitate was collected by filtration and washed with diethyl ether then dried in vacuo to afford 2-(diethylamino)ethyl-4-nitrophenylcarbonate hydrochloride (2.3 g, 77%). $^1$H NMR (400 MHz, CDCl$_3$): 8.28 (d, 2H), 7.43 (d, 2H), 4.86-4.83 (d, 2H), 3.49-3.43 (m, 2H), 3.31-3.15 (br m, 4H), 1.45 (t, 6H); MS (EI) for $C_{13}H_{18}N_2O_5$: 283 (MH$^+$).

To a suspension of 2-(diethylamino)ethyl-4-nitrophenylcarbonate hydrochloride (275 mg, 0.862 mmol) and 2-methyl-2-thiopseudourea sulfate (120 mg, 0.862 mmol) in acetonitrile (5 mL) was slowly added triethylamine (365 µL, 2.58 mmol) at room temperature. The reaction mixture was heated to 50° C. and stirred for 16 h, at which time it was concentrated in vacuo. The residue was dissolved in aqueous hydrochloric acid (0.5 M, 5 mL) and washed with ethyl acetate. The aqueous layer was basified with sodium bicarbonate powder until pH reached 7 and was added chloroform. The organic layer was separated, washed with brine and dried over anhydrous magnesium sulfate, filtered and the filtrated concentrated in vacuo to afford 2-(diethylamino)ethyl[imino (methylthio)methyl]carbamate (102 mg, 50%) as a yellow oil. MS (EI) for $C_9H_{19}N_3O_2S$: 234 (MH$^+$).

A solution of 2-(3-chloro-2-fluorophenyl)-3-(3,4-diaminophenyl)-3-hydroxy-2,3-dihydro-1H-isoindol-1-one (100 mg, 0.26 mmol) and 2-(diethylamino)ethyl[imino(methylthio)methyl]carbamate (102 mg, 0.437 mmol) in acetic acid (2.0 mL) was heated to 80° C. and stirred for 25 min. The reaction mixture was allowed to cool to room temperature and partitioned between aqueous saturated sodium bicarbonate and ethyl acetate. The organic layer was washed with brine, dried over anhydrous magnesium sulfate, filtered and the filtrate concentrated in vacuo. The residue was purified by reverse phase HPLC to afford 2-(diethylamino)ethyl{5-[2-(3-chloro-2-fluorophenyl)-1-hydroxy-3-oxo-2,3-dihydro-1H-isoindol-1-yl]-1H-benzimidazol-2-yl}carbamate trifluoroacetate salt (29 mg). $^1$H NMR (400 MHz, $d_6$-DMSO): 7.85 (d, 1H), 7.75 (s, 1H), 7.67-7.58 (m, 2H), 7.49-7.45 (m, 1H), 7.42 (s, 1H), 7.31-7.27 (m, 2H), 7.23 (d, 1H), 7.15 (t, 1H), 6.90 (d, 1H), 4.16 (t, 2H), 2.66-2.62 (m, 4H), 2.46 (t, 2H), 1.85 (s, 1H), 0.93 (t, 6H); MS (EI) for $C_{28}H_{27}ClFN_5O_4$: 574 (MNa$^+$).

Using the same or analogous synthetic techniques and/or substituting with alternative reagents, the following compounds of the invention were prepared:

2-piperidin-1-ylethyl{5-[2-(4-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.82 (d, 1H), 7.64 (s, 1H), 7.60-7.55 (m, 2H), 7.46-7.42 (m, 4H), 7.24 (t, 2H), 7.08 (t, 2H), 6.93 (d, 1H), 4.21 (t, 2H), 2.45-2.37 (m, 6H), 1.87 (s, 3H), 1.46-1.44 (m, 6H), 1.34 (br m, 2H); MS (EI) for $C_{29}H_{28}FN_5O_4$: 530 (MH$^+$).

2-(diethylamino)ethyl{5-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.85 (d, 1H), 7.75 (s, 1H), 7.67-7.58 (m, 2H), 7.49-7.45 (m, 1H), 7.42 (s, 1H), 7.31-7.27 (m, 2H), 7.23 (d, 1H), 7.15 (t, 1H), 6.90 (d, 1H), 4.16 (t, 2H), 2.66-2.62 (m, 4H), 2.46 (t, 2H), 1.85 (s, 1H), 0.93 (t, 6H); MS (EI) for $C_{28}H_{27}ClFN_5O_4$: 574 (MNa$^+$).

2-piperidin-1-ylethyl{5-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.81 (d, 1H), 7.73 (s, 1H), 7.61-7.54 (m, 2H), 7.44-7.38 (m, 2H), 7.27-7.22 (m, 2H), 7.19 (d, 1H), 7.11 (t, 1H), 6.85 (d, 1H), 4.17 (t, 2H), 2.49 (t, 2H), 2.33 (br m, 4H), 1.83 (s, 1H), 1.42-1.39 (m, 4H), 1.29 (br m, 2H); MS (EI) for $C_{29}H_{27}ClFN_5O_4$: 586 (MNa$^+$).

2-[methyl(phenylmethyl)amino]ethyl{5-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.87 (d, 1H), 7.81 (s, 1H), 7.69-7.60 (m, 2H), 7.55-7.52 (m, 2H), 7.47-7.46 (m, 5H), 7.35 (t, 1H), 7.29-7.18 (m, 2H), 7.20 (t, 1H), 6.99 (d, 1H), 4.52 (br s, 2H), 4.39 (br s, 2H), 3.45 (br s, 2H), 2.75 (s, 3H); MS (EI) for $C_{32}H_{27}ClFN_5O_4$: 600 (MH$^{30}$)

2-(dimethylamino)ethyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.87 (d, 1H), 7.73 (s, 1H), 7.64 (m, 2H), 7.49 (t, 1H), 7.44 (broad s, 1H), 7.33 (d, 1H), 7.31 (d, 1H), 7.24 (d, 1H), 7.17 (t, 1H), 6.91 (d, 1H), 4.23 (t, 2H), 2.55 (t, 2H), 2.21 (s, 6H); MS (EI) for $C_{26}H_{23}N_5O_4ClF$: 524 (MH$^+$).

2-morpholin-4-ylethyl{6-[2-(3-chloro-2-fluorophenyl)-1-hydroxy-3-oxo-2,3-dihydro-1H-isoindol-1-yl]-1H-benzimidazol-2-yl}carbamate: $^1$H NMR (400 MHz, $d_6$-DMSO): 7.88 (d, 1H), 7.82 (s, 1H), 7.64 (m, 2H), 7.50 (m, 2H), 7.26-7.36 (m, 3H), 7.17 (m, 1H), 7.01 (m, 1H), 4.49 (t, 1H), 4.44 (t, 1H), 4.33 (t, 1H), 3.71-3.97 (m, 3H), 3.20-3.48 (m, 6H); MS (EI) for $C_{28}H_{25}N_5O_5FCl$: 566 (MH$^+$).

2-piperidin-1-ylethyl{6-[2-(3-bromophenyl)-3-oxo-2,3-dihydro-1H-isoindol-1-yl]-1H-benzimidazol-2-yl}carbamate. $^1$H NMR (400 MHz, DMSO-$d_6$): 11.56 (s, 1H), 8.07 (d, 1H), 7.87 (d, 1H), 7.65 (m, 2H), 7.60 (d, 1H), 7.55 (t, 1H), 7.27 (m, 4H), 6.95 (d, 1H), 6.69 (s, 1H), 4.23 (t, 2H), 3.35 (s, 2H), 2.54 (t, 1H), 2.38 (br.s, 1H), 1.46 (m, 4H), 1.35 (m, 1H); MS (EI) for $C_{29}H_{28}BrN_5O_3$: 575 (MH$^+$).

Example 27

Methyl[6-({2-[(phenylcarbonyl)amino]phenyl}carbonyl)-1H-benzimidazol-2-yl]carbamate A solution of [5-(2-benzylcarbanoyl-benzoyl)-1H-benzoimidazol-2-yl]-carbamic acid methyl ester (21.4 g, 49.8 mmol) in tetrahydrofuran (150 mL) was cooled in an ice bath. To the solution was added di-tert-butyl dicarbonate (33 g, 150 mmol). This was followed by the drop wise addition of a solution of N,N-dimethylaminopyridine (6.1 g, 50 mmole) and Hunig's base (8.7 mL, 50 mmol) in tetrahydrofuran (80 mL). The solution was stirred at 0° C. for 40 minutes, then quenched by pouring over crushed ice and hydrochloric acid 1N (2:1). The mixture was partition and extracted using diethyl ether (200 mL). The organic portion was washed with water, saturated sodium bicarbonate, dried over sodium sulfate, filtered and concentrated in-vacuo. The resultant residue was purified by column chromatography (silica gel, ethyl acetate/hexanes). The isolated product was concentrated in-vacuo to afford, 25 g, 40 mmol (80%) of a colorless oil, which was diluted in ethyl acetate (150 mL). To the solution was added catalytic Palladium on carbon (wet 5%), and the solution was stirred under 1 atmosphere of hydrogen gas at ambient temperature for 18 hr. The solution was filtered through Celite and concentrated in-vacuo to afford 24 g, 39 mmol (95%) of a pale yellow oil, which was diluted in dichloromethane (150 mL) and cooled to 0° C. To the solution was added pyridine (3.6 ml, 39 mmol) followed by the drop wise addition of cyanuric fluoride (6.6 g, 49 mmol). The solution was stirred at ambient temperatures for 3 hr, and then was quenched by adding water (25 mL). The mixture was stirred at ambient temperatures for 30 minutes. The mixture was filtered through celite and washed with dichloromethane (2×50 mL). The filtrate was partitioned and the organic portion was washed with ice-cold 0.5N hydrochloric acid, water and brine, dried over sodium sulfate, and filtered through a silica gel plug column. The product was isolated and concentrated in-vacuo to afford 16.9 g, 31 mmol (62% over 3 steps) of a white solid, of which 500 mg, 0.92 mmol of the white solid was dissolved in dichloromethane (15 mL). To the solution was added sodium azide (600 mg, 9.23 mmol). The mixture was stirred at room temperature for 15 hrs, and then partitioned between water and ethyl acetate. The aqueous portion was extracted with ethyl acetate. The combined organic portion was washed with brine, dried over sodium sulfate, filtered and concentrated in-vacuo to afford, 520 mg, 0.92 mmol (100%) of a white solid, which was dissolved in toluene (10 mL). To the solution was added benzyl alcohol (190 μl, 1.84 mmol). The solution was stirred at 105° C. for 4 hrs, then cooled to room temperature and partitioned between water and ethyl acetate. The organic portion was washed with brine, dried over sodium sulfate, filtered and concentrated in-vacuo to afford a yellow oil, which was purified by column chromatography (silica gel, 20-40% ethyl acetate in hexanes). The product was collected to afford 300 mg, 0.47 mmol (50%) of a colorless oil, which was diluted in ethyl acetate (5 mL). To the solution was added Palladium (5 wt. %, (dry basis) on activated carbon, wet) and the solution was stirred at room temperature under a hydrogen gas filled balloon (1 atm) for 3 hrs. The mixture was filtered and the filtrate was concentrated in-vacuo to afford 194 mg, 0.38 mmol (95%) of a bright yellow solid. The solid was dissolved in 1,2-dichloroenthane (2 mL). To the solution was added benzoyl chloride (7 μl, 0.06 mmol), and the solution was stirred at room temperature for 30 minutes. To the solution was added trifluoroacetic acid (300 μl), and the solution was stirred at room temperature for a further 30 minutes. The solution was then concentrated in-vacuo to afford an orange residue which was purified by reverse phase HPLC (acetonitrile/water, 0.1% TFA eluent). The product was collected and afforded 20.2 mg, 0.04 mmol (4% over 5 steps) of methyl[6-({2-[(phenylcarbonyl)amino]phenyl}carbonyl)-1H-benzimidazol-2-yl]carbamate trifluoroacetate as a white solid. $^1$H NMR (400 MHz, $d_6$-DMSO): 10.68 (s, 1H), 7.88-7.86 (m, 2H), 7.70 (d, 2H), 7.66-7.58 (m, 2H), 7.55-7.48 (m, 3H), 7.46-7.42 (m, 2H), 7.35-7.31 (m, 1H), 3.80 (s, 3H); MS (EI) for $C_{23}H_{18}N_4O_4$: 414 (MH$^+$).

Example 28

Methyl{5-[2-(3-ethynyl-2-fluorophenyl)-4,7-difluoro-1-hydroxy-3-oxo-2,3-dihydro-1H-isoindol-1-yl]-1H-benzimidazol-2-yl}carbamate To a solution of 3,6-difluorophthalic anhydride (3.0 g, 16.00 mmol) in 1,1,2,2-tetrachloroethane (30 mL) chlorobenzene (2.0 mL, 18.00 mmol) was added followed by the addition of aluminum chloride (4.40 g, 33.00 mmol). The reaction mixture was stirred at room temperature for 120 minutes followed by the stirring at 60° C. for an additional 90 minutes. It was cooled to room temperature, poured into ice water (300 mL) and diluted with 1M aqueous hydrochloric acid. The aqueous slurry was extracted with ethyl acetate (300 mL) and the organic layer was washed with water (70 mL), brine (70 mL) and dried over anhydrous sodium sulfate. Filtration and concentration resulted in a crude product, which was crystallized from ethyl acetate by the addition of hexane. The product was collected by filtration and dried in vacuo to give 2-[(4-chlorophenyl)carbonyl]-3,6-difluorobenzoic acid (3.52 g, 73% yield). $^1$HMR (400 MHz, CD$_3$OD): 7.77 (s, 1H), 7.75 (s, 1H), 7.53 (s, 1H), 7.51 (s, 1H), 7.53-7.34 (m, 2H). MS (EI) for $C_{14}H_7ClF_2O_3$: 281 (M–H$_2$O).

2-[(4-chlorophenyl)carbonyl]-3,6-difluorobenzoic acid (3.20 g, 11.00 mmol) was dissolved while heating in concentrated.sulfuric acid (15 ml) and it was cooled to 0° C. A solution of fuming nitric acid (0.5 ml, 11.00 mmol) in concentrated.sulfuric acid (3.0 mL) was added dropwise and the reaction mixture was stirred at 0° C. for 60 minutes. It was poured into crushed ice. The product was precipitated. It was collected by filtration then it was dissolved in ethyl acetate (100 mL); it was washed with water (2×40 mL), brine (40 mL) and dried over anhydrous sodium sulfate. Filtration and concentration resulted in a crude product, which was triturated with hexane. The crystalline product was collected by filtration to give 2-[(4-chloro-3-nitrophenyl)carbonyl]-3,6-difluorobenzoic acid (2.73 g, 74% yield). $^1$H NMR (400 MHz, CD$_3$OD): 8.28 (s, 1H), 7.91 (d, J=8.8 Hz, 1H), 7.79 (d, J=8.4 Hz, 1H), 7.53-7.42 (m, 2H); MS (EI) for $C_{14}H_7ClF_2NO_5$: 341 (M$^-$).

To a solution of 2-[(4-chloro-3-nitrophenyl)carbonyl]-3,6-difluorobenzoic acid (7.0 g, 22.00 mmol) at 0° C. in anhydrous dichloromethane (40 mL) pyridine (1.70 ml, 22.00 mmol) was added, followed by the addition of cyanuric fluoride (1.90 ml, 24.20 mmol). The reaction mixture was stirred for 120 minutes at. 0° C. Water (35 mL) was added to the reaction mixture and it was stirred for 10 min at 0° C. The resulting slurry was filtered through a pad of Celite and washed with dichloromethane. The filtrate was partitioned with water and the organic layer was washed with water. It was dried over anhydrous sodium sulfate. Filtration and concentration gave a crystalline product. It was collected by filtration and dried in vacuo, to give 3-(4-chloro-3-nitrophenyl)-3,4,7-trifluoro-2-benzofuran-1(3H)-one (5.77 g, 82% yield). MS (EI) for $C_{14}H_5ClF_3NO_4$: 342 (M$^-$).

To a solution of 3-(4-chloro-3-nitrophenyl)-3,4,7-trifluoro-2-benzofuran-1(3H)-one (2.70 g, 7.85 mmol) in 1,2-dichloroethane (30.0 mL) 2-fluoro-3-alkyne aniline (1.11 g, 8.25 mmol), was added, followed by addition of N,N-dimethylaniline (1.20 mL, 9.42 mmol). The reaction mixture was stirred for 15 hours, at 75° C. The solvent was evaporated and the residue was dissolved in ethyl acetate (350 mL). It was washed with 1M hydrochloric acid (2×100 mL), water (3×100 mL), saturated aqueous sodium bicarbonate (100 mL), brine (100 mL), and dried over anhydrous sodium sulfate. Filtration and concentration gave a semisolid residue, which was crystallized from diethyl ether by the addition of hexane. The product was collected by filtration and it was dried in vacuo, to give 3-(4-chloro-3-nitrophenyl)-2-(3-ethynyl-2-fluorophenyl)-4,7-difluoro-3-hydroxy-2,3-dihydro-1H-isoindol-1-one (2.47 g, 68% yield). $^1$H NMR (400 MHz, CD$_3$OD): 8.01 (s, 1H), 7.60 (s, 2H), 7.51-7.42 (m, 3H), 7.32 (t, J=6.4 Hz, 1H), 7.15 (t, J=8 Hz, 1H), 3.80 (s, 1H); MS (EI) for $C_{22}H_{10}ClF_3N_2O_4$: 459 (MH$^+$).

To a solution of 3-(4-chloro-3-nitrophenyl)-2-(3-ethynyl-2-fluorophenyl)-4,7-difluoro-3-hydroxy-2,3-dihydro-1H-isoindol-1-one (2.45 g, 5.34 mmol) in N,N-dimethylformamide (30.0 mL) sodium azide (1.05 g, 16.0 mmol) was added and the reaction mixture was stirred at 40° C. for 20 hours. The reaction mixture was cooled to room temperature, and poured into ice water. A precipitate was formed, which was collected by filtration. It was washed with water and dried in vacuo to give 3-(4-azido-3-nitrophenyl)-2-(3-ethynyl-2-fluorophenyl)-4,7-difluoro-3-hydroxy-2,3-dihydro-1H-isoindol-1-one (1.87 g, 75% yield). $^1$H NMR (400 MHz, CD$_3$OD): 8.00 (d, J=2 Hz, 1H), 7.64 (dd, J$_1$=8.4 Hz, J$_2$=1.6 Hz, 1H), 7.47-7.41 (m, 4H), 7.35 (t, J=7.2 Hz, 1H), 7.14 (t, J=8 Hz, 1H), 3.80 (s, 1H); MS (EI) for $C_{22}H_{10}F_3N_5O_4$: 464 (M$^-$).

To a solution of 3-(4-azido-3-nitrophenyl)-2-(3-ethynyl-2-fluorophenyl)-4,7-difluoro-3-hydroxy-2,3-dihydro-1H-isoindol-1-one (1.50 mg, 3.20 mmol) in a mixture tetrahydrofurane-water (1:1, 30.0 mL) ammonium formate (2.0 g, 32.0 mmol) was added followed by the addition of iron (1.45 g, 26.0 mmol). The mixture was heated to reflux and stirred for 180 minutes. It was cooled to room temperature and diluted with ethyl acetate. The resulting slurry was filtered through a pad of Celite, and washed with ethyl acetate. It was partitioned with water and the organic layer was washed with water, brine and dried over anhydrous sodium sulfate. Filtration and concentration resulted in an oily product. It was crystallized from diethyl ether by the addition of hexane. The product was collected by filtration, dried in vacuo, to provide 3-(3,4-diaminophenyl)-2-(3-ethynyl-2-fluorophenyl)-4,7-difluoro-3-hydroxy-2,3-dihydro-1H-isoindol-1-one (1.16 g, 88% yield). $^1$H NMR (400 MHz, CD$_3$OD): 7.57 (s, 1H), 7.42-7.23 (m, 3H), 7.16 (m, 2H), 6.75 (s, 1H), 6.61-6.57 (m, 1H), 3.78 (d, J=8.4 Hz, 1H); MS (EI) for C$_{22}$H$_{14}$F$_3$N$_3$O$_2$: 408 (M$^-$).

A solution of 3-(3,4-diaminophenyl)-2-(3-ethynyl-2-fluorophenyl)-4,7-difluoro-3-hydroxy-2,3-dihydro-1H-isoindol-1-one (1.15 g, 2.80 mmol) and 1,3-bis(methoxycarbonyl)-2-methyl-2-thiopseudourea (0.58 g, 2.80 mmol) was heated to 80° C. for 30 minutes in glacial acetic acid (15.0 mL). The reaction mixture was cooled to room temperature and it was pored into ice water. The pH was adjusted to 8 by the addition of 2M aqueous sodium hydroxide. The precipitated product was extracted with ethyl acetate (350 mL) and the organic layer was washed with brine and dried over anhydrous sodium sulfate. Filtration and evaporation resulted in a crude product. It was purified by reverse phase preparative HPLC (CH$_3$CN/25 mM aqueous ammonium acetate). The fractions were collected, and the solvent was concentrated. The residue was partitioned with ethyl acetate. The organic layer was washed with saturated aqueous sodium bicarbonate, brine and dried over anhydrous sodium sulfate. Filtration and concentration resulted in an amorphous residue, which was freeze-dried from a mixture of acetonitrile-water (35.0 mL) to give methyl{5-[2-(3-ethynyl-2-fluorophenyl)-4,7-difluoro-1-hydroxy-3-oxo-2,3-dihydro-1H-isoindol-1-yl]-1H-benzimidazol-2-yl}carbamate (1.15 g, 83% yield). $^1$H NMR (400 MHz, CD$_3$OD): 7.79 (s, 1H), 7.50 (d, J=8.4 Hz, 1H), 7.43-7.36 (m, 4H), 7.31 (t, J=7.2 Hz, 1H), 7.07 (t, J=7.6 Hz, 1H), 3.92 (s, 3H), 3.78 (s, 3H); MS (EI) for C$_{25}$H$_{15}$F$_3$N$_4$O$_4$: 493 (MH$^+$).

Using the same or analogous synthetic techniques and/or substituting with alternative reagents, the following compounds of the invention were prepared:

methyl{6-[4,7-dichloro-2-(3-chloro-2-fluorophenyl)-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 8.03-8.02 (b, 1H), 7.71 (s, 2H), 7.53-7.49 (m, 1H), 7.38-7.36 (d, 1H), 7.22-7.15 (m, 3H), 3.78 (s, 3H); MS (EI) for C$_{23}$H$_{14}$Cl$_3$FN$_4$O$_4$: 535 (MH$^+$).

methyl{6-[2-(3-bromophenyl)-4,7-difluoro-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 8.29 (s, 0.8H) close, 7.88 (s, 0.2H) open, 7.78-7.76 (m, 1H), 7.70-7.60 (m, 1H), 7.53-7.20 (m, 7H), 3.82 (s, 2.4H) close, 3.78 (s, 0.6H) open; MS (EI) for C$_{23}$H$_{15}$BrF$_2$N$_4$O$_4$: 529 (MH$^+$).

methyl{6-[2-(5-chloro-2-methylphenyl)-4,7-difluoro-1-hydroxy-3-oxo-2,3-dihydro-1H-isoindol-1-yl]-1H-benzimidazol-2-yl}carbamate: $^1$H NMR (400 MHz, d$_6$-DMSO): 10.28 (s, 0.3H) open, 7.88-7.83 (m, 1H), 7.65-7.57 (m, 3H), 7.37-7.19 (m, 2.4H), 7.15-7.07 (m, 1H), 6.90-6.82 (m, 1H), 5.99-5.97 (b, 0.3H) open, 3.78 (s, 0.9H) open, 3.73 (s, 2.1H) close, 2.10 (s, 0.9H) open, 1.45 (s, 2.1H) closed; MS (EI) for C$_{24}$H$_{17}$ClF$_2$N$_4$O$_4$: 499 (MH$^+$).

methyl{6-[2-(3-chloro-2-fluorophenyl)-7-fluoro-1-hydroxy-3-oxo-2,3-dihydro-1H-isoindol-1-yl]-1H-benzimidazol-2-yl}carbamate hydrochloride: $^1$H NMR (400 MHz, d$_6$-DMSO): 8.22-8.20 (b, 1H), 7.77-7.75 (d, 1H), 7.72-7.68 (m, 1H), 7.64-7.62 (b, 1H), 7.53-7.44 (m, 3H), 7.32-7.29 (dd, 1H), 7.20-7.16 (dd, 2H), 3.81 (s, 3H); MS (EI) for C$_{23}$H$_{15}$ClF$_2$N$_4$O$_4$: 485 (MH$^+$).

Methyl{6-[2-(3-bromophenyl)-5,6-dichloro-1-hydroxy-3-oxo-2,3-dihydro-1H-isoindol-1-yl]-1H-benzimidazol-2-yl}carbamate trifluoroacetic acid salt: MS (EI) for C$_{23}$H$_{15}$N$_4$O$_4$Cl$_2$Br: 563 (MH$^+$).

methyl{5-[2-(3-ethynyl-2-fluorophenyl)-7-fluoro-1-hydroxy-3-oxo-2,3-dihydro-1H-isoindol-1-yl]-1H-benzimidazol-2-yl}carbamate: $^1$H NMR (400 MHz, d$_6$-DMSO): 7.94 (s, 1H), 7.75 (d, 1H), 7.67-7.72 (m, 1H), 7.43-7.50 (m, 4H), 7.32 (t, 1H), 7.25 (d, 1H), 7.14 (t, 1H), 6.94 (d, 1H), 4.51 (s, 1H), 3.73 (s, 3H); MS (EI) for C$_{25}$H$_{16}$N$_4$O$_4$F$_2$: 475 (MH$^+$).

methyl{5-[2-(5-chloro-2-methylphenyl)-7-fluoro-1-hydroxy-3-oxo-2,3-dihydro-1H-isoindol-1-yl]-1H-benzimidazol-2-yl}carbamate: $^1$H NMR (400 MHz, d$_6$-DMSO): 11.64 (broad s, 1H), 7.54 (s, 2H), 7.46-7.62 (m, 2H), 7.16-7.26 (m, 2H), 7.07 (d, 1H), 6.77 (d, 1H), 3.77 (s, 0.6H) open, 3.72 (s, 2.4H) closed, 3.35 (s, 3H); MS (EI) for C$_{24}$H$_{18}$N$_4$O$_4$FCl: 481 (MH$^+$).

methyl{6-[2-(3-chloro-2-fluorophenyl)-4,7-difluoro-1-hydroxy-3-oxo-2,3-dihydro-1H-isoindol-1-yl]-1H-benzimidazol-2-yl}carbamate. $^1$H NMR (400 MHz, DMSO-d$_6$): 11.60 (br.s, 1H), 8.06 (s, 1H), 7.63 (m, 1H) open, 7.53 (m, 4H), 7.38 (t, 1H) open, 7.25 (m, 2H), 7.17 (m, 1H), 7.14 (t, 1H) open, 6.97 (d, 1H), 3.77 (s, 3H) open, 3.73 (s, 3H) closed; MS (EI) for C$_{23}$H$_{14}$ClF$_3$N$_4$O$_4$: 503 (MIT).

Example 29

5-[2-(3-Chloro-2-fluorophenyl)-1-hydroxy-3-oxo-2,3-dihydro-1H-isoindol-1-yl]-1,3-dihydro-2H-benzimidazol-2-one To a solution of 2-(3-chloro-2-fluorophenyl)-3-(3,4-diaminophenyl)-3-hydroxy-2,3-dihydro-1H-isoindol-1-one (100 mg, 0.26 mmol) in tetrahydrofuran (3 mL) was added 1,1'-carbonyldiimidazole (63 mg, 0.39 mmol) at room temperature. The reaction mixture was stirred for 2 h, at which time the solvent was evaporated. The residue was purified by reverse phase HPLC to afford 5-[2-(3-chloro-2-fluorophenyl)-1-hydroxy-3-oxo-2,3-dihydro-1H-isoindol-1-yl]-1,3-dihydro-2H-benzimidazol-2-one (34 mg). $^1$H NMR (400 MHz, d$_6$-DMSO): 10.63 (s, 1H), 10.52 (s, 1H), 7.84 (d, 1H), 7.72 (d, 1H), 7.68-7.58 (m, 2H), 7.50 (dt, 1H), 7.31-7.29 (m, 2H), 7.19 (t, 1H), 6.84-6.77 (m, 3H); MS (EI) for C$_{21}$H$_{13}$ClFN$_3$O$_3$: 408 (MH$^-$).

Example 30

Methyl{6-[1-(3-bromophenyl)-5-oxopyrrolidin-2-yl]-1H-benzimidazol-2-yl}carbamate 3,4-Dinitrobenzaldehyde (634.5 mg, 3.24 mmol.) was taken into dichloromethane (20 mL) and the resulting solution was cooled to 0° C. under a nitrogen atmosphere. [(1-Ethoxycyclopropyl)oxy]trimethylsilane (0.85 mL, 4.21 mmol.) was added by syringe followed by addition of titanium tetrachloride (0.4 mL, 3.56 mmol.) and the resulting mixture was allowed to slowly warm to room temperature over 12 hours then stirred an additional 3 days. The solution was partitioned with water and the organic layer was dried over anhydrous sodium sulfate. Filtration and concentration followed by purification of the residue using silica gel flash chromatography (1:1 to 3:1 ethyl acetate:hexane eluent) gave a less polar fraction ethyl 4-chloro-4-(3,4-dinitrophenyl)butanone (379 mg, 37% yield) as an amorphous residue and 5-(3,4-dinitrophenyl)dihydrofuran-2(3H)-one as a more polar fraction (338 mg, 41% yield). $^1$H NMR (400 MHz, CDCl$_3$): 7.98 (d, 1H), 7.96 (d, 1H), 7.80 (dd, 1H), 5.11 (dd, 1H), 4.15 (q, 2H), 2.66-2.50 (m, 2H), 2.42-2.28 (m, 2H), 1.27 (tr, 3H).

Ethyl 4-chloro-4-(3,4-dinitrophenyl)butanone (366.3 mg, 1.2 mmol.), 3-bromoaniline (220 mg, 1.3 mmol) and N,N-dimethylacetamide (0.3 mL) were combined and heated to 120° C. over 17 hours under a nitrogen atmosphere. The mixture was then cooled to room temperature and partitioned with ethyl acetate and water. The organic layer was washed twice with additional water, then brine and dried over anhydrous sodium sulfate. Filtration and concentration followed by purification of the residue by silica gel flash chromatography (100% ethyl acetate eluent) gave 1-(3-bromophenyl)-5-(3,4-dinitrophenyl)pyrrolidin-2-one (132 mg, 28% yield) as an amorphous residue. The material thus obtained is contaminated by variable amounts of 5-(3,4-dinitrophenyl)dihydrofuran-2(3H)-one as a side product and is carried forward without further purification. MS (EI) for $C_{16}H_{12}N_3O_5Br$: 407 (MH+).

1-(3-Bromophenyl)-5-(3,4-dinitrophenyl)pyrrolidin-2-one (132 mg, 0.33 mmol.) was taken into acetic acid (5.0 mL) was the resulting solution was warmed to 50° C. followed by addition of tin (II) chloride dihydrate (368 mg, 1.65 mmol.). After one hour at 50° C. a second aliquot of tin (II) chloride dihydrate was added and heating was continued another three hours. The resulting solution was concentrated and the residue was partitioned with ethyl acetate and 1M aqueous sodium hydroxide. The organic phase was allowed to separate from the resulting emulsion and washed an additional time with saturated aqueous sodium bicarbonate followed by brine. The solution was then dried over anhydrous sodium sulfate, filtered and concentrated. The residue was purified by silica gel flash chromatography (100% ethyl acetate eluent) to afford 1-(3-bromophenyl)-5-(3,4-aminophenyl)pyrrolidin-2-one (16.4 mg, 15% yield) as an amorphous residue. MS (EI) for $C_{16}H_{16}N_3O_3Br$: 347 (MH+).

1-(3-Bromophenyl)-5-(3,4-aminophenyl)pyrrolidin-2-one (16.4 mg, 0.05 mmol.) was taken into acetic acid (1.0 mL) followed by addition of 1,3-bis(methoxycarbonyl)-2-methyl-2-thiopseudourea (14.5 mg, 0.07 mmol.) and the mixture was heated to 80° C. for one hour. The solution was then concentrated and the residue partitioned with saturated aqueous sodium bicarbonate and ethyl acetate. The organic layer was washed once with brine, dried over anhydrous sodium sulfate then filtered and concentrated. The residue was purified by silica gel flash chromatography (100% ethyl acetate eluent) to afford methyl{6-[1-(3-bromophenyl)-5-oxopyrrolidin-2-yl]-1H-benzimidazol-2-yl}carbamate (12.9 mg, 64% yield) as a white solid. $^1$H NMR (400 MHz, d$_6$-DMSO): 7.82 (s, 1H), 7.36-7.30 (m, 2H), 7.27 (s, 1H), 7.22-7.16 (m, 2H), 7.00 (d, 1H), 5.53 (tr, 1H), 3.73 (s, 3H), 2.70-2.50 (m, 4H). MS (EI) for $C_{19}H_{17}N_4O_3Br$: 430 (MH+).

Example 31

Methyl({6-[2-(3-chloro-2-fluorophenyl)-1-hydroxy-3-oxo-2,3-dihydro-1H-isoindol-1-yl]-1H-benzimidazol-2-yl}amino)(oxo)acetate To a suspension of 2-methyl-2-thiopseudourea sulfate (1.50 g, 10.80 mmol) in dichloromethane (50 mL) and pyridine (1.76 mL, 21.60 mmol) at 0° C. a solution of methyl chlorooxoacetate (1.0 mL, 10.80 mmol) in dichloromethane (10.0 mL) was added and the reaction mixture was stirred for 15 hours at room temperature. Ethyl acetate (150 mL) was added into the mixture and it was washed with 1M aqueous hydrochloric acid and brine. The solvent was dried over anhydrous sodium sulfate. Filtration and concentration, followed by purification of the crude product by silica gel flash chromatography (hexane:ethyl acetate 4:3 to 3:2 eluent) gave methyl{[(1Z)-{[(methyloxy)(oxo)acetyl]amino}(methylthio)methylidene]amino}(oxo)acetate (0.87 g, 31% yield).

$^1$H NMR (400 MHz, DMSO-d$_6$): 12.48 (br.s, 2H), 3.81 (s, 3H), 2.41 (s, 3H); MS (EI) for $C_8H_{10}N_2O_6S$: 263 (MH+).

A solution of 2-(3-chloro-2-fluorophenyl)-3-(3,4-diaminophenyl)-3-hydroxy-2,3-dihydro-1H-isoindol-1-one (0.10 g, 0.26 mmol) and methyl{[(1Z)-{[(methyloxy)(oxo)acetyl]amino}(methylthio)methylidene]amino}(oxo)acetate (67 mg, 0.26 mmol) in n-butanol (2.0 mL) was heated to 80° C. for 5 hours. The reaction mixture was cooled to room temperature and the solvent was evaporated. The resulting crude product was purified by reverse phase preparative HPLC (CH$_3$CN/25 mM aqueous ammonium acetate). The fractions were collected, and the solvent was concentrated. The aqueous residue was partitioned with ethyl acetate. The organic layer was washed with saturated aqueous sodium bicarbonate, brine and dried over anhydrous sodium sulfate. Filtration and concentration resulted in an oily residue, which was lyophillized from a mixture of acetonitrile-water (5.0 mL) to give methyl({6-[2-(3-chloro-2-fluorophenyl)-1-hydroxy-3-oxo-2,3-dihydro-1H-isoindol-1-yl]-1H-benzimidazol-2-yl}amino)(oxo)acetate (48 mg, 38% yield. $^1$H NMR (400 MHz, DMSO-d$_6$): 11.86 (d, 1H), 7.87 (d, 1H), 7.65 (m, 2H), 7.53 (t, 1H), 7.33 (t, 1H), 7.30 (d, 1H), 7.25 (s, 1H), 7.20 (t, 1H), 6.99 (d, 1H), 6.91 (d, 1H), 3.57 (s, 3H); $^{13}$C NMR (400 MHz, DMSO-d$_6$): 67.0, 92.5, 110.0, 113.8, 114.1, 115.7, 120.8, 121.4, 123.9, 125.3, 125.6, 126.0, 126.2, 129.5, 129.8, 130.5, 130.7, 134.3, 134.8, 150.3, 155.7, 155.8, 163.5, 166.2; MS (EI) for $C_{24}H_{16}ClFN_4O_4$: 436 (M−CO$_2$CH$_3$).

Example 32

2-(3-Chloro-2-fluorophenyl)-3-hydroxy-3-[2-(1,3-thiazol-2-ylamino)-1H-benzimidazol-5-yl]-2,3-dihydro-1H-isoindol-1-one To a solution of 2-aminothiazole (630 mg, 6.29 mmol) in acetone (30 mL) was slowly added benzoyl isothiocyanate (845 μL, 6.29 mmol) at room temperature. The reaction mixture was heated to a gentle reflux for 6.5 h, at which time it was cooled to room temperature and concentrated in vacuo. The residue was added acetonitrile (50 mL) and the yellow precipitate was filtered. The filtrate was concentrated in vacuo and the residue was taken up in 10% aqueous sodium hydroxide (50 mL). The heterogeneous reaction mixture was heated to a gentle reflux for 1 h then cooled to room temperature and stirred for 16 h. To the reaction mixture was added 6 N hydrochloric acid until pH reached 7. To the aqueous layer was added ammonium hydroxide (50 mL) followed by ethyl acetate then separated. The organic layer was washed with brine then dried over anhydrous magnesium sulfate, filtered and the filtrate concentrated in vacuo to afford N-1,3-thiazol-2-ylthiourea (717 mg, 71%) as a pale yellow powder. The powder was then taken up in chloroform (50 mL) and to this suspension was added iodomethane (281 μL, 4.50 mmol). The reaction mixture was heated to reflux for 2 h, at which time it was cooled to room temperature and concentrated in vacuo. The residue was purified by column chromatography (SiO$_2$, hexanes/ethyl acetate) to afford methyl N-1,3-thiazol-2-ylimidothiocarbamate (200 mg, 26%). MS (EI) for $C_5H_7N_3S_2$: 174 (MH+).

A solution of 2-(3-chloro-2-fluorophenyl)-3-(3,4-diaminophenyl)-3-hydroxy-2,3-dihydro-1H-isoindol-1-one (30 mg, 0.078 mmol) and methyl N-1,3-thiazol-2-ylimidothiocarbamate (200 mg, 1.15 mmol) in acetic acid (1.5 mL) was heated to 80° C. and stirred for 1 h. The reaction mixture was cooled to room temperature and partitioned between saturated aqueous sodium bicarbonate and ethyl acetate. The organic layer was washed with brine then dried over magnesium sulfate, filtered and the filtrate concentrated in vacuo. The residue was purified by reverse phase HPLC to afford 2-(3-chloro-2-fluorophenyl)-3-hydroxy-3-[2-(1,3-thiazol-2-ylamino)-1H-benzimidazol-5-yl]-2,3-dihydro-1H-isoindol-1-one trifluoroacetate salt (6.6 mg). $^1$H NMR (400 MHz, d$_6$-DMSO): 8.02 (d, 0.5H), 7.86 (d, 1H), 7.73 (s, 1H), 7.66-7.61 (m, 3H), 7.52-7.47 (m, 2H), 7.35-7.27 (m, 4H), 7.21-7.15 (m, 2H), 6.92 (br s, 1H); MS (EI) for C$_{24}$H$_{15}$ClFN$_5$O$_2$S: 492 (MH$^+$).

Using the same or analogous synthetic techniques and/or substituting with alternative reagents, the following compounds of the invention were prepared:

3-(2-{[4,6-bis(methyloxy)pyrimidin-2-yl]amino}-1H-benzimidazol-5-yl)-2-(3-chloro-2-fluorophenyl)-3-hydroxy-2,3-dihydro-1H-isoindol-1-one: $^1$H NMR (400 MHz, d$_6$-DMSO): 10.52 (s, 1H), 7.89 (d, 1H), 7.79 (s, 1H), 7.65 (m, 2H), 7.51 (m, 2H), 7.34 (m, 3H), 7.18 (t, 1H) closed, 7.12 (t, 1H) open, 6.99 (d, 1H), 5.89 (s, 1H) open, 5.88 (s, 1H) closed, 3.95 (s, 6H) open, 3.94 (s, 6H) closed; MS (EI) for C$_{27}$H$_{20}$ClFN$_6$O$_4$: 547 (MH$^+$).

2-(3-chloro-2-fluorophenyl)-3-hydroxy-3-(2-{[4-methyl-6-(methyloxy)pyrimidin-2-yl]amino}-1H-benzimidazol-5-yl)-2,3-dihydro-1H-isoindol-1-one: $^1$H NMR (400 MHz, d$_6$-DMSO): 10.54 (s, 1H), 7.88 (d, 1H), 7.76 (s, 1H), 7.66 (m, 2H), 7.50 (m, 2H), 7.33 (m, 3H), 7.17 (t, 1H), 6.96 (d, 1H), 6.41 (s, 1H) open, 6.37 (s, 1H) closed, 3.94 (s, 3H), 2.44 (s, 3H) open, 2.41 (s, 3H) closed; MS (EI) for C$_{27}$H$_{20}$ClFN$_6$O$_3$: 531 (MH$^+$).

2-(3-chloro-2-fluorophenyl)-3-hydroxy-3-[2-(pyridin-2-ylamino)-1H-benzimidazol-5-yl]-2,3-dihydro-1H-isoindol-1-one: $^1$H NMR (400 MHz, d$_6$-DMSO): 8.29 (s, 1H), 7.88 (d, 1H), 7.73-7.47 (m, 4H), 7.49 (t, 2H), 7.33-7.31 (m, 3H), 7.19-7.15 (m, 2H), 6.98 (s, 1H); MS (EI) for C$_{26}$H$_{17}$ClFN$_5$O$_2$: 486 (MH$^+$).

2-(3-chloro-2-fluorophenyl)-3-hydroxy-3-[2-(pyrimidin-2-ylamino)-1H-benzimidazol-5-yl]-2,3-dihydro-1H-isoindol-1-one: $^1$H NMR (400 MHz, d$_6$-DMSO): 8.59-8.58 (m, 2H), 7.87 (dd, 1H), 7.70 (s, 1H), 7.66-7.61 (m, 2H), 7.48 (br m, 2H), 7.33-7.31 (m, 4H), 7.18-7.16 (m, 1H), 7.04-7.02 (m, 1H), 6.94 (br s, 1H); MS (EI) for C$_{25}$H$_{16}$ClFN$_6$O$_2$: 487 (MH$^+$).

2-(3-chloro-2-fluorophenyl)-3-hydroxy-3-[2-(1,3-thiazol-2-ylamino)-1H-benzimidazol-5-yl]-2,3-dihydro-1H-isoindol-1-one: $^1$H NMR (400 MHz, d$_6$-DMSO): 8.02 (d, 0.5H), 7.86 (d, 1H), 7.73 (s, 1H), 7.66-7.61 (m, 3H), 7.52-7.47 (m, 2H), 7.35-7.27 (m, 4H), 7.21-7.15 (m, 2H), 6.92 (br s, 1H); MS (EI) for C$_{24}$H$_{15}$ClFN$_5$O$_2$S: 492 (MH$^+$).

2-(3-chloro-2-fluorophenyl)-3-hydroxy-3-[2-(pyrazin-2-ylamino)-1H-benzimidazol-5-yl]-2,3-dihydro-1H-isoindol-1-one: $^1$H NMR (400 MHz, d$_6$-DMSO): 8.57 (s, 1H), 8.24 (s, 1H), 8.12 (s, 1H), 7.88 (d, 1H), 7.72 (s, 1H), 7.69-7.60 (m, 3H), 7.49 (t, 1H), 7.32 (d, 2H), 7.17 (t, 1H), 6.95 (s, 1H); MS (EI) for C$_{25}$H$_{16}$ClFN$_6$O$_2$: 487 (MH$^+$).

2-(3-ethynyl-2-fluorophenyl)-3-hydroxy-3-[2-(pyrimidin-2-ylamino)-1H-benzimidazol-5-yl]-2,3-dihydro-1H-isoindol-1-one: $^1$H NMR (400 MHz, d$_6$-DMSO): 12.17 (s, 1H), 11.18 (s, 1H), 8.62-8.57 (m, 2H), 7.87 (d, 1H), 7.69-7.59 (m, 3H), 7.43 (t, 2H), 7.41-7.34 (m, 1H), 7.32 (d, 1H), 7.14 (t, 1H), 7.04 (t, 1H), 6.94 (br s, 1H), 4.49 (s, 1H); MS (EI) for C$_{27}$H$_{17}$FN$_6$O$_2$: 477 (MH$^+$).

2-(3-chloro-2-fluorophenyl)-3-{2-[(6-chloropyridazin-3-yl)amino]-1H-benzimidazol-5-yl}-3-hydroxy-2,3-dihydro-1H-isoindol-1-one: MS (EI) for C$_{25}$H$_{15}$Cl$_2$FN$_6$O$_2$: 521 (M$^+$).

2-(3-chloro-2-fluorophenyl)-3-{2-[(5-chloropyrimidin-2-yl)amino]-1H-benzimidazol-5-yl}-3-hydroxy-2,3-dihydro-1H-isoindol-1-one: $^1$H NMR (400 MHz, d$_6$-DMSO): 8.79-8.74 (m, 2H), 7.92-7.85 (m, 2H), 7.71-7.61 (m, 3H), 7.59-7.56 (m, 1H), 7.53-7.46 (m, 1H), 7.44-7.40 (m, 1H), 7.38-7.30 (m, 3H), 7.23-7.17 (m, 1H), 7.14-7.09 (m, 1H); MS (EI) for C$_{25}$H$_{15}$Cl$_2$FN$_6$O$_2$: 521 (M$^+$).

3-hydroxy-2-(3-methylphenyl)-3-[2-(pyrimidin-2-ylamino)-1H-benzimidazol-6-yl]-2,3-dihydro-1H-isoindol-1-one: $^1$H NMR (400 MHz, d$_6$-DMSO): 8.60 (d, 2H), 7.82 (d, 1H), 7.57 (m, 5H), 7.43 (s, 1H), 7.28 (m, 3H), 7.11 (t, 1H), 7.04 (t, 1H), 6.91 (d, 1H), 2.20 (s, 3H); MS (EI) for C$_{26}$H$_{20}$N$_6$O$_2$: 449 (MH$^+$).

2-(5-chloro-2-methylphenyl)-3-hydroxy-3-[2-(pyrimidin-2-ylamino)-1H-benzimidazol-6-yl]-2,3-dihydro-1H-isoindol-1-one: $^1$H NMR (400 MHz, d$_6$-DMSO): 8.59 (m, 2H), 7.87 (d, 1H), 7.68 (m, 5H), 7.50 (s, 1H), 7.26 (m, 3H), 7.10 (m, 1H), 7.04 (m, 1H), 6.75 (m, 1H); MS (EI) for C$_{26}$H$_{19}$N$_6$O$_2$Cl: 483 (MH$^+$).

3-hydroxy-2-(3-methylphenyl)-3-[2-(pyrazin-2-ylamino)-1H-benzimidazol-6-yl]-2,3-dihydro-1H-isoindol-1-one: $^1$H NMR (400 MHz, d$_6$-DMSO): 8.57 (broad s, 1H), 8.24 (s, 1H), 8.11 (s, 1H), 7.83 (d, 1H), 7.56 (m, 3H), 7.43 (s, 1H), 7.27 (m, 3H), 7.11 (t, 1H), 7.09 (broad s, 1H), 6.92 (d, 1H), 6.56 (s, open), 2.15 (s, 3H); MS (EI) for C$_{26}$H$_{20}$N$_6$O$_2$: 449 (MH$^+$).

2-(5-chloro-2-methylphenyl)-3-hydroxy-3-[2-(pyrazin-2-ylamino)-1H-benzimidazol-6-yl]-2,3-dihydro-1H-isoindol-1-one: $^1$H NMR (400 MHz, d$_6$-DMSO): 8.56 (broad s, 1H), 8.24 (s, 1H), 8.12 (d, 1H), 7.87 (d, 1H), 7.69 (m, 3H), 7.50 (s, 1H), 7.45 (m, 1H), 7.03-7.25 (m, 4H), 6.75 (broad s, 1H), 6.56 (s, open); MS (EI) for C$_{26}$H$_{19}$N$_6$O$_2$Cl: 483 (MH$^+$).

3-hydroxy-2-[3-(methyloxy)phenyl]-3-[2-(pyrimidin-2-ylamino)-1H-benzimidazol-6-yl]-2,3-dihydro-1H-isoindol-1-one: $^1$H NMR (400 MHz, d$_6$-DMSO): 8.62 (dd, 1H), 7.83 (d, 1H), 7.53-7.62 (m, 5H), 7.28 (d, 2H), 7.20 (m, 2H), 7.14 (m, 2H), 7.04 (t, 1H), 6.56-6.69 (m, 3H), 3.61 (s, 3H); MS (EI) for C$_{26}$H$_{20}$N$_6$O$_3$: 465 (MH$^+$).

3-hydroxy-2-[3-(methyloxy)phenyl]-3-[2-(pyrazin-2-ylamino)-1H-benzimidazol-5-yl]-2,3-dihydro-1H-isoindol-1-one: $^1$H NMR (400 MHz, d$_6$-DMSO): 7.80 (m, 5H), 7.48-7.67 (m, 3H), 7.11-7.28 (m, 5H), 6.78 (s, 1H), 6.58 (s, 1H), 3.74 (s, 3H); MS (EI) for C$_{26}$H$_{20}$N$_6$O$_3$: 465 (MH$^+$).

2-(3-chloro-2-fluorophenyl)-4,7-difluoro-3-hydroxy-3-[2-(pyrimidin-2-ylamino)-1H-benzimidazol-5-yl]-2,3-dihydro-1H-isoindol-1-one. $^1$H NMR (400 MHz, CD$_3$OD): 8.61 (s, 1H), 8.60 (s, 1H), 7.61 (s, 1H), 7.40-7.36 (m, 3H), 7.34 (m, 1H), 7.10-7.05 (m, 2H), 7.02 (t, J=4.8 Hz, 2H); MS (EI) for C$_{25}$H$_{14}$ClF$_3$N$_6$O$_2$: 523 (MH$^+$).

2-(3-chloro-2-fluorophenyl)-3-hydroxy-3-{2-[(4-methylpyrimidin-2-yl)amino]-1H-benzimidazol-5-yl}-2,3-dihydro-1H-isoindol-1-one acetate: $^1$H NMR (400 MHz, d$_6$-DMSO): 8.45-8.41 (d, 1H), 7.89-7.85 (d, 1H), 7.69-7.58 (m, 2H), 7.51-7.46 (m, 2H), 7.35-7.28 (d, 2H), 7.20-7.14 (m, 2H), 6.95-6.90 (m, 2H), 5.48-5.46 (s, 1H), 1.89-1.87 (s, 3H); MS (EI) for C$_{26}$H$_{18}$ClFN$_6$O$_2$: 501 (MH$^+$).

Example 33

2-(3-Chloro-2-fluorophenyl)-3-hydroxy-3-[2-(phenylamino)-1H-benzimidazol-5-yl]-2,3-dihydro-1H-isoindol-1-one To a solution of 2-(3-chloro-2-fluorophenyl)-3-(3,4-diaminophenyl)-3-hydroxy-2,3-dihydro-1H-isoindol-1-one (575 mg, 1.49 mmol) in tetrahydrofuran (2.0 mL) was added 1,1'-thiocarbonyldiimidazole (400 mg, 2.25 mmol) at room temperature and stirred for 4 h. The reaction mixture was concentrated in vacuo and the residue was purified by column chromatography (SiO$_2$, hexanes/ethyl acetate) to afford 2-(3-chloro-2-fluorophenyl)-3-hydroxy-3-(2-thioxo-2,3-dihyro-1H-benzimidazol-5-yl)-2,3-dihyro-1H-isoindol-1-one (530 mg, 84%) as an off-white powder. $^1$H NMR (400 MHz, d$_6$-DMSO): 12.58 (s, 1H), 12.50 (s, 1H), 7.90 (s, 1H), 7.89 (s, 1H), 7.70-7.60 (m, 2H), 7.51 (t, 1H), 7.32 (d, 1H), 7.30 (t, 1H), 7.19 (t, 1H), 7.14 (s, 1H), 7.05 (d, 1H), 6.94 (d, 1H); MS (EI) for C$_{21}$H$_{13}$ClFN$_3$O$_2$S: 426 (MH$^+$).

A solution of 2-(3-chloro-2-fluorophenyl)-3-hydroxy-3-(2-thioxo-2,3-dihyro-1H-benzimidazol-5-yl)-2,3-dihyro-1H-isoindol-1-one (500 mg, 1.17 mmol) and iodomethane (200 mL, 3.20 mmol) in tetrahydrofuran (10 mL) was heated to 50° C. The reaction mixture was stirred for 1 h, at which time it was cooled to room temperature. The white precipitate was collected by filtration and further rinsed with ethyl acetate (30 mL) to afford 2-(3-chloro-2-fluorophenyl)-3-hydroxy-3-[2-(methylthio)-1H-benzimidazol-5-yl]-2,3-dihydro-1H-isoindolin-1-one (510 mg, 98%). $^1$H NMR (400 MHz, d$_6$-DMSO): 7.96 (br s, 1H), 7.90 (d, 1H), 7.69-7.62 (m, 2H), 7.55 (s, 1H), 7.51 (t, 1H), 7.45 (d, 1H), 7.37 (t, 1H), 7.30 (d, 1H), 7.21 (t, 1H), 7.09 (d, 1H), 2.76 (s, 3H); MS (EI) for C$_{22}$H$_{15}$ClFN$_3$O$_2$S: 440 (MH$^+$).

A neat solution of 2-(3-chloro-2-fluorophenyl)-3-hydroxy-3-[2-(methylthio)-1H-benzimidazol-5-yl]-2,3-dihydro-1H-isoindolin-1-one (50 mg, 0.114 mmol) and aniline (103 mL, 1.13 mmol) was heated to 140° C. for 1 h, at which time it was cooled to room temperature. The residue was purified by reverse phase HPLC to afford 2-(3-chloro-2-fluorophenyl)-3-hydroxy-3-[2-(phenylamino)-1H-benzimidazol-5-yl]-2,3-dihydro-1H-isoindol-1-one trifluoroacetate salt (8.2 mg). MS (EI) for C$_{27}$H$_{18}$ClFN$_4$O$_2$: 485 (MH$^+$).

Example 34

Ethyl{5-[2-(3-chloro-2-fluorophenyl)-1-hydroxy-3-oxo-2,3-dihydro-1H-isoindol-1-yl]-1,3-benzoxazol-2-yl}carbamate To a solution of 2-[(4-hydroxy-3-nitrophenyl)carbonyl]benzoic acid (9.7 g, 30 mmol) in DMF (100 mL) was added cesium carbonate (9.8 g, 30 mmol) and benzyl bromide (3.6 mL, 30 mmol). The reaction mixture was stirred at rt for 4 h. Water, 10% citric acid, and ethyl acetate were added, and then the phases were partitioned. The aqueous phase was extracted with ethyl acetate. The organic extracts were combined, dried over magnesium sulfate, filtered, and concentrated. The residue was purified by flash chromatography (50% hexanes: 50% ethyl acetate). The product-containing fractions were combined and concentrated. Impurities were removed from the solid residue by trituration with ether. The desired phenylmethyl 2-[(4-hydroxy-3-nitrophenyl)carbonyl]benzoate was obtained as powdery yellow solid (6.17 g, 16.3 mmol, 54% yield. $^1$H NMR (400 MHz, CDCl$_3$): 10.89 (s, 1H), 8.25 (d, 1H), 8.16 (dd, 1H), 7.91 (dd, 1H), 7.69 (m, 1H), 7.62 (m, 1H), 7.35 (m, 1H), 7.27-7.23 (m, 3H), 7.20-7.17 (m, 2H), 7.10 (d, 1H), 5.13 (s, 2H); MS (EI) for C$_{21}$H$_{15}$NO$_6$: 400 (MNa$^+$).

A solution of phenylmethyl 2-[(4-hydroxy-3-nitrophenyl)carbonyl]benzoate (5.78 g, 15.3 mmol) in acetic acid (50 mL) was treated with iron powder (8.5 g, 153 mmol) at 50° C. for 30 min. After cooling to rt, the mixture was diluted with ethyl acetate, and the solids were removed by filtration though celite. The organic filtrate was washed with saturated sodium bicarbonate, which lead to further precipitation of solid contaminants. These solids were removed by filtration. The resulting organic filtrate was dried over magnesium sulfate, filtered, and concentrated to a brown foam. This material was taken up in DMF (30 mL). To this solution was added ethoxycarbonyl isothiocyanate (2.6 mL, 23 mmol). After stirring for 35 min, EDC (4.4 g, 23 mmol) was added to the reaction mixture. The mixture was stirred at rt for 35 min and then was stirred for a further 1 h at 65° C., and then it was cooled to rt. To the mixture was added 10% aqueous citric acid, and the resulting aqueous mixture was extracted twice with ethyl acetate. The organic extracts were combined, washed with brine, dried over magnesium sulfate, filtered, and concentrated to a brown solid. Contaminants were removed by trituration with methanol. Desired phenylmethyl 2-[(2-{[(ethyloxy)carbonyl]amino}-1,3-benzoxazol-5-yl)carbonyl]benzoate was isolated as a white solid (637 mg, 1.4 mmol, 9.4% yield). A sample was further purified by reverse phase HPLC. $^1$H NMR (400 MHz, CDCl$_3$): 10.91 (br s, 1H), 8.12 (m 1H), 7.95 (br s, 1H), 7.67 (m, 1H), 7.63-7.52 (m, 3H), 7.47-7.38 (m, 2H), 7.26-7.13 (m, 5H), 5.08 (s, 2H), 4.29 (q, 2H), 1.38 (t, 3H); MS (EI) for C$_{25}$H$_{20}$N$_2$O$_6$: 445 (MH$^+$).

To a solution of phenylmethyl 2-[(2-{[(ethyloxy)carbonyl]amino}-1,3-benzoxazol-5-yl)carbonyl]benzoate (637 mg, 1.4 mmol) in ethyl acetate (10 mL), THF (2 mL) and methanol (4 mL) was added 10% palladium on carbon (wet) (200 mg). The mixture was subjected to an atmosphere of hydrogen gas at 30 psi for 2.5 h. The catalyst was then removed by filtration through a pad of celite. The filtrate was concentrated in vacuo to provide 198 mg of product contaminated with an unidentified byproduct. A portion of this material was used in the subsequent reaction without further purification. To the contaminated acid (85 mg, <0.24 mmol) was added DCM (1.8 mL), pyridine (20 µL, 0.24 mmol), and cyanuric fluoride (25 µL, 0.29 mmol). The mixture was stirred for 30 min at rt. Water and DCM were then added, and the layers were partitioned. The organic extract was dried over magnesium sulfate, filtered, and concentrated to a white solid (73 mg, <0.12 mmol). This solid was dissolved in dichloroethane (2 mL), and then N,N-dimethylaniline (51 mL, 0.4 mmol) and 3-chloro-2-fluoroaniline (35 mg, 0.24 mmol) were added. The mixture was heated to 75° C. for 4 h and was then cooled to rt. The solvent was removed in vacuo, and the residue was purified by preparative HPLC. The clean product-containing fractions neutralized with saturated sodium bicarbonate. The organic solvents were removed in vacuo, and the resulting aqueous solution was extracted with ethyl acetate. The organic extracts were dried over magnesium sulfate, filtered, and concentrated yielding ethyl{5-[2-(3-chloro-2-fluorophenyl)-1-hydroxy-3-oxo-2,3-dihydro-1H-isoindol-1-yl]-1,3-benzoxazol-2-yl}carbamate as a white solid (8.5 mg, 0.018 mmol). $^1$H NMR (400 MHz, d$_6$-DMSO): 11.58 (s, 1H), 7.91 (s, 1H), 7.90-7.88 (m, 1H), 7.71-7.62 (m, 2H), 7.54-7.47 (m, 3H), 7.40-7.33 (m, 2H), 7.20 (m, 1H), 7.09 (dd, 1H), 4.17 (q, 2H), 1.25 (t, 3H); MS (EI) for C$_{24}$H$_{17}$ClFN$_3$O$_5$: 482, 484 (MH$^+$).

Example 35

5-chloro-3-ethynyl-2-methylaniline

4-Chloro-2-nitrotoluene (10 g, 58.3 mmol) was dissolved in concentrated sulfuric acid (60 mL) and cooled in an ice-bath. N-Iodosuccinimide (23.6 g, 105 mmol) was added over 0.1 h and the cooled mixture was stirred for 2 h. The mixture was poured into ice-water (~200 mL) and extracted with twice with ethyl acetate. The combined organic portion was washed three times with 1 M sodium thiosulfate solution, twice with saturated sodium bicarbonate solution, brine, dried over sodium sulfate, filtered and concentrated in vacuo to afford a yellow-brown oil (17.6 g) which was dissolved in acetic acid (80 mL). Tin (II) chloride dihydrate (52.3 g, 232 mmol) was added and the mixture was stirred for 2 h and then was concentrated in vacuo. The residue was transferred to an Erlenmeyer flask using a little ethyl acetate and diluted with ether (120 mL). The mixture was stirred while cooling in an ice-water bath and sodium hydroxide (50% solution in water) (60 mL) was added dropwise. The solid which formed was removed by filtration and was washed with hot ethyl acetate. The combined filtrate was concentrated in vacuo and the residue was partitioned between ethyl acetate and water. The organic portion was washed twice with 1N sodium hydroxide, brine, dried over sodium sulfate, filtered and concentrated in vacuo to afford an orange oil which was purified by Biotage normal phase column chromatography using the 75 pre-packed chromatography column (gradient: hexanes to ethyl acetate-hexanes 9:1) to afford 5-chloro-3-iodo-2-methylaniline as yellow crystals (7.48 g, 28.0 mmol, 47% yield). $^1$H NMR (400 MHz, CDCl$_3$): 7.27-7.25 (m, 1H), 6.64 (d, 1H), 3.78 (br s, 2H), 2.28 (s, 3H); MS (EI) for C$_7$H$_7$Cl$_1$N: 268 (MH$^+$).

5-Chloro-3-iodo-2-methylaniline (7.44 g, 27.8 mmol) was dissolved in tetrahydrofuran (80 mL) and di-tert-butyl dicarbonate (6.37 g, 29.2 mmol) was added. The mixture was stirred at room temperature for 15 h and then a few crystals of 4-dimethylaminopyridine were added and the mixture was stirred for a further 1 h. Di-tert-butyl dicarbonate (6.37 g, 29.2 mmol) was added and the mixture was stirred for a further 56.5 h. The mixture was concentrated in vacuo and the residue was partitioned between ethyl acetate and citric acid (20% aqueous solution). The organic portion was washed with brine, dried over sodium sulfate, filtered and concentrated in vacuo to afford an orange-brown oil (~13.5 g), which was diluted with acetone (100 mL). To the solution was added water (5 mL) and potassium carbonate (5 g). The mixture was stirred at ambient temperature for 1 hr, and then concentrated in vacuo. The resultant residue was partitioned between water and ethyl acetate. The aqueous portion was extracted twice using ethyl acetate and the combined organic portions were washed with brine, dried over sodium sulfate, filtered and concentrated in vacuo to afford 7.6 g, 0.02 mol (34%) of 1,1-dimethylethyl (5-chloro-3-iodo-2-methylphenyl)carbamate as a white solid. $^1$H NMR (400 MHz, CDCl$_3$): 7.79 (d, 1H), 7.11 (d, 1H), 2.28 (s, 3H), 1.41 (s, 9H); MS (EI) for C$_{12}$H$_{15}$Cl$_1$NO$_2$: 368 (MH$^+$).

To a solution of 1,1-dimethylethyl (5-chloro-3-iodo-2-methylphenyl)carbamate (5 g, 13.6 mmol) in dichloromethane (50 mL) was added trifluoroacetic acid (10 mL). The solution was stirred at ambient temperature for 2 hours, then concentrated in-vacuo. The resultant residue was partitioned between saturated sodium bicarbonate and ethyl acetate. The aqueous portion was extracted twice with ethyl acetate. The combined organic portions were washed with brine, dried over sodium sulfate, filtered and concentrated in-vacuo to afford an orange residue which was purified by column chromatography (silica gel, 5% ethyl acetate in hexane). The product was isolated to afford 3.05 g, 11.4 mmol (84%) of 5-chloro-3-iodo-2-methylaniline as a yellow solid. $^1$H NMR (400 MHz, CDCl$_3$): 7.26 (d, 1H), 6.64 (d, 1H), 3.78 (br s, 2H), 2.28 (s, 3H); MS (EI) for C$_7$H$_7$Cl$_1$N: 268 (MH$^+$).

A solution of 1,1-dimethylethyl (5-chloro-3-iodo-2-methylphenyl)carbamate (610 mg, 1.7 mmol), 2-methyl-3-butyn-2-ol (245 μl, 2.5 mmol), and triphenylphosphine (30 mg, 0.12 mmol) in acetonitrile (2 mL) was deoxygenated for 20 minutes. The solution was cooled to 0° C., followed by the addition of copper(I)iodide (12 mg, 0.07 mmol), and palladium (II)dichloride (13 mg, 0.06 mmol). The mixture was stirred at reflux for 1.5 hours, then cooled to room temperature and concentrated in-vacuo. The resultant residue was partitioned between water and ethyl acetate. The aqueous portion was extracted twice with ethyl acetate. The combined organic portions were washed with brine, dried over sodium sulfate, filtered and concentrated in-vacuo to afford a brown residue which was purified by column chromatography (silica gel, 20% ethyl acetate in hexanes). The product was collected to afford 504 mg, 1.56 mmol (94%) of 1,1-dimethylethyl[5-chloro-3-(3-hydroxy-3-methylbut-1-yn-1-yl)-2-methylphenyl]carbamate as a yellow solid. $^1$H NMR (400 MHz, CDCl$_3$): 7.36 (d, 1H), 7.06 (d, 1H), 2.26 (s, 3H), 1.63 (s, 6H), 1.41 (s, 9H); MS (EI) for C$_{17}$H$_{22}$ClNO$_3$: 324 (MH$^+$).

To a solution of 1,1-dimethylethyl[5-chloro-3-(3-hydroxy-3-methylbut-1-yn-1-yl)-2-methylphenyl]carbamate (504 mg 1.56 mmol) in toluene (3 mL) was added potassium carbonate (215 mg, 1.56 mmol) and 18-crown-6 (82 mg, 0.31 mmol). The mixture was stirred at reflux for 5 hours, then was cooled to room temperature and partitioned between water and ethyl acetate. The aqueous portion was extracted twice with ethyl acetate. The combined organic portions were washed with brine, dried over sodium sulfate, filtered and concentrated in-vacuo to afford a brown residue which was purified by column chromatography (silica gel, 5% ethyl acetate in hexane). The product was collected to afford 242 mg, 0.91 mmol (58%) of 1,1-dimethylethyl (5-chloro-3-ethynyl-2-methylphenyl)carbamate as a tan solid. $^1$H NMR (400 MHz, CDCl$_3$): 7.40 (d, 1H), 7.07 (d, 1H), 3.32 (s, 1H), 2.25 (s, 3H), 1.39 (s, 9H); MS (EI) for C$_{14}$H$_{16}$ClNO$_2$: 266 (MH$^+$).

To a solution of 1,1-dimethylethyl (5-chloro-3-ethynyl-2-methylphenyl)carbamate (242 mg, 0.91 mmol) in dichloromethane (2 mL) was added trifluoroacetic acid (500 μl). The solution was stirred at ambient temperature for 1 hour. The solution was partitioned between saturated sodium bicarbonate and dichloromethane. The aqueous layer was extracted twice with dichloromethane. The combined organic portions were washed with brine, dried over sodium sulfate, filtered and concentrated in-vacuo to afford an orange oil which was purified by column chromatography (silica gel, 50% dichloromethane in hexane). The product was collected to afford 60 mg, 0.36 mmol (40%) of 5-chloro-3-ethynyl-2-methylaniline as a white solid. $^1$H NMR (400 MHz, CDCl$_3$): 6.90 (d, 1H), 6.63 (d, 1H), 3.71 (br s, 2H), 3.24 (s, 1H), 2.23 (s, 3H); MS (EI) for C$_9$H$_8$ClN: 166 (MH$^+$).

Example 36

3-ethenyl-2-fluoroaniline

A solution of 1,1-dimethylethyl (3-bromo-2-fluorophenyl) carbamate (500 mg, 1.72 mmol) and 2,6-ditert-4-methylphenol (3 mg, 0.02 mmol) in toluene (3 mL) was deoxygenated for 10 minutes. Tetrakis(triphenylphosphine)palladium(0) (100 mg, 0.09 mmol) and tributyl(vinyl)tin (708 μl, 2.43 mmol) were added to the solution, which was then stirred at refluxed for 4 hrs. The mixture was cooled to room temperature, and then filtered through a pad of celite. The filtrate was concentrated in-vacuo to afford an orange residue, which was purified by column chromatography (silica gel, 5% ether in hexane). The product was isolated as a colorless oil, and was then diluted in dichloromethane (2 mL). To the solution was added trifluoroacetic acid (500 μl), and the solution was stirred at ambient temperature for 1 hour. The solution was partitioned between saturated sodium bicarbonate and dichloromethane. The aqueous portion was extracted twice with dichloromethane, and the combined organic portions were washed with brine, dried over sodium sulfate, filtered, and concentrated in-vacuo to afford 138 mg, 1.0 mmol, (58% over two steps) of 3-ethenyl-2-fluoroaniline as a colorless oil.

¹H NMR (400 MHz, CDCl₃): 6.92-6.82 (m, 3H), 6.71-6.66 (m, 1H), 5.80 (d, 1H), 5.35 (d, 1H); 3.72 (br s, 2H); MS (EI) for $C_8H_8FN$: 138 (MH⁺).

Example 37

3-ethynyl-2-fluoroaniline

A solution of 3-bromo-2-fluorobenzoic acid (18.9 g, 86.3 mmol) in thionyl chloride (125 mL) was stirred at reflux for 1 hr. The solution was cooled to room temperature, and concentrated in-vacuo. The resultant residue was azeotroped twice with benzene, then diluted with dichloromethane. The organic portion was dried over sodium sulfate, filtered and concentrated in-vacuo to afford 20.3 g, 85.4 mmol (99%) of a pale yellow oil, which was diluted in acetonitrile (100 mL). The solution was cooled in an ice bath and sodium azide (8.5 g, 130 mmol) was added in portions. The mixture was stirred at ambient temperature for 1.5 hrs, and then concentrated in-vacuo. The resultant residue was partitioned between water and ether. The organic portion was washed twice with water, brine, dried over sodium sulfate, filtered and concentrated in-vacuo to afford 19.9 g, 81.6 mmol (96%) of an off white solid. The solid was dissolved in toluene (50 mL) and added dropwise over the course of 1 hr, to tent-butanol (100 mL) stirring at 90° C. Upon addition the solution was stirred for a further 30 minutes at 90° C. The solution was cooled to room temperature and concentrated in-vacuo. The resultant residue was azeotroped twice with benzene, to afford 23.3 g, 80.31 mmol (93%) of 1,1-dimethylethyl (3-bromo-2-fluorophenyl)carbamate as a pale yellow solid. ¹H NMR (400 MHz, d₆-DMSO): 9.21 (s, 1H), 7.63-7.58 (m, 1H), 7.42-7.37 (m, 1H), 7.11-7.07 (m, 1H), 1.46 (s, 9H); MS (EI) for $C_{11}H_{13}BrFNO_2$: 291 (MH⁺).

To a solution of 1,1-dimethylethyl (3-bromo-2-fluorophenyl)carbamate (15.7 g, 54.1 mmol), in triethylamine (60 mL) was added 3-methyl-butyn-2-ol (7.9 mL, 81.2 mmol), triphenylphosphine (568 mg, 2.2 mmol), copper(I)iodide (419 mg, 2.2 mmol) and palladium(II)dichloride (767 mg, 4.33 mmol). The mixture was stirred at reflux for 2 hrs, and then was cooled to room temperature. The mixture was filtered through a plug of silica, and eluted using ether/hexane (1:1). The product was isolated to afford 19.4 g, 66.1 mmol (122%) of a brown oil which was diluted in toluene (60 mL). To the solution was added tert-butoxide (25 g, 270.5 mmol), and the mixture was stirred at reflux for 1 hr. The mixture was cooled to room temperature, and partitioned between 20% citric acid and toluene. The aqueous portion was extracted twice with ethyl acetate. The combined organic portions were washed with water, brine, dried over sodium sulfate, filtered and concentrated in-vacuo to afford a brown residue, which was purified by column chromatography (silica gel, 10% ether in hexanes). The product was isolated to afford 10.5 g, 44.6 mmol (83% over 2 steps) of 1,1-dimethylethyl (3-ethynyl-2-fluorophenyl)carbamate as a yellow oil. ¹H NMR (400 MHz, d₆-DMSO): 9.10 (s, 1H), 7.64-7.60 (m, 1H), 7.24-7.20 (m, 1H), 7.12-7.08 (m, 1H), 4.48 (s, 1H), 1.44 (s, 9H); MS (EI) for $C_{13}H_{14}FNO_2$: 236 (MH⁺).

To a solution of 1,1-dimethylethyl (3-ethynyl-2-fluorophenyl)carbamate (10.5 g, 44.6 mmol) in dichloromethane (100 mL) was added trifluoroacetic acid (20 mL). The solution was stirred at room temperature for 1 hr, and was then concentrated in-vacuo. The resultant residue was partition between sodium bicarbonate and ether. The organic portion was washed with brine, dried over sodium sulfate, filtered and concentrated in-vacuo to afford a brown residue. The residue was diluted with isopropanol (10 mL) and 4N HCl in dioxane (8 mL) was added. The recrystallized product was collected by vacuum filtration to afford 3.7 g, 21 mmol (68%) of 3-ethynyl-2-fluoroaniline hydrochloride as a pale brown solid. ¹H NMR (400 MHz, d₆-DMSO): 7.08-6.91 (m, 3H), 4.45 (s, 1H); MS (EI) for $C_8H_6FN$: 136 (MH⁺).

Example 38

3-ethyl-4-fluoroaniline

To a solution of 3-ethynyl-4-fluoroaniline (220 mg, 1.62 mmol) in ethyl acetate (10 mL) was added 10% palladium on carbon (wet). The resulting mixture was subjected to an atmosphere of hydrogen for approximately 1 h. The palladium on carbon was removed by filtration through celite. The filtrate was concentrated in vacuo to provide 3-ethyl-4-fluoroaniline (154 mg, 1.11 mmol, 69% yield) as a brown oil. ¹H NMR (400 MHz, CDCl₃): 6.77 (dd, 1H), 6.50 (dd, 1H), 6.45-6.41 (m, 1H), 3.47 (br s, 2H), 2.57 (q, 2H), 1.19 (t, 3H); MS (EI) for $C_8H_{10}FN$: 140 (MH⁺).

Example 39

1-(3-chloro-2-methylphenyl)ethanamine: (1Z)-1-(3-chloro-2-methylphenyl)ethanone oxime 1-(3-Chloro-2-methyl-phenyl)-ethanone (390 mg, 2.3 mmol) was dissolved in ethanol (6 ml) and hydroxylamine hydrochloride (433 µL, 10.4 mmol) was added. The mixture was stirred at 80° C. for 1.5 hours. Reaction mixture was concentrated in vacuo and partitioned between water and ethyl acetate. The aqueous portion was extracted with ethyl acetate. The combined organic portions were washed with brine, dried over sodium sulfate and concentrated in vacuo to give (1Z)-1-(3-chloro-2-methylphenyl)ethanone oxime as a yellow oil (383 mg, 2.08 mmol, 90% yield). ¹H NMR (400 MHz, CDCl₃): 6.95-7.37 (m, 3H), 2.36 (s, 3H), 2.26 (s, 1H), 2.21 (s, 3H); MS (EI) for $C_9H_{10}ClNO$: 184 (MH⁺).

1-(3-chloro-2-methylphenyl)ethanamine

To (1Z)-1-(3-chloro-2-methylphenyl)ethanone oxime (383 mg, 2.08 mmol) in acetic acid (10 ml) was added zinc dust (2.72 g, 41.6 mmol) and the resulting mixture was stirred at 40° C. for 3 hours. The reaction mixture was diluted with methanol and filtered. The filtrate was concentrated in vacuo and the obtained residue was partitioned between 1 N hydrochloric acid and ethyl acetate. The aqueous portion was neutralized with sodium bicarbonate and extracted with ethyl acetate. The organic layer was washed with brine, dried over sodium sulfate and concentrated in vacuo to give 1-(3-chloro-2-methylphenyl)ethanamine as a clear oil (290 mg, 1.7 mmol, 82% yield). ¹H NMR (400 MHz, CDCl₃): 8.98 (s, 1H), 7.11-7.44 (m, 3H), 2.37 (s, 3H), 1.81 (s, 3H); MS (EI) for $C_9H_{12}ClN$: 170 (MH⁺).

Example 40

N-Ethyl-N-phenylbenzene-1,3-diamine

1-Bromo 3-nitrobenzene (500 mg, 2.5 mmol) and N-ethylaniline (375 µL, 3.0 mmol) were dissolved in toluene (15 ml) and sodium butoxide (193 mg, 2.0 mmol), Xantphos (143 mg, 0.25 mmol) and tris (dibenzylideneacetone) dipalladium (57 mg, 0.06 mmol) were added. The reaction mixture was stirred at 110° C. for 16 hours. The mixture was filtered through celite and the filtrate was concentrated to give crude product, which was purified by column chromatography (9:1 hexanes-ethyl acetate) to give N-ethyl-3-nitro-N-phenylaniline as colorless oil (400 mg, 1.65 mmol, 67% yield). $^1$H NMR (400 MHz, CDCl$_3$): 6.99-7.59 (m, 8H), 6.58-6.69 (m, 1H), 3.79 (q, 2H), 1.25 (t, 3H); MS (EI) for C$_{14}$H$_{14}$N$_2$O$_2$: 242 (MH$^+$).

N-Ethyl-3-nitro-N-phenylaniline (400 mg, 1.65 mmol) was dissolved in acetic acid (5 ml) at 40° C. followed by slow addition of tin (II) chloride dihydrate (1.50 g, 6.60 mmol). The reaction mixture was stirred at 40° C. for 2 hours and then for a further 2 hours at 75° C. The mixture was concentrated in vacuo and the obtained residue was diluted with ether (10 ml). Aqueous sodium hydroxide solution (2 ml) was added dropwise to the cooled (0° C.) solution. A solid formed was separated by filtration and was rinsed twice with hot ethyl acetate (25 ml). The filtrate was concentrated to approximately 30 ml and washed with 1 N sodium hydroxide, brine, dried over sodium sulfate and concentrated in vacuo to give N-ethyl-N-phenylbenzene-1,3-diamine as a yellow oil (117 mg, 1.04 mmol, 63% yield). $^1$H NMR (400 MHz, CDCl$_3$): 6.87-7.28 (m, 7H), 6.28-6.83 (m, 2H), 3.74 (q, 2H), 3.59 (s, 2H), 1.20 (t, 3H); MS (EI) for C$_{14}$H$_{16}$N$_2$: 212 (MH$^+$).

Analogously the following reagents were synthesized:
N-methyl-N-phenylbenzene-1,3-diamine: $^1$H NMR (400 MHz, CDCl$_3$): 6.94-7.29 (m, 8H), 6.29-6.43 (m, 3H), 3.28 (s, 3H); MS (EI) for C$_{13}$H$_{14}$N$_2$: 198 (MH$^+$).
N-cyclohexyl-N-methylbenzene-1,3-diamine: $^1$H NMR (400 MHz, CDCl$_3$): 6.98-7.02 (m, 1H), 6.05-6.25 (m, 3H), 3.49-3.57 (m, 2H), 2.73 (s, 3H), 1.10-2.05 (m, 11H); MS (EI) for C$_{13}$H$_{20}$N$_2$: 204 (MH$^+$).

Example 41

5-ethynyl-2-methylaniline

To a solution of 4-bromo-1-methyl-2-nitrobenzene (1.0 g, 4.6 mmol) in triethylamine (5 mL) was added 2-methyl-3-butyn-2-ol (680 mL, 6.9 mmol), triphenylphosphine (97 mg, 0.37 mmol), copper(I) iodide (34 mg, 0.18 mmol), and palladium(II) chloride (32 mg, 0.18 mmol). The mixture was heated to reflux and stirred for 45 min. After cooling, the mixture was filtered through celite, and the filtrate was concentrated in vacuo. The residue was purified by flash chromatography (65% hexanes: 35% ethyl acetate) quantitatively yielding 2-methyl-4-(4-methyl-3-nitrophenyl)but-3-yn-2-ol as an orange oil. $^1$H NMR (400 MHz, CDCl$_3$): 8.02 (d, 1H), 7.52 (dd, 1H), 7.29 (d, 1H), 2.60 (s, 3H), 1.63 (s, 6H); GCMS for C$_{12}$H$_{13}$NO$_3$: 219 (M$^+$).

To a solution of 2-methyl-4-(4-methyl-3-nitrophenyl)but-3-yn-2-ol (1.0 g, 4.6 mmol) in acetic acid (15 mL) at 50° C. was added iron powder (2.6 g, 46 mmol). The mixture was stirred at 50° C. for 45 min, after which the mixture was heated to 70° C. for a further 16 h. The mixture was cooled to rt, diluted with ethyl acetate, and filtered through celite with multiple ethyl acetate rinses. The filtrate was concentrated in vacuo. The residue was taken up in ethyl acetate and saturated sodium bicarbonate at which point a precipitate formed. The solid was removed by filtration, and the filtrate was partitioned. The organic phase was dried over magnesium sulfate, filtered, and concentrated. The residue was purified by flash chromatography (50% hexanes: 50% ethyl acetate) yielding 4-(3-amino-4-methylphenyl)-2-methylbut-3-yn-2-ol as an orange oil (509 mg, 2.7 mmol, 58% yield over two steps). $^1$H NMR (400 MHz, CDCl$_3$): 6.97 (d, 1H), 6.77 (d, 1H), 6.74 (s, 1H), 2.15 (s, 3H), 1.60 (s, 6H); GCMS for C$_{12}$H$_{15}$NO: 189 (M$^+$).

A solution of 4-(3-amino-4-methylphenyl)-2-methylbut-3-yn-2-ol (509 mg, 2.7 mmol) in toluene (2 mL) was treated with potassium hydroxide (1.0 g, 18 mmol) at reflux for 20 min. After cooling to rt, water and ether were added, and the layers were partitioned. The organic phase was acidified with 4 N hydrochloric acid in dioxane (700 μL). The volatile materials were removed in vacuo providing a yellow/brown solid. The solid was taken up in ether and washed with saturated sodium bicarbonate. The organic phase was dried over magnesium sulfate, filtered, and concentrated carefully to avoid loss of the moderately volatile product. Desired 5-ethynyl-2-methylaniline was isolated as an oil in quantitative yield, contaminated with 10% ether by mass. $^1$H NMR (400 MHz, CDCl$_3$): 6.99 (d, 1H), 6.85 (dd, 1H), 6.81 (d, 1H), 3.61 (br s, 2H), 2.98 (s, 1H), 2.16 (s, 3H); GCMS for C$_9$H$_9$N: 131 (M$^+$).

Example 42

1-(5-chloro-2-thienyl)ethanamine

To a toluene (12 mL) solution of 1-(5-methyl-2-thienyl)ethanol (983 mg, 6.05 mmol) was added DBU (1.09 mL, 7.26 mmol) followed by diphenylphosphoryl azide (1.56 mL, 3.96 mmol). The resulting mixture was stirred for 18 h at rt. Water and ethyl acetate were then added, and the resulting biphasic mixture was partitioned. The organic phase was dried over magnesium sulfate, filtered, and then concentrated in vacuo. The residue was purified by flash chromatography (95% hexanes:5% ethyl acetate) yielding the desired 1-(5-chloro-2-thienyl)ethyl azide (991 mg, 5.3 mmol, 87%) as a colorless oil. $^1$H NMR (400 MHz, CDCl$_3$): 6.79 (m, 2H), 4.71 (q, 1H), 1.58 (d, 3H).

A mixture of 1-(5-chloro-2-thienyl)ethyl azide (991 mg, 5.3 mmol) and triphenylphosphine (1.4 g, 5.3 mmol) in THF (10 mL) and water (0.4 mL) was heated to 60° C. for 1 h. After cooling to rt, the solution was concentrated in vacuo. The resulting residue was purified by flash chromatography (90% DCM:10% methanol) to provide the desired 1-(5-chloro-2-thienyl)ethanamine (646 mg, 4.0 mmol, 75% yield) as a pink liquid. $^1$H NMR (400 MHz, CDCl$_3$): 6.71 (d, 1H), 6.64 (d, 1H), 4.26 (q, 1H), 1.64 (br s, 2H), 1.44 (d, 3H).

Example 43

5-chloro-2,3-difluoroaniline

To acetic anhydride (20 mL) was added 2-chloro-4,5-difluoroaniline (4.7 g, 29 mmol), and the resulting solution was stirred at 100° C. for 1 h. After cooling to rt, the mixture was stored in a freezer overnight. A white crystalline precipitate formed, and it was collected by filtration. Residual acetic anhydride was removed in vacuo. The desired N-(2-chloro-4,5-difluorophenyl)acetamide (4.69 g, 22.8 mmol, 79% yield) was isolated as a white crystalline solid. $^1$H NMR (400 MHz, CDCl$_3$): 8.38 (dd, 1H), 7.53 (br s, 1H), 7.23 (dd, 1H), 2.25 (s, 3H); MS (EI) for C$_8$H$_6$ClF$_2$NO: 206 (MH$^+$).

A solution of N-(2-chloro-4,5-difluorophenyl)acetamide (4.69 g, 22.8 mmol) in acetic acid (4.5 mL) and concentrated sulfuric acid (15 ml) was cooled to 0° C. To the solution was added a mixture of fuming nitric acid (2 mL) and acetic acid (0.5 mL). After stirring for 1.5 h at 0° C., the mixture was poured into ice. A precipitate formed, and it was collected by filtration. The filtrate was extracted with ether, and the organic phase was dried over magnesium sulfate, filtered, and concentrated to sticky yellow syrup. The solid and the syrup were combined, and to the resulting residue was added concentrated hydrochloric acid (30 mL). This mixture was heated to 120° C. for 1.25 h. It was then cooled to rt and subsequently poured onto ice. The aqueous solution was extracted with ethyl acetate. The organics were washed with saturated sodium bicarbonate, dried over magnesium sulfate, filtered, and concentrated. The residue was purified by flash chromatography (80% hexanes: 20% ethyl acetate) to provide the desired 6-chloro-3,4-difluoro-2-nitroaniline (3.30 g, 15.8 mmol, 69% yield). $^1$H NMR (400 MHz, CDCl$_3$): 7.43 (dd, 1H), 5.86 (br s, 2H); GCMS for $C_6H_3ClF_2N_2O_2$: 208 (M$^+$).

A solution of 6-chloro-3,4-difluoro-2-nitroaniline (3.30 g, 15.8 mmol) in concentrated sulfuric acid (8.3 mL) was stirred at rt for 3 h and was then cooled to 0° C. A solution of sodium nitrite (1.3 g, 18.8 mmol) concentrated sulfuric acid (6.7 mL) was added slowly followed by phosphoric acid (85%, 15 mL) added drop wise. A dark brown precipitate formed, and the resulting slurry was stirred for 1 h at 0° C. A suspension of copper(I) oxide (2.4 g, 30 mmol) and sodium hypophosphite hydrate (5.6 g, 64 mmol) in water (6.7 mL) was then added slowly with the temperature remaining at 0° C. Substantial gas evolution was observed during the addition. When the reaction was complete, the mixture was diluted with water and ether. Celite was added to help adsorb insoluble solids. The mixture was filtered, and the filtrate was partitioned. The organic phase was dried over magnesium sulfate, filtered, and concentrated in vacuo. The residue was purified by flash chromatography (90% hexanes: 10% ethyl acetate) to provide the desired 5-chloro-1,2-difluoro-3-nitrobenzene (1.62 g, 8.4 mmol, 53% yield) as a yellow crystalline solid. $^1$H NMR (400 MHz, CDCl$_3$): 7.88 (m, 1H), 7.53 (m, 1H); GCMS for $C_6H_2ClF_2NO_2$: 193 (M$^+$).

To a solution of 5-chloro-1,2-difluoro-3-nitrobenzene (1.62 g, 8.4 mmol) in acetic acid (30 mL) was added tin(II) dichloride dihydrate (11.4 g, 50.4 mmol). The mixture was stirred for 1.25 h at rt, and then the acetic acid was removed in vacuo. The residue was transferred to a 500-mL Erlenmeyer flask in a minimal amount of ethyl acetate. The resulting suspension was then diluted with approximately 200 mL of ether, and then the flask was placed into an ice bath. To the vigorously stirring mixture was added 50% aqueous sodium hydroxide (10 mL), and a pale yellow solid formed. Celite and sodium sulfate were added to adsorb and dry the precipitate. All the solids were removed by filtration, rinsed with ethyl acetate, and discarded. The filtrate was concentrated, and the residue was purified by flash chromatography (80% hexanes: 20% ethyl acetate). The desired 5-chloro-2,3-difluoroaniline was isolated as an orange oil (913 mg, 5.6 mmol, 66% yield). $^1$H NMR (400 MHz, CDCl$_3$): 6.57-6.52 (m, 2H), 3.91 (br s, 2H); GCMS for $C_6H_4ClF_2N$: 163 (M$^+$).

Example 44

3-chloro-2,6-difluoroaniline

To a solution of 3-chloro-2,6-difluorobenzoic acid (500 mg, 2.6 mmol) in DMF (7.5 mL) was added triethylamine (362 µL, 2.6 mmol) and diphenylphosphoryl azide (560 µL, 2.6 mmol). After the mixture was stirred at rt for 1.25 h, 2-methyl-2-propanol (2.5 mL) was added, and the mixture was heated to 90° C. for 2 h. Upon cooling to rt, the solvents were removed in vacuo. The residue was partitioned between water and ethyl acetate. The aqueous was extracted with ethyl acetate. The combined organic extracts were washed with brine, dried over magnesium sulfate, filtered, and concentrated. The residue was purified by flash chromatography (80% hexanes: 20% ethyl acetate) yielding 1,1-dimethylethyl (3-chloro-2,6-difluorophenyl)carbamate as a white waxy solid (contaminated with approximately 20% of the aniline).

$^1$H NMR (400 MHz, CDCl$_3$): 7.24 (m, 1H), 6.91 (m, 1H), 5.99 (br s, 1H), 1.51 (s, 9H); GCMS for $C_{11}H_{12}ClF_2NO_2$: 263 (M$^+$).

A solution of 1,1-dimethylethyl (3-chloro-2,6-difluorophenyl)carbamate (437 mg, 1.66 mmol) in methanol (2 mL) was treated with 4 N hydrochloric acid in dioxane (2 mL) and heated for 1 min with a heat gun. After cooling, the volatile materials were removed in vacuo. The resulting residue was taken up in ethyl acetate and washed with sodium bicarbonate (sat). The organic phase was dried over magnesium sulfate, filtered, and concentrated yielding 3-chloro-2,6-difluoroaniline as a white solid (250 mg, 1.53 mmol, 92%). MS (EI) for $C_6H_4ClF_2N$: 164 (MH$^+$).

Example 45

Methyl{5-[(2-{[(phenylmethyl)amino]carbonylphenyl)carbonyl]-1H-benzimid-azol-2-yl}carbamate A solution of 2-(4-chloro-3-nitrobenzoyl)benzoic acid (5.0 g, 16.36 mmol) was heated to reflux in 28-30% aq. ammonium hydroxide (100 mL) for 18 h. The solution was cooled to room temperature followed by addition of 6N aq. hydrochloric acid until pH to 7. The precipitated yellow solid was collected by filtration and washed with water then dried in vacuo to provide 2-[(4-amino-3-nitrophenyl)carbonyl]benzoic acid (4.60 g, 98%). MS (EI) for $C_{14}H_{10}N_2O_5$: 288 (MH$^+$).

A solution of 2-[(4-amino-3-nitrophenyl)carbonyl]benzoic acid (4.60 g, 16.00 mmol) in methanol (300 mL) in the presence of catalytic amount of cc. sulfuric acid was heated to reflux for 18 h. The solution was cooled to room temperature and the solvent was evaporated. The yellow precipitate formed was collected by filtration, washed with water and dried in vacuo to provide methyl 2-[(4-amino-3-nitrophenyl)carbonyl]benzoate (4.8 g, quantitative). MS (EI) for $C_{15}H_{12}N_2O_5$: 301 (MH$^+$).

A solution of methyl 2-[(4-amino-3-nitrophenyl)carbonyl]benzoate (420 mg, 1.39 mmol) in a mixture of terahydrofuran-ethyl acetate (1:1, 20 mL) was hydrogenated over 10% Pd—C (10 mg) for 18 h. The catalyst removed by filtration and the filtrate concentrated to give methyl 2-[(3,4-diaminophenyl)carbonyl]benzoate (370 mg, 98%) as a brown powder. MS (EI) for $C_{15}H_{14}N_2O_3$: 293 (M+Na).

To a solution of methyl 2-[(3,4-diaminophenyl)carbonyl]benzoate (134 mg, 0.50 mmol) in a mixture of acetonitrile-benzene (1:1, 5 mL) methyl isothiocyanatidocarbonate (70 mg, 0.60 mmol) was added followed by the addition of DCC (153 mg, 0.75 mmol) and the reaction mixture was heated to reflux for 18 h. After cooling to room temperature the reaction mixture was concentrated. The residue was triturated with diethyl ether (2×, 10 mL) and the pale orange solid was collected by filtration to give methyl 2-[(2-{[(methoxy)carbonyl]amino}-1H-benzimidazol-5-yl)carbonyl]benzoate (125 mg, 71%). MS (EI) for $C_{18}H_{15}N_3O_5$: 354 (M+H).

Methyl 2-[(2-{[(methoxy)carbonyl]amino}-1H-benzimidazol-5-yl)carbonyl]benzoate (125 mg, 0.35 mmol) was dissolved in a mixture of tetrahydrofuran-methanol (3:1, 12 mL) and a 3.0 M aq. solution of lithium hydroxide (0.12 mL) was added. The solution was heated to reflux for 10 min then cooled to room temperature and the solvent was concentrated. An excess of hydrogen chloride (4M in dioxane) was added and the acidic mixture was concentrated to dryness. The resulting crude, 2-[(2-{[(methoxy)carbonyl]amino}-1H-benzimidazol-5-yl)carbonyl]benzoic acid (120 mg), was used without further purification. MS (EI) for $C_{17}H_{13}N_3O_5$: 340 (M+H).

To a solution of 2-[(2-{[(methoxy)carbonyl]amino}-1H-benzimidazol-5-yl)carbonyl]benzoic acid (120 mg, 0.35 mmol), HOAt (0.5 M in DMF, 1.06 mL, 0.53 mmol), N-methylmorpholine (98 uL, 0.71 mmol) and HATU (175 mg, 0.46 mmol) was added benzylamine (64 uL, 0.60 mmol) and the reaction mixture was stirred at 60° C. for 18 h. The mixture was cooled to room temperature and the solvent was evaporated. The residue was dissolved in a mixture of acetonitrile-chloroform (1:1, 50 mL) and the organic layer was washed with water and brine then dried over anhydrous sodium sulfate, filtered and the filtrate concentrated in vacuo. The residue was purified by reverse phase HPLC to afford the title compound (5.7 mg). MS (EI) for $C_{17}H_{13}N_3O_5$: 429 (M+H).

Example 46

2-[(3-oxo-3,4-dihydro-2H-1,4-benzoxazine-6-yl)carbonyl]-N-(phenylmethyl)benzamide To a solution of 2-[(3-oxo-3,4-dihydro-2H-1,4-benzoxazine-6-yl)carbonylbenzoic acid (100 mg, 033 mmol) in N,N-dimethylformamide (2.00 mL) was added N-methylmorpholine (0.14 mL 1.32 mmol) followed by addition of HOAt (55 mg, 0.40 mmol) and HATU (130 mg, 0.33 mmol). The mixture was stirred for 30 minutes at room temperature followed by the addition of benzylamine (36 uL, 0.33 mmol). The reaction mixture was then heated to 60° C. for 18 h. The mixture was cooled to room temperature and the solvent was evaporated. The residue was dissolved in ethyl acetate the organic layer was washed with brine, 1.0 M aq. hydrochloric acid, brine, saturated aq. sodium-hydrogencarbonate and brine. The organic layer was separated dried over anhydrous sodium sulfate, filtered and the filtrate concentrated in vacuo. The residue was purified by column chromatography (SiO$_2$, hexanes/ethyl acetate) to afford the title compound (0.27 g, 80%). MS (EI) for $C_{23}H_{18}N_2O_4$: 387 (M+H).

Using the same or analogous synthetic techniques and/or substituting with alternative reagents, the following compounds of the invention were prepared:

N-{[4-(methoxy)phenyl]methyl}-2-[(3-oxo-3,4-dihydro-2H-1,4-benzoxazine-6-yl)carbonyl]benzamide MS (EI) for $C_{24}H_{20}N_2O_5$: 399 (M-16 fragment)

N-{[3-(methoxy)phenyl]methyl}-2-[(3-oxo-3,4-dihydro-2H-1,4-benzoxazine-6-yl)carbonyl]benzamide MS (EI) for $C_{24}H_{20}N_2O_5$: 399 (M-16 fragment), 417 (M+H)

N-[(4-bromophenyl)methyl]-2-[(3-oxo-3,4-dihydro-2H-1,4-benzoxazine-6-yl)carbonyl]benzamide MS (EI) for $C_{23}H_{17}BrN_2O_4$: 467 (M+H)

N-[(3-bromophenyl)methyl]-2-[(3-oxo-3,4-dihydro-2H-1,4-benzoxazine-6-yl)carbonyl]benzamide MS (EI) for $C_{23}H_{17}BrN_2O_4$: 467 (M+H)

N-[(4-chlorophenyl)methyl]-2-[(3-oxo-3,4-dihydro-2H-1,4-benzoxazine-6-yl)carbonyl]benzamide MS (EI) for $C_{22}H_{15}ClN_2O_4$: 443 (M+Na)

N-[(3,4-dichlorophenyl)methyl]-2-[(3-oxo-3,4-dihydro-2H-1,4-benzoxazine-6-yl)carbonyl]benzamide MS (EI) for $C_{23}H_{16}Cl_2N_2O_4$: 455 (M+H)

N-[(4-fluorophenyl)methyl]-2-[(3-oxo-3,4-dihydro-2H-1,4-benzoxazine-6-yl)carbonyl]benzamide MS (EI) for $C_{23}H_{17}FN_2O_4$: 405 (M+H)

N-{[4-chloro-3-(trifluoromethyl)phenyl]methyl}-2-[(3-oxo-3,4-dihydro-2H-1,4-benzoxazine-6-yl)carbonyl]benzamide MS (EI) for $C_{24}H_{16}ClF_3N_2O_4$: 489 (M+H)

N-[(4-methylphenyl)methyl]-2-[(3-oxo-3,4-dihydro-2H-1,4-benzoxazine-6-yl)carbonyl]benzamide MS (EI) for $C_{24}H_{20}N_2O_4$: 423 (M+Na)

N-[(3,4-dimethylphenyl)methyl]-2-[(3-oxo-3,4-dihydro-2H-1,4-benzoxazine-6-yl)carbonyl]benzamide MS (EI) for $C_{25}H_{22}N_2O_4$: 416 (M+H)

N-{[4-(dimethylamino)phenyl]methyl}-2-[(3-oxo-3,4-dihydro-2H-1,4-benzoxazine-6-yl)carbonyl]benzamide MS (EI) for $C_{25}H_{23}N_3O_4$: 444 (M+Na)

2-[(3-oxo-3,4-dihydro-2H-1,4-benzoxazine-6-yl)carbonyl]-N-(3-phenylpropyl)benzamide MS (EI) for $C_{25}H_{22}N_2O_4$: 437 (M+Na)

2-[(3-oxo-3,4-dihydro-2H-1,4-benzoxazine-6-yl)carbonyl]-N-(2-phenylethyl)benzamide MS (EI) for $C_{24}H_{20}N_2O_4$: 401 (M+H), 384 (M-16 fragment); $^1$H NMR (400 MHz, d$_6$-DMSO): 10.60 (s, 1H), 7.76 (d, 1H), 7.58 (dd, 2H), 7.12-7.36 (m, 6H), 6.85 (m, 3H), 4.54 (s, 2H), 3.52 (m, 1H), 3.16 (m, 1H), 2.82 (m, 1H), 2.62 (m, 1H).

2-[(3-oxo-3,4-dihydro-2H-1,4-benzoxazine-6-yl)carbonyl]-N-phenylbenzamide MS (EI) for $C_{22}H_{16}N_2O_4$: 373 (M+H)

N-(3-chlorophenyl)-2-[(3-oxo-3,4-dihydro-2H-1,4-benzoxazine-6-yl)carbonyl]benzamide MS (EI) for $C_{22}H_{15}ClN_2O_4$: 429 (M+Na)

N-(4-chlorophenyl)-2-[(3-oxo-3,4-dihydro-2H-1,4-benzoxazine-6-yl)carbonyl]benzamide MS (EI) for $C_{22}H_{15}ClN_2O_4$: 407 (M+H)

N-butyl-2-[(3-oxo-3,4-dihydro-2H-1,4-benzoxazine-6-yl)carbonyl]benzamide MS (EI) for $C_{20}H_{20}N_2O_4$: 353 (M+H)

N-(1-methylethyl)-2-[(3-oxo-3,4-dihydro-2H-1,4-benzoxazine-6-yl)carbonyl]benzamide MS (EI) for $C_{19}H_{18}N_2O_4$: 361 (M+Na)

Generally, the compounds listed above were identified by LC-MS, and/or isolated, and characterized by $^1$H-NMR (most typically 400 MHz). Liquid chromatography-mass spectral (LC-MS) analyses were performed using at least one of: a Hewlett-Packard Series 1100 MSD, an Agilent 1100 Series LC/MSD (available from Agilent Technologies Deutschland GmbH of Waldbronn Germany), or a Waters 8-Channel MUX System (available from Waters Corporation of Milford, Mass.). Compounds were identified according to either their observed mass [M+1] ion (positive mode) or [M−1] ion (negative mode). $^1$H-NMR data for compounds was taken with a Varian AS400 Spectrometer (400 MHz, available from Varian GmbH, Darmstadt, Germany).

Additional examples of compounds that were made according to the methods and procedures described above are set forth in Table 1. Each of these compounds are further aspects of this invention.

Assays

For assay of activity, generally Raf, or a compound according to the invention is non-diffusably bound to an insoluble support having isolated sample-receiving areas (e.g., a microtiter plate, an array, etc.). The insoluble support may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Exemplary methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

One measure of inhibition is $K_i$. For compounds with $IC_{50}$'s less than 1 µM, the $K_i$ or $K_d$ is defined as the dissociation rate constant for the interaction of the agent with a Raf. Exemplary compositions have $K_i$'s of, for example, less than about 100 µM, less than about 10 µM, less than about 1 µM, and further for example having $K_i$'s of less than about 100 nM, and still further, for example, less than about 10 nM. The $K_i$ for a compound is determined from the $IC_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate data (i.e. compound concentration) are fitted to the equation:

$$V = V_{max} E_0 \left[ 1 - \frac{(E_0 + I_0 + K_d) - \sqrt{(E_0 + I_0 + K_d)^2 - 4E_0 I_0}}{2E_0} \right]$$

where V is the observed rate, $V_{max}$, is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Exemplary compounds have $GI_{50}$'s of, for example, less than about 1 mM, less than about 10 µM, less than about 1 µM, and further, for example, having $GI_{50}$'s of less than about 100 nM, still further having $GI_{50}$'s of less than about 10 nM. Measurement of $GI_{50}$ is done using a cell proliferation assay.

Tyrosine kinase activity is determined by 1) measurement of kinase-dependent ATP consumption by in the presence of a generic substrate such as polyglutamine, tyrosine (pEY), by luciferase/luciferin-mediated chemiluminescence or; 2) incorporation of radioactive phosphate derived from $^{33}$P-ATP into a generic substrate which has been adsorbed onto the well surface of polystyrene microtiter plates. Phosphorylated substrate products are quantified by scintillation spectrometry.

Luciferase-Coupled Chemiluminescence Assay Protocol

Kinase activity is measured as the percent of ATP consumed following the kinase reaction using luciferase-luciferin-coupled chemiluminescence. Reactions were conducted in 384-well white, medium binding microtiter plates (Greiner). Kinase reactions were initiated by combining test compounds, ATP and kinase in a 20 uL volume. The reaction mixture was incubated at ambient temperature for 3 hrs. For c-Raf, B-Raf, and B-RafV599E, 2.5-5 nM of the enzyme was pre-incubated with compound in 20 mM Tris pH 7.5, 10 mM MgCl2, 0.03% TX-100, and 1 mM DTT for 30 minutes at room temperature. Following the kinase reaction, a 20 µL aliquot of luciferase-luciferin mix was added and the chemiluminescence signal measured using a Victor$^2$ plate reader (Perkin Elmer). The luciferase-luciferin mix contained 50 mM HEPES, pH 7.8, 67 mM oxalic acid (pH 7.8), 5 (or 50) mM DTT, 0.4% Triton X-100, 0.25 mg/mL coenzyme A, 63 µM AMP, 28 µg/mL luciferin and 40,000 units/mL luciferase. Total ATP consumption was limited to 25-60% and the $IC_{50}$ values correlate well with those determined by radiometric assays.

$^{33}$P-Phosphoryl Transfer Kinase Assay Protocol II

Direct c-Raf Kinase activity was measured as incorporated $^{33}$P in the method described below. Reactions were performed in a 96-well polypropylene V-bottom plate. Samples were incubated for 30 minutes and then transferred to a 96-well P81 Unifilter plate (Whatman). Each reaction contained 50 nM c-Raf with 5 uM ATP and $^{33}$P-γ-ATP (3.3 µCi/nmol) in 20 mM Tris pH 7.5, 10 mM MgCl2, 0.03% TX-100, and 1 mM DTT. Plates were washed 10 times with 0.075% phosphoric acid. 100 ul of scintillation fluid was added and incorporated $^{33}$P was measured by liquid scintillation spectrometry using a MicroBeta scintillation counter (Perkin Elmer).

Structure Activity Relationships

Table 1 shows structure activity relationship data for selected compounds of the invention. Inhibition is indicated as $IC_{50}$ with following key: A=$IC_{50}$ less than 100 nM, B=$IC_{50}$ greater than 100 nM, but less than or equal to 1000 nM, C=$IC_{50}$ greater than 1000 nM, but less than 10,000 nM, D=$IC_{50}$ 10,000 nM or greater. An empty cell indicates lack of data only.

TABLE 1

| Entry | Name | cRaf-1 | bRaf |
|---|---|---|---|
| 1 | 6-(2-butyl-1-hydroxy-3-oxo-2,3-dihydro-1H-isoindol-1-yl)-2H-1,4-benzoxazin-3(4H)-one | C | C |
| 2 | 6-[1-hydroxy-3-oxo-2-(2-phenylethyl)-2,3-dihydro-1H-isoindol-1-yl]-2H-1,4-benzoxazin-3(4H)-one | D | D |
| 3 | 6-(1-hydroxy-2-{[4-(methyloxy)phenyl]methyl}-3-oxo-2,3-dihydro-1H-isoindol-1-yl)-2H-1,4-benzoxazin-3(4H)-one | D | D |
| 4 | 6-(1-hydroxy-2-{[3-(methyloxy)phenyl]methyl}-3-oxo-2,3-dihydro-1H-isoindol-1-yl)-2H-1,4-benzoxazin-3(4H)-one | D | D |
| 5 | 6-{2-[(4-fluorophenyl)methyl]-1-hydroxy-3-oxo-2,3-dihydro-1H-isoindol-1-yl}-2H-1,4-benzoxazin-3(4H)-one | D | D |
| 6 | 6-(1-hydroxy-3-oxo-2-phenyl-2,3-dihydro-1H-isoindol-1-yl)-2H-1,4-benzoxazin-3(4H)-one | B | B |
| 7 | 6-{2-[(3-bromophenyl)methyl]-1-hydroxy-3-oxo-2,3-dihydro-1H-isoindol-1-yl}-2H-1,4-benzoxazin-3(4H)-one | C | C |

TABLE 1-continued

| Entry | Name | cRaf-1 | bRaf |
|---|---|---|---|
| 8 | 6-{2-[(4-bromophenyl)methyl]-1-hydroxy-3-oxo-2,3-dihydro-1H-isoindol-1-yl}-2H-1,4-benzoxazin-3(4H)-one | D | D |
| 9 | 6-[1-hydroxy-3-oxo-2-(3-phenylpropyl)-2,3-dihydro-1H-isoindol-1-yl]-2H-1,4-benzoxazin-3(4H)-one | D | D |
| 10 | 6-{2-[(3,4-dichlorophenyl)methyl]-1-hydroxy-3-oxo-2,3-dihydro-1H-isoindol-1-yl}-2H-1,4-benzoxazin-3(4H)-one | D | D |
| 11 | 6-{1-hydroxy-2-[(4-methylphenyl)methyl]-3-oxo-2,3-dihydro-1H-isoindol-1-yl}-2H-1,4-benzoxazin-3(4H)-one | D | D |
| 12 | 6-{2-[(4-chlorophenyl)methyl]-1-hydroxy-3-oxo-2,3-dihydro-1H-isoindol-1-yl}-2H-1,4-benzoxazin-3(4H)-one | D | D |
| 13 | 6-[1-hydroxy-2-(1-methylethyl)-3-oxo-2,3-dihydro-1H-isoindol-1-yl]-2H-1,4-benzoxazin-3(4H)-one | D | D |
| 14 | methyl {5-[1-hydroxy-3-oxo-2-(phenylmethyl)-2,3-dihydro-1H-isoindol-1-yl]-1H-benzimidazol-2-yl}carbamate | A | A |
| 15 | 6-{2-[(3,4-dimethylphenyl)methyl]-1-hydroxy-3-oxo-2,3-dihydro-1H-isoindol-1-yl}-2H-1,4-benzoxazin-3(4H)-one | D | D |
| 16 | 6-(2-{[4-chloro-3-(trifluoromethyl)phenyl]methyl}-1-hydroxy-3-oxo-2,3-dihydro-1H-isoindol-1-yl)-2H-1,4-benzoxazin-3(4H)-one | D | D |
| 17 | 6-(2-{[4-(dimethylamino)phenyl]methyl}-1-hydroxy-3-oxo-2,3-dihydro-1H-isoindol-1-yl)-2H-1,4-benzoxazin-3(4H)-one | D | D |
| 18 | 6-[2-(3-chlorophenyl)-1-hydroxy-3-oxo-2,3-dihydro-1H-isoindol-1-yl]-2H-1,4-benzoxazin-3(4H)-one | B | A |
| 19 | 6-[2-(4-chlorophenyl)-1-hydroxy-3-oxo-2,3-dihydro-1H-isoindol-1-yl]-2H-1,4-benzoxazin-3(4H)-one | C | C |
| 20 | 6-[2-(3,4-dichlorophenyl)-1-hydroxy-3-oxo-2,3-dihydro-1H-isoindol-1-yl]-2H-1,4-benzoxazin-3(4H)-one | C | C |
| 21 | 6-[1-hydroxy-2-(4-methylphenyl)-3-oxo-2,3-dihydro-1H-isoindol-1-yl]-2H-1,4-benzoxazin-3(4H)-one | D | D |
| 22 | 3-(2-{[3,5-bis(methyloxy)phenyl]amino}-1H-benzimidazol-5-yl)-3-(methyloxy)-2-(phenylmethyl)-2,3-dihydro-1H-isoindol-1-one | D | D |
| 23 | 3-(2-{[3,5-bis(methyloxy)phenyl]amino}-1H-benzimidazol-5-yl)-2-(1-methylethyl)-3-(methyloxy)-2,3-dihydro-1H-isoindol-1-one | D | D |
| 24 | 3-(2-{[3,5-bis(methyloxy)phenyl]amino}-1H-benzimidazol-5-yl)-3-hydroxy-2-phenyl-2,3-dihydro-1H-isoindol-1-one | C | D |
| 25 | 3-(2-{[3,5-bis(methyloxy)phenyl]amino}-1H-benzimidazol-5-yl)-3-hydroxy-2-(phenylmethyl)-2,3-dihydro-1H-isoindol-1-one | D | D |
| 26 | methyl {5-[1-hydroxy-3-oxo-2-(phenylmethyl)-2,3-dihydro-1H-isoindol-1-yl]-1-methyl-1H-benzimidazol-2-yl}carbamate | D | D |
| 27 | 3-(1H-benzimidazol-5-yl)-3-hydroxy-2-(phenylmethyl)-2,3-dihydro-1H-isoindol-1-one | C | C |
| 28 | 5-[1-hydroxy-3-oxo-2-(phenylmethyl)-2,3-dihydro-1H-isoindol-1-yl]-N-methyl-1H-benzimidazole-2-carboxamide | C | C |
| 29 | 3-hydroxy-3-(2-methyl-1H-benzimidazol-5-yl)-2-(phenylmethyl)-2,3-dihydro-1H-isoindol-1-one | D | D |
| 30 | 7-[1-hydroxy-3-oxo-2-(phenylmethyl)-2,3-dihydro-1H-isoindol-1-yl]-3,4-dihydroquinoxalin-2(1H)-one | C | C |
| 31 | 7-[2-(3-chlorophenyl)-1-hydroxy-3-oxo-2,3-dihydro-1H-isoindol-1-yl]-3,4-dihydroquinoxalin-2(1H)-one | D | D |
| 32 | 1,1-dimethylethyl 4-{[1-hydroxy-3-oxo-1-(3-oxo-3,4-dihydro-2H-1,4-benzoxazin-6-yl)-1,3-dihydro-2H-isoindol-2-yl]methyl}piperidine-1-carboxylate | D | D |
| 33 | 6-(1-hydroxy-2-{[2-(methyloxy)phenyl]methyl}-3-oxo-2,3-dihydro-1H-isoindol-1-yl)-2H-1,4-benzoxazin-3(4H)-one | D | D |

TABLE 1-continued

| Entry | Name | cRaf-1 | bRaf |
|---|---|---|---|
| 34 | 6-{2-[(3-chlorophenyl)methyl]-1-hydroxy-3-oxo-2,3-dihydro-1H-isoindol-1-yl}-2H-1,4-benzoxazin-3(4H)-one | C | C |
| 35 | 6-{2-[(2-chlorophenyl)methyl]-1-hydroxy-3-oxo-2,3-dihydro-1H-isoindol-1-yl}-2H-1,4-benzoxazin-3(4H)-one | C | D |
| 36 | 6-{2-[(3-fluorophenyl)methyl]-1-hydroxy-3-oxo-2,3-dihydro-1H-isoindol-1-yl}-2H-1,4-benzoxazin-3(4H)-one | C | C |
| 37 | 6-{2-[(2-bromophenyl)methyl]-1-hydroxy-3-oxo-2,3-dihydro-1H-isoindol-1-yl}-2H-1,4-benzoxazin-3(4H)-one | D | D |
| 38 | 6-{2-[(2-fluorophenyl)methyl]-1-hydroxy-3-oxo-2,3-dihydro-1H-isoindol-1-yl}-2H-1,4-benzoxazin-3(4H)-one | C | D |
| 39 | 6-[2-(3-fluorophenyl)-1-hydroxy-3-oxo-2,3-dihydro-1H-isoindol-1-yl]-2H-1,4-benzoxazin-3(4H)-one | B | C |
| 40 | 6-[1-hydroxy-2-(3-iodophenyl)-3-oxo-2,3-dihydro-1H-isoindol-1-yl]-2H-1,4-benzoxazin-3(4H)-one | A | B |
| 41 | 6-[2-(3-bromophenyl)-1-hydroxy-3-oxo-2,3-dihydro-1H-isoindol-1-yl]-2H-1,4-benzoxazin-3(4H)-one | A | B |
| 42 | 6-[1-hydroxy-2-(3-nitrophenyl)-3-oxo-2,3-dihydro-1H-isoindol-1-yl]-2H-1,4-benzoxazin-3(4H)-one | B | C |
| 43 | 6-{1-hydroxy-2-[3-(methyloxy)phenyl]-3-oxo-2,3-dihydro-1H-isoindol-1-yl}-2H-1,4-benzoxazin-3(4H)-one | B | B |
| 44 | 6-[1-hydroxy-2-(3-methylphenyl)-3-oxo-2,3-dihydro-1H-isoindol-1-yl]-2H-1,4-benzoxazin-3(4H)-one | B | B |
| 45 | 3-hydroxy-3-(1H-indol-5-yl)-2-(phenylmethyl)-2,3-dihydro-1H-isoindol-1-one | D | D |
| 46 | methyl [6-(1-hydroxy-3-oxo-2-phenyl-2,3-dihydro-1H-isoindol-1-yl)-1H-benzimidazol-2-yl]carbamate | A | A |
| 47 | 6-[2-(2-aminophenyl)-1-hydroxy-3-oxo-2,3-dihydro-1H-isoindol-1-yl]-2H-1,4-benzoxazin-3(4H)-one | B | B |
| 48 | 6-{[2-(3-phenyl-1,2,4-oxadiazol-5-yl)phenyl]carbonyl}-2H-1,4-benzoxazin-3(4H)-one | D | D |
| 49 | 6-{[2-(1H-benzimidazol-2-yl)phenyl]carbonyl}-2H-1,4-benzoxazin-3(4H)-one | D | D |
| 50 | 6-(1-hydroxy-3-oxo-2-{[2-(trifluoromethyl)phenyl]methyl}-2,3-dihydro-1H-isoindol-1-yl)-2H-1,4-benzoxazin-3(4H)-one | D | D |
| 51 | 6-{2-[(5-bromo-2-fluorophenyl)methyl]-1-hydroxy-3-oxo-2,3-dihydro-1H-isoindol-1-yl}-2H-1,4-benzoxazin-3(4H)-one | C | C |
| 52 | 6-{1-hydroxy-2-[(3-nitrophenyl)methyl]-3-oxo-2,3-dihydro-1H-isoindol-1-yl}-2H-1,4-benzoxazin-3(4H)-one | C | C |
| 53 | 6-(1-hydroxy-3-oxo-2-{[3-(trifluoromethyl)phenyl]methyl}-2,3-dihydro-1H-isoindol-1-yl)-2H-1,4-benzoxazin-3(4H)-one | D | D |
| 54 | 6-(2-{[2,3-bis(methyloxy)phenyl]methyl}-1-hydroxy-3-oxo-2,3-dihydro-1H-isoindol-1-yl)-2H-1,4-benzoxazin-3(4H)-one | D | D |
| 55 | 6-{1-hydroxy-2-[(3-iodophenyl)methyl]-3-oxo-2,3-dihydro-1H-isoindol-1-yl}-2H-1,4-benzoxazin-3(4H)-one | C | C |
| 56 | 6-[1-hydroxy-3-oxo-2-({3-[(trifluoromethyl)oxy]phenyl}methyl)-2,3-dihydro-1H-isoindol-1-yl]-2H-1,4-benzoxazin-3(4H)-one | D | D |
| 57 | 6-(1-hydroxy-2-{[2-(methylthio)phenyl]methyl}-3-oxo-2,3-dihydro-1H-isoindol-1-yl)-2H-1,4-benzoxazin-3(4H)-one | D | D |
| 58 | 6-[2-(3,4-difluorophenyl)-1-hydroxy-3-oxo-2,3-dihydro-1H-isoindol-1-yl]-2H-1,4-benzoxazin-3(4H)-one | C | C |
| 59 | 6-{1-hydroxy-2-[3-(1-methylethyl)phenyl]-3-oxo-2,3-dihydro-1H-isoindol-1-yl}-2H-1,4-benzoxazin-3(4H)-one | B | B |

TABLE 1-continued

| Entry | Name | cRaf-1 | bRaf |
|---|---|---|---|
| 60 | 6-(1-hydroxy-3-oxo-2-{3-[(trifluoromethyl)oxy]phenyl}-2,3-dihydro-1H-isoindol-1-yl)-2H-1,4-benzoxazin-3(4H)-one | D | D |
| 61 | 6-{1-hydroxy-3-oxo-2-[3-(trifluoromethyl)phenyl]-2,3-dihydro-1H-isoindol-1-yl}-2H-1,4-benzoxazin-3(4H)-one | B | C |
| 62 | 3-[1-hydroxy-3-oxo-1-(3-oxo-3,4-dihydro-2H-1,4-benzoxazin-6-yl)-1,3-dihydro-2H-isoindol-2-yl]benzenesulfonamide | C | D |
| 63 | 6-{2-[5-chloro-2-(methyloxy)phenyl]-1-hydroxy-3-oxo-2,3-dihydro-1H-isoindol-1-yl}-2H-1,4-benzoxazin-3(4H)-one | D | C |
| 64 | 6-{2-[4-fluoro-3-(trifluoromethyl)phenyl]-1-hydroxy-3-oxo-2,3-dihydro-1H-isoindol-1-yl}-2H-1,4-benzoxazin-3(4H)-one | D | D |
| 65 | 3-hydroxy-3-(1H-indol-6-yl)-2-(phenylmethyl)-2,3-dihydro-1H-isoindol-1-one | D | D |
| 66 | 6-[2-(3-fluoro-5-iodophenyl)-1-hydroxy-3-oxo-2,3-dihydro-1H-isoindol-1-yl]-2H-1,4-benzoxazin-3(4H)-one | C | C |
| 67 | 6-[2-(3-aminophenyl)-1-hydroxy-3-oxo-2,3-dihydro-1H-isoindol-1-yl]-2H-1,4-benzoxazin-3(4H)-one | B | B |
| 68 | 6-[2-(3,5-difluorophenyl)-1-hydroxy-3-oxo-2,3-dihydro-1H-isoindol-1-yl]-2H-1,4-benzoxazin-3(4H)-one | C | C |
| 69 | 6-{1-hydroxy-2-[3-(methylsulfonyl)phenyl]-3-oxo-2,3-dihydro-1H-isoindol-1-yl}-2H-1,4-benzoxazin-3(4H)-one | D | D |
| 70 | ethyl 3-[1-hydroxy-3-oxo-1-(3-oxo-3,4-dihydro-2H-1,4-benzoxazin-6-yl)-1,3-dihydro-2H-isoindol-2-yl]benzoate | D | D |
| 71 | 3-[1-hydroxy-3-oxo-1-(3-oxo-3,4-dihydro-2H-1,4-benzoxazin-6-yl)-1,3-dihydro-2H-isoindol-2-yl]benzonitrile | C | C |
| 72 | 6-[2-(2-chlorophenyl)-1-hydroxy-3-oxo-2,3-dihydro-1H-isoindol-1-yl]-2H-1,4-benzoxazin-3(4H)-one | C | C |
| 73 | 6-[2-(3-amino-5-chlorophenyl)-1-hydroxy-3-oxo-2,3-dihydro-1H-isoindol-1-yl]-2H-1,4-benzoxazin-3(4H)-one | A | A |
| 74 | 6-[2-(5-chloro-2-methylphenyl)-1-hydroxy-3-oxo-2,3-dihydro-1H-isoindol-1-yl]-2H-1,4-benzoxazin-3(4H)-one | A | A |
| 75 | 6-[2-(3-chloro-2-methylphenyl)-1-hydroxy-3-oxo-2,3-dihydro-1H-isoindol-1-yl]-2H-1,4-benzoxazin-3(4H)-one | B | B |
| 76 | 6-[2-(3-ethylphenyl)-1-hydroxy-3-oxo-2,3-dihydro-1H-isoindol-1-yl]-2H-1,4-benzoxazin-3(4H)-one | B | B |
| 77 | 6-[2-(3-ethynylphenyl)-1-hydroxy-3-oxo-2,3-dihydro-1H-isoindol-1-yl]-2H-1,4-benzoxazin-3(4H)-one | B | B |
| 78 | 6-[1-hydroxy-2-(3-hydroxyphenyl)-3-oxo-2,3-dihydro-1H-isoindol-1-yl]-2H-1,4-benzoxazin-3(4H)-one | C | C |
| 79 | 6-{1-hydroxy-3-oxo-2-[3-(phenyloxy)phenyl]-2,3-dihydro-1H-isoindol-1-yl}-2H-1,4-benzoxazin-3(4H)-one | B | C |
| 80 | 6-(1-hydroxy-3-oxo-2-{3-[(phenylmethyl)oxy]phenyl}-2,3-dihydro-1H-isoindol-1-yl)-2H-1,4-benzoxazin-3(4H)-one | D | D |
| 81 | 3-[1-hydroxy-3-oxo-1-(3-oxo-3,4-dihydro-2H-1,4-benzoxazin-6-yl)-1,3-dihydro-2H-isoindol-2-yl]benzamide | C | C |
| 82 | 6-{1-hydroxy-2-[3-(hydroxymethyl)phenyl]-3-oxo-2,3-dihydro-1H-isoindol-1-yl}-2H-1,4-benzoxazin-3(4H)-one | C | C |
| 83 | 6-[2-(2-fluorophenyl)-1-hydroxy-3-oxo-2,3-dihydro-1H-isoindol-1-yl]-2H-1,4-benzoxazin-3(4H)-one | C | B |
| 84 | 3-hydroxy-3-[2-(methylamino)-1H-benzimidazol-5-yl]-2-(phenylmethyl)-2,3-dihydro-1H-isoindol-1-one | C | C |
| 85 | 6-(2-biphenyl-3-yl-1-hydroxy-3-oxo-2,3-dihydro-1H-isoindol-1-yl)-2H-1,4-benzoxazin-3(4H)-one | D | D |

TABLE 1-continued

| Entry | Name | cRaf-1 | bRaf |
|---|---|---|---|
| 86 | 6-(2-{3-[(dimethylamino)methyl]phenyl}-1-hydroxy-3-oxo-2,3-dihydro-1H-isoindol-1-yl)-2H-1,4-benzoxazin-3(4H)-one | C | C |
| 87 | 6-[2-(3,5-dichlorophenyl)-1-hydroxy-3-oxo-2,3-dihydro-1H-isoindol-1-yl]-2H-1,4-benzoxazin-3(4H)-one | C | C |
| 88 | 6-(1-hydroxy-3-oxo-2-piperidin-4-yl-2,3-dihydro-1H-isoindol-1-yl)-2H-1,4-benzoxazin-3(4H)-one | D | D |
| 89 | 6-[2-(3-{[2-(dimethylamino)ethyl]oxy}phenyl)-1-hydroxy-3-oxo-2,3-dihydro-1H-isoindol-1-yl]-2H-1,4-benzoxazin-3(4H)-one | D | D |
| 90 | 6-[1-hydroxy-2-(2-methylphenyl)-3-oxo-2,3-dihydro-1H-isoindol-1-yl]-2H-1,4-benzoxazin-3(4H)-one | C | C |
| 91 | N-methyl-2-[(3-oxo-3,4-dihydro-2H-1,4-benzoxazin-6-yl)carbonyl]-N-phenylbenzamide | D | D |
| 92 | methyl {5-[1-(ethyloxy)-3-oxo-2-(phenylmethyl)-2,3-dihydro-1H-isoindol-1-yl]-1H-benzimidazol-2-yl}carbamate | B | B |
| 93 | Phenylmethyl 2-[(2-{[(methyloxy)carbonyl]amino}-1H-benzimidazol-5-yl)carbonyl]benzoate | B | B |
| 94 | 3-hydroxy-3-(1H-indazol-5-yl)-2-(phenylmethyl)-2,3-dihydro-1H-isoindol-1-one | B | B |
| 95 | 3-hydroxy-3-(1H-indazol-6-yl)-2-(phenylmethyl)-2,3-dihydro-1H-isoindol-1-one | D | D |
| 96 | ethyl {5-[1-hydroxy-3-oxo-2-(phenylmethyl)-2,3-dihydro-1H-isoindol-1-yl]-1H-benzimidazol-2-yl}carbamate | D | D |
| 97 | 2-methylpropyl {5-[1-hydroxy-3-oxo-2-(phenylmethyl)-2,3-dihydro-1H-isoindol-1-yl]-1H-benzimidazol-2-yl}carbamate | B | B |
| 98 | methyl {5-[1-hydroxy-3-oxo-2-(2-thienylmethyl)-2,3-dihydro-1H-isoindol-1-yl]-1H-benzimidazol-2-yl}carbamate | A | A |
| 99 | methyl {5-[1-hydroxy-3-oxo-2-(2-phenylethyl)-2,3-dihydro-1H-isoindol-1-yl]-1H-benzimidazol-2-yl}carbamate | C | C |
| 100 | 3-[2-amino-1-(1,1-dimethylethyl)-1H-benzimidazol-5-yl]-3-hydroxy-2-(phenylmethyl)-2,3-dihydro-1H-isoindol-1-one | D | D |
| 101 | 3-(2-amino-1H-benzimidazol-5-yl)-3-hydroxy-2-(phenylmethyl)-2,3-dihydro-1H-isoindol-1-one | C | C |
| 102 | methyl [5-(1-hydroxy-3-oxo-2,3-dihydro-1H-isoindol-1-yl)-1H-benzimidazol-2-yl]carbamate | D | D |
| 103 | 3-(methyloxy)butyl {5-[1-hydroxy-3-oxo-2-(phenylmethyl)-2,3-dihydro-1H-isoindol-1-yl]-1H-benzimidazol-2-yl}carbamate | A | A |
| 104 | methyl (5-{1-hydroxy-3-oxo-2-[(1R)-1-phenylethyl]-2,3-dihydro-1H-isoindol-1-yl}-1H-benzimidazol-2-yl)carbamate | A | A |
| 105 | methyl (5-{1-hydroxy-3-oxo-2-[(1S)-1-phenylethyl]-2,3-dihydro-1H-isoindol-1-yl}-1H-benzimidazol-2-yl)carbamate | C | C |
| 106 | 2-(methyloxy)ethyl {5-[1-hydroxy-3-oxo-2-(phenylmethyl)-2,3-dihydro-1H-isoindol-1-yl]-1H-benzimidazol-2-yl}carbamate | A | A |
| 107 | methyl {6-[1-hydroxy-3-oxo-2-(phenylmethyl)-2,3-dihydro-1H-isoindol-1-yl]-1-methyl-1H-benzimidazol-2-yl}carbamate | D | D |
| 108 | prop-2-yn-1-yl {5-[1-hydroxy-3-oxo-2-(phenylmethyl)-2,3-dihydro-1H-isoindol-1-yl]-1H-benzimidazol-2-yl}carbamate | A | A |
| 109 | but-2-yn-1-yl {5-[1-hydroxy-3-oxo-2-(phenylmethyl)-2,3-dihydro-1H-isoindol-1-yl]-1H-benzimidazol-2-yl}carbamate | A | A |
| 110 | 1-methylethyl {5-[1-hydroxy-3-oxo-2-(phenylmethyl)-2,3-dihydro-1H-isoindol-1-yl]-1H-benzimidazol-2-yl}carbamate | A | A |
| 111 | methyl {5-[2-(2,3-dihydro-1H-inden-2-yl)-1-hydroxy-3-oxo-2,3-dihydro-1H-isoindol-1-yl]-1H-benzimidazol-2-yl}carbamate | D | D |
| 112 | methyl {5-[1-hydroxy-3-oxo-2-(pyridin-4-ylmethyl)-2,3-dihydro-1H-isoindol-1-yl]-1H-benzimidazol-2-yl}carbamate | C | D |
| 113 | methyl {5-[1-hydroxy-3-oxo-2-(pyridin-3-ylmethyl)-2,3-dihydro-1H-isoindol-1-yl]-1H-benzimidazol-2-yl}carbamate | B | B |

TABLE 1-continued

| Entry | Name | cRaf-1 | bRaf |
|---|---|---|---|
| 114 | methyl (6-{2-[(3-fluorophenyl)methyl]-1-hydroxy-3-oxo-2,3-dihydro-1H-isoindol-1-yl}-1H-benzimidazol-2-yl)carbamate | A | A |
| 115 | methyl {5-[1-hydroxy-2-(3-methylphenyl)-3-oxo-2,3-dihydro-1H-isoindol-1-yl]-1H-benzimidazol-2-yl}carbamate | A | A |
| 116 | methyl [5-(1-hydroxy-2-{[2-(methyloxy)phenyl]methyl}-3-oxo-2,3-dihydro-1H-isoindol-1-yl)-1H-benzimidazol-2-yl]carbamate | C | C |
| 117 | methyl [5-(1-hydroxy-2-{[3-(methyloxy)phenyl]methyl}-3-oxo-2,3-dihydro-1H-isoindol-1-yl)-1H-benzimidazol-2-yl]carbamate | B | B |
| 118 | methyl [5-(1-hydroxy-2-{[4-(methyloxy)phenyl]methyl}-3-oxo-2,3-dihydro-1H-isoindol-1-yl)-1H-benzimidazol-2-yl]carbamate | D | D |
| 119 | methyl (6-{2-[(4-fluorophenyl)methyl]-1-hydroxy-3-oxo-2,3-dihydro-1H-isoindol-1-yl}-1H-benzimidazol-2-yl)carbamate | B | B |
| 120 | methyl (6-{2-[(3-bromophenyl)methyl]-1-hydroxy-3-oxo-2,3-dihydro-1H-isoindol-1-yl}-1H-benzimidazol-2-yl)carbamate | A | A |
| 121 | methyl (5-{1-hydroxy-2-[(3-iodophenyl)methyl]-3-oxo-2,3-dihydro-1H-isoindol-1-yl}-1H-benzimidazol-2-yl)carbamate | B | B |
| 122 | methyl (5-{2-[(3-chlorophenyl)methyl]-1-hydroxy-3-oxo-2,3-dihydro-1H-isoindol-1-yl}-1H-benzimidazol-2-yl)carbamate | A | A |
| 123 | methyl (5-{2-[(2-fluorophenyl)methyl]-1-hydroxy-3-oxo-2,3-dihydro-1H-isoindol-1-yl}-1H-benzimidazol-2-yl)carbamate | A | A |
| 124 | methyl {5-[1-hydroxy-3-oxo-2-(pyridin-2-ylmethyl)-2,3-dihydro-1H-isoindol-1-yl]-1H-benzimidazol-2-yl}carbamate | B | B |
| 125 | phenylmethyl {5-[1-hydroxy-3-oxo-2-(phenylmethyl)-2,3-dihydro-1H-isoindol-1-yl]-1H-benzimidazol-2-yl}carbamate | A | A |
| 126 | 2-fluoroethyl {5-[1-hydroxy-3-oxo-2-(phenylmethyl)-2,3-dihydro-1H-isoindol-1-yl]-1H-benzimidazol-2-yl}carbamate | A | A |
| 127 | propyl {5-[1-hydroxy-3-oxo-2-(phenylmethyl)-2,3-dihydro-1H-isoindol-1-yl]-1H-benzimidazol-2-yl}carbamate | A | A |
| 128 | methyl (5-{1-hydroxy-2-[4-(methyloxy)phenyl]-3-oxo-2,3-dihydro-1H-isoindol-1-yl}-1H-benzimidazol-2-yl)carbamate | C | C |
| 129 | methyl (5-{2-[(2-chlorophenyl)methyl]-1-hydroxy-3-oxo-2,3-dihydro-1H-isoindol-1-yl}-1H-benzimidazol-2-yl)carbamate | A | B |
| 130 | methyl (5-{2-[(2-bromophenyl)methyl]-1-hydroxy-3-oxo-2,3-dihydro-1H-isoindol-1-yl}-1H-benzimidazol-2-yl)carbamate | B | B |
| 131 | methyl (5-{1-hydroxy-2-[(3-methylphenyl)methyl]-3-oxo-2,3-dihydro-1H-isoindol-1-yl}-1H-benzimidazol-2-yl)carbamate | A | A |
| 132 | methyl (5-{1-hydroxy-2-[(4-methylphenyl)methyl]-3-oxo-2,3-dihydro-1H-isoindol-1-yl}-1H-benzimidazol-2-yl)carbamate | B | C |
| 133 | methyl (5-{1-hydroxy-2-[(2-methylphenyl)methyl]-3-oxo-2,3-dihydro-1H-isoindol-1-yl}-1H-benzimidazol-2-yl)carbamate | A | A |
| 134 | methyl {5-[2-(3-bromophenyl)-1-hydroxy-3-oxo-2,3-dihydro-1H-isoindol-1-yl]-1H-benzimidazol-2-yl}carbamate | A | A |
| 135 | methyl {5-[2-(3-chlorophenyl)-1-hydroxy-3-oxo-2,3-dihydro-1H-isoindol-1-yl]-1H-benzimidazol-2-yl}carbamate | A | A |
| 136 | methyl {5-[2-(3-fluorophenyl)-1-hydroxy-3-oxo-2,3-dihydro-1H-isoindol-1-yl]-1H-benzimidazol-2-yl}carbamate | A | A |
| 137 | methyl (5-{1-hydroxy-2-[3-(methyloxy)phenyl]-3-oxo-2,3-dihydro-1H-isoindol-1-yl}-1H-benzimidazol-2-yl)carbamate | A | A |
| 138 | methyl {5-[2-(4-bromophenyl)-1-hydroxy-3-oxo-2,3-dihydro-1H-isoindol-1-yl]-1H-benzimidazol-2-yl}carbamate | B | B |

TABLE 1-continued

| Entry | Name | cRaf-1 | bRaf |
|---|---|---|---|
| 139 | methyl {5-[2-(4-chlorophenyl)-1-hydroxy-3-oxo-2,3-dihydro-1H-isoindol-1-yl]-1H-benzimidazol-2-yl}carbamate | A | A |
| 140 | methyl {5-[2-(4-fluorophenyl)-1-hydroxy-3-oxo-2,3-dihydro-1H-isoindol-1-yl]-1H-benzimidazol-2-yl}carbamate | A | A |
| 141 | methyl {5-[2-(3,5-dimethylphenyl)-1-hydroxy-3-oxo-2,3-dihydro-1H-isoindol-1-yl]-1H-benzimidazol-2-yl}carbamate | A | A |
| 142 | methyl {5-[2-(2-fluorophenyl)-1-hydroxy-3-oxo-2,3-dihydro-1H-isoindol-1-yl]-1H-benzimidazol-2-yl}carbamate | A | A |
| 143 | methyl {5-[2-(2-chlorophenyl)-1-hydroxy-3-oxo-2,3-dihydro-1H-isoindol-1-yl]-1H-benzimidazol-2-yl}carbamate | A | A |
| 144 | methyl {5-[1-hydroxy-2-(2-methylphenyl)-3-oxo-2,3-dihydro-1H-isoindol-1-yl]-1H-benzimidazol-2-yl}carbamate | A | A |
| 145 | methyl (5-{1-hydroxy-2-[2-(methyloxy)phenyl]-3-oxo-2,3-dihydro-1H-isoindol-1-yl}-1H-benzimidazol-2-yl)carbamate | A | A |
| 146 | methyl {5-[1-hydroxy-2-(4-methylphenyl)-3-oxo-2,3-dihydro-1H-isoindol-1-yl]-1H-benzimidazol-2-yl}carbamate | B | B |
| 147 | methyl (5-{1-hydroxy-3-oxo-2-[3-(trifluoromethyl)phenyl]-2,3-dihydro-1H-isoindol-1-yl}-1H-benzimidazol-2-yl)carbamate | A | A |
| 148 | but-2-yn-1-yl (5-{1-hydroxy-3-oxo-2-[(1R)-1-phenylethyl]-2,3-dihydro-1H-isoindol-1-yl}-1H-benzimidazol-2-yl)carbamate | A | A |
| 149 | N-ethyl-N'-{5-[1-hydroxy-3-oxo-2-(phenylmethyl)-2,3-dihydro-1H-isoindol-1-yl]-1H-benzimidazol-2-yl}urea | A | A |
| 150 | phenylmethyl (5-{1-hydroxy-3-oxo-2-[(1R)-1-phenylethyl]-2,3-dihydro-1H-isoindol-1-yl}-1H-benzimidazol-2-yl)carbamate | A | A |
| 151 | methyl {6-[2-(3-amino-5-chlorophenyl)-1-hydroxy-3-oxo-2,3-dihydro-1H-isoindol-1-yl]-1H-benzimidazol-2-yl}carbamate | A | A |
| 152 | piperidin-4-ylmethyl {5-[1-hydroxy-3-oxo-2-(phenylmethyl)-2,3-dihydro-1H-isoindol-1-yl]-1H-benzimidazol-2-yl}carbamate | B | A |
| 153 | methyl {5-[2-(cyclopropylmethyl)-1-hydroxy-3-oxo-2,3-dihydro-1H-isoindol-1-yl]-1H-benzimidazol-2-yl}carbamate | B | B |
| 154 | methyl {5-[2-(2,2-dimethylpropyl)-1-hydroxy-3-oxo-2,3-dihydro-1H-isoindol-1-yl]-1H-benzimidazol-2-yl}carbamate | C | C |
| 155 | methyl {5-[2-(3,5-dichlorophenyl)-1-hydroxy-3-oxo-2,3-dihydro-1H-isoindol-1-yl]-1H-benzimidazol-2-yl}carbamate | A | A |
| 156 | methyl {5-[2-(3,5-difluorophenyl)-1-hydroxy-3-oxo-2,3-dihydro-1H-isoindol-1-yl]-1H-benzimidazol-2-yl}carbamate | B | B |
| 157 | N-ethyl-N'-(5-{1-hydroxy-3-oxo-2-[(1R)-1-phenylethyl]-2,3-dihydro-1H-isoindol-1-yl}-1H-benzimidazol-2-yl)urea | A | A |
| 158 | N'-{5-[1-hydroxy-3-oxo-2-(phenylmethyl)-2,3-dihydro-1H-isoindol-1-yl]-1H-benzimidazol-2-yl}-N,N-dimethylurea | A | A |
| 159 | methyl {5-[2-(3-{[2-(dimethylamino)ethyl]oxy}phenyl)-1-hydroxy-3-oxo-2,3-dihydro-1H-isoindol-1-yl]-1H-benzimidazol-2-yl}carbamate | B | C |
| 160 | 3-(4-methylpiperazin-1-yl)propyl {6-[1-hydroxy-3-oxo-2-(phenylmethyl)-2,3-dihydro-1H-isoindol-1-yl]-1H-benzimidazol-2-yl}carbamate | A | A |
| 161 | methyl {5-[2-(cyclohexylmethyl)-1-hydroxy-3-oxo-2,3-dihydro-1H-isoindol-1-yl]-1H-benzimidazol-2-yl}carbamate | A | A |
| 162 | methyl {5-[1-hydroxy-2-(2-methylpropyl)-3-oxo-2,3-dihydro-1H-isoindol-1-yl]-1H-benzimidazol-2-yl}carbamate | B | B |
| 163 | methyl {5-[1-hydroxy-3-oxo-2-(1,3-thiazol-2-ylmethyl)-2,3-dihydro-1H-isoindol-1-yl]-1H-benzimidazol-2-yl}carbamate | B | B |

TABLE 1-continued

| Entry | Name | cRaf-1 | bRaf |
|---|---|---|---|
| 164 | methyl {5-[2-(3,4-difluorophenyl)-1-hydroxy-3-oxo-2,3-dihydro-1H-isoindol-1-yl]-1H-benzimidazol-2-yl}carbamate | A | A |
| 165 | methyl (5-{2-[1-(3,5-difluorophenyl)ethyl]-1-hydroxy-3-oxo-2,3-dihydro-1H-isoindol-1-yl}-1H-benzimidazol-2-yl)carbamate | B | C |
| 166 | methyl (5-{2-[1-(3-fluorophenyl)ethyl]-1-hydroxy-3-oxo-2,3-dihydro-1H-isoindol-1-yl}-1H-benzimidazol-2-yl)carbamate | B | A |
| 167 | methyl [5-(2-cyclohexyl-1-hydroxy-3-oxo-2,3-dihydro-1H-isoindol-1-yl)-1H-benzimidazol-2-yl]carbamate | A | A |
| 168 | methyl {-[2-(2,5-difluorophenyl)-1-hydroxy-3-oxo-2,3-dihydro-1H-isoindol-1-yl]-1H-benzimidazol-2-yl}carbamate | A | A |
| 169 | N-{5-[1-hydroxy-3-oxo-2-(phenylmethyl)-2,3-dihydro-1H-isoindol-1-yl]-1H-benzimidazol-2-yl}-N'-(phenylmethyl)urea | A | A |
| 170 | piperidin-4-yl {5-[1-hydroxy-3-oxo-2-(phenylmethyl)-2,3-dihydro-1H-isoindol-1-yl]-1H-benzimidazol-2-yl}carbamate | A | A |
| 171 | N-{5-[1-hydroxy-3-oxo-2-(phenylmethyl)-2,3-dihydro-1H-isoindol-1-yl]-1H-benzimidazol-2-yl}-N'-methylurea | A | A |
| 172 | methyl (5-{2-[1-(2-fluorophenyl)ethyl]-1-hydroxy-3-oxo-2,3-dihydro-1H-isoindol-1-yl}-1H-benzimidazol-2-yl)carbamate | C | C |
| 173 | methyl (5-{1-hydroxy-3-oxo-2-[1-(2-thienyl)ethyl]-2,3-dihydro-1H-isoindol-1-yl}-1H-benzimidazol-2-yl)carbamate | A | A |
| 174 | methyl (5-{2-[1-(3-chlorophenyl)ethyl]-1-hydroxy-3-oxo-2,3-dihydro-1H-isoindol-1-yl}-1H-benzimidazol-2-yl)carbamate | B | A |
| 175 | methyl (5-{1-hydroxy-2-[3-methyl-5-(trifluoromethyl)phenyl]-3-oxo-2,3-dihydro-1H-isoindol-1-yl}-1H-benzimidazol-2-yl)carbamate | A | A |
| 176 | N-{5-[1-hydroxy-3-oxo-2-(phenylmethyl)-2,3-dihydro-1H-isoindol-1-yl]-1H-benzimidazol-2-yl}propanamide | A | A |
| 177 | methyl {5-[2-(3,4-dichlorophenyl)-1-hydroxy-3-oxo-2,3-dihydro-1H-isoindol-1-yl]-1H-benzimidazol-2-yl}carbamate | A | A |
| 178 | methyl {5-[2-(3-ethylphenyl)-1-hydroxy-3-oxo-2,3-dihydro-1H-isoindol-1-yl]-1H-benzimidazol-2-yl}carbamate | A | A |
| 179 | methyl {5-[2-(3-ethynylphenyl)-1-hydroxy-3-oxo-2,3-dihydro-1H-isoindol-1-yl]-1H-benzimidazol-2-yl}carbamate | A | A |
| 180 | methyl {5-[2-(4-chloro-3-methylphenyl)-1-hydroxy-3-oxo-2,3-dihydro-1H-isoindol-1-yl]-1H-benzimidazol-2-yl}carbamate | A | A |
| 181 | methyl [5-(1-hydroxy-3-oxo-2-{1-[3-(trifluoromethyl)phenyl]ethyl}-2,3-dihydro-1H-isoindol-1-yl)-1H-benzimidazol-2-yl]carbamate | C | C |
| 182 | methyl (5-{1-hydroxy-3-oxo-2-[(1R)-1-phenylpropyl]-2,3-dihydro-1H-isoindol-1-yl}-1H-benzimidazol-2-yl)carbamate | B | B |
| 183 | methyl [5-(1-hydroxy-3-oxo-2-{2-[(trifluoromethyl)oxy]phenyl}-2,3-dihydro-1H-isoindol-1-yl)-1H-benzimidazol-2-yl]carbamate | B | A |
| 184 | methyl {-[2-(2,3-difluorophenyl)-1-hydroxy-3-oxo-2,3-dihydro-1H-isoindol-1-yl]-1H-benzimidazol-2-yl}carbamate | A | A |
| 185 | cyclohexyl {5-[1-hydroxy-3-oxo-2-(phenylmethyl)-2,3-dihydro-1H-isoindol-1-yl]-1H-benzimidazol-2-yl}carbamate | B | B |
| 186 | tetrahydrofuran-2-ylmethyl {5-[1-hydroxy-3-oxo-2-(phenylmethyl)-2,3-dihydro-1H-isoindol-1-yl]-1H-benzimidazol-2-yl}carbamate | A | A |
| 187 | cyclopropylmethyl {5-[1-hydroxy-3-oxo-2-(phenylmethyl)-2,3-dihydro-1H-isoindol-1-yl]-1H-benzimidazol-2-yl}carbamate | A | A |
| 188 | N-{5-[1-hydroxy-3-oxo-2-(phenylmethyl)-2,3-dihydro-1H-isoindol-1-yl]-1H-benzimidazol-2-yl}morpholine-4-carboxamide | B | C |
| 189 | methyl {5-[2-(cyclopentylmethyl)-1-hydroxy-3-oxo-2,3-dihydro-1H-isoindol-1-yl]-1H-benzimidazol-2-yl}carbamate | A | A |

TABLE 1-continued

| Entry | Name | cRaf-1 | bRaf |
|---|---|---|---|
| 190 | methyl {5-[2-(2,3-dimethylphenyl)-1-hydroxy-3-oxo-2,3-dihydro-1H-isoindol-1-yl]-1H-benzimidazol-2-yl}carbamate | A | A |
| 191 | methyl {5-[2-(2,3-dihydro-1H-inden-1-yl)-1-hydroxy-3-oxo-2,3-dihydro-1H-isoindol-1-yl]-1H-benzimidazol-2-yl}carbamate | A | A |
| 192 | methyl (2S)-cyclohexyl[1-hydroxy-1-(2-{[(methyloxy)carbonyl]amino}-1H-benzimidazol-5-yl)-3-oxo-1,3-dihydro-2H-isoindol-2-yl]ethanoate | C | C |
| 193 | methyl {5-[2-(2,6-difluorophenyl)-1-hydroxy-3-oxo-2,3-dihydro-1H-isoindol-1-yl]-1H-benzimidazol-2-yl}carbamate | A | A |
| 194 | methyl {5-[2-(3-chloro-4-fluorophenyl)-1-hydroxy-3-oxo-2,3-dihydro-1H-isoindol-1-yl]-1H-benzimidazol-2-yl}carbamate | A | A |
| 195 | but-3-en-1-yl {5-[1-hydroxy-3-oxo-2-(phenylmethyl)-2,3-dihydro-1H-isoindol-1-yl]-1H-benzimidazol-2-yl}carbamate | A | A |
| 196 | 2,2,2-trifluoroethyl {5-[1-hydroxy-3-oxo-2-(phenylmethyl)-2,3-dihydro-1H-isoindol-1-yl]-1H-benzimidazol-2-yl}carbamate | A | A |
| 197 | methyl {5-[2-(5-chloro-2-fluorophenyl)-1-hydroxy-3-oxo-2,3-dihydro-1H-isoindol-1-yl]-1H-benzimidazol-2-yl}carbamate | A | A |
| 198 | methyl (5-{2-[1-(5-chloro-2-methylphenyl)ethyl]-1-hydroxy-3-oxo-2,3-dihydro-1H-isoindol-1-yl}-1H-benzimidazol-2-yl)carbamate | C | C |
| 199 | methyl (5-{1-hydroxy-3-oxo-2-[(1S)-1-phenylpropyl]-2,3-dihydro-1H-isoindol-1-yl}-1H-benzimidazol-2-yl)carbamate | C | C |
| 200 | methyl (5-{2-[1-(3-chloro-2-methylphenyl)ethyl]-1-hydroxy-3-oxo-2,3-dihydro-1H-isoindol-1-yl}-1H-benzimidazol-2-yl)carbamate | C | C |
| 201 | methyl (5-{1-hydroxy-2-[1-(5-methyl-2-thienyl)ethyl]-3-oxo-2,3-dihydro-1H-isoindol-1-yl}-1H-benzimidazol-2-yl)carbamate | A | A |
| 202 | methyl (5-{2-[1-(5-chloro-2-thienyl)ethyl]-1-hydroxy-3-oxo-2,3-dihydro-1H-isoindol-1-yl}-1H-benzimidazol-2-yl)carbamate | A | A |
| 203 | methyl {5-[1-hydroxy-2-(3-iodophenyl)-3-oxo-2,3-dihydro-1H-isoindol-1-yl]-1H-benzimidazol-2-yl}carbamate | A | A |
| 204 | methyl (5-{1-hydroxy-2-[3-(1-methylethyl)phenyl]-3-oxo-2,3-dihydro-1H-isoindol-1-yl}-1H-benzimidazol-2-yl)carbamate | A | A |
| 205 | methyl {5-[2-(furan-2-ylmethyl)-1-hydroxy-3-oxo-2,3-dihydro-1H-isoindol-1-yl]-1H-benzimidazol-2-yl}carbamate | A | A |
| 219 | methyl (5-{1-hydroxy-2-[3-(methylsulfonyl)phenyl]-3-oxo-2,3-dihydro-1H-isoindol-1-yl}-1H-benzimidazol-2-yl)carbamate | B | B |
| 220 | methyl (5-{1-hydroxy-3-oxo-2-[3-(phenyloxy)phenyl]-2,3-dihydro-1H-isoindol-1-yl}-1H-benzimidazol-2-yl)carbamate | A | A |
| 221 | methyl [5-(1-hydroxy-3-oxo-2-{3-[(phenylmethyl)oxy]phenyl}-2,3-dihydro-1H-isoindol-1-yl)-1H-benzimidazol-2-yl]carbamate | A | B |
| 222 | methyl [5-(2-biphenyl-3-yl-1-hydroxy-3-oxo-2,3-dihydro-1H-isoindol-1-yl)-1H-benzimidazol-2-yl]carbamate | C | C |
| 223 | 2,2-dimethyl-3-[(phenylmethyl)oxy]propyl {5-[1-hydroxy-3-oxo-2-(phenylmethyl)-2,3-dihydro-1H-isoindol-1-yl]-1H-benzimidazol-2-yl}carbamate | A | B |
| 224 | methyl {5-[2-(3-chloro-2-fluorophenyl)-1-hydroxy-3-oxo-2,3-dihydro-1H-isoindol-1-yl]-1H-benzimidazol-2-yl}carbamate | A | A |
| 225 | methyl {5-[2-(3-cyanophenyl)-1-hydroxy-3-oxo-2,3-dihydro-1H-isoindol-1-yl]-1H-benzimidazol-2-yl}carbamate | B | B |
| 226 | methyl {5-[2-(3-ethynyl-4-fluorophenyl)-1-hydroxy-3-oxo-2,3-dihydro-1H-isoindol-1-yl]-1H-benzimidazol-2-yl}carbamate | A | A |
| 227 | methyl {5-[2-(4-fluoro-3-methylphenyl)-1-hydroxy-3-oxo-2,3-dihydro-1H-isoindol-1-yl]-1H-benzimidazol-2-yl}carbamate | A | A |

TABLE 1-continued

| Entry | Name | cRaf-1 | bRaf |
|---|---|---|---|
| 228 | methyl {6-[2-(3,4-dichloro-2-fluorophenyl)-1-hydroxy-3-oxo-2,3-dihydro-1H-isoindol-1-yl]-1H-benzimidazol-2-yl}carbamate | A | A |
| 229 | [(4S)-2,2-dimethyl-1,3-dioxolan-4-yl]methyl {5-[1-hydroxy-3-oxo-2-(phenylmethyl)-2,3-dihydro-1H-isoindol-1-yl]-1H-benzimidazol-2-yl}carbamate | A | A |
| 230 | methyl {5-[2-(5-bromo-2-fluorophenyl)-1-hydroxy-3-oxo-2,3-dihydro-1H-isoindol-1-yl]-1H-benzimidazol-2-yl}carbamate | A | A |
| 231 | methyl (5-{2-[3-(acetylamino)phenyl]-1-hydroxy-3-oxo-2,3-dihydro-1H-isoindol-1-yl}-1H-benzimidazol-2-yl)carbamate | A | A |
| 232 | methyl (5-{1-hydroxy-3-oxo-2-[3-(phenylmethyl)phenyl]-2,3-dihydro-1H-isoindol-1-yl}-1H-benzimidazol-2-yl)carbamate | A | A |
| 233 | methyl (5-{2-[1-(4-chloro-2-thienyl)ethyl]-1-hydroxy-3-oxo-2,3-dihydro-1H-isoindol-1-yl}-1H-benzimidazol-2-yl)carbamate | A | A |
| 234 | methyl (5-{1-hydroxy-3-oxo-2-[3-(phenylcarbonyl)phenyl]-2,3-dihydro-1H-isoindol-1-yl}-1H-benzimidazol-2-yl)carbamate | B | C |
| 235 | methyl [5-(2-{3-[(dimethylamino)methyl]phenyl}-1-hydroxy-3-oxo-2,3-dihydro-1H-isoindol-1-yl)-1H-benzimidazol-2-yl]carbamate | B | B |
| 236 | methyl (5-{2-[3-(aminosulfonyl)phenyl]-1-hydroxy-3-oxo-2,3-dihydro-1H-isoindol-1-yl}-1H-benzimidazol-2-yl)carbamate | B | B |
| 237 | methyl {5-[2-(3-acetylphenyl)-1-hydroxy-3-oxo-2,3-dihydro-1H-isoindol-1-yl]-1H-benzimidazol-2-yl}carbamate | A | A |
| 238 | methyl {5-[2-(3-ethyl-4-fluorophenyl)-1-hydroxy-3-oxo-2,3-dihydro-1H-isoindol-1-yl]-1H-benzimidazol-2-yl}carbamate | A | A |
| 239 | methyl {5-[2-(3-chloro-5-fluorophenyl)-1-hydroxy-3-oxo-2,3-dihydro-1H-isoindol-1-yl]-1H-benzimidazol-2-yl}carbamate | A | A |
| 240 | N-{6-[1-hydroxy-3-oxo-2-(phenylmethyl)-2,3-dihydro-1H-isoindol-1-yl]-1H-benzimidazol-2-yl}-2-methylpropanamide | B | B |
| 241 | methyl (5-{2-[1-(3-chloro-2-thienyl)ethyl]-1-hydroxy-3-oxo-2,3-dihydro-1H-isoindol-1-yl}-1H-benzimidazol-2-yl)carbamate | C | C |
| 242 | methyl [5-(1-hydroxy-3-oxo-2-pyridin-3-yl-2,3-dihydro-1H-isoindol-1-yl)-1H-benzimidazol-2-yl]carbamate | A | B |
| 243 | methyl (5-{1-hydroxy-3-oxo-2-[3-(phenylamino)phenyl]-2,3-dihydro-1H-isoindol-1-yl}-1H-benzimidazol-2-yl)carbamate | B | B |
| 244 | methyl {5-[2-(5-bromo-2,4-difluorophenyl)-1-hydroxy-3-oxo-2,3-dihydro-1H-isoindol-1-yl]-1H-benzimidazol-2-yl}carbamate | A | A |
| 245 | methyl {5-[2-(5-chloro-2,4-difluorophenyl)-1-hydroxy-3-oxo-2,3-dihydro-1H-isoindol-1-yl]-1H-benzimidazol-2-yl}carbamate | A | A |
| 246 | methyl {5-[2-(3,5-dichloro-4-fluorophenyl)-1-hydroxy-3-oxo-2,3-dihydro-1H-isoindol-1-yl]-1H-benzimidazol-2-yl}carbamate | B | C |
| 247 | 2,2-dimethyl-3-(methyloxy)propyl {5-[1-hydroxy-3-oxo-2-(phenylmethyl)-2,3-dihydro-1H-isoindol-1-yl]-1H-benzimidazol-2-yl}carbamate | B | B |
| 248 | 3-hydroxy-2,2-dimethylpropyl {5-[1-hydroxy-3-oxo-2-(phenylmethyl)-2,3-dihydro-1H-isoindol-1-yl]-1H-benzimidazol-2-yl}carbamate | B | B |
| 249 | methyl (5-{2-[1-(5-bromo-2-thienyl)ethyl]-1-hydroxy-3-oxo-2,3-dihydro-1H-isoindol-1-yl}-1H-benzimidazol-2-yl)carbamate | A | A |
| 250 | methyl {5-[2-(4,5-dichloro-2-fluorophenyl)-1-hydroxy-3-oxo-2,3-dihydro-1H-isoindol-1-yl]-1H-benzimidazol-2-yl}carbamate | A | A |
| 251 | methyl {5-[2-(3-bromo-2-fluorophenyl)-1-hydroxy-3-oxo-2,3-dihydro-1H-isoindol-1-yl]-1H-benzimidazol-2-yl}carbamate | A | A |
| 252 | methyl {5-[2-(3-chloro-2,4-difluorophenyl)-1-hydroxy-3-oxo-2,3-dihydro-1H-isoindol-1-yl]-1H-benzimidazol-2-yl}carbamate | A | A |

TABLE 1-continued

| Entry | Name | cRaf-1 | bRaf |
|---|---|---|---|
| 253 | N-{6-[1-hydroxy-3-oxo-2-(phenylmethyl)-2,3-dihydro-1H-isoindol-1-yl]-1H-benzimidazol-2-yl}pent-4-ynamide | A | A |
| 254 | methyl (6-{1-methyl-3-oxo-2-[3-(trifluoromethyl)phenyl]-2,3-dihydro-1H-isoindol-1-yl}-1H-benzimidazol-2-yl)carbamate | A | A |
| 255 | methyl [5-(1-hydroxy-3-oxo-2-{3-[(1,1,2,2-tetrafluoroethyl)oxy]phenyl}-2,3-dihydro-1H-isoindol-1-yl)-1H-benzimidazol-2-yl]carbamate | C | C |
| 256 | methyl {5-[1-hydroxy-3-oxo-2-(3-piperidin-4-ylphenyl)-2,3-dihydro-1H-isoindol-1-yl]-1H-benzimidazol-2-yl}carbamate | B | B |
| 257 | methyl {5-[2-(3-ethenylphenyl)-1-hydroxy-3-oxo-2,3-dihydro-1H-isoindol-1-yl]-1H-benzimidazol-2-yl}carbamate | A | A |
| 258 | methyl (5-{2-[3-(dimethylamino)phenyl]-1-hydroxy-3-oxo-2,3-dihydro-1H-isoindol-1-yl}-1H-benzimidazol-2-yl)carbamate | A | A |
| 259 | 2,2-difluoro-N-{6-[1-hydroxy-3-oxo-2-(phenylmethyl)-2,3-dihydro-1H-isoindol-1-yl]-1H-benzimidazol-2-yl}cyclopropanecarboxamide | A | A |
| 260 | N-ethyl-N'-{6-[2-(4-fluorophenyl)-1-hydroxy-3-oxo-2,3-dihydro-1H-isoindol-1-yl]-1H-benzimidazol-2-yl}urea | A | A |
| 261 | methyl {5-[2-(3-aminophenyl)-1-hydroxy-3-oxo-2,3-dihydro-1H-isoindol-1-yl]-1H-benzimidazol-2-yl}carbamate | A | A |
| 262 | N-{5-[1-hydroxy-3-oxo-2-(phenylmethyl)-2,3-dihydro-1H-isoindol-1-yl]-1H-benzimidazol-2-yl}-4-[(phenylmethyl)oxy]butanamide | A | A |
| 263 | N-{5-[1-hydroxy-3-oxo-2-(phenylmethyl)-2,3-dihydro-1H-isoindol-1-yl]-1H-benzimidazol-2-yl}-4-piperidin-1-ylbutanamide | A | A |
| 264 | N-{5-[1-hydroxy-3-oxo-2-(phenylmethyl)-2,3-dihydro-1H-isoindol-1-yl]-1H-benzimidazol-2-yl}-4-(4-methylpiperazin-1-yl)butanamide | A | A |
| 265 | N-{6-[2-(4-fluorophenyl)-1-hydroxy-3-oxo-2,3-dihydro-1H-isoindol-1-yl]-1H-benzimidazol-2-yl}butanamide | A | A |
| 266 | methyl {6-[2-(3-bromophenyl)-5,6-dichloro-1-hydroxy-3-oxo-2,3-dihydro-1H-isoindol-1-yl]-1H-benzimidazol-2-yl}carbamate | C | C |
| 267 | methyl [5-(1-hydroxy-2-{3-[methyl(phenyl)amino]phenyl}-3-oxo-2,3-dihydro-1H-isoindol-1-yl)-1H-benzimidazol-2-yl]carbamate | A | A |
| 268 | methyl {5-[1-hydroxy-3-oxo-2-(phenylsulfonyl)-2,3-dihydro-1H-isoindol-1-yl]-1H-benzimidazol-2-yl}carbamate | C | C |
| 269 | methyl {5-[(2-{[(phenylamino)carbonyl]amino}phenyl)carbonyl]-1H-benzimidazol-2-yl}carbamate | B | B |
| 270 | methyl (5-{[2-({[(phenylmethyl)oxy]carbonyl}amino)phenyl]carbonyl}-1H-benzimidazol-2-yl)carbamate | C | C |
| 271 | methyl [5-({2-[(2-phenylhydrazino)carbonyl]phenyl}carbonyl)-1H-benzimidazol-2-yl]carbamate | B | B |
| 272 | methyl {5-[(2-{[(phenyloxy)amino]carbonyl}phenyl)carbonyl]-1H-benzimidazol-2-yl}carbamate | A | A |
| 273 | but-2-yn-1-yl {5-[2-(4-fluorophenyl)-1-hydroxy-3-oxo-2,3-dihydro-1H-isoindol-1-yl]-1H-benzimidazol-2-yl}carbamate | A | A |
| 274 | N-{5-[1-hydroxy-3-oxo-2-(phenylmethyl)-2,3-dihydro-1H-isoindol-1-yl]-1H-benzimidazol-2-yl}-3-piperidin-1-ylpropanamide | A | A |
| 275 | N-{6-[2-(4-fluorophenyl)-1-hydroxy-3-oxo-2,3-dihydro-1H-isoindol-1-yl]-1H-benzimidazol-2-yl}propanamide | A | A |
| 276 | N-(4-fluorophenyl)-2-{[2-(pent-4-ynylamino)-1H-benzimidazol-6-yl]carbonyl}benzamide | A | A |
| 277 | 4-(diethylamino)-N-{5-[1-hydroxy-3-oxo-2-(phenylmethyl)-2,3-dihydro-1H-isoindol-1-yl]-1H-benzimidazol-2-yl}butanamide | A | A |
| 278 | N-{5-[1-hydroxy-3-oxo-2-(phenylmethyl)-2,3-dihydro-1H-isoindol-1-yl]-1H-benzimidazol-2-yl}-4-pyrrolidin-1-ylbutanamide | A | A |

TABLE 1-continued

| Entry | Name | cRaf-1 | bRaf |
|---|---|---|---|
| 279 | 3-piperidin-1-ylpropyl {6-[2-(4-fluorophenyl)-1-hydroxy-3-oxo-2,3-dihydro-1H-isoindol-1-yl]-1H-benzimidazol-2-yl}carbamate | A | B |
| 280 | 3-(4-methylpiperazin-1-yl)propyl {6-[2-(4-fluorophenyl)-1-hydroxy-3-oxo-2,3-dihydro-1H-isoindol-1-yl]-1H-benzimidazol-2-yl}carbamate | A | A |
| 281 | methyl {5-[2-(3-bromophenyl)-3-oxo-2,3-dihydro-1H-isoindol-1-yl]-1H-benzimidazol-2-yl}carbamate | A | A |
| 282 | methyl {5-[2-(3-ethynyl-2-fluorophenyl)-1-hydroxy-3-oxo-2,3-dihydro-1H-isoindol-1-yl]-1H-benzimidazol-2-yl}carbamate | A | A |
| 283 | 2-piperidin-1-ylethyl {5-[2-(4-fluorophenyl)-1-hydroxy-3-oxo-2,3-dihydro-1H-isoindol-1-yl]-1H-benzimidazol-2-yl}carbamate | A | B |
| 284 | methyl {5-[2-(3-chloro-2-methylphenyl)-1-hydroxy-3-oxo-2,3-dihydro-1H-isoindol-1-yl]-1H-benzimidazol-2-yl}carbamate | A | A |
| 285 | methyl {5-[2-(5-chloro-2-methylphenyl)-1-hydroxy-3-oxo-2,3-dihydro-1H-isoindol-1-yl]-1H-benzimidazol-2-yl}carbamate | A | A |
| 286 | N-{6-[1-hydroxy-3-oxo-2-(phenylmethyl)-2,3-dihydro-1H-isoindol-2-yl]-1H-benzimidazol-2-yl}-2,2-dimethyl-3-piperidin-1-ylpropanamide | C | C |
| 287 | N-{5-[2-(4-fluorophenyl)-1-hydroxy-3-oxo-2,3-dihydro-1H-isoindol-1-yl]-1H-benzimidazol-2-yl}-4-piperidin-1-ylbutanamide | A | A |
| 288 | N-{5-[2-(3-chloro-2-fluorophenyl)-1-hydroxy-3-oxo-2,3-dihydro-1H-isoindol-1-yl]-1H-benzimidazol-2-yl}-4-piperidin-1-ylbutanamide | A | A |
| 289 | methyl [6-({2-[(phenylcarbonyl)amino]phenyl}carbonyl)-1H-benzimidazol-2-yl]carbamate | C | C |
| 290 | methyl {5-[1-hydroxy-2-(3-morpholin-4-ylphenyl)-3-oxo-2,3-dihydro-1H-isoindol-1-yl]-1H-benzimidazol-2-yl}carbamate | C | C |
| 291 | 2-(dimethylamino)ethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 292 | 2-(diethylamino)ethyl {5-[2-(3-chloro-2-fluorophenyl)-1-hydroxy-3-oxo-2,3-dihydro-1H-isoindol-1-yl]-1H-benzimidazol-2-yl}carbamate | A | A |
| 293 | 2-piperidin-1-ylethyl {5-[2-(3-chloro-2-fluorophenyl)-1-hydroxy-3-oxo-2,3-dihydro-1H-isoindol-1-yl]-1H-benzimidazol-2-yl}carbamate | A | A |
| 294 | 3-piperidin-1-ylpropyl {6-[2-(3-chloro-2-fluorophenyl)-1-hydroxy-3-oxo-2,3-dihydro-1H-isoindol-1-yl]-1H-benzimidazol-2-yl}carbamate | C | C |
| 295 | 2-piperidin-1-ylethyl {6-[2-(3-bromophenyl)-3-oxo-2,3-dihydro-1H-isoindol-1-yl]-1H-benzimidazol-2-yl}carbamate | A | B |
| 296 | methyl {6-[2-(3-bromophenyl)-4,7-difluoro-1-hydroxy-3-oxo-2,3-dihydro-1H-isoindol-1-yl]-1H-benzimidazol-2-yl}carbamate | A | A |
| 297 | 2-[methyl(phenylmethyl)amino]ethyl {5-[2-(3-chloro-2-fluorophenyl)-1-hydroxy-3-oxo-2,3-dihydro-1H-isoindol-1-yl]-1H-benzimidazol-2-yl}carbamate | A | A |
| 298 | methyl {5-[1-hydroxy-3-oxo-2-(3-pyrrolidin-1-ylphenyl)-2,3-dihydro-1H-isoindol-1-yl]-1H-benzimidazol-2-yl}carbamate | C | C |
| 299 | methyl {5-[2-(5-chloro-2,3-difluorophenyl)-1-hydroxy-3-oxo-2,3-dihydro-1H-isoindol-1-yl]-1H-benzimidazol-2-yl}carbamate | A | A |
| 300 | methyl {5-[1-hydroxy-3-oxo-2-(pyrrolidin-2-ylmethyl)-2,3-dihydro-1H-isoindol-1-yl]-1H-benzimidazol-2-yl}carbamate | C | C |
| 301 | methyl {5-[1-hydroxy-3-oxo-2-(pyrrolidin-3-ylmethyl)-2,3-dihydro-1H-isoindol-1-yl]-1H-benzimidazol-2-yl}carbamate | C | C |
| 302 | (1-methylpiperidin-2-yl)methyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 303 | [(2S)-1-methylpyrrolidin-2-yl]methyl {6-[2-(3-chloro-2-fluorophenyl)-1-hydroxy-3-oxo-2,3-dihydro-1H-isoindol-1-yl]-1H-benzimidazol-2-yl}carbamate | A | A |

TABLE 1-continued

| Entry | Name | cRaf-1 | bRaf |
|---|---|---|---|
| 304 | octahydro-2H-quinolizin-1-ylmethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 305 | methyl {5-[2-(5-bromo-2-methylphenyl)-1-hydroxy-3-oxo-2,3-dihydro-1H-isoindol-1-yl]-1H-benzimidazol-2-yl}carbamate | A | A |
| 306 | 5-[2-(3-chloro-2-fluorophenyl)-1-hydroxy-3-oxo-2,3-dihydro-1H-isoindol-1-yl]-1,3-dihydro-2H-benzimidazol-2-one | C | C |
| 307 | methyl {5-[2-(3-bromo-2,5-difluorophenyl)-1-hydroxy-3-oxo-2,3-dihydro-1H-isoindol-1-yl]-1H-benzimidazol-2-yl}carbamate | A | A |
| 308 | 2-morpholin-4-ylethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 309 | (1-methylpiperidin-3-yl)methyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 310 | methyl (5-{2-[5-chloro-2-(methyloxy)phenyl]-1-hydroxy-3-oxo-2,3-dihydro-1H-isoindol-1-yl}-1H-benzimidazol-2-yl)carbamate | A | A |
| 311 | methyl [5-(2-{3-[cyclohexyl(methyl)amino]phenyl}-1-hydroxy-3-oxo-2,3-dihydro-1H-isoindol-1-yl)-1H-benzimidazol-2-yl]carbamate | A | A |
| 312 | 8-azabicyclo[3.2.1]oct-3-ylmethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 313 | methyl {6-[1-(3-bromophenyl)-5-oxopyrrolidin-2-yl]-1H-benzimidazol-2-yl}carbamate | C | C |
| 314 | (1-methylpiperidin-4-yl)methyl {5-[1-hydroxy-3-oxo-2-(phenylmethyl)-2,3-dihydro-1H-isoindol-1-yl]-1H-benzimidazol-2-yl}carbamate | A | A |
| 315 | 1,1-dimethylethyl 4-({[({5-[1-hydroxy-3-oxo-2-(phenylmethyl)-2,3-dihydro-1H-isoindol-1-yl]-1H-benzimidazol-2-yl}amino)carbonyl]oxy}methyl)piperidine-1-carboxylate | B | B |
| 316 | (1-methylpiperidin-4-yl)methyl {5-[2-(3-chloro-2-fluorophenyl)-1-hydroxy-3-oxo-2,3-dihydro-1H-isoindol-1-yl]-1H-benzimidazol-2-yl}carbamate | A | A |
| 317 | 2-(1-methylpiperidin-4-yl)ethyl {5-[2-(3-chloro-2-fluorophenyl)-1-hydroxy-3-oxo-2,3-dihydro-1H-isoindol-1-yl]-1H-benzimidazol-2-yl}carbamate | A | A |
| 318 | methyl ({6-[2-(3-chloro-2-fluorophenyl)-1-hydroxy-3-oxo-2,3-dihydro-1H-isoindol-1-yl]-1H-benzimidazol-2-yl}amino)(oxo)acetate | C | C |
| 319 | N-(5-{1-hydroxy-3-oxo-2-[3-(phenyloxy)phenyl]-2,3-dihydro-1H-isoindol-1-yl}-1H-benzimidazol-2-yl)-4-piperidin-1-ylbutanamide | A | A |
| 320 | methyl {6-[2-(3-bromophenyl)-1-methyl-3-oxo-2,3-dihydro-1H-isoindol-1-yl]-1H-benzimidazol-2-yl}carbamate | A | A |
| 321 | 4-(diethylamino)but-2-yn-1-yl {6-[2-(3-chloro-2-fluorophenyl)-1-hydroxy-3-oxo-2,3-dihydro-1H-isoindol-1-yl]-1H-benzimidazol-2-yl}carbamate | A | A |
| 322 | methyl {5-[2-(3-chloro-2,6-difluorophenyl)-1-hydroxy-3-oxo-2,3-dihydro-1H-isoindol-1-yl]-1H-benzimidazol-2-yl}carbamate | A | A |
| 323 | 2-(2-oxopyrrolidin-1-yl)ethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 324 | 2-(2,5-dioxopyrrolidin-1-yl)ethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 325 | 2,2,3,3-tetrafluorocyclobutyl {5-[2-(3-chloro-2-fluorophenyl)-1-hydroxy-3-oxo-2,3-dihydro-1H-isoindol-1-yl]-1H-benzimidazol-2-yl}carbamate | A | A |
| 326 | 1-acetyl-N-{5-[2-(3-chloro-2-fluorophenyl)-1-hydroxy-3-oxo-2,3-dihydro-1H-isoindol-1-yl]-1H-benzimidazol-2-yl}piperidine-4-carboxamide | A | A |
| 327 | N-{5-[2-(3-chloro-2-fluorophenyl)-1-hydroxy-3-oxo-2,3-dihydro-1H-isoindol-1-yl]-1H-benzimidazol-2-yl}cyclobutanecarboxamide | A | A |
| 328 | methyl [5-(2-{3-[ethyl(phenyl)amino]phenyl}-1-hydroxy-3-oxo-2,3-dihydro-1H-isoindol-1-yl)-1H-benzimidazol-2-yl]carbamate | B | B |

TABLE 1-continued

| Entry | Name | cRaf-1 | bRaf |
|---|---|---|---|
| 329 | N-{6-[2-(3-chloro-2-fluorophenyl)-1-hydroxy-3-oxo-2,3-dihydro-1H-isoindol-1-yl]-1H-benzimidazol-2-yl}-2,2-difluorocyclopropanecarboxamide | A | A |
| 330 | cyclobutyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 331 | 2,2-difluoroethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 332 | 2-(3-chloro-2-fluorophenyl)-3-hydroxy-3-[2-(pyridin-2-ylamino)-1H-benzimidazol-5-yl]-2,3-dihydro-1H-isoindol-1-one | A | A |
| 333 | 1-methylethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 334 | cyclopropylmethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 335 | N-{5-[2-(3-chloro-2-fluorophenyl)-1-hydroxy-3-oxo-2,3-dihydro-1H-isoindol-1-yl]-1H-benzimidazol-2-yl}cyclopropanecarboxamide | A | A |
| 336 | 2-(methyloxy)ethyl {5-[2-(3-chloro-2-fluorophenyl)-1-hydroxy-3-oxo-2,3-dihydro-1H-isoindol-1-yl]-1H-benzimidazol-2-yl}carbamate | A | A |
| 337 | tetrahydrofuran-2-ylmethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 338 | N-{5-[2-(3-chloro-2-fluorophenyl)-1-hydroxy-3-oxo-2,3-dihydro-1H-isoindol-1-yl]-1H-benzimidazol-2-yl}-2-(2-thienyl)acetamide | A | A |
| 339 | methyl {6-[2-(3-chloro-2-fluorophenyl)-4,7-difluoro-1-hydroxy-3-oxo-2,3-dihydro-1H-isoindol-1-yl]-1H-benzimidazol-2-yl}carbamate | A | A |
| 340 | ethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 341 | 2-fluoroethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 342 | methyl (5-{1-hydroxy-3-oxo-2-[2-(phenyloxy)phenyl]-2,3-dihydro-1H-isoindol-1-yl}-1H-benzimidazol-2-yl)carbamate | B | B |
| 343 | N'-{5-[2-(3-chloro-2-fluorophenyl)-1-hydroxy-3-oxo-2,3-dihydro-1H-isoindol-1-yl]-1H-benzimidazol-2-yl}-N,N-diethylpentanediamide | A | A |
| 344 | cyclobutylmethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 345 | 2,2,2-trifluoroethyl {6-[2-(3-chloro-2-fluorophenyl)-1-hydroxy-3-oxo-2,3-dihydro-1H-isoindol-1-yl]-1H-benzimidazol-2-yl}carbamate | A | A |
| 346 | methyl (5-{2-[3-(1,1-dimethylethyl)phenyl]-1-hydroxy-3-oxo-2,3-dihydro-1H-isoindol-1-yl}-1H-benzimidazol-2-yl)carbamate | A | A |
| 347 | methyl {6-[2-(3-chloro-2-fluorophenyl)-7-fluoro-1-hydroxy-3-oxo-2,3-dihydro-1H-isoindol-1-yl]-1H-benzimidazol-2-yl}carbamate | A | A |
| 348 | 2-(3-chloro-2-fluorophenyl)-3-hydroxy-3-[2-(phenylamino)-1H-benzimidazol-5-yl]-2,3-dihydro-1H-isoindol-1-one | C | C |
| 349 | methyl {6-[4,7-dichloro-2-(3-chloro-2-fluorophenyl)-1-hydroxy-3-oxo-2,3-dihydro-1H-isoindol-1-yl]-1H-benzimidazol-2-yl}carbamate | C | C |
| 350 | phenylmethyl 2-[(2-{[(ethyloxy)carbonyl]amino}-1,3-benzoxazol-5-yl)carbonyl]benzoate | C | C |
| 351 | methyl {5-[2-(5-chloro-3-ethynyl-2-methylphenyl)-1-hydroxy-3-oxo-2,3-dihydro-1H-isoindol-1-yl]-1H-benzimidazol-2-yl}carbamate | B | A |
| 352 | methyl {5-[2-(5-ethynyl-2,4-difluorophenyl)-1-hydroxy-3-oxo-2,3-dihydro-1H-isoindol-1-yl]-1H-benzimidazol-2-yl}carbamate | A | A |
| 353 | methyl {5-[2-(3-ethynyl-2,4-difluorophenyl)-1-hydroxy-3-oxo-2,3-dihydro-1H-isoindol-1-yl]-1H-benzimidazol-2-yl}carbamate | A | A |
| 354 | 2-(3-chloro-2-fluorophenyl)-3-hydroxy-3-[2-(pyrimidin-2-ylamino)-1H-benzimidazol-5-yl]-2,3-dihydro-1H-isoindol-1-one | A | A |

TABLE 1-continued

| Entry | Name | cRaf-1 | bRaf |
|---|---|---|---|
| 355 | methyl {5-[2-(3-ethynyl-2-fluorophenyl)-4,7-difluoro-1-hydroxy-3-oxo-2,3-dihydro-1H-isoindol-1-yl]-1H-benzimidazol-2-yl}carbamate | A | A |
| 356 | 2-(3-chloro-2-fluorophenyl)-3-hydroxy-3-[2-(1,3-thiazol-2-ylamino)-1H-benzimidazol-5-yl]-2,3-dihydro-1H-isoindol-1-one | A | A |
| 357 | ethyl {5-[2-(3-chloro-2-fluorophenyl)-1-hydroxy-3-oxo-2,3-dihydro-1H-isoindol-1-yl]-1,3-benzoxazol-2-yl}carbamate | B | A |
| 358 | methyl {5-[2-(5-chloro-3-iodo-2-methylphenyl)-1-hydroxy-3-oxo-2,3-dihydro-1H-isoindol-1-yl]-1H-benzimidazol-2-yl}carbamate | B | B |
| 359 | methyl {5-[2-(3-ethyl-2-fluorophenyl)-1-hydroxy-3-oxo-2,3-dihydro-1H-isoindol-1-yl]-1H-benzimidazol-2-yl}carbamate | A | A |
| 360 | methyl {5-[2-(5-ethynyl-2-methylphenyl)-1-hydroxy-3-oxo-2,3-dihydro-1H-isoindol-1-yl]-1H-benzimidazol-2-yl}carbamate | A | A |
| 361 | 2-(3-chloro-2-fluorophenyl)-3-hydroxy-3-[2-(pyrazin-2-ylamino)-1H-benzimidazol-5-yl]-2,3-dihydro-1H-isoindol-1-one | A | A |
| 362 | methyl {5-[2-(2-fluoro-3-iodophenyl)-1-hydroxy-3-oxo-2,3-dihydro-1H-isoindol-1-yl]-1H-benzimidazol-2-yl}carbamate | A | A |
| 363 | methyl {6-[2-(5-ethynyl-2-fluorophenyl)-1-hydroxy-3-oxo-2,3-dihydro-1H-isoindol-1-yl]-1H-benzimidazol-2-yl}carbamate | A | A |
| 364 | 2-(3-ethynyl-2-fluorophenyl)-3-hydroxy-3-[2-(pyrimidin-2-ylamino)-1H-benzimidazol-5-yl]-2,3-dihydro-1H-isoindol-1-one | A | A |
| 365 | methyl {5-[2-(2,5-dimethylphenyl)-1-hydroxy-3-oxo-2,3-dihydro-1H-isoindol-1-yl]-1H-benzimidazol-2-yl}carbamate | A | A |
| 366 | methyl {5-[2-(3-ethenyl-2-fluorophenyl)-1-hydroxy-3-oxo-2,3-dihydro-1H-isoindol-1-yl]-1H-benzimidazol-2-yl}carbamate | A | A |
| 367 | methyl (6-{2-[2-fluoro-3-(methyloxy)phenyl]-1-hydroxy-3-oxo-2,3-dihydro-1H-isoindol-1-yl}-1H-benzimidazol-2-yl)carbamate | B | A |
| 368 | methyl (5-{1-hydroxy-2-[2-methyl-5-(methyloxy)phenyl]-3-oxo-2,3-dihydro-1H-isoindol-1-yl}-1H-benzimidazol-2-yl)carbamate | A | A |
| 369 | methyl {5-[2-(3-ethynyl-2-fluorophenyl)-7-fluoro-1-hydroxy-3-oxo-2,3-dihydro-1H-isoindol-1-yl]-1H-benzimidazol-2-yl}carbamate | A | A |
| 370 | methyl {5-[2-(2-fluoro-3-prop-1-yn-1-ylphenyl)-1-hydroxy-3-oxo-2,3-dihydro-1H-isoindol-1-yl]-1H-benzimidazol-2-yl}carbamate | B | B |
| 371 | methyl {5-[2-(5-chloro-2-methylphenyl)-7-fluoro-1-hydroxy-3-oxo-2,3-dihydro-1H-isoindol-1-yl]-1H-benzimidazol-2-yl}carbamate | A | A |
| 372 | methyl {5-[2-(3-ethynyl-2-methylphenyl)-1-hydroxy-3-oxo-2,3-dihydro-1H-isoindol-1-yl]-1H-benzimidazol-2-yl}carbamate | A | A |
| 373 | 3-hydroxy-2-[3-(methyloxy)phenyl]-3-[2-(pyrimidin-2-ylamino)-1H-benzimidazol-6-yl]-2,3-dihydro-1H-isoindol-1-one | A | A |
| 374 | 3-hydroxy-2-(3-methylphenyl)-3-[2-(pyrimidin-2-ylamino)-1H-benzimidazol-6-yl]-2,3-dihydro-1H-isoindol-1-one | A | A |
| 375 | 2-(5-chloro-2-methylphenyl)-3-hydroxy-3-[2-(pyrimidin-2-ylamino)-1H-benzimidazol-6-yl]-2,3-dihydro-1H-isoindol-1-one | A | A |
| 376 | methyl {6-[2-(5-chloro-2-methylphenyl)-4,7-difluoro-1-hydroxy-3-oxo-2,3-dihydro-1H-isoindol-1-yl]-1H-benzimidazol-2-yl}carbamate | A | A |
| 377 | methyl {5-[2-(3-ethynyl-2-fluorophenyl)-3-oxo-2,3-dihydro-1H-isoindol-1-yl]-1H-benzimidazol-2-yl}carbamate | A | A |
| 378 | 2-(3-chloro-2-fluorophenyl)-3-{2-[(6-chloropyridazin-3-yl)amino]-1H-benzimidazol-5-yl}-3-hydroxy-2,3-dihydro-1H-isoindol-1-one | B | B |
| 379 | 2-(3-chloro-2-fluorophenyl)-4,7-difluoro-3-hydroxy-3-[2-(pyrimidin-2-ylamino)-1H-benzimidazol-5-yl]-2,3-dihydro-1H-isoindol-1-one | A | A |

TABLE 1-continued

| Entry | Name | cRaf-1 | bRaf |
|---|---|---|---|
| 380 | methyl {5-[2-(2-fluoro-5-methylphenyl)-1-hydroxy-3-oxo-2,3-dihydro-1H-isoindol-1-yl]-1H-benzimidazol-2-yl}carbamate | A | A |
| 381 | methyl (5-{2-[2-fluoro-5-(methyloxy)phenyl]-1-hydroxy-3-oxo-2,3-dihydro-1H-isoindol-1-yl}-1H-benzimidazol-2-yl)carbamate | A | A |
| 382 | methyl (5-{1-hydroxy-2-[5-methyl-2-(methyloxy)phenyl]-3-oxo-2,3-dihydro-1H-isoindol-1-yl}-1H-benzimidazol-2-yl)carbamate | A | A |
| 383 | methyl {5-[2-(3-ethynyl-5-methylphenyl)-1-hydroxy-3-oxo-2,3-dihydro-1H-isoindol-1-yl]-1H-benzimidazol-2-yl}carbamate | A | A |
| 384 | 2-(3-chloro-2-fluorophenyl)-3-{2-[(5-chloropyrimidin-2-yl)amino]-1H-benzimidazol-5-yl}-3-hydroxy-2,3-dihydro-1H-isoindol-1-one | A | A |
| 385 | 2-(3-chloro-2-fluorophenyl)-3-hydroxy-3-{2-[(4-methylpyrimidin-2-yl)amino]-1H-benzimidazol-5-yl}-2,3-dihydro-1H-isoindol-1-one | A | A |
| 386 | 3-(2-{[4,6-bis(methyloxy)pyrimidin-2-yl]amino}-1H-benzimidazol-5-yl)-2-(3-chloro-2-fluorophenyl)-3-hydroxy-2,3-dihydro-1H-isoindol-1-one | A | A |
| 387 | 2-(3-chloro-2-fluorophenyl)-3-hydroxy-3-(2-{[4-methyl-6-(methyloxy)pyrimidin-2-yl]amino}-1H-benzimidazol-5-yl)-2,3-dihydro-1H-isoindol-1-one | A | A |
| 388 | 3-hydroxy-2-(3-methylphenyl)-3-[2-(pyrazin-2-ylamino)-1H-benzimidazol-6-yl]-2,3-dihydro-1H-isoindol-1-one | A | A |
| 389 | 2-(5-chloro-2-methylphenyl)-3-hydroxy-3-[2-(pyrazin-2-ylamino)-1H-benzimidazol-6-yl]-2,3-dihydro-1H-isoindol-1-one | A | A |
| 390 | methyl {6-[2-(2-fluoro-3-methylphenyl)-1-hydroxy-3-oxo-2,3-dihydro-1H-isoindol-1-yl]-1H-benzimidazol-2-yl}carbamate | A | A |
| 391 | 3-hydroxy-2-[3-(methyloxy)phenyl]-3-[2-(pyrazin-2-ylamino)-1H-benzimidazol-5-yl]-2,3-dihydro-1H-isoindol-1-one | A | A |
| 392 | methyl {6-[(2-{[(2-thienylmethyl)amino]carbonyl}phenyl)carbonyl]-1H-benzimidazol-2-yl}carbamate | A | A |
| 393 | methyl {6-[(2-{[(3-methylphenyl)amino]carbonyl}phenyl)carbonyl]-1H-benzimidazol-2-yl}carbamate |  | A |
| 394 | methyl {6-[(2-{[(3-bromophenyl)amino]carbonyl}phenyl)carbonyl]-1H-benzimidazol-2-yl}carbamate | A | A |
| 395 | methyl {6-[(2-{[(3-chlorophenyl)amino]carbonyl}phenyl)carbonyl]-1H-benzimidazol-2-yl}carbamate | A | A |
| 396 | methyl {6-[(2-{[(3-fluorophenyl)amino]carbonyl}phenyl)carbonyl]-1H-benzimidazol-2-yl}carbamate |  | A |
| 397 | methyl (6-{[2-({[3-(methyloxy)phenyl]amino}carbonyl)phenyl]carbonyl}-1H-benzimidazol-2-yl)carbamate | A | A |
| 398 | methyl (6-{[2-({[3-(trifluoromethyl)phenyl]amino}carbonyl)phenyl]carbonyl}-1H-benzimidazol-2-yl)carbamate | A | A |
| 399 | methyl {6-[(2-{[(3-ethylphenyl)amino]carbonyl}phenyl)carbonyl]-1H-benzimidazol-2-yl}carbamate |  | A |
| 400 | methyl {6-[(2-{[(3-ethynylphenyl)amino]carbonyl}phenyl)carbonyl]-1H-benzimidazol-2-yl}carbamate |  | A |
| 401 | methyl {6-[(2-{[(3-chloro-4-fluorophenyl)amino]carbonyl}phenyl)carbonyl]-1H-benzimidazol-2-yl}carbamate | A | A |
| 402 | methyl {6-[(2-{[(5-chloro-2-fluorophenyl)amino]carbonyl}phenyl)carbonyl]-1H-benzimidazol-2-yl}carbamate | A | A |
| 403 | methyl {6-[(2-{[(3-iodophenyl)amino]carbonyl}phenyl)carbonyl]-1H-benzimidazol-2-yl}carbamate |  | A |

TABLE 1-continued

| Entry | Name | cRaf-1 | bRaf |
|---|---|---|---|
| 404 | methyl (6-{[2-({[3-(1-methylethyl)phenyl]amino}carbonyl)phenyl]carbonyl}-1H-benzimidazol-2-yl)carbamate | | A |
| 405 | methyl {6-[(2-{[(3-thienylmethyl)amino]carbonyl}phenyl)carbonyl]-1H-benzimidazol-2-yl}carbamate | | A |
| 406 | methyl {6-[(2-{[(3-bromo-4-fluorophenyl)amino]carbonyl}phenyl)carbonyl]-1H-benzimidazol-2-yl}carbamate | A | A |
| 407 | methyl {6-[(2-{[(3-chloro-2-fluorophenyl)amino]carbonyl}phenyl)carbonyl]-1H-benzimidazol-2-yl}carbamate | A | A |
| 408 | methyl {6-[(2-{[(4-fluoro-3-methylphenyl)amino]carbonyl}phenyl)carbonyl]-1H-benzimidazol-2-yl}carbamate | A | A |
| 409 | methyl {6-[(2-{[(5-bromo-2-fluorophenyl)amino]carbonyl}phenyl)carbonyl]-1H-benzimidazol-2-yl}carbamate | | A |
| 410 | methyl {6-[(2-{[(5-bromo-2,4-difluorophenyl)amino]carbonyl}phenyl)carbonyl]-1H-benzimidazol-2-yl}carbamate | A | A |
| 411 | methyl {6-[(2-{[(5-chloro-2,4-difluorophenyl)amino]carbonyl}phenyl)carbonyl]-1H-benzimidazol-2-yl}carbamate | A | A |
| 412 | methyl {6-[(2-{[(3-bromo-2-fluorophenyl)amino]carbonyl}phenyl)carbonyl]-1H-benzimidazol-2-yl}carbamate | | A |
| 413 | methyl {6-[(2-{[(3-ethenylphenyl)amino]carbonyl}phenyl)carbonyl]-1H-benzimidazol-2-yl}carbamate | A | A |
| 414 | methyl {6-[(2-{[(3-ethynyl-2-fluorophenyl)amino]carbonyl}phenyl)carbonyl]-1H-benzimidazol-2-yl}carbamate | A | A |
| 415 | methyl {6-[(2-{[(5-chloro-2-methylphenyl)amino]carbonyl}phenyl)carbonyl]-1H-benzimidazol-2-yl}carbamate | | A |
| 416 | methyl {6-[(2-{[(5-bromo-2-methylphenyl)amino]carbonyl}phenyl)carbonyl]-1H-benzimidazol-2-yl}carbamate | | A |
| 417 | methyl {6-[(2-{[(2-fluoro-3-iodophenyl)amino]carbonyl}phenyl)carbonyl]-1H-benzimidazol-2-yl}carbamate | | A |
| 418 | methyl {6-[(2-{[(3-ethenyl-2-fluorophenyl)amino]carbonyl}phenyl)carbonyl]-1H-benzimidazol-2-yl}carbamate | A | A |
| 419 | methyl {6-[(2-{[(2-fluoro-5-methylphenyl)amino]carbonyl}phenyl)carbonyl]-1H-benzimidazol-2-yl}carbamate | A | A |

As discussed above, the names of the compounds are generated using the nomenclature engine published by ACD/Labs of Toronto Canada. In order to further describe the compounds of the present invention, a representative number of compounds set forth in Table 1 are provided below in Table 2, wherein the structure of the compound is provided as well as the name generated by the nomenclature engine. These examples are provided to further clarify the compounds of the present invention.

TABLE 2

| Name | Structure |
|---|---|
| 6-(2-butyl-1-hydroxy-3-oxo-2,3-dihydro-1H-isoindol-1-yl)-2H-1,4-benzoxazin-3(4H)-one | 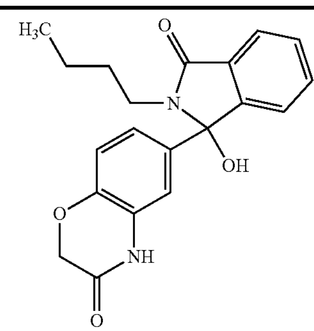 |

TABLE 2-continued

| Name | Structure |
| --- | --- |
| methyl {6-[1-hydroxy-3-oxo-2-(phenylmethyl)-2,3-dihydro-1H-isoindol-1-yl]-1-methyl-1H-benzimidazol-2-yl}carbamate | 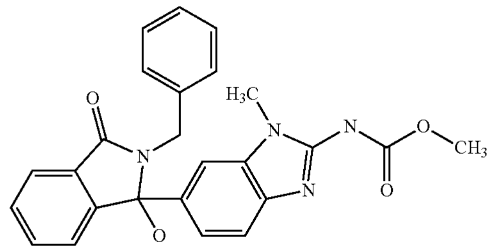 [SMILES: COC(=O)Nc1nc2ccc(C3(O)c4ccccc4C(=O)N3Cc3ccccc3)cc2n1C] |
| 1-methylethyl {5-[1-hydroxy-3-oxo-2-(phenylmethyl)-2,3-dihydro-1H-isoindol-1-yl]-1H-benzimidazol-2-yl}carbamate | 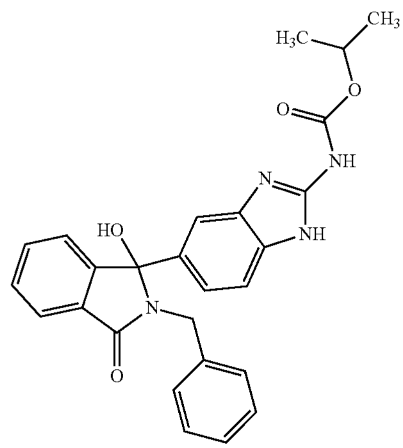 [SMILES: CC(C)OC(=O)Nc1nc2cc(C3(O)c4ccccc4C(=O)N3Cc3ccccc3)ccc2[nH]1] |
| methyl {5-[1-hydroxy-2-(3-methylphenyl)-3-oxo-2,3-dihydro-1H-isoindol-1-yl]-1H-benzimidazol-2-yl}carbamate | 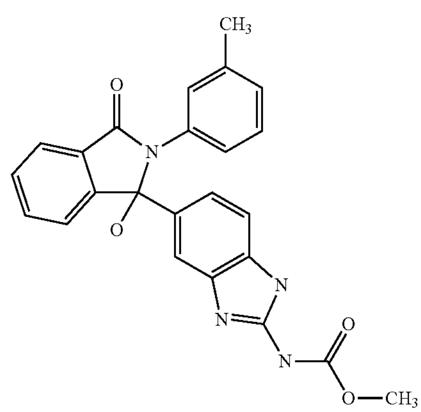 [SMILES: COC(=O)Nc1nc2cc(C3(O)c4ccccc4C(=O)N3c3cccc(C)c3)ccc2[nH]1] |
| methyl {5-[1-hydroxy-3-oxo-2-(tetrahydrofuran-2-ylmethyl)-2,3-dihydro-1H-isoindol-1-yl]-1H-benzimidazol-2-yl}carbamate | 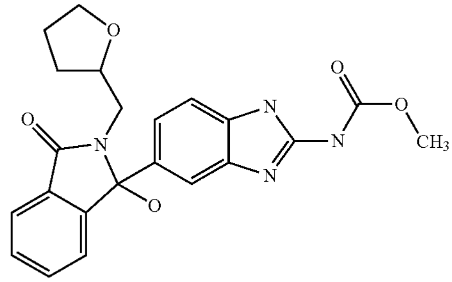 [SMILES: COC(=O)Nc1nc2cc(C3(O)c4ccccc4C(=O)N3CC3CCCO3)ccc2[nH]1] |

TABLE 2-continued

| Name | Structure |
|---|---|
| methyl (5-{1-hydroxy-3-oxo-2-[3-(phenylamino)phenyl]-2,3-dihydro-1H-isoindol-1-yl}-1H-benzimidazol-2-yl)carbamate | 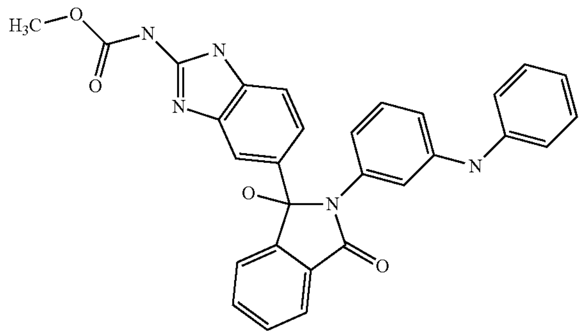 [SMILES: COC(=O)Nc1nc2cc(C3(O)c4ccccc4C(=O)N3c3cccc(Nc4ccccc4)c3)ccc2[nH]1] |
| methyl {5-[2-(5-bromo-2,4-difluorophenyl)-1-hydroxy-3-oxo-2,3-dihydro-1H-isoindol-1-yl]-1H-benzimidazol-2-yl}carbamate | 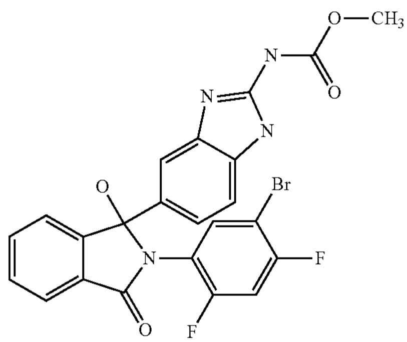 [SMILES: COC(=O)Nc1nc2cc(C3(O)c4ccccc4C(=O)N3c3cc(Br)c(F)cc3F)ccc2[nH]1] |
| methyl {5-[2-(5-chloro-2,4-difluorophenyl)-1-hydroxy-3-oxo-2,3-dihydro-1H-isoindol-1-yl]-1H-benzimidazol-2-yl}carbamate | 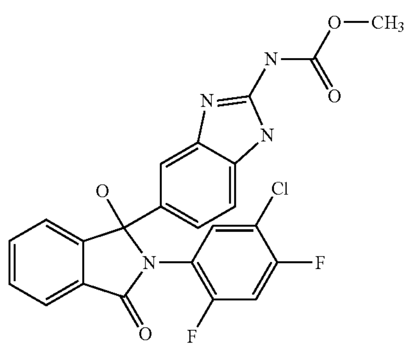 [SMILES: COC(=O)Nc1nc2cc(C3(O)c4ccccc4C(=O)N3c3cc(Cl)c(F)cc3F)ccc2[nH]1] |
| methyl {5-[2-(3,5-dichloro-4-fluorophenyl)-1-hydroxy-3-oxo-2,3-dihydro-1H-isoindol-1-yl]-1H-benzimidazol-2-yl}carbamate | 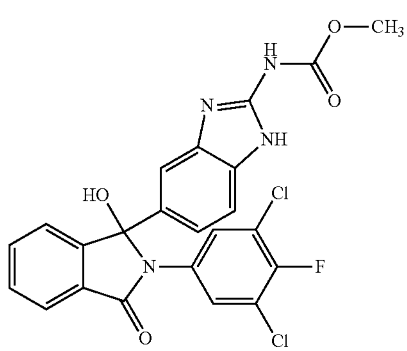 [SMILES: COC(=O)Nc1nc2cc(C3(O)c4ccccc4C(=O)N3c3cc(Cl)c(F)c(Cl)c3)ccc2[nH]1] |

TABLE 2-continued

| Name | Structure |
|---|---|
| 2,2-dimethyl-3-(methyloxy)propyl {5-[1-hydroxy-3-oxo-2-(phenylmethyl)-2,3-dihydro-1H-isoindol-1-yl]-1H-benzimidazol-2-yl}carbamate | 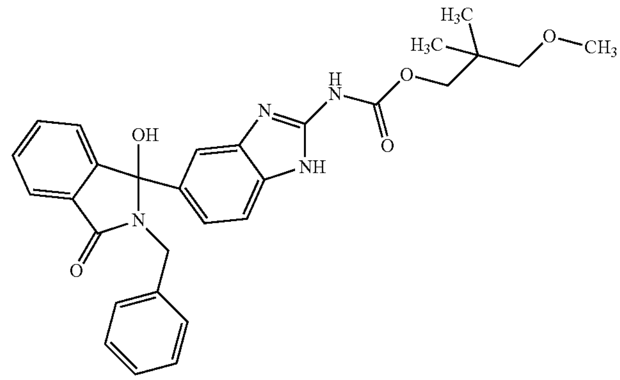 [SMILES: COCC(C)(C)COC(=O)Nc1nc2cc(C3(O)c4ccccc4C(=O)N3Cc3ccccc3)ccc2[nH]1] |
| 3-hydroxy-2,2-dimethylpropyl {5-[1-hydroxy-3-oxo-2-(phenylmethyl)-2,3-dihydro-1H-isoindol-1-yl]-1H-benzimidazol-2-yl}carbamate | 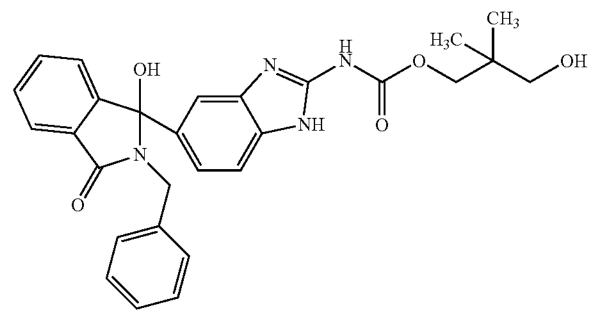 [SMILES: CC(C)(CO)COC(=O)Nc1nc2cc(C3(O)c4ccccc4C(=O)N3Cc3ccccc3)ccc2[nH]1] |
| methyl (5-{2-[1-(5-bromo-2-thienyl)ethyl]-1-hydroxy-3-oxo-2,3-dihydro-1H-isoindol-1-yl}-1H-benzimidazol-2-yl)carbamate | 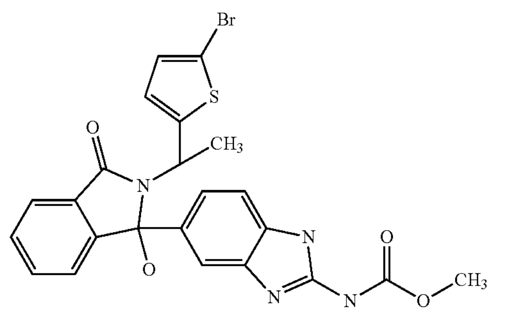 [SMILES: COC(=O)Nc1nc2cc(C3(O)c4ccccc4C(=O)N3C(C)c3ccc(Br)s3)ccc2[nH]1] |
| 3-(4-methylpiperazin-1-yl)propyl {6-[2-(4-fluorophenyl)-1-hydroxy-3-oxo-2,3-dihydro-1H-isoindol-1-yl]-1H-benzimidazol-2-yl}carbamate | 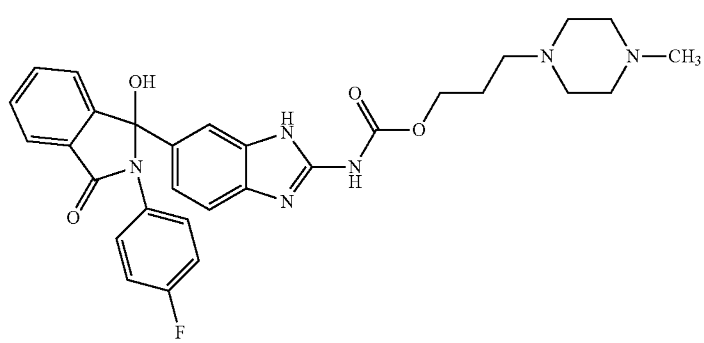 [SMILES: CN1CCN(CCCOC(=O)Nc2nc3ccc(C4(O)c5ccccc5C(=O)N4c4ccc(F)cc4)cc3[nH]2)CC1] |
| methyl {5-[2-(3-ethynyl-2-fluorophenyl)-1-hydroxy-3-oxo-2,3-dihydro-1H-isoindol-1-yl]-1H-benzimidazol-2-yl}carbamate | 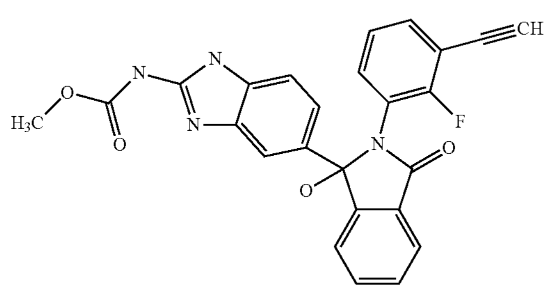 [SMILES: C#Cc1cccc(N2C(=O)c3ccccc3C2(O)c2ccc3[nH]c(NC(=O)OC)nc3c2)c1F] |

TABLE 2-continued

| Name | Structure |
|---|---|
| methyl {5-[2-(3-chloro-2-methylphenyl)-1-hydroxy-3-oxo-2,3-dihydro-1H-isoindol-1-yl]-1H-benzimidazol-2-yl}carbamate | 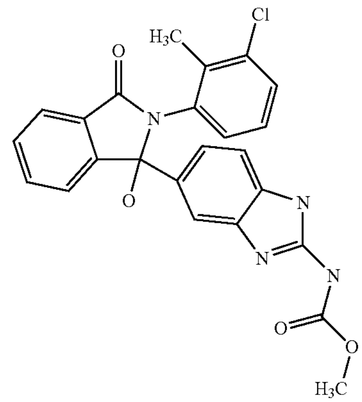 [SMILES: COC(=O)Nc1nc2cc(C3(O)c4ccccc4C(=O)N3c3cccc(Cl)c3C)ccc2[nH]1] |
| methyl {5-[2-(5-chloro-2-methylphenyl)-1-hydroxy-3-oxo-2,3-dihydro-1H-isoindol-1-yl]-1H-benzimidazol-2-yl}carbamate | 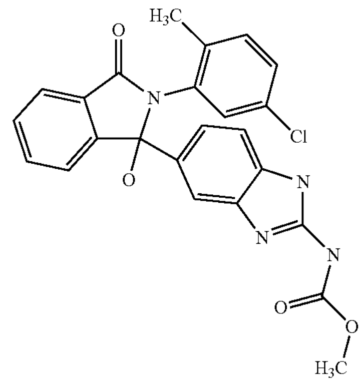 [SMILES: COC(=O)Nc1nc2cc(C3(O)c4ccccc4C(=O)N3c3cc(Cl)ccc3C)ccc2[nH]1] |
| N-{6-[1-hydroxy-3-oxo-2-(phenylmethyl)-2,3-dihydro-1H-isoindol-1-yl]-1H-benzimidazol-2-yl}-2,2-dimethyl-3-piperidin-1-ylpropanamide | 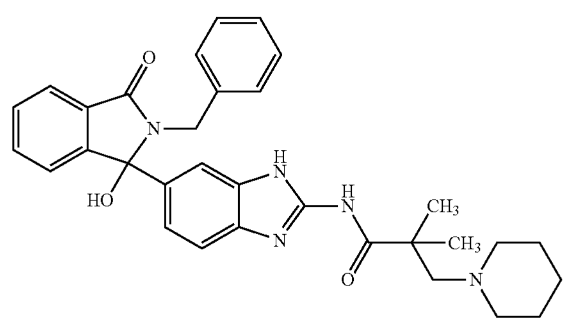 [SMILES: CC(C)(CN1CCCCC1)C(=O)Nc1nc2ccc(C3(O)c4ccccc4C(=O)N3Cc3ccccc3)cc2[nH]1] |
| 3-hydroxy-2-[3-(methyloxy)phenyl]-3-[2-(pyrazin-2-ylamino)-1H-benzimidazol-5-yl]-2,3-dihydro-1H-isoindol-1-one | 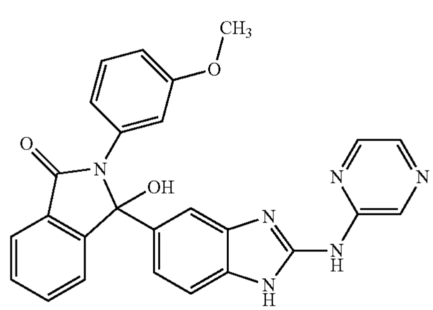 [SMILES: COc1cccc(N2C(=O)c3ccccc3C2(O)c2ccc3[nH]c(Nc4cnccn4)nc3c2)c1] |

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A method of inhibiting activity of Raf kinase for the treatment of solid tumors, the method comprising administering to a mammalian patient in need of the treatment a therapeutically effective amount of a compound according to Formula IX,

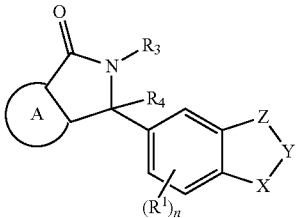

IX or a pharmaceutically acceptable salt thereof, wherein
A is ortho-phenylene;
n is zero to three;
each $R^1$ is independently selected from —H, halogen, —CN, —NO$_2$, —OR$^3$, —N(R$^3$)R$^3$, —S(O)$_{0-2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —C(O)R$^3$, —OC(O)R$^3$, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;
Z and X are each independently selected from —C(R$^2$)═, —N═, —N(R$^2$)—, —S(O)$_{0-2}$—, and —O—;
Y is selected from —C(R$^2$)(R$^2$)—, —C(═O)—, —C(R$^2$)═ and —N═, but Y is not —N═ when both Z and X are —N═;
each $R^2$ is independently selected from R$^3$, —C(O)N(R$^3$)R$^3$, —N(R$^3$)CO$_2$R$^3$, —N(R$^3$)C(O)N(R$^3$)R$^3$, and —N(R$^3$)C(O)R$^3$;
each $R^3$ is independently selected from —H, optionally substituted C$_{1-6}$alkyl, optionally substituted aryl, optionally substituted aryl C$_{1-3}$alkyl, optionally substituted heterocyclyl, and optionally substituted heterocyclyl C$_{1-3}$alkyl;
optionally two of $R^3$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P;
$R^4$ is selected from —H, —OH, optionally substituted C$_{1-6}$alkyl and optionally substituted C$_{1-6}$alkoxy; and
wherein each optionally substituted alkyl, aryl, and heterocyclyl group can independently be substituted with one to three groups selected from C$_{1-6}$alkyl, aryl, arylC$_{1-6}$alkyl, heterocyclylC$_{1-6}$alkyl, heterocyclyl, alkoxy, amino, amidino, aryloxy, arylalkyloxy, carboxy, acyloxy, carboxyalkyl, carboxamido, benzyloxycarbonylamino, cyano, acyl, halogen, hydroxy, nitro, alkylsulfanyl, alkylsulfinyl, alkylsulfonyl, thiol, oxo, carbamyl, acylamino, hydrazino, hydroxylamino, and sulfonamido.

2. A method of treating rheumatoid arthritis, atherosclerosis, myocardioinfarction, ischemia, stroke, restenosis, or diabetic retinopathy associated with activity of a Raf kinase in a mammalian patient, the method comprising administering to the mammalian patient in need of the treatment a therapeutically effective amount of a compound according to Formula IX,

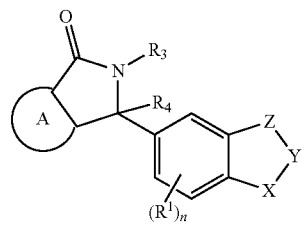

IX or a pharmaceutically acceptable salt thereof, wherein
A is ortho-phenylene;
n is zero to three;
each $R^1$ is independently selected from —H, halogen, —CN, —NO$_2$, —OR$^3$, —N(R$^3$)R$^3$, —S(O)$_{0-2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —C(O)R$^3$, —OC(O)R$^3$, optionally substituted C$_{1-6}$alkyl, optionally substituted aryl, optionally substituted aryl C$_{1-6}$alkyl, optionally substituted heterocyclyl, and optionally substituted heterocyclyl C$_{1-6}$alkyl;
Z and X are each independently selected from —C(R$^2$)═, —N═, —N(R$^2$)—, —S(O)$_{0-2}$—, and —O—;
Y is selected from —C(R$^2$)(R$^2$)—, —C(═O)—, —C(R$^2$)═ and —N═, but Y is not —N═ when both Z and X are —N═;
each $R^2$ is independently selected from R$^3$, —C(O)N(R$^3$)R$^3$, —N(R$^3$)CO$_2$R$^3$, —N(R$^3$)C(O)N(R$^3$)R$^3$, and —N(R$^3$)C(O)R$^3$;
each $R^3$ is independently selected from —H, optionally substituted C$_{1-6}$alkyl, optionally substituted aryl, optionally substituted aryl C$_{1-3}$alkyl, optionally substituted heterocyclyl, and optionally substituted heterocyclyl C$_{1-3}$alkyl;
optionally two of $R^3$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P;
$R^4$ is selected from —H, —OH, optionally substituted C$_{1-6}$ alkyl and optionally substituted C$_{1-6}$alkoxy; and
wherein each optionally substituted alkyl, aryl, and heterocyclyl group can independently be substituted with one to three groups selected from C$_{1-6}$alkyl, aryl, arylC$_{1-6}$alkyl, heterocyclylC$_{1-6}$alkyl, heterocyclyl, alkoxy, amino, amidino, aryloxy, arylalkyloxy, carboxy, acyloxy, carboxyalkyl, carboxamido, benzyloxycarbonylamino, cyano, acyl, halogen, hydroxy, nitro, alkylsulfanyl, alkylsulfinyl, alkylsulfonyl, thiol, oxo, carbamyl, acylamino, hydrazino, hydroxylamino, and sulfonamido.

3. The method according to claim 1, wherein the compound is selected from
6-(2-butyl-1-hydroxy-3-oxo-2,3-dihydro-1H-isoindol-1-yl)-2H-1,4-benzoxazin-3(4H)-one
6-(1-hydroxy-3-oxo-2-phenyl-2,3-dihydro-1H-isoindol-1-yl)-2H-1,4-benzoxazin-3(4H)-one
6-{2-[(3-bromophenyl)methyl]-1-hydroxy-3-oxo-2,3-dihydro-1H-isoindol-1-yl}-2H-1,4-benzoxazin-3(4H)-one
methyl{5-[1-hydroxy-3-oxo-2-(phenylmethyl)-2,3-dihydro-1H-isoindol-1-yl]-1H-benzimidazol-2-yl}carbamate 6-[2-(3-chlorophenyl)-1-hydroxy-3-oxo-2,3-dihydro-1H-isoindol-1-yl]-2H-1,4-benzoxazin-3(4H)-one
3-(2-{[3,5-bis(methyloxy)phenyl]amino}-1H-benzimidazol-5-yl)-3-hydroxy-2-phenyl-2,3-dihydro-1H-isoindol-1-one
5-[1-hydroxy-3-oxo-2-(phenylmethyl)-2,3-dihydro-1H-isoindol-1-yl]-N-methyl-1H-benzimidazole-2-carboxamide
7-[1-hydroxy-3-oxo-2-(phenylmethyl)-2,3-dihydro-1H-isoindol-1-yl]-3,4-dihydroquinoxalin-2(1H)-one
6-{2-[(3-chlorophenyl)methyl]-1-hydroxy-3-oxo-2,3-dihydro-1H-isoindol-1-yl}-2H-1,4-benzoxazin-3(4H)-one
6-{2-[(2-chlorophenyl)methyl]-1-hydroxy-3-oxo-2,3-dihydro-1H-isoindol-1-yl}-2H-1,4-benzoxazin-3(4H)-one
6-{2-[(3-fluorophenyl)methyl]-1-hydroxy-3-oxo-2,3-dihydro-1H-isoindol-1-yl}-2H-1,4-benzoxazin-3(4H)-one
6-{2-[(2-fluorophenyl)methyl]-1-hydroxy-3-oxo-2,3-dihydro-1H-isoindol-1-yl}-2H-1,4-benzoxazin-3(4H)-one
6-[2-(3-fluorophenyl)-1-hydroxy-3-oxo-2,3-dihydro-1H-isoindol-1-yl]-2H-1,4-benzoxazin-3(4H)-one
6-[1-hydroxy-2-(3-iodophenyl)-3-oxo-2,3-dihydro-1H-isoindol-1-yl]-2H-1,4-benzoxazin-3(4H)-one
6-[2-(3-bromophenyl)-1-hydroxy-3-oxo-2,3-dihydro-1H-isoindol-1-yl]-2H-1,4-benzoxazin-3(4H)-one
6-[1-hydroxy-2-(3-nitrophenyl)-3-oxo-2,3-dihydro-1H-isoindol-1-yl]-2H-1,4-benzoxazin-3(4H)-one
6-{1-hydroxy-2-[3-(methyloxy)phenyl]-3-oxo-2,3-dihydro-1H-isoindol-1-yl}-2H-1,4-benzoxazin-3(4H)-one
6-[1-hydroxy-2-(3-methylphenyl)-3-oxo-2,3-dihydro-1H-isoindol-1-yl]-2H-1,4-benzoxazin-3(4H)-one
methyl[6-(1-hydroxy-3-oxo-2-phenyl-2,3-dihydro-1H-isoindol-1-yl)-1H-benzimidazol-2-yl]carbamate
6-[2-(2-aminophenyl)-1-hydroxy-3-oxo-2,3-dihydro-1H-isoindol-1-yl]-2H-1,4-benzoxazin-3(4H)-one
6-{[2-(3-phenyl-1,2,4-oxadiazol-5-yl)phenyl]carbonyl}-2H-1,4-benzoxazin-3(4H)-one
6-{[2-(1H-benzimidazol-2-yl)phenyl]carbonyl}-2H-1,4-benzoxazin-3(4H)-one
6-(1-hydroxy-3-oxo-2-{[2-(trifluoromethyl)phenyl]methyl}-2,3-dihydro-1H-isoindol-1-yl)-2H-1,4-benzoxazin-3(4H)-one
6-{2-[(5-bromo-2-fluorophenyl)methyl]-1-hydroxy-3-oxo-2,3-dihydro-1H-isoindol-1-yl}-2H-1,4-benzoxazin-3(4H)-one
6-{1-hydroxy-2-[(3-nitrophenyl)methyl]-3-oxo-2,3-dihydro-1H-isoindol-1-yl}-2H-1,4-benzoxazin-3(4H)-one
6-{1-hydroxy-2-[(3-iodophenyl)methyl]-3-oxo-2,3-dihydro-1H-isoindol-1-yl}-2H-1,4-benzoxazin-3(4H)-one
6-[2-(3,4-difluorophenyl)-1-hydroxy-3-oxo-2,3-dihydro-1H-isoindol-1-yl]-2H-1,4-benzoxazin-3(4H)-one
6-{1-hydroxy-2-[3-(1-methylethyl)phenyl]-3-oxo-2,3-dihydro-1H-isoindol-1-yl}-2H-1,4-benzoxazin-3(4H)-one
6-{1-hydroxy-3-oxo-2-[3-(trifluoromethyl)phenyl]-2,3-dihydro-1H-isoindol-1-yl}-2H-1,4-benzoxazin-3(4H)-one
3-[1-hydroxy-3-oxo-1-(3-oxo-3,4-dihydro-2H-1,4-benzoxazin-6-yl)-1,3-dihydro-2H-isoindol-2-yl]benzenesulfonamide
6-{2-[5-chloro-2-(methyloxy)phenyl]-1-hydroxy-3-oxo-2,3-dihydro-1H-isoindol-1-yl}-2H-1,4-benzoxazin-3(4H)-one
6-[2-(3-fluoro-5-iodophenyl)-1-hydroxy-3-oxo-2,3-dihydro-1H-isoindol-1-yl]-2H-1,4-benzoxazin-3(4H)-one
6-[2-(3-aminophenyl)-1-hydroxy-3-oxo-2,3-dihydro-1H-isoindol-1-yl]-2H-1,4-benzoxazin-3(4H)-one
6-[2-(3,5-difluorophenyl)-1-hydroxy-3-oxo-2,3-dihydro-1H-isoindol-1-yl]-2H-1,4-benzoxazin-3(4H)-one
3-[1-hydroxy-3-oxo-1-(3-oxo-3,4-dihydro-2H-1,4-benzoxazin-6-yl)-1,3-dihydro-2H-isoindol-2-yl]benzonitrile
6-[2-(2-chlorophenyl)-1-hydroxy-3-oxo-2,3-dihydro-1H-isoindol-1-yl]-2H-1,4-benzoxazin-3(4H)-one
6-[2-(3-amino-5-chlorophenyl)-1-hydroxy-3-oxo-2,3-dihydro-1H-isoindol-1-yl]-2H-1,4-benzoxazin-3(4H)-one
6-[2(5-chloro-2-methylphenyl)-1-hydroxy-3-oxo-2,3-dihydro-1H-isoindol-1-yl]-2H-1,4-benzoxazin-3(4H)-one
6-[2-(3-chloro-2-methylphenyl)-1-hydroxy-3-oxo-2,3-dihydro-1H-isoindol-1yl]-2H-1,4-benzoxazin-3(4H)-one
6-[2-(3-ethylphenyl)-1-hydroxy-3-oxo-2,3-dihydro-1H-isoindol-1-yl]-2H-1,4-benzoxazin-3(4H)-one
6-[2-(3-ethynylphenyl)-1-hydroxy-3-oxo-2,3-dihydro-1H-isoindol-1-yl]-2H-1,4-benzoxazin-3(4H)-one
6-[1-hydroxy-2-(3-hydroxyphenyl)-3-oxo-2,3-dihydro-1H-isoindol-1-yl]-2H-1,4-benzoxazin-3(4H)-one
6-{1-hydroxy-3-oxo-2-[3-(phenyloxy)phenyl]-2,3-dihydro-1H-isoindol-1-yl}-2H-1,4-benzoxazin-3(4H)-one
3-[1-hydroxy-3-oxo-1-(3-oxo-3,4-dihydro-2H-1,4-benzoxazin-6-yl)-1,3-dihydro-2H-isoindol-2-yl]benzamide
6-{1-hydroxy-2-[3-(hydroxymethyl)phenyl]-3-oxo-2,3-dihydro-1H-isoindol-1-yl}-2H-1,4-benzoxazin-3(4H)-one
6-[2-(2-fluorophenyl)-1-hydroxy-3-oxo-2,3-dihydro-1H-isoindol-1-yl]-2H-1,4-benzoxazin-3(4H)-one
3-hydroxy-3-[2-(methylamino)-1H-benzimidazol-5-yl]-2-(phenylmethyl)-2,3-dihydro-1H-isoindol-1-one
6-(2-{3-[(dimethylamino)methyl]phenyl}-1-hydroxy-3-oxo-2,3-dihydro-1H-isoindol-1-yl)-2H-1,4-benzoxazin-3(4H)-one
6-[2-(3,5-dichlorophenyl)-1-hydroxy-3-oxo-2,3-dihydro-1H-isoindol-1-yl]-2H-1,4-benzoxazin-3(4H)-one
6-[1-hydroxy-2-(2-methylphenyl)-3-oxo-2,3-dihydro-1H-isoindol-1-yl]-2H-1,4-benzoxazin-3(4H)-one
N-methyl-2-[(3-oxo-3,4-dihydro-2H-1,4-benzoxazin-6-yl)carbonyl]-N-phenylbenzamide
methyl{5-[1-(ethyloxy)-3-oxo-2-(phenylmethyl)-2,3-dihydro-1H-isoindol-1-yl]-1H-benzimidazol-2-yl}carbamate
Phenylmethyl2-[(2-{[(methyloxy)carbonyl]amino}-1H-benzimidazol-5-yl)carbonyl]enzoate
3-hydroxy-3-(1H-indazol-5-yl)-2-(phenylmethyl)-2,3-dihydro-1H-isoindol-1-one
ethyl{5-[1-hydroxy-3-oxo-2-(phenylmethyl)-2,3-dihydro-1H-isoindol-1-yl]-1H-benzimidazol-2-yl}carbamate
2-methylpropyl{5-[1-hydroxy-3-oxo-2-(phenylmethyl)-2,3-dihydro-1H-isoindol-1-yl]-1H-benzimidazol-2-yl}carbamate
methyl{5-[1-hydroxy-3-oxo-2-(2-thienylmethyl)-2,3-dihydro-1H-isoindol-1-yl]-1H-benzimidazol-2-yl}carbamate
3-(2-amino-1H-benzimidazol-5-yl)-3-hydroxy-2-(phenylmethyl)-2,3-dihydro-1H-isoindol-1-one
3-(methyloxy)butyl{5-[1-hydroxy-3-oxo-2-(phenylmethyl)-2,3-dihydro-1H-isoindol-1-yl]-1H-benzimidazol-2-yl}carbamate methyl(5-{1-hydroxy-3-oxo-2-[(1R)-1-phenylethyl]-2,3-dihydro-1H-isoindol-1-yl}-1H-benzimidazol-2-yl)carbamate methyl(5-{1-hydroxy-3-oxo-2-[(1S)-1-phenylethyl]-2,3-dihydro-1H-isoindol-1-yl}-1H-benzimidazol-2-yl)carbamate 2-(methyloxy)ethyl{5-[1-hydroxy-3-oxo-2-(phenylmethyl)-2,3-dihydro-1H-isoindol-1-yl]-1H-benzimidazol-2-yl}carbamate prop-2-yn-1-yl{5-[1-hydroxy-3-oxo-2-(phenylmethyl)-2,3-dihydro-1H-isoindol-1-yl]-1H-benzimidazol-2-yl}carbamate but-2-yn-1-yl{5-[1-hydroxy-3-oxo-2-(phenylmethyl)-2,3-dihydro-1H-isoindol-1-yl]-1H-benzimidazol-2-yl}carbamate 1-methylethyl{5-[1-hydroxy-3-oxo-2-(phenylmethyl)-2,3-dihydro-1H-isoindol-1-yl]-1H-benzimidazol-2-yl}carbamate methyl{5-[2-(2,3-dihydro-1H-inden-2-yl)-1-hydroxy-3-oxo-2,3-dihydro-1H-isoindol-1-yl]-1H-benzimidazol-2-yl}carbamate methyl{5-[1-hydroxy-3-oxo-2-(pyridin-4-ylmethyl)-2,3-dihydro-1H-isoindol-1-yl]-1H-benzimidazol-2-yl}carbamate methyl{5-[1-hydroxy-3-oxo-2-(pyridin-3-ylmethyl)-2,3-dihydro-1H-isoindol-1-yl]-1H-benzimidazol-2-yl}carbamate methyl(6-{2-[(3-fluorophenyl)methyl]-1-hydroxy-3-oxo-2,3-dihydro-1H-isoindol-1-yl}-1H-benzimidazol-2-yl)carbamate methyl{5-[1-hydroxy-2-(3-methylphenyl)-3-oxo-2,3-dihydro-1H-isoindol-1-yl]-1H-benzimidazol-2-yl}carbamate methyl[5-(1-hydroxy-2-{[2-(methyloxy)phenyl]methyl}-3-oxo-2,3-dihydro-1H-isoindol-1-yl)-1H-benzimidazol-2-yl]carbamate methyl[5-(1-hydroxy-2-{[3-(methyloxy)phenyl]methyl}-3-oxo-2,3-dihydro-1H-isoindol-1-yl)-1H-benzimidazol-2-yl]carbamate methyl(6-{2-[(4-fluorophenyl)methyl]-1-hydroxy-3-oxo-2,3-dihydro-1H-isoindol-1-yl}-1H-benzimidazol-2-yl)carbamate methyl(6-{2-[(3-bromophenyl)methyl]-1-hydroxy-3-oxo-2,3-dihydro-1H-isoindol-1-yl}-1H-benzimidazol-2-yl)carbamate methyl(5-{1-hydroxy-2-[(3-iodophenyl)methyl]-3-oxo-2,3-dihydro-1H-isoindol-1-yl}-1H-benzimidazol-2-yl)carbamate methyl(5-{2-[(3-chlorophenyl)methyl]-1-hydroxy-3-oxo-2,3-dihydro-1H-isoindol-1-yl}-1H-benzimidazol-2-yl)carbamate methyl(5-{2-[(2-fluorophenyl)methyl]-1-hydroxy-3-oxo-2,3-dihydro-1H-isoindol-1-yl}-1H-benzimidazol-2-yl)carbamate methyl{5-[1-hydroxy-3-oxo-2-(pyridin-2-ylmethyl)-2,3-dihydro-1H-isoindol-1-yl]-1H-benzimidazol-2-yl}carbamate phenylmethyl{5-[1-hydroxy-3-oxo-2-(phenylmethyl)-2,3-dihydro-1H-isoindol-1-yl]-1H-benzimidazol-2-yl}carbamate 2-fluoroethyl{5-[1-hydroxy-3-oxo-2-(phenylmethyl)-2,3-dihydro-1H-isoindol-1-yl]-1H-benzimidazol-2-yl}carbamate propyl{5-[1-hydroxy-3-oxo-2-(phenylmethyl)-2,3-dihydro-1H-isoindol-1-yl]-1H-benzimidazol-2-yl}carbamate methyl(5-{1-hydroxy-2-[4-(methyloxy)phenyl]-3-oxo-2,3-dihydro-1H-isoindol-1-yl}-1H-benzimidazol-2-yl)carbamate methyl(5-{2-[(2-chlorophenyl)methyl]-1-hydroxy-3-oxo-2,3-dihydro-1H-isoindol-1-yl}-1H-benzimidazol-2-yl)carbamate methyl(5-{2-[(2-bromophenyl)methyl]-1-hydroxy-3-oxo-2,3-dihydro-1H-isoindol-1-yl}-1H-benzimidazol-2-yl)carbamate methyl(5-{1-hydroxy-2-[(3-methylphenyl)methyl]-3-oxo-2,3-dihydro-1H-isoindol-1-yl}-1H-benzimidazol-2-yl)carbamate methyl(5-{1-hydroxy-2-[(4-methylphenyl)methyl]-3-oxo-2,3-dihydro-1H-isoindol-1-yl}-1H-benzimidazol-2-yl)carbamate methyl(5-{1-hydroxy-2-[(2-methylphenyl)methyl]-3-oxo-2,3-dihydro-1H-isoindol-1-yl}-1H-benzimidazol-2-yl)carbamate methyl{5-[2-(3-bromophenyl)-1-hydroxy-3-oxo-2,3-dihydro-1H-isoindol-1-yl]-1H-benzimidazol-2-yl}carbamate methyl{5-[2-(3-chlorophenyl)-1-hydroxy-3-oxo-2,3-dihydro-1H-isoindol-1-yl]-1H-benzimidazol-2-yl}carbamate methyl{5-[2-(3-fluorophenyl)-1-hydroxy-3-oxo-2,3-dihydro-1H-isoindol-1-yl]-1H-benzimidazol-2-yl}carbamate methyl(5-{1-hydroxy-2-[3-(methyloxy)phenyl]-3-oxo-2,3-dihydro-1H-isoindol-1-yl}-1H-benzimidazol-2-yl)carbamate methyl{5-[2-(4-bromophenyl)-1-hydroxy-3-oxo-2,3-dihydro-1H-isoindol-1-yl]-1H-benzimidazol-2-yl}carbamate methyl{5-[2-(4-chlorophenyl)-1-hydroxy-3-oxo-2,3-dihydro-1H-isoindol-1-yl]-1H-benzimidazol-2-yl}carbamate methyl{5-[2-(4-fluorophenyl)-1-hydroxy-3-oxo-2,3-dihydro-1H-isoindol-1-yl]-1H-benzimidazol-2-yl}carbamate methyl{5-[2-(3,5-dimethylphenyl)-1-hydroxy-3-oxo-2,3-dihydro-1H-isoindol-1-yl]-1H-benzimidazol-2-yl}carbamate methyl{5-[2-(2-fluorophenyl)-1-hydroxy-3-oxo-2,3-dihydro-1H-isoindol-1-yl]-1H-benzimidazol-2-yl}carbamate methyl{5-[2-(2-chlorophenyl)-1-hydroxy-3-oxo-2,3-dihydro-1H-isoindol-1-yl]-1H-benzimidazol-2-yl}carbamate methyl{5-[1-hydroxy-2-(2-methylphenyl)-3-oxo-2,3-dihydro-1H-isoindol-1-yl]-1H-benzimidazol-2-yl}carbamate methyl(5-{1-hydroxy-2-[2-(methyloxy)phenyl]-3-oxo-2,3-dihydro-1H-isoindol-1-yl}-1H-benzimidazol-2-yl)carbamate methyl{5-[1-hydroxy-2-(4-methylphenyl)-3-oxo-2,3-dihydro-1H-isoindol-1-yl]-1H-benzimidazol-2-yl}carbamate methyl(5-{1-hydroxy-3-oxo-2-[3-(trifluoromethyl)phenyl]-2,3-dihydro-1H-isoindol-1-yl}-1H-benzimidazol-2-yl)carbamate but-2-yn-1-yl(5-{1-hydroxy-3-oxo-2-[(1R)-1-phenylethyl]-2,3-dihydro-1H-isoindol-1-yl}-1H-benzimidazol-2-yl)carbamate N-ethyl-N'-{5-[1-hydroxy-3-oxo-2-(phenylmethyl)-2,3-dihydro-1H-isoindol-1-yl]-1H-benzimidazol-2-yl}urea phenylmethyl(5-{1-hydroxy-3-oxo-2-[(1R)-1-phenylethyl]-2,3-dihydro-1H-isoindol-1-yl}-1H-benzimidazol-2-yl)carbamate methyl{6-[2-(3-amino-5-chlorophenyl)-1-hydroxy-3-oxo-2,3-dihydro-1H-isoindol-1-yl]-1H-benzimidazol-2-yl}carbamate piperidin-4-ylmethyl{5-[1-hydroxy-3-oxo-2-(phenylmethyl)-2,3-dihydro-1H-isoindol-1-yl]-1H-benzimidazol-2-yl}carbamate methyl{5-[2-(cyclopropylmethyl)-1-hydroxy-3-oxo-2,3-dihydro-1H-isoindol-1-yl]-1H-benzimidazol-2-yl}carbamate methyl{5-[2-(2,2-dimethylpropyl)-1-hydroxy-3-oxo-2,3-dihydro-1H-isoindol-1-yl]-1H-benzimidazol-2-yl}carbamate methyl{5-[2-(3,5-dichlorophenyl)-1-hydroxy-3-oxo-2,3-dihydro-1H-isoindol-1-yl]-1H-benzimidazol-2-yl}carbamate methyl{5-[2-(3,5-difluorophenyl)-1-hydroxy-3-oxo-2,3-dihydro-1H-isoindol-1-yl]-1H-benzimidazol-2-yl}carbamate N-ethyl-N'-(5-{1-hydroxy-3-oxo-2-[(1R)-1-phenylethyl]-2,3-dihydro-1H-isoindol-1-yl}-1H-benzimidazol-2-yl)urea N'-{5-[1-hydroxy-3-oxo-2-(phenylmethyl)-2,3-dihydro-1H-isoindol-1-yl]-1H-benzimidazol-2-yl}-N,N-dimethylurea methyl{5-[2-(3-{[2-(dimethylamino)ethyl]oxy}phenyl)-1-hydroxy-3-oxo-2,3-dihydro-1H-isoindol-1-yl]-1H-benzimidazol-2-yl}carbamate 3-(4-methylpiperazin-1-yl)propyl{6-[1-hydroxy-3-oxo-2-(phenylmethyl)-2,3-dihydro-1H-isoindol-1-yl]-1H-benzimidazol-2-yl}carbamate methyl{5-[2-(cyclohexylmethyl)-1-hydroxy-3-oxo-2,3-dihydro-1H-isoindol-1-yl]-1H-benzimidazol-2-yl}carbamate methyl{5-[1-hydroxy-2-(2-methylpropyl)-3-oxo-2,3-dihydro-1H-isoindol-1-yl]-1H-benzimidazol-2-yl}carbamate methyl{5-[1-hydroxy-3-oxo-2-(1,3-thiazol-2-ylmethyl)-2,3-dihydro-1H-isoindol-1-yl]-1H-benzimidazol-2-yl}carbamate methyl{5-[2-(3,4-difluorophenyl)-1-hydroxy-3-oxo-2,3-dihydro-1H-isoindol-1-yl]-1H-benzimidazol-2-yl}carbamate methyl(5-{2-[1-(3,5-difluorophenyl)ethyl]-1-hydroxy-3-oxo-2,3-dihydro-1H-isoindol-1-yl}-1H-benzimidazol-2-yl)carbamate methyl(5-{2-[1-(3-fluorophenyl)ethyl]-1-hydroxy-3-oxo-2,3-dihydro-1H-isoindol-1-yl}-1H-benzimidazol-2-yl)carbamate methyl[5-(2-cyclohexyl-1-hydroxy-3-oxo-2,3-dihydro-1H-isoindol-1-yl)-1H-benzimidazol-2-yl]carbamate methyl{5-[2-(2,5-difluorophenyl)-1-hydroxy-3-oxo-2,3-dihydro-1H-isoindol-1-yl]-1H-benzimidazol-2-yl}carbamate N-{5-[1-hydroxy-3-oxo-2-(phenylmethyl)-2,3-dihydro-1H-isoindol-1-yl]-1H-benzimidazol-2-yl}-N'-(phenylmethyl)urea piperidin-4-yl{5-[1-hydroxy-3-oxo-2-(phenylmethyl)-2,3-dihydro-1H-isoindol-1-yl]-1H-benzimidazol-2-yl}carbamate N-{5-[1-hydroxy-3-oxo-2-(phenylmethyl)-2,3-dihydro-1H-isoindol-1-yl]-1H-benzimidazol-2-yl}-N'-methylurea methyl(5-{2-[1-(2-fluorophenyl)ethyl]-1-hydroxy-3-oxo-2,3-dihydro-1H-isoindol-1-yl}-1H-benzimidazol-2-yl)carbamate methyl(5-{1-hydroxy-3-oxo-2-[1-(2-thienyl)ethyl]-2,3-dihydro-1H-isoindol-1-yl}-1H-benzimidazol-2-yl)carbamate methyl(5-{2-[1-(3-chlorophenyl)ethyl]-1-hydroxy-3-oxo-2,3-dihydro-1H-isoindol-1-yl}-1H-benzimidazol-2-yl)carbamate methyl(5-{1-hydroxy-2-[3-methyl-5-(trifluoromethyl)phenyl]-3-oxo-2,3-dihydro-1H-isoindol-1-yl}-1H-benzimidazol-2-yl)carbamate N-{5-[1-hydroxy-3-oxo-2-(phenylmethyl)-2,3-dihydro-1H-isoindol-1-yl]-1H-benzimidazol-2-yl}propanamide methyl{5-[2-(3,4-dichlorophenyl)-1-hydroxy-3-oxo-2,3-dihydro-1H-isoindol-1-yl]-1H-benzimidazol-2-yl}carbamate methyl{5-[2-(3-ethylphenyl)-1-hydroxy-3-oxo-2,3-dihydro-1H-isoindol-1-yl]-1H-benzimidazol-2-yl}carbamate methyl{5-[2-(3-ethynylphenyl)-1-hydroxy-3-oxo-2,3-dihydro-1H-isoindol-1-yl]-1H-benzimidazol-2-yl}carbamate methyl{5-[2-(4-chloro-3-methylphenyl)-1-hydroxy-3-oxo-2,3-dihydro-1H-isoindol-1-yl]-1H-benzimidazol-2-yl}carbamate methyl[5-(1-hydroxy-3-oxo-2-{1-[3-(trifluoromethyl)phenyl]ethyl}-2,3-dihydro-1H-isoindol-1-yl)-1H-benzimidazol-2-yl]carbamate methyl(5-{1-hydroxy-3-oxo-2-[(1R)-1-phenylpropyl]-2,3-dihydro-1H-isoindol-1-yl}-1H-benzimidazol-2-yl)carbamate methyl[5-(1-hydroxy-3-oxo-2-{2-[(trifluoromethyl)oxy]phenyl}-2,3-dihydro-1H-isoindol-1-yl)-1H-benzimidazol-2-yl]carbamate methyl{5-[2-(2,3-difluorophenyl)-1-hydroxy-3-oxo-2,3-dihydro-1H-isoindol-1-yl]-1H-benzimidazol-2-yl}carbamate cyclohexyl{5-[1-hydroxy-3-oxo-2-(phenylmethyl)-2,3-dihydro-1H-isoindol-1-yl]-1H-benzimidazol-2-yl}carbamate tetrahydrofuran-2-ylmethyl{5-[1-hydroxy-3-oxo-2-(phenylmethyl)-2,3-dihydro-1H-isoindol-1-yl]-1H-benzimidazol-2-yl}carbamate cyclopropylmethyl{5-[1-hydroxy-3-oxo-2-(phenylmethyl)-2,3-dihydro-1H-isoindol-1-yl]-1H-benzimidazol-2-yl}carbamate N-{5-[1-hydroxy-3-oxo-2-(phenylmethyl)-2,3-dihydro-1H-isoindol-1-yl]-1H-benzimidazol-2-yl}morpholine-4-carboxamide methyl{5-[2-(cyclopentylmethyl)-1-hydroxy-3-oxo-2,3-dihydro-1H-isoindol-1-yl]-1H-benzimidazol-2-yl}carbamate methyl{5-[2-(2,3-dimethylphenyl)-1-hydroxy-3-oxo-2,3-dihydro-1H-isoindol-1-yl]-1H-benzimidazol-2-yl}carbamate methyl{5-[2-(2,3-dihydro-1H-inden-1-yl)-1-hydroxy-3-oxo-2,3-dihydro-1H-isoindol-1-yl]-1H-benzimidazol-2-yl}carbamate methyl(2S)-cyclohexyl[1-hydroxy-1-(2-{[(methyloxy)carbonyl]amino}-1H-benzimidazol-5-yl)-3-oxo-1,3-dihydro-2H-isoindol-2-yl]ethanoate methyl{5-[2-(2,6-difluorophenyl)-1-hydroxy-3-oxo-2,3-dihydro-1H-isoindol-1-yl]-1H-benzimidazol-2-yl}carbamate methyl{5-[2-(3-chloro-4-fluorophenyl)-1-hydroxy-3-oxo-2,3-dihydro-1H-isoindol-1-yl]-1H-benzimidazol-2-yl}carbamate
but-3-en-1-yl{5-[1-hydroxy-3-oxo-2-(phenylmethyl)-2,3-dihydro-1H-isoindol-1-yl]-1H-benzimidazol-2-yl}carbamate
2,2,2-trifluoroethyl{5-[1-hydroxy-3-oxo-2-(phenylmethyl)-2,3-dihydro-1H-isoindol-1-yl]-1H-benzimidazol-2-yl}carbamate
methyl{5-[2-(5-chloro-2-fluorophenyl)-1-hydroxy-3-oxo-2,3-dihydro-1H-isoindol-1-yl]-1H-benzimidazol-2-yl}carbamate
methyl(5-{2-[1-(5-chloro-2-methylphenyl)ethyl]-1-hydroxy-3-oxo-2,3-dihydro-1H-isoindol-1-yl}-1H-benzimidazol-2-yl)carbamate
methyl(5-{1-hydroxy-3-oxo-2-[(1S)-1-phenylpropyl]-2,3-dihydro-1H-isoindol-1-yl}-1H-benzimidazol-2-yl)carbamate
methyl(5-{2-[1-(3-chloro-2-methylphenyl)ethyl]-1-hydroxy-3-oxo-2,3-dihydro-1H-isoindol-1-yl}-1H-benzimidazol-2-yl)carbamate
methyl(5-{1-hydroxy-2-[1-(5-methyl-2-thienyl)ethyl]-3-oxo-2,3-dihydro-1H-isoindol-1-yl}-1H-benzimidazol-2-yl)carbamate
methyl(5-{2-[1-(5-chloro-2-thienyl)ethyl]-1-hydroxy-3-oxo-2,3-dihydro-1H-isoindol-1-yl}-1H-benzimidazol-2-yl)carbamate
methyl{5-[1-hydroxy-2-(3-iodophenyl)-3-oxo-2,3-dihydro-1H-isoindol-1-yl]-1H-benzimidazol-2-yl}carbamate
methyl(5-{1-hydroxy-2-[3-(1-methylethyl)phenyl]-3-oxo-2,3-dihydro-1H-isoindol-1-yl}-1H-benzimidazol-2-yl)carbamate
methyl{5-[2-(furan-2-ylmethyl)-1-hydroxy-3-oxo-2,3-dihydro-1H-isoindol-1-yl]-1H-benzimidazol-2-yl}carbamate
methyl{5-[1-hydroxy-3-oxo-2-(3-thienylmethyl)-2,3-dihydro-1H-isoindol-1-yl]-1H-benzimidazol-2-yl}carbamate
methyl{5-[2-(cyclobutylmethyl)-1-hydroxy-3-oxo-2,3-dihydro-1H-isoindol-1-yl]-1H-benzimidazol-2-yl}carbamate
3,3,3-trifluoro-2-hydroxy-N-{5-[1-hydroxy-3-oxo-2-(phenylmethyl)-2,3-dihydro-1H-isoindol-1-yl]-1H-benzimidazol-2-yl}-2-(trifluoromethyl)propanamide
methyl(5-{1-hydroxy-2-[1-(4-methyl-2-thienyl)ethyl]-3-oxo-2,3-dihydro-1H-isoindol-1-yl}-1H-benzimidazol-2-yl)carbamate
methyl(5-{2-[1-(4-bromo-2-thienyl)ethyl]-1-hydroxy-3-oxo-2,3-dihydro-1H-isoindol-1-yl}-1H-benzimidazol-2-yl)carbamate
methyl{5-[1-hydroxy-2-(3-{[2-(methyloxy)ethyl]oxy}phenyl)-3-oxo-2,3-dihydro-1H-isoindol-1-yl]-1H-benzimidazol-2-yl}carbamate
tetrahydrofuran-3-ylmethyl{5-[1-hydroxy-3-oxo-2-(phenylmethyl)-2,3-dihydro-1H-isoindol-1-yl]-1H-benzimidazol-2-yl}carbamate
N-{5-[1-hydroxy-3-oxo-2-(phenylmethyl)-2,3-dihydro-1H-isoindol-1-yl]-1H-benzimidazol-2-yl}piperidine-1-carboxamide
methyl{5-[2-(3-bromo-4-fluorophenyl)-1-hydroxy-3-oxo-2,3-dihydro-1H-isoindol-1-yl]-1H-benzimidazol-2-yl}carbamate
2,3-dihydroxypropyl{5-[1-hydroxy-3-oxo-2-(phenylmethyl)-2,3-dihydro-1H-isoindol-1-yl]-1H-benzimidazol-2-yl}carbamate
methyl{5-[1-hydroxy-3-oxo-2-(tetrahydrofuran-2-ylmethyl)-2,3-dihydro-1H-isoindol-1-yl]-1H-benzimidazol-2-yl}carbamate
methyl(5-{2-[3-(aminocarbonyl)phenyl]-1-hydroxy-3-oxo-2,3-dihydro-1H-isoindol-1-yl}-1H-benzimidazol-2-yl)carbamate
4,4,4-trifluoro-3-hydroxy-N-{5-[1-hydroxy-3-oxo-2-(phenylmethyl)-2,3-dihydro-1H-isoindol-1-yl]-1H-benzimidazol-2-yl}-3-(trifluoromethyl)butanamide
methyl(5-{1-hydroxy-2-[3-(methylsulfonyl)phenyl]-3-oxo-2,3-dihydro-1H-isoindol-1-yl}-1H-benzimidazol-2-yl)carbamate
methyl(5-{1-hydroxy-3-oxo-2-[3-(phenyloxy)phenyl]-2,3-dihydro-1H-isoindol-1-yl}-1H-benzimidazol-2-yl)carbamate
methyl[5-(1-hydroxy-3-oxo-2-{3-[(phenylmethyl)oxy]phenyl}-2,3-dihydro-1H-isoindol-1-yl)-1H-benzimidazol-2-yl]carbamate
methyl[5-(2-biphenyl-3-yl-1-hydroxy-3-oxo-2,3-dihydro-1H-isoindol-1-yl)-1H-benzimidazol-2-yl]carbamate
2,2-dimethyl-3-[(phenylmethyl)oxy]propyl{5-[1-hydroxy-3-oxo-2-(phenylmethyl)-2,3-dihydro-1H-isoindol-1-yl]-1H-benzimidazol-2-yl}carbamate
methyl{5-[2-(3-chloro-2-fluorophenyl)-1-hydroxy-3-oxo-2,3-dihydro-1H-isoindol-1-yl]-1H-benzimidazol-2-yl}carbamate
methyl{5-[2-(3-cyanophenyl)-1-hydroxy-3-oxo-2,3-dihydro-1H-isoindol-1-yl]-1H-benzimidazol-2-yl}carbamate
methyl{5-[2-(3-ethynyl-4-fluorophenyl)-1-hydroxy-3-oxo-2,3-dihydro-1H-isoindol-1-yl]-1H-benzimidazol-2-yl}carbamate
methyl{5-[2-(4-fluoro-3-methylphenyl)-1-hydroxy-3-oxo-2,3-dihydro-1H-isoindol-1-yl]-1H-benzimidazol-2-yl}carbamate
methyl{6-[2-(3,4-dichloro-2-fluorophenyl)-1-hydroxy-3-oxo-2,3-dihydro-1H-isoindol-1-yl]-1H-benzimidazol-2-yl}carbamate
[(4S)-2,2-dimethyl-1,3-dioxolan-4-yl]methyl{5-[1-hydroxy-3-oxo-2-(phenylmethyl)-2,3-dihydro-1H-isoindol-1-yl]-1H-benzimidazol-2-yl}carbamate
methyl{5-[2-(5-bromo-2-fluorophenyl)-1-hydroxy-3-oxo-2,3-dihydro-1H-isoindol-1-yl]-1H-benzimidazol-2-yl}carbamate
methyl(5-{2-[3-(acetylamino)phenyl]-1-hydroxy-3-oxo-2,3-dihydro-1H-isoindol-1-yl}-1H-benzimidazol-2-yl)carbamate
methyl(5-{1-hydroxy-3-oxo-2-[3-(phenylmethyl)phenyl]-2,3-dihydro-1H-isoindol-1-yl}-1H-benzimidazol-2-yl)carbamate
methyl(5-{2-[1-(4-chloro-2-thienyl)ethyl]-1-hydroxy-3-oxo-2,3-dihydro-1H-isoindol-1-yl}-1H-benzimidazol-2-yl)carbamate
methyl(5-{1-hydroxy-3-oxo-2-[3-(phenylcarbonyl)phenyl]-2,3-dihydro-1H-isoindol-1-yl}-1H-benzimidazol-2-yl)carbamate
methyl[5-(2-{3-[(dimethylamino)methyl]phenyl}-1-hydroxy-3-oxo-2,3-dihydro-1H-isoindol-1-yl)-1H-benzimidazol-2-yl]carbamate
methyl(5-{2-[3-(aminosulfonyl)phenyl]-1-hydroxy-3-oxo-2,3-dihydro-1H-isoindol-1-yl}-1H-benzimidazol-2-yl)carbamate
methyl{5-[2-(3-acetylphenyl)-1-hydroxy-3-oxo-2,3-dihydro-1H-isoindol-1-yl]-1H-benzimidazol-2-yl}carbamate methyl{5-[2-(3-ethyl-4-fluorophenyl)-1-hydroxy-3-oxo-2,3-dihydro-1H-isoindol-1-yl]-1H-benzimidazol-2-yl}carbamate
methyl{5-[2-(3-chloro-5-fluorophenyl)-1-hydroxy-3-oxo-2,3-dihydro-1H-isoindol-1-yl]-1H-benzimidazol-2-yl}carbamate
N-{6-[1-hydroxy-3-oxo-2-(phenylmethyl)-2,3-dihydro-1H-isoindol-1-yl]-1H-benzimidazol-2-yl}-2-methylpropanamide
methyl(5-{2-[1-(3-chloro-2-thienyl)ethyl]-1-hydroxy-3-oxo-2,3-dihydro-1H-isoindol-1-yl}-1H-benzimidazol-2-yl)carbamate
methyl[5-(1-hydroxy-3-oxo-2-pyridin-3-yl-2,3-dihydro-1H-isoindol-1-yl)-1H-benzimidazol-2-yl]carbamate
methyl(5-{1-hydroxy-3-oxo-2-[3-(phenylamino)phenyl]-2,3-dihydro-1H-isoindol-1-yl}-1H-benzimidazol-2-yl)carbamate
methyl{5-[2-(5-bromo-2,4-difluorophenyl)-1-hydroxy-3-oxo-2,3-dihydro-1H-isoindol-1-yl]-1H-benzimidazol-2-yl}carbamate
methyl{5-[2-(5-chloro-2,4-difluorophenyl)-1-hydroxy-3-oxo-2,3-dihydro-1H-isoindol-1-yl]-1H-benzimidazol-2-yl}carbamate
methyl{5-[2-(3,5-dichloro-4-fluorophenyl)-1-hydroxy-3-oxo-2,3-dihydro-1H-isoindol-1-yl]-1H-benzimidazol-2-yl}carbamate
2,2-dimethyl-3-(methyloxy)propyl{5-[1-hydroxy-3-oxo-2-(phenylmethyl)-2,3-dihydro-1H-isoindol-1-yl]-1H-benzimidazol-2-yl}carbamate
3-hydroxy-2,2-dimethylpropyl{5-[1-hydroxy-3-oxo-2-(phenylmethyl)-2,3-dihydro-1H-isoindol-1-yl]-1H-benzimidazol-2-yl}carbamate
methyl(5-{2-[1-(5-bromo-2-thienyl)ethyl]-1-hydroxy-3-oxo-2,3-dihydro-1H-isoindol-1-yl}-1H-benzimidazol-2-yl)carbamate
methyl{5-[2-(4,5-dichloro-2-fluorophenyl)-1-hydroxy-3-oxo-2,3-dihydro-1H-isoindol-1-yl]-1H-benzimidazol-2-yl}carbamate
methyl{5-[2-(3-bromo-2-fluorophenyl)-1-hydroxy-3-oxo-2,3-dihydro-1H-isoindol-1-yl]-1H-benzimidazol-2-yl}carbamate
methyl{5-[2-(3-chloro-2,4-difluorophenyl)-1-hydroxy-3-oxo-2,3-dihydro-1H-isoindol-1-yl]-1H-benzimidazol-2-yl}carbamate
N-{6-[1-hydroxy-3-oxo-2-(phenylmethyl)-2,3-dihydro-1H-isoindol-1-yl]-1H-benzimidazol-2-yl}pent-4-ynamide
methyl(6-{1-methyl-3-oxo-2-[3-(trifluoromethyl)phenyl]-2,3-dihydro-1H-isoindol-1-yl}-1H-benzimidazol-2-yl)carbamate
methyl[5-(1-hydroxy-3-oxo-2-{3-[(1,1,2,2-tetrafluoroethyl)oxy]phenyl}-2,3-dihydro-1H-isoindol-1-yl)-1H-benzimidazol-2-yl]carbamate
methyl{5-[1-hydroxy-3-oxo-2-(3-piperidin-4-ylphenyl)-2,3-dihydro-1H-isoindol-1-yl]-1H-benzimidazol-2-yl}carbamate
methyl{5-[2-(3-ethenylphenyl)-1-hydroxy-3-oxo-2,3-dihydro-1H-isoindol-1-yl]-1H-benzimidazol-2-yl}carbamate
methyl(5-{2-[3-(dimethylamino)phenyl]-1-hydroxy-3-oxo-2,3-dihydro-1H-isoindol-1-yl}-1H-benzimidazol-2-yl)carbamate
2,2-difluoro-N-{6-[1-hydroxy-3-oxo-2-(phenylmethyl)-2,3-dihydro-1H-isoindol-1-yl]-1H-benzimidazol-2-yl}cyclopropanecarboxamide
N-ethyl-N'-{6-[2-(4-fluorophenyl)-1-hydroxy-3-oxo-2,3-dihydro-1H-isoindol-1-yl]-1H-benzimidazol-2-yl}urea
methyl{5-[2-(3-aminophenyl)-1-hydroxy-3-oxo-2,3-dihydro-1H-isoindol-1-yl]-1H-benzimidazol-2-yl}carbamate
N-{5-[1-hydroxy-3-oxo-2-(phenylmethyl)-2,3-dihydro-1H-isoindol-1-yl]-1H-benzimidazol-2-yl}-4-[(phenylmethyl)oxy]butanamide
N-{5-[1-hydroxy-3-oxo-2-(phenylmethyl)-2,3-dihydro-1H-isoindol-1-yl]-1H-benzimidazol-2-yl}-4-piperidin-1-ylbutanamide
N-{5-[1-hydroxy-3-oxo-2-(phenylmethyl)-2,3-dihydro-1H-isoindol-1-yl]-1H-benzimidazol-2-yl}-4-(4-methylpiperazin-1-yl)butanamide
N-{6-[2-(4-fluorophenyl)-1-hydroxy-3-oxo-2,3-dihydro-1H-isoindol-1-yl]-1H-benzimidazol-2-yl}butanamide
methyl{6-[2-(3-bromophenyl)-5,6-dichloro-1-hydroxy-3-oxo-2,3-dihydro-1H-isoindol-1-yl]-1H-benzimidazol-2-yl}carbamate
methyl[5-(1-hydroxy-2-{3-[methyl(phenyl)amino]phenyl}-3-oxo-2,3-dihydro-1H-isoindol-1-yl)-1H-benzimidazol-2-yl]carbamate
methyl{5-[1-hydroxy-3-oxo-2-(phenylsulfonyl)-2,3-dihydro-1H-isoindol-1-yl]-1H-benzimidazol-2-yl}carbamate
methyl{5-[(2-{[(phenylamino)carbonyl]amino}phenyl)carbonyl]-1H-benzimidazol-2-yl}carbamate
methyl(5-{[2-({[(phenylmethyl)oxy]carbonyl}amino)phenyl]carbonyl}-1H-benzimidazol-2-yl)carbamate
methyl[5-({2-[(2-phenylhydrazino)carbonyl]phenyl}carbonyl)-1H-benzimidazol-2-yl]carbamate
methyl{5-[(2-{[(phenyloxy)amino]carbonyl}phenyl)carbonyl]-1H-benzimidazol-2-yl}carbamate
but-2-yn-1-yl{5-[2-(4-fluorophenyl)-1-hydroxy-3-oxo-2,3-dihydro-1H-isoindol-1-yl]-1H-benzimidazol-2-yl}carbamate
N-{5-[1-hydroxy-3-oxo-2-(phenylmethyl)-2,3-dihydro-1H-isoindol-1-yl]-1H-benzimidazol-2-yl}-3-piperidin-1-ylpropanamide
N-{6-[2-(4-fluorophenyl)-1-hydroxy-3-oxo-2,3-dihydro-1H-isoindol-1-yl]-1H-benzimidazol-2-yl}propanamide
N-(4-fluorophenyl)-2-{[2-(pent-4-ynoylamino)-1H-benzimidazol-6-yl]carbonyl}benzamide
4-(diethylamino)-N-{5-[1-hydroxy-3-oxo-2-(phenylmethyl)-2,3-dihydro-1H-isoindol-1-yl]-1H-benzimidazol-2-yl}butanamide
N-{5-[1-hydroxy-3-oxo-2-(phenylmethyl)-2,3-dihydro-1H-isoindol-1-yl]-1H-benzimidazol-2-yl}-4-pyrrolidin-1-ylbutanamide
3-piperidin-1-ylpropyl{6-[2-(4-fluorophenyl)-1-hydroxy-3-oxo-2,3-dihydro-1H-isoindol-1-yl]-1H-benzimidazol-2-yl}carbamate
3-(4-methylpiperazin-1-yl)propyl{6-[2-(4-fluorophenyl)-1-hydroxy-3-oxo-2,3-dihydro-1H-isoindol-1-yl]-1H-benzimidazol-2-yl}carbamate
methyl{5-[2-(3-bromophenyl)-3-oxo-2,3-dihydro-1H-isoindol-1-yl]-1H-benzimidazol-2-yl}carbamate
methyl{5-[2-(3-ethynyl-2-fluorophenyl)-1-hydroxy-3-oxo-2,3-dihydro-1H-isoindol-1-yl]-1H-benzimidazol-2-yl}carbamate
2-piperidin-1-ylethyl{5-[2-(4-fluorophenyl)-1-hydroxy-3-oxo-2,3-dihydro-1H-isoindol-1-yl]-1H-benzimidazol-2-yl}carbamate
methyl{5-[2-(3-chloro-2-methylphenyl)-1-hydroxy-3-oxo-2,3-dihydro-1H-isoindol-1-yl]-1H-benzimidazol-2-yl}carbamate
methyl{5-[2-(5-chloro-2-methylphenyl)-1-hydroxy-3-oxo-2,3-dihydro-1H-isoindol-1-yl]-1H-benzimidazol-2-yl}carbamate N-{6-[1-hydroxy-3-oxo-2-(phenylmethyl)-2,3-dihydro-1H-isoindol-1-yl]-1H-benzimidazol-2-yl}-2,2-dimethyl-3-piperidin-1-ylpropanamide N-{5-[2-(4-fluorophenyl)-1-hydroxy-3-oxo-2,3-dihydro-1H-isoindol-1-yl]-1H-benzimidazol-2-yl}-4-piperidin-1-ylbutanamide N-{5-[2-(3-chloro-2-fluorophenyl)-1-hydroxy-3-oxo-2,3-dihydro-1H-isoindol-1-yl]-1H-benzimidazol-2-yl}-4-piperidin-1-ylbutanamide methyl[6-({2-[(phenylcarbonyl)amino]phenyl}carbonyl)-1H-benzimidazol-2-yl]carbamate methyl{5-[1-hydroxy-2-(3-morpholin-4-ylphenyl)-3-oxo-2,3-dihydro-1H-isoindol-1-yl]-1H-benzimidazol-2-yl}carbamate 2-(dimethylamino)ethyl{6-[2-(3-chloro-2-fluorophenyl)-1-hydroxy-3-oxo-2,3-dihydro-1H-isoindol-1-yl]-1H-benzimidazol-2-yl}carbamate 2-(diethylamino)ethyl{5-[2-(3-chloro-2-fluorophenyl)-1-hydroxy-3-oxo-2,3-dihydro-1H-isoindol-1-yl]-1H-benzimidazol-2-yl}carbamate 2-piperidin-1-ylethyl{5-[2-(3-chloro-2-fluorophenyl)-1-hydroxy-3-oxo-2,3-dihydro-1H-isoindol-1-yl]-1H-benzimidazol-2-yl}carbamate 3-piperidin-1-ylpropyl{6-[2-(3-chloro-2-fluorophenyl)-1-hydroxy-3-oxo-2,3-dihydro-1H-isoindol-1-yl]-1H-benzimidazol-2-yl}carbamate 2-piperidin-1-ylethyl{6-[2-(3-bromophenyl)-3-oxo-2,3-dihydro-1H-isoindol-1-yl]-1H-benzimidazol-2-yl}carbamate methyl{6-[2-(3-bromophenyl)-4,7-difluoro-1-hydroxy-3-oxo-2,3-dihydro-1H-isoindol-1-yl]-1H-benzimidazol-2-yl}carbamate 2-[methyl(phenylmethyl)amino]ethyl{5-[2-(3-chloro-2-fluorophenyl)-1-hydroxy-3-oxo-2,3-dihydro-1H-isoindol-1-yl]-1H-benzimidazol-2-yl}carbamate methyl{5-[1-hydroxy-3-oxo-2-(3-pyrrolidin-1-ylphenyl)-2,3-dihydro-1H-isoindol-1-yl]-1H-benzimidazol-2-yl}carbamate methyl{5-[2-(5-chloro-2,3-difluorophenyl)-1-hydroxy-3-oxo-2,3-dihydro-1H-isoindol-1-yl]-1H-benzimidazol-2-yl}carbamate methyl{5-[1-hydroxy-3-oxo-2-(pyrrolidin-2-ylmethyl)-2,3-dihydro-1H-isoindol-1-yl]-1H-benzimidazol-2-yl}carbamate methyl{5-[1-hydroxy-3-oxo-2-(pyrrolidin-3-ylmethyl)-2,3-dihydro-1H-isoindol-1-yl]-1H-benzimidazol-2-yl}carbamate (1-methylpiperidin-2-yl)methyl{6-[2-(3-chloro-2-fluorophenyl)-1-hydroxy-3-oxo-2,3-dihydro-1H-isoindol-1-yl]-1H-benzimidazol-2-yl}carbamate

[(2S)-1-methylpyrrolidin-2-yl]methyl{6-[2-(3-chloro-2-fluorophenyl)-1-hydroxy-3-oxo-2,3-dihydro-1H-isoindol-1-yl]-1H-benzimidazol-2-yl}carbamate octahydro-2H-quinolizin-1-ylmethyl{6-[2-(3-chloro-2-fluorophenyl)-1-hydroxy-3-oxo-2,3-dihydro-1H-isoindol-1-yl]-1H-benzimidazol-2-yl}carbamate methyl{5-[2-(5-bromo-2-methylphenyl)-1-hydroxy-3-oxo-2,3-dihydro-1H-isoindol-1-yl]-1H-benzimidazol-2-yl}carbamate 5-[2-(3-chloro-2-fluorophenyl)-1-hydroxy-3-oxo-2,3-dihydro-1H-isoindol-1-yl]-1,3-dihydro-2H-benzimidazol-2-one methyl{5-[2-(3-bromo-2,5-difluorophenyl)-1-hydroxy-3-oxo-2,3-dihydro-1H-isoindol-1-yl]-1H-benzimidazol-2-yl}carbamate 2-morpholin-4-ylethyl{6-[2-(3-chloro-2-fluorophenyl)-1-hydroxy-3-oxo-2,3-dihydro-1H-isoindol-1-yl]-1H-benzimidazol-2-yl}carbamate (1-methylpiperidin-3-yl)methyl{6-[2-(3-chloro-2-fluorophenyl)-1-hydroxy-3oxo-2,3-dihydro-1H-isoindol-1-yl]-1H-benzimidazol-2-yl}carbamate methyl(5-{2-[5-chloro-2-(methyloxy)phenyl]-1-hydroxy-3-oxo-2,3-dihydro-1H-isoindol-1-yl}-1H-benzimidazol-2-yl)carbamate methyl[5-(2-{3-[cyclohexyl(methyl)amino]phenyl}-1-hydroxy-3-oxo-2,3-dihydro-1H-isoindol-1-yl)-1H-benzimidazol-2-yl]carbamate 8-azabicyclo[3.2.1]oct-3-ylmethyl{6-[2-(3-chloro-2-fluorophenyl)-1-hydroxy-3-oxo-2,3-dihydro-1H-isoindol-1-yl]-1H-benzimidazol-2-yl}carbamate methyl{6-[1-(3-bromophenyl)-5-oxopyrrolidin-2-yl]-1H-benzimidazol-2-yl}carbamate (1-methylpiperidin-4-yl)methyl{5-[1-hydroxy-3-oxo-2-(phenylmethyl)-2,3-dihydro-1H-isoindol-1-yl]-1H-benzimidazol-2-yl}carbamate 1,1-dimethylethyl4-({[({5-[1-hydroxy-3-oxo-2-(phenylmethyl)-2,3-dihydro-1H-isoindol-1-yl]-1H-benzimidazol-2-yl}amino)carbonyl]oxy}methyl)piperidine-1-carboxylate (1-methylpiperidin-4-yl)methyl{5-[2-(3-chloro-2-fluorophenyl)-1-hydroxy-3-oxo-2,3-dihydro-1H-isoindol-1-yl]-1H-benzimidazol-2-yl}carbamate 2-(1-methylpiperidin-4-yl)ethyl{5-[2-(3-chloro-2-fluorophenyl)-1-hydroxy-3-oxo-2,3-dihydro-1H-isoindol-1-yl]-1H-benzimidazol-2-yl}carbamate methyl({6-[2-(3-chloro-2-fluorophenyl)-1-hydroxy-3-oxo-2,3-dihydro-1H-isoindol-1-yl]-1H-benzimidazol-2-yl}amino)(oxo)acetate N-(5-{1-hydroxy-3-oxo-2-[3-(phenyloxy)phenyl]-2,3-dihydro-1H-isoindol-1-yl}-1H-benzimidazol-2-yl)-4-piperidin-1-ylbutanamide methyl{6-[2-(3-bromophenyl)-1-methyl-3-oxo-2,3-dihydro-1H-isoindol-1-yl]-1H-benzimidazol-2-yl}carbamate 4-(diethylamino)but-2-yn-1-yl{6-[2-(3-chloro-2-fluorophenyl)-1-hydroxy-3-oxo-2,3-dihydro-1H-isoindol-1-yl]-1H-benzimidazol-2-yl}carbamate methyl{5-[2-(3-chloro-2,6-difluorophenyl)-1-hydroxy-3-oxo-2,3-dihydro-1H-isoindol-1-yl]-1H-benzimidazol-2-yl}carbamate 2-(2-oxopyrrolidin-1-yl)ethyl{6-[2-(3-chloro-2-fluorophenyl)-1-hydroxy-3-oxo-2,3-dihydro-1H-isoindol-1-yl]-1H-benzimidazol-2-yl}carbamate 2-(2,5-dioxopyrrolidin-1-yl)ethyl{6-[2-(3-chloro-2-fluorophenyl)-1-hydroxy-3-oxo-2,3-dihydro-1H-isoindol-1-yl]-1H-benzimidazol-2-yl}carbamate 2,2,3,3-tetrafluorocyclobutyl{5-[2-(3-chloro-2-fluorophenyl)-1-hydroxy-3-oxo-2,3-dihydro-1H-isoindol-1-yl]-1H-benzimidazol-2-yl}carbamate 1-acetyl-N-{5-[2-(3-chloro-2-fluorophenyl)-1-hydroxy-3-oxo-2,3-dihydro-1H-isoindol-1-yl]-1H-benzimidazol-2-yl}piperidine-4-carboxamide N-{5-[2-(3-chloro-2-fluorophenyl)-1-hydroxy-3-oxo-2,3-dihydro-1H-isoindol-1-yl]-1H-benzimidazol-2-yl}cyclobutanecarboxamide methyl[5-(2-{3-[ethyl(phenyl)amino]phenyl}-1-hydroxy-3-oxo-2,3-dihydro-1H-isoindol-1-yl)-1H-benzimidazol-2-yl]carbamate N-{6-[2-(3-chloro-2-fluorophenyl)-1-hydroxy-3-oxo-2,3-dihydro-1H-isoindol-1-yl]-1H-benzimidazol-2-yl}-2,2-difluorocyclopropanecarboxamide cyclobutyl{6-[2-(3-chloro-2-fluorophenyl)-1-hydroxy-3-oxo-2,3-dihydro-1H-isoindol-1-yl]-1H-benzimidazol-2-yl}carbamate 2,2-difluoroethyl{6-[2-(3-chloro-2-fluorophenyl)-1-hydroxy-3-oxo-2,3-dihydro-1H-isoindol-1-yl]-1H-benzimidazol-2-yl}carbamate 2-(3-chloro-2-fluorophenyl)-3-hydroxy-3-[2-(pyridin-2-ylamino)-1H-benzimidazol-5-yl]-2,3-dihydro-1H-isoindol-1-one 1-methylethyl{6-[2-(3-chloro-2-fluorophenyl)-1-hydroxy-3-oxo-2,3-dihydro-1H-isoindol-1-yl]-1H-benzimidazol-2-yl}carbamate cyclopropylmethyl{6-[2-(3-chloro-2-fluorophenyl)-1-hydroxy-3-oxo-2,3-dihydro-1H-isoindol-1-yl]-1H-benzimidazol-2-yl}carbamate N-{5-[2-(3-chloro-2-fluorophenyl)-1-hydroxy-3-oxo-2,3-dihydro-1H-isoindol-1-yl]-1H-benzimidazol-2-yl}cyclopropanecarboxamide 2-(methyloxy)ethyl{5-[2-(3-chloro-2-fluorophenyl)-1-hydroxy-3-oxo-2,3-dihydro-1H-isoindol-1-yl]-1H-benzimidazol-2-yl}carbamate tetrahydrofuran-2-ylmethyl{6-[2-(3-chloro-2-fluorophenyl)-1-hydroxy-3-oxo-2,3-dihydro-1H-isoindol-1-yl]-1H-benzimidazol-2-yl}carbamate N-{5-[2-(3-chloro-2-fluorophenyl)-1-hydroxy-3-oxo-2,3-dihydro-1H-isoindol-1-yl]-1H-benzimidazol-2-yl}-2-(2-thienyl)acetamide methyl{6-[2-(3-chloro-2-fluorophenyl)-4,7-difluoro-1-hydroxy-3-oxo-2,3-dihydro-1H-isoindol-1-yl]-1H-benzimidazol-2-yl}carbamate ethyl{6-[2-(3-chloro-2-fluorophenyl)-1-hydroxy-3-oxo-2,3-dihydro-1H-isoindol-1-yl]-1H-benzimidazol-2-yl}carbamate 2-fluoroethyl{6-[2-(3-chloro-2-fluorophenyl)-1-hydroxy-3-oxo-2,3-dihydro-1H-isoindol-1-yl]-1H-benzimidazol-2-yl}carbamate methyl(5-{1-hydroxy-3-oxo-2-[2-(phenyloxy)phenyl]-2,3-dihydro-1H-isoindol-1-yl}-1H-benzimidazol-2-yl)carbamate N'-{5-[2-(3-chloro-2-fluorophenyl)-1-hydroxy-3-oxo-2,3-dihydro-1H-isoindol-1-yl]-1H-benzimidazol-2-yl}-N,N-diethylpentanediamide cyclobutylmethyl{6-[2-(3-chloro-2-fluorophenyl)-1-hydroxy-3-oxo-2,3-dihydro-1H-isoindol-1-yl]-1H-benzimidazol-2-yl}carbamate 2,2,2-trifluoroethyl{6-[2-(3-chloro-2-fluorophenyl)-1-hydroxy-3-oxo-2,3-dihydro-1H-isoindol-1-yl]-1H-benzimidazol-2-yl}carbamate methyl(5-{2-[3-(1,1-dimethylethyl)phenyl]-1-hydroxy-3-oxo-2,3-dihydro-1H-isoindol-1-yl}-1H-benzimidazol-2-yl)carbamate methyl{6-[2-(3-chloro-2-fluorophenyl)-7-fluoro-1-hydroxy-3-oxo-2,3-dihydro-1H-isoindol-1-yl]-1H-benzimidazol-2-yl}carbamate 2-(3-chloro-2-fluorophenyl)-3-hydroxy-3-[2-(phenylamino)-1H-benzimidazol-5-yl]-2,3-dihydro-1H-isoindol-1-one methyl{6-[4,7-dichloro-2-(3-chloro-2-fluorophenyl)-1-hydroxy-3-oxo-2,3-dihydro-1H-isoindol-1-yl]-1H-benzimidazol-2-yl}carbamate phenylmethyl2-[(2-{[(ethyloxy)carbonyl]amino}-1,3-benzoxazol-5-yl)carbonyl]benzoate methyl{5-[2-(5-chloro-3-ethynyl-2-methylphenyl)-1-hydroxy-3-oxo-2,3-dihydro-1H-isoindol-1-yl]-1H-benzimidazol-2-yl}carbamate methyl{5-[2-(5-ethynyl-2,4-difluorophenyl)-1-hydroxy-3-oxo-2,3-dihydro-1H-isoindol-1-yl]-1H-benzimidazol-2-yl}carbamate methyl{5-[2-(3-ethynyl-2,4-difluorophenyl)-1-hydroxy-3-oxo-2,3-dihydro-1H-isoindol-1-yl]-1H-benzimidazol-2-yl}carbamate 2-(3-chloro-2-fluorophenyl)-3-hydroxy-3-[2-(pyrimidin-2-ylamino)-1H-benzimidazol-5-yl]-2,3-dihydro-1H-isoindol-1-one methyl{5-[2-(3-ethynyl-2-fluorophenyl)-4,7-difluoro-1-hydroxy-3-oxo-2,3-dihydro-1H-isoindol-1-yl]-1H-benzimidazol-2-yl}carbamate 2-(3-chloro-2-fluorophenyl)-3-hydroxy-3-[2-(1,3-thiazol-2-ylamino)-1H-benzimidazol-5-yl]-2,3-dihydro-1H-isoindol-1-one ethyl{5-[2-(3-chloro-2-fluorophenyl)-1-hydroxy-3-oxo-2,3-dihydro-1H-isoindol-1-yl]-1,3-benzoxazol-2-yl}carbamate methyl{5-[2-(5-chloro-3-iodo-2-methylphenyl)-1-hydroxy-3-oxo-2,3-dihydro-1H-isoindol-1-yl]-1H-benzimidazol-2-yl}carbamate methyl{5-[2-(3-ethyl-2-fluorophenyl)-1-hydroxy-3-oxo-2,3-dihydro-1H-isoindol-1-yl]-1H-benzimidazol-2-yl}carbamate methyl{5-[2-(5-ethynyl-2-methylphenyl)-1-hydroxy-3-oxo-2,3-dihydro-1H-isoindol-1-yl]-1H-benzimidazol-2-yl}carbamate 2-(3-chloro-2-fluorophenyl)-3-hydroxy-3-[2-(pyrazin-2-ylamino)-1H-benzimidazol-5-yl]-2,3-dihydro-1H-isoindol-1-one methyl{5-[2-(2-fluoro-3-iodophenyl)-1-hydroxy-3-oxo-2,3-dihydro-1H-isoindol-1-yl]-1H-benzimidazol-2-yl}carbamate methyl{6-[2-(5-ethynyl-2-fluorophenyl)-1-hydroxy-3-oxo-2,3-dihydro-1H-isoindol-1-yl]-1H-benzimidazol-2-yl}carbamate 2-(3-ethynyl-2-fluorophenyl)-3-hydroxy-3-[2-(pyrimidin-2-ylamino)-1H-benzimidazol-5-yl]-2,3-dihydro-1H-isoindol-1-one methyl{5-[2-(2,5-dimethylphenyl)-1-hydroxy-3-oxo-2,3-dihydro-1H-isoindol-1-yl]-1H-benzimidazol-2-yl}carbamate methyl{5-[2-(3-ethenyl-2-fluorophenyl)-1-hydroxy-3-oxo-2,3-dihydro-1H-isoindol-1-yl]-1H-benzimidazol-2-yl}carbamate methyl(6-{2-[2-fluoro-3-(methyloxy)phenyl]-1-hydroxy-3-oxo-2,3-dihydro-1H-isoindol-1-yl}-1H-benzimidazol-2-yl)carbamate methyl(5-{1-hydroxy-2-[2-methyl-5-(methyloxy)phenyl]-3-oxo-2,3-dihydro-1H-isoindol-1-yl}-1H-benzimidazol-2-yl)carbamate methyl{5-[2-(3-ethynyl-2-fluorophenyl)-7-fluoro-1-hydroxy-3-oxo-2,3-dihydro-1H-isoindol-1-yl]-1H-benzimidazol-2-yl}carbamate methyl{5-[2-(2-fluoro-3-prop-1-yn-1-ylphenyl)-1-hydroxy-3-oxo-2,3-dihydro-1H-isoindol-1-yl]-1H-benzimidazol-2-yl}carbamate methyl{5-[2-(5-chloro-2-methylphenyl)-7-fluoro-1-hydroxy-3-oxo-2,3-dihydro-1H-isoindol-1-yl]-1H-benzimidazol-2-yl}carbamate methyl{5-[2-(3-ethynyl-2-methylphenyl)-1-hydroxy-3-oxo-2,3-dihydro-1H-isoindol-1-yl]-1H-benzimidazol-2-yl}carbamate 3-hydroxy-2-[3-(methyloxy)phenyl]-3-[2-(pyrimidin-2-ylamino)-1H-benzimidazol-6-yl]-2,3-dihydro-1H-isoindol-1-one 3-hydroxy-2-(3-methylphenyl)-3-[2-(pyrimidin-2-ylamino)-1H-benzimidazol-6-yl]-2,3-dihydro-1H-isoindol-1-one 2-(5-chloro-2-methylphenyl)-3-hydroxy-3-[2-(pyrimidin-2-ylamino)-1H-benzimidazol-6-yl]-2,3-dihydro-1H-isoindol-1-one methyl{6-[2-(5-chloro-2-methylphenyl)-4,7-difluoro-1-hydroxy-3-oxo-2,3-dihydro-1H-isoindol-1-yl]-1H-benzimidazol-2-yl}carbamate methyl{5-[2-(3-ethynyl-2-fluorophenyl)-3-oxo-2,3-dihydro-1H-isoindol-1-yl]-1H-benzimidazol-2-yl}carbamate 2-(3-chloro-2-fluorophenyl)-3-{2-[(6-chloropyridazin-3-yl)amino]-1H-benzimidazol-5-yl}-3-hydroxy-2,3-dihydro-1H-isoindol-1-one 2-(3-chloro-2-fluorophenyl)-4,7-difluoro-3-hydroxy-3-[2-(pyrimidin-2-ylamino)-1H-benzimidazol-5-yl]-2,3-dihydro-1H-isoindol-1-one methyl{5-[2-(2-fluoro-5-methylphenyl)-1-hydroxy-3-oxo-2,3-dihydro-1H-isoindol-1-yl]-1H-benzimidazol-2-yl}carbamate methyl(5-{2-[2-fluoro-5-(methyloxy)phenyl]-1-hydroxy-3-oxo-2,3-dihydro-1H-isoindol-1-yl}-1H-benzimidazol-2-yl)carbamate methyl(5-{1-hydroxy-2-[5-methyl-2-(methyloxy)phenyl]-3-oxo-2,3-dihydro-1H-isoindol-1-yl}-1H-benzimidazol-2-yl)carbamate methyl{5-[2-(3-ethynyl-5-methylphenyl)-1-hydroxy-3-oxo-2,3-dihydro-1H-isoindol-1-yl]-1H-benzimidazol-2-yl}carbamate 2-(3-chloro-2-fluorophenyl)-3-{2-[(5-chloropyrimidin-2-yl)amino]-1H-benzimidazol-5-yl}-3-hydroxy-2,3-dihydro-1H-isoindol-1-one 2-(3-chloro-2-fluorophenyl)-3-hydroxy-3-{2-[(4-methylpyrimidin-2-yl)amino]-1H-benzimidazol-5-yl}-2,3-dihydro-1H-isoindol-1-one 3-(2-{[4,6-bis(methyloxy)pyrimidin-2-yl]amino}-1H-benzimidazol-5-yl)-2-(3-chloro-2-fluorophenyl)-3-hydroxy-2,3-dihydro-1H-isoindol-1-one 2-(3-chloro-2-fluorophenyl)-3-hydroxy-3-(2-{[4-methyl-6-(methyloxy)pyrimidin-2-yl]amino}-1H-benzimidazol-5-yl)-2,3-dihydro-1H-isoindol-1-one 3-hydroxy-2-(3-methylphenyl)-3-[2-(pyrazin-2-ylamino)-1H-benzimidazol-6-yl]-2,3-dihydro-1H-isoindol-1-one 2-(5-chloro-2-methylphenyl)-3-hydroxy-3-[2-(pyrazin-2-ylamino)-1H-benzimidazol-6-yl]-2,3-dihydro-1H-isoindol-1-one methyl{6-[2-(2-fluoro-3-methylphenyl)-1-hydroxy-3-oxo-2,3-dihydro-1H-isoindol-1-yl]-1H-benzimidazol-2-yl}carbamate 3-hydroxy-2-[3-(methyloxy)phenyl]-3-[2-(pyrazin-2-ylamino)-1H-benzimidazol-5-yl]-2,3-dihydro-1H-isoindol-1-one methyl{6-[(2-{[(2-thienylmethyl)amino]carbonyl}phenyl)carbonyl]-1H-benzimidazol-2-yl}carbamate methyl{6-[(2-{[(3-methylphenyl)amino]carbonyl}phenyl)carbonyl]-1H-benzimidazol-2-yl}carbamate methyl{6-[(2-{[(3-bromophenyl)amino]carbonyl}phenyl)carbonyl]-1H-benzimidazol-2-yl}carbamate methyl{6-[(2-{[(3-chlorophenyl)amino]carbonyl}phenyl]-1H-benzimidazol-2-yl}carbamate methyl{6-[(2-{[(3-fluorophenyl)amino]carbonyl}phenyl)carbonyl]-1H-benzimidazol-2-yl}carbamate methyl(6-{[2-({[3-(methyloxy)phenyl]amino}carbonyl)phenyl]carbonyl}-1H-benzimidazol-2-yl)carbamate methyl(6-{[2-({[3-(trifluoromethyl)phenyl]amino}carbonyl)phenyl]carbonyl}-1H-benzimidazol-2-yl)carbamate methyl{6-[(2-{[(3-ethylphenyl)amino]carbonyl}phenyl)carbonyl]-1H-benzimidazol-2-yl}carbamate methyl{6-[(2-{[(3-ethynylphenyl)amino]carbonyl}phenyl)carbonyl]-1H-benzimidazol-2-yl}carbamate methyl{6-[(2-{[(3-chloro-4-fluorophenyl)amino]carbonyl}phenyl)carbonyl]-1H-benzimidazol-2-yl}carbamate methyl{6-[(2-{[(5-chloro-2-fluorophenyl)amino]carbonyl}phenyl)carbonyl]-1H-benzimidazol-2-yl}carbamate methyl{6-[(2-{[(3-iodophenyl)amino]carbonyl}phenyl)carbonyl]-1H-benzimidazol-2-yl}carbamate methyl(6-{[2-({[3-(1-methylethyl)phenyl]amino}carbonyl)phenyl]carbonyl}-1H-benzimidazol-2-yl)carbamate methyl{6-[(2-{[(3-thienylmethyl)amino]carbonyl}phenyl)carbonyl]-1H-benzimidazol-2-yl}carbamate methyl{6-[(2-{[(3-bromo-4-fluorophenyl)amino]carbonyl}phenyl)carbonyl]-1H-benzimidazol-2-yl}carbamate methyl{6-[(2-{[(3-chloro-2-fluorophenyl)amino]carbonyl}phenyl)carbonyl]-1H-benzimidazol-2-yl}carbamate methyl{6-[(2-{[(4-fluoro-3-methylphenyl)amino]carbonyl}phenyl)carbonyl]-1H-benzimidazol-2-yl}carbamate methyl{6-[(2-{[(5-bromo-2-fluorophenyl)amino]carbonyl}phenyl)carbonyl]-1H-benzimidazol-2-yl}carbamate methyl{6-[(2-{[(5-bromo-2,4-difluorophenyl)amino]carbonyl}phenyl)carbonyl]-1H-benzimidazol-2-yl}carbamate methyl{6-[(2-{[(5-chloro-2,4-difluorophenyl)amino]carbonyl}phenyl)carbonyl]-1H-benzimidazol-2-yl}carbamate methyl{6-[(2-{[(3-bromo-2-fluorophenyl)amino]carbonyl}phenyl)carbonyl]-1H-benzimidazol-2-yl}carbamate methyl{6-[(2-{[(3-ethenylphenyl)amino]carbonyl}phenyl)carbonyl]-1H-benzimidazol-2-yl}carbamate methyl{6-[(2-{[(3-ethynyl-2-fluorophenyl)amino]carbonyl}phenyl)carbonyl]-1H-benzimidazol-2-yl}carbamate methyl{6-[(2-{[(5-chloro-2-methylphenyl)amino]carbonyl}phenyl)carbonyl]-1H-benzimidazol-2-yl}carbamate methyl{6-[(2-{[(5-bromo-2-methylphenyl)amino]carbonyl}phenyl)carbonyl]-1H-benzimidazol-2-yl}carbamate methyl{6-[(2-{[(2-fluoro-3-iodophenyl)amino]carbonyl}phenyl)carbonyl]-1H-benzimidazol-2-yl}carbamate methyl{6-[(2-{[(3-ethenyl-2-fluorophenyl)amino]carbonyl}phenyl)carbonyl]-1H-benzimidazol-2-yl}carbamate; or methyl{6-[(2-{[(2-fluoro-5-methylphenyl)amino]carbonyl}phenyl)carbonyl]-1H-benzimidazol-2-yl}carbamate;

or a pharmaceutically acceptable salt of any of the above compounds.

4. The method according to claim 2, wherein the compound is selected from:

6-(2-butyl-1-hydroxy-3-oxo-2,3-dihydro-1H-isoindol-1-yl)-2H-1,4-benzoxazin-3(4H)-one
6-(1-hydroxy-3-oxo-2-phenyl-2,3-dihydro-1H-isoindol-1-yl)-2H-1,4-benzoxazin-3(4H)-one
6-{2-[(3-bromophenyl)methyl]-1-hydroxy-3-oxo-2,3-dihydro-1H-isoindol-1-yl}-2H-1,4-benzoxazin-3(4H)-one
methyl{5-[1-hydroxy-3-oxo-2-(phenylmethyl)-2,3-dihydro-1H-isoindol-1-yl]-1H-benzimidazol-2-yl}carbamate
6-[2-(3-chlorophenyl)-1-hydroxy-3-oxo-2,3-dihydro-1H-isoindol-1-yl]-2H-1,4-benzoxazin-3(4H)-one
3-(2-{[3,5-bis(methyloxy)phenyl]amino}-1H-benzimidazol-5-yl)-3-hydroxy-2-phenyl-2,3-dihydro-1H-isoindol-1-one
5-[1-hydroxy-3-oxo-2-(phenylmethyl)-2,3-dihydro-1H-isoindol-1-yl]-N-methyl-1H-benzimidazole-2-carboxamide
7-[1-hydroxy-3-oxo-2-(phenylmethyl)-2,3-dihydro-1H-isoindol-1-yl]-3,4-dihydroquinoxalin-2(1H)-one
6-{2-[(3-chlorophenyl)methyl]-1-hydroxy-3-oxo-2,3-dihydro-1H-isoindol-1-yl}-2H-1,4-benzoxazin-3(4H)-one
6-{2-[(2-chlorophenyl)methyl]-1-hydroxy-3-oxo-2,3-dihydro-1H-isoindol-1-yl}-2H-1,4-benzoxazin-3(4H)-one
6-{2-[(3-fluorophenyl)methyl]-1-hydroxy-3-oxo-2,3-dihydro-1H-isoindol-1-yl}-2H-1,4-benzoxazin-3(4H)-one
6-{2-[(2-fluorophenyl)methyl]-1-hydroxy-3-oxo-2,3-dihydro-1H-isoindol-1-yl}-2H-1,4-benzoxazin-3(4H)-one
6-[2-(3-fluorophenyl)-1-hydroxy-3-oxo-2,3-dihydro-1H-isoindol-1-yl]-2H-1,4-benzoxazin-3(4H)-one
6-[1-hydroxy-2-(3-iodophenyl)-3-oxo-2,3-dihydro-1H-isoindol-1-yl]-2H-1,4-benzoxazin-3(4H)-one
6-[2-(3-bromophenyl)-1-hydroxy-3-oxo-2,3-dihydro-1H-isoindol-1-yl]-2H-1,4-benzoxazin-3(4H)-one
6-[1-hydroxy-2-(3-nitrophenyl)-3-oxo-2,3-dihydro-1H-isoindol-1-yl]-2H-1,4-benzoxazin-3(4H)-one
6-{1-hydroxy-2-[3-(methyloxy)phenyl]-3-oxo-2,3-dihydro-1H-isoindol-1-yl}-2H-1,4-benzoxazin-3(4H)-one
6-[1-hydroxy-2-(3-methylphenyl)-3-oxo-2,3-dihydro-1H-isoindol-1-yl]-2H-1,4-benzoxazin-3(4H)-one
methyl[6-(1-hydroxy-3-oxo-2-phenyl-2,3-dihydro-1H-isoindol-1-yl)-1H-benzimidazol-2-yl]carbamate
6-[2-(2-aminophenyl)-1-hydroxy-3-oxo-2,3-dihydro-1H-isoindol-1-yl]-2H-1,4-benzoxazin-3(4H)-one
6-{[2-(3-phenyl-1,2,4-oxadiazol-5-yl)phenyl]carbonyl}-2H-1,4-benzoxazin-3(4H)-one
6-{[2-(1H-benzimidazol-2-yl)phenyl]carbonyl}-2H-1,4-benzoxazin-3(4H)-one
6-(1-hydroxy-3-oxo-2-{[2-(trifluoromethyl)phenyl]methyl}-2,3-dihydro-1H-isoindol-1-yl)-2H-1,4-benzoxazin-3(4H)-one
6-{2-[(5-bromo-2-fluorophenyl)methyl]-1-hydroxy-3-oxo-2,3-dihydro-1H-isoindol-1-yl}-2H-1,4-benzoxazin-3(4H)-one
6-{1-hydroxy-2-[(3-nitrophenyl)methyl]-3-oxo-2,3-dihydro-1H-isoindol-1-yl}-2H-1,4-benzoxazin-3(4H)-one
6-{1-hydroxy-2-[(3-iodophenyl)methyl]-3-oxo-2,3-dihydro-1H-isoindol-1-yl}-2H-1,4-benzoxazin-3(4H)-one
6-[2-(3,4-difluorophenyl)-1-hydroxy-3-oxo-2,3-dihydro-1H-isoindol-1-yl]-2H-1,4-benzoxazin-3(4H)-one
6-{1-hydroxy-2-[3-(1-methylethyl)phenyl]-3-oxo-2,3-dihydro-1H-isoindol-1-yl}-2H-1,4-benzoxazin-3(4H)-one
6-{1-hydroxy-3-oxo-2-[3-(trifluoromethyl)phenyl]-2,3-dihydro-1H-isoindol-1-yl}-2H-1,4-benzoxazin-3(4H)-one
3-[1-hydroxy-3-oxo-1-(3-oxo-3,4-dihydro-2H-1,4-benzoxazin-6-yl)-1,3-dihydro-2H-isoindol-2-yl]benzenesulfonamide
6-{2-[5-chloro-2-(methyloxy)phenyl]-1-hydroxy-3-oxo-2,3-dihydro-1H-isoindol-1-yl}-2H-1,4-benzoxazin-3(4H)-one
6-[2-(3-fluoro-5-iodophenyl)-1-hydroxy-3-oxo-2,3-dihydro-1H-isoindol-1-yl]-2H-1,4-benzoxazin-3(4H)-one
6-[2-(3-aminophenyl)-1-hydroxy-3-oxo-2,3-dihydro-1H-isoindol-1-yl]-2H-1,4-benzoxazin-3(4H)-one
6-[2-(3,5-difluorophenyl)-1-hydroxy-3-oxo-2,3-dihydro-1H-isoindol-1-yl]-2H-1,4-benzoxazin-3(4H)-one
3-[1-hydroxy-3-oxo-1-(3-oxo-3,4-dihydro-2H-1,4-benzoxazin-6-yl)-1,3-dihydro-2H-isoindol-2-yl]benzonitrile
6-[2-(2-chlorophenyl)-1-hydroxy-3-oxo-2,3-dihydro-1H-isoindol-1-yl]-2H-1,4-benzoxazin-3(4H)-one
6-[2-(3-amino-5-chlorophenyl)-1-hydroxy-3-oxo-2,3-dihydro-1H-isoindol-1-yl]-2H-1,4-benzoxazin-3(4H)-one
6-[2-(5-chloro-2-methylphenyl)-1-hydroxy-3-oxo-2,3-dihydro-1H-isoindol-1-yl]-2H-1,4-benzoxazin-3(4H)-one
6-[2-(3-chloro-2-methylphenyl)-1-hydroxy-3-oxo-2,3-dihydro-1H-isoindol-1-yl]-2H-1,4-benzoxazin-3(4H)-one
6-[2-(3-ethylphenyl)-1-hydroxy-3-oxo-2,3-dihydro-1H-isoindol-1-yl]-2H-1,4-benzoxazin-3(4H)-one
6-[2-(3-ethynylphenyl)-1-hydroxy-3-oxo-2,3-dihydro-1H-isoindol-1-yl]-2H-1,4-benzoxazin-3(4H)-one
6-[1-hydroxy-2-(3-hydroxyphenyl)-3-oxo-2,3-dihydro-1H-isoindol-1-yl]-2H-1,4-benzoxazin-3(4H)-one
6-{1-hydroxy-3-oxo-2-[3-(phenyloxy)phenyl]-2,3-dihydro-1H-isoindol-1-yl}-2H-1,4-benzoxazin-3(4H)-one
3-[1-hydroxy-3-oxo-1-(3-oxo-3,4-dihydro-2H-1,4-benzoxazin-6-yl)-1,3-dihydro-2H-isoindol-2-yl]benzamide
6-{1-hydroxy-2-[3-(hydroxymethyl)phenyl]-3-oxo-2,3-dihydro-1H-isoindol-1-yl}-2H-1,4-benzoxazin-3(4H)-one
6-[2-(2-fluorophenyl)-1-hydroxy-3-oxo-2,3-dihydro-1H-isoindol-1-yl]-2H-1,4-benzoxazin-3(4H)-one
3-hydroxy-3-[2-(methylamino)-1H-benzimidazol-5-yl]-2-(phenylmethyl)-2,3-dihydro-1H-isoindol-1-one
6-(2-{3-[(dimethylamino)methyl]phenyl}-1-hydroxy-3-oxo-2,3-dihydro-1H-isoindol-1-yl)-2H-1,4-benzoxazin-3(4H)-one
6-[2-(3,5-dichlorophenyl)-1-hydroxy-3-oxo-2,3-dihydro-1H-isoindol-1-yl]-2H-1,4-benzoxazin-3(4H)-one
6-[1-hydroxy-2-(2-methylphenyl)-3-oxo-2,3-dihydro-1H-isoindol-1-yl]-2H-1,4-benzoxazin-3(4H)-one
N-methyl-2-[(3-oxo-3,4-dihydro-2H-1,4-benzoxazin-6-yl)carbonyl]-N-phenylbenzamide
methyl{5-[1-(ethyloxy)-3-oxo-2-(phenylmethyl)-2,3-dihydro-1H-isoindol-1-yl]-1H-benzimidazol-2-yl}carbamate
Phenylmethyl2-[(2-{[(methyloxy)carbonyl]amino}-1H-benzimidazol-5-yl)carbonyl]benzoate 3-hydroxy-3-(1H-indazol-5-yl)-2-(phenylmethyl)-2,3-dihydro-1H-isoindol-1-one
ethyl{5-[1-hydroxy-3-oxo-2-(phenylmethyl)-2,3-dihydro-1H-isoindol-1-yl]-1H-benzimidazol-2-yl}carbamate
2-methylpropyl{5-[1-hydroxy-3-oxo-2-(phenylmethyl)-2,3-dihydro-1H-isoindol-1-yl]-1H-benzimidazol-2-yl}carbamate
methyl{5-[1-hydroxy-3-oxo-2-(2-thienylmethyl)-2,3-dihydro-1H-isoindol-1-yl]-1H-benzimidazol-2-yl}carbamate
3-(2-amino-1H-benzimidazol-5-yl)-3-hydroxy-2-(phenylmethyl)-2,3-dihydro-1H-isoindol-1-one
3-(methyloxy)butyl{5-[1-hydroxy-3-oxo-2-(phenylmethyl)-2,3-dihydro-1H-isoindol-1-yl]-1H-benzimidazol-2-yl}carbamate
methyl(5-{1-hydroxy-3-oxo-2-[(1R)-1-phenylethyl]-2,3-dihydro-1H-isoindol-1-yl}-1H-benzimidazol-2-yl)carbamate
methyl(5-{1-hydroxy-3-oxo-2-[(1S)-1-phenylethyl]-2,3-dihydro-1H-isoindol-1-yl}-1H-benzimidazol-2-yl)carbamate
2-(methyloxy)ethyl{5-[1-hydroxy-3-oxo-2-(phenylmethyl)-2,3-dihydro-1H-isoindol-1-yl]-1H-benzimidazol-2-yl}carbamate
prop-2-yn-1-yl{5-[1-hydroxy-3-oxo-2-(phenylmethyl)-2,3-dihydro-1H-isoindol-1-yl]-1H-benzimidazol-2-yl}carbamate
but-2-yn-1-yl{5-[1-hydroxy-3-oxo-2-(phenylmethyl)-2,3-dihydro-1H-isoindol-1-yl]-1H-benzimidazol-2-yl}carbamate
1-methylethyl{5-[1-hydroxy-3-oxo-2-(phenylmethyl)-2,3-dihydro-1H-isoindol-1-yl]-1H-benzimidazol-2-yl}carbamate
methyl{5-[2-(2,3-dihydro-1H-inden-2-yl)-1-hydroxy-3-oxo-2,3-dihydro-1H-isoindol-1-yl]-1H-benzimidazol-2-yl}carbamate
methyl{5-[1-hydroxy-3-oxo-2-(pyridin-4-ylmethyl)-2,3-dihydro-1H-isoindol-1-yl]-1H-benzimidazol-2-yl}carbamate
methyl{5-[1-hydroxy-3-oxo-2-(pyridin-3-ylmethyl)-2,3-dihydro-1H-isoindol-1-yl]-1H-benzimidazol-2-yl}carbamate
methyl(6-{2-[(3-fluorophenyl)methyl]-1-hydroxy-3-oxo-2,3-dihydro-1H-isoindol-1-yl}-1H-benzimidazol-2-yl)carbamate
methyl{5-[1-hydroxy-2-(3-methylphenyl)-3-oxo-2,3-dihydro-1H-isoindol-1-yl]-1H-benzimidazol-2-yl}carbamate
methyl[5-(1-hydroxy-2-{[2-(methyloxy)phenyl]methyl}-3-oxo-2,3-dihydro-1H-isoindol-1-yl)-1H-benzimidazol-2-yl]carbamate
methyl[5-(1-hydroxy-2-{[3-(methyloxy)phenyl]methyl}-3-oxo-2,3-dihydro-1H-isoindol-1-yl)-1H-benzimidazol-2-yl]carbamate
methyl(6-{2-[(4-fluorophenyl)methyl]-1-hydroxy-3-oxo-2,3-dihydro-1H-isoindol-1-yl}-1H-benzimidazol-2-yl)carbamate
methyl(6-{2-[(3-bromophenyl)methyl]-1-hydroxy-3-oxo-2,3-dihydro-1H-isoindol-1-yl}-1H-benzimidazol-2-yl)carbamate
methyl(5-{1-hydroxy-2-[(3-iodophenyl)methyl]-3-oxo-2,3-dihydro-1H-isoindol-1-yl}-1H-benzimidazol-2-yl)carbamate
methyl(5-{2-[(3-chlorophenyl)methyl]-1-hydroxy-3-oxo-2,3-dihydro-1H-isoindol-1-yl}-1H-benzimidazol-2-yl)carbamate
methyl(5-{2-[(2-fluorophenyl)methyl]-1-hydroxy-3-oxo-2,3-dihydro-1H-isoindol-1-yl}-1H-benzimidazol-2-yl)carbamate
methyl{5-[1-hydroxy-3-oxo-2-(pyridin-2-ylmethyl)-2,3-dihydro-1H-isoindol-1-yl]-1H-benzimidazol-2-yl}carbamate
phenylmethyl{5-[1-hydroxy-3-oxo-2-(phenylmethyl)-2,3-dihydro-1H-isoindol-1-yl]-1H-benzimidazol-2-yl}carbamate
2-fluoroethyl{5-[1-hydroxy-3-oxo-2-(phenylmethyl)-2,3-dihydro-1H-isoindol-1-yl]-1H-benzimidazol-2-yl}carbamate
propyl{5-[1-hydroxy-3-oxo-2-(phenylmethyl)-2,3-dihydro-1H-isoindol-1-yl]-1H-benzimidazol-2-yl}carbamate
methyl(5-{1-hydroxy-2-[4-(methyloxy)phenyl]-3-oxo-2,3-dihydro-1H-isoindol-1-yl}-1H-benzimidazol-2-yl)carbamate
methyl(5-{2-[(2-chlorophenyl)methyl]-1-hydroxy-3-oxo-2,3-dihydro-1H-isoindol-1-yl}-1H-benzimidazol-2-yl)carbamate
methyl(5-{2-[(2-bromophenyl)methyl]-1-hydroxy-3-oxo-2,3-dihydro-1H-isoindol-1-yl}-1H-benzimidazol-2-yl)carbamate
methyl(5-{1-hydroxy-2-[(3-methylphenyl)methyl]-3-oxo-2,3-dihydro-1H-isoindol-1-yl}-1H-benzimidazol-2-yl)carbamate
methyl(5-{1-hydroxy-2-[(4-methylphenyl)methyl]-3-oxo-2,3-dihydro-1H-isoindol-1-yl}-1H-benzimidazol-2-yl)carbamate
methyl(5-{1-hydroxy-2-[(2-methylphenyl)methyl]-3-oxo-2,3-dihydro-1H-isoindol-1-yl}-1H-benzimidazol-2-yl)carbamate
methyl{5-[2-(3-bromophenyl)-1-hydroxy-3-oxo-2,3-dihydro-1H-isoindol-1-yl]-1H-benzimidazol-2-yl}carbamate
methyl{5-[2-(3-chlorophenyl)-1-hydroxy-3-oxo-2,3-dihydro-1H-isoindol-1-yl]-1H-benzimidazol-2-yl}carbamate
methyl{5-[2-(3-fluorophenyl)-1-hydroxy-3-oxo-2,3-dihydro-1H-isoindol-1-yl]-1H-benzimidazol-2-yl}carbamate
methyl(5-{1-hydroxy-2-[3-(methyloxy)phenyl]-3-oxo-2,3-dihydro-1H-isoindol-1-yl}-1H-benzimidazol-2-yl)carbamate
methyl{5-[2-(4-bromophenyl)-1-hydroxy-3-oxo-2,3-dihydro-1H-isoindol-1-yl]-1H-benzimidazol-2-yl}carbamate
methyl{5-[2-(4-chlorophenyl)-1-hydroxy-3-oxo-2,3-dihydro-1H-isoindol-1-yl]-1H-benzimidazol-2-yl}carbamate
methyl{5-[2-(4-fluorophenyl)-1-hydroxy-3-oxo-2,3-dihydro-1H-isoindol-1-yl]-1H-benzimidazol-2-yl}carbamate
methyl{5-[2-(3,5-dimethylphenyl)-1-hydroxy-3-oxo-2,3-dihydro-1H-isoindol-1-yl]-1H-benzimidazol-2-yl}carbamate
methyl{5-[2-(2-fluorophenyl)-1-hydroxy-3-oxo-2,3-dihydro-1H-isoindol-1-yl]-1H-benzimidazol-2-yl}carbamate
methyl{5-[2-(2-chlorophenyl)-1-hydroxy-3-oxo-2,3-dihydro-1H-isoindol-1-yl]-1H-benzimidazol-2-yl}carbamate
methyl{5-[1-hydroxy-2-(2-methylphenyl)-3-oxo-2,3-dihydro-1H-isoindol-1-yl]-1H-benzimidazol-2-yl}carbamate methyl(5-{1-hydroxy-2-[2-(methyloxy)phenyl]-3-oxo-2,3-dihydro-1H-isoindol-1-yl}-1H-benzimidazol-2-yl)carbamate methyl{5-[1-hydroxy-2-(4-methylphenyl)-3-oxo-2,3-dihydro-1H-isoindol-1-yl]-1H-benzimidazol-2-yl}carbamate methyl(5-{1-hydroxy-3-oxo-2-[3-(trifluoromethyl)phenyl]-2,3-dihydro-1H-isoindol-1-yl}-1H-benzimidazol-2-yl)carbamate but-2-yn-1-yl(5-{1-hydroxy-3-oxo-2-[(1R)-1-phenylethyl]-2,3-dihydro-1H-isoindol-1-yl}-1H-benzimidazol-2-yl)carbamate N-ethyl-N'-{5-[1-hydroxy-3-oxo-2-(phenylmethyl)-2,3-dihydro-1H-isoindol-1-yl]-1H-benzimidazol-2-yl}urea phenylmethyl(5-{1-hydroxy-3-oxo-2-[(1R)-1-phenylethyl]-2,3-dihydro-1H-isoindol-1-yl}-1H-benzimidazol-2-yl)carbamate methyl{6-[2-(3-amino-5-chlorophenyl)-1-hydroxy-3-oxo-2,3-dihydro-1H-isoindol-1-yl]-1H-benzimidazol-2-yl}carbamate piperidin-4-ylmethyl{5-[1-hydroxy-3-oxo-2-(phenylmethyl)-2,3-dihydro-1H-isoindol-1-yl]-1H-benzimidazol-2-yl}carbamate methyl{5-[2-(cyclopropylmethyl)-1-hydroxy-3-oxo-2,3-dihydro-1H-isoindol-1-yl]-1H-benzimidazol-2-yl}carbamate methyl{5-[2-(2,2-dimethylpropyl)-1-hydroxy-3-oxo-2,3-dihydro-1H-isoindol-1-yl]-1H-benzimidazol-2-yl}carbamate methyl{5-[2-(3,5-dichlorophenyl)-1-hydroxy-3-oxo-2,3-dihydro-1H-isoindol-1-yl]-1H-benzimidazol-2-yl}carbamate methyl{5-[2-(3,5-difluorophenyl)-1-hydroxy-3-oxo-2,3-dihydro-1H-isoindol-1-yl]-1H-benzimidazol-2-yl}carbamate N-ethyl-N'-(5-{1-hydroxy-3-oxo-2-[(1R)-1-phenylethyl]-2,3-dihydro-1H-isoindol-1-yl}-1H-benzimidazol-2-yl)urea N'-{5-[1-hydroxy-3-oxo-2-(phenylmethyl)-2,3-dihydro-1H-isoindol-1-yl]-1H-benzimidazol-2-yl}-N,N-dimethylurea methyl{5-[2-(3-{[2-(dimethylamino)ethyl]oxy}phenyl)-1-hydroxy-3-oxo-2,3-dihydro-1H-isoindol-1-yl]-1H-benzimidazol-2-yl}carbamate 3-(4-methylpiperazin-1-yl)propyl{6-[1-hydroxy-3-oxo-2-(phenylmethyl)-2,3-dihydro-1H-isoindol-1-yl]-1H-benzimidazol-2-yl}carbamate methyl{5-[2-(cyclohexylmethyl)-1-hydroxy-3-oxo-2,3-dihydro-1H-isoindol-1-yl]-1H-benzimidazol-2-yl}carbamate methyl{5-[1-hydroxy-2-(2-methylpropyl)-3-oxo-2,3-dihydro-1H-isoindol-1-yl]-1H-benzimidazol-2-yl}carbamate methyl{5-[1-hydroxy-3-oxo-2-(1,3-thiazol-2-ylmethyl)-2,3-dihydro-1H-isoindol-1-yl]-1H-benzimidazol-2-yl}carbamate methyl{5-[2-(3,4-difluorophenyl)-1-hydroxy-3-oxo-2,3-dihydro-1H-isoindol-1-yl]-1H-benzimidazol-2-yl}carbamate methyl(5-{2-[1-(3,5-difluorophenyl)ethyl]-1-hydroxy-3-oxo-2,3-dihydro-1H-isoindol-1-yl}-1H-benzimidazol-2-yl)carbamate methyl(5-{2-[1-(3-fluorophenyl)ethyl]-1-hydroxy-3-oxo-2,3-dihydro-1H-isoindol-1-yl}-1H-benzimidazol-2-yl)carbamate methyl[5-(2-cyclohexyl-1-hydroxy-3-oxo-2,3-dihydro-1H-isoindol-1-yl]-1H-benzimidazol-2-yl]carbamate methyl{5-[2-(2,5-difluorophenyl)-1-hydroxy-3-oxo-2,3-dihydro-1H-isoindol-1-yl]-1H-benzimidazol-2-yl}carbamate N-{5-[1-hydroxy-3-oxo-(phenylmethyl)-2,3-dihydro-1H-isoindol-1-yl]-1H-benzimidazol-2-yl}-N'-(phenylmethyl)urea piperidin-4-yl{5-[1-hydroxy-3-oxo-2-(phenylmethyl)-2,3-dihydro-1H-isoindol-1-yl]-1H-benzimidazol-2-yl}carbamate N-{5-[1-hydroxy-3-oxo-2-(phenylmethyl)-2,3-dihydro-1H-isoindol-1-yl]-1H-benzimidazol-2-yl}-N'-methylurea methyl(5-{2-[1-(2-fluorophenyl)ethyl]-1-hydroxy-3-oxo-2,3-dihydro-1H-isoindol-1-yl}-1H-benzimidazol-2-yl)carbamate methyl(5-{1-hydroxy-3-oxo-2-[1-(2-thienyl)ethyl]-2,3-dihydro-1H-isoindol-1-yl}-1H-benzimidazol-2-yl)carbamate methyl(5-{2-[1-(3-chlorophenyl)ethyl]-1-hydroxy-3-oxo-2,3-dihydro-1H-isoindol-1-yl}-1H-benzimidazol-2-yl)carbamate methyl(5-{1-hydroxy-2-[3-methyl-5-(trifluoromethyl)phenyl]-3-oxo-2,3-dihydro-1H-isoindol-1-yl}-1H-benzimidazol-2-yl)carbamate N-{5-[1-hydroxy-3-oxo-2-(phenylmethyl)-2,3-dihydro-1H-isoindol-1-yl]-1H-benzimidazol-2-yl}propanamide methyl{5-[2-(3,4-dichlorophenyl)-1-hydroxy-3-oxo-2,3-dihydro-1H-isoindol-1-yl]-1H-benzimidazol-2-yl}carbamate methyl{5-[2-(3-ethylphenyl)-1-hydroxy-3-oxo-2,3-dihydro-1H-isoindol-1-yl]-1H-benzimidazol-2-yl}carbamate methyl{5-[2-(3-ethynylphenyl)-1-hydroxy-3-oxo-2,3-dihydro-1H-isoindol-1-yl]-1H-benzimidazol-2-yl}carbamate methyl{5-[2-(4-chloro-3-methylphenyl)-1-hydroxy-3-oxo-2,3-dihydro-1H-isoindol-1-yl]-1H-benzimidazol-2-yl}carbamate methyl[5-(1-hydroxy-3-oxo-2-{1-[3-(trifluoromethyl)phenyl]ethyl}-2,3-dihydro-1H-isoindol-1-yl)-1H-benzimidazol-2-yl]carbamate methyl(5-{1-hydroxy-3-oxo-2-[(1R)-1-phenylpropyl]-2,3-dihydro-1H-isoindol-1-yl}-1H-benzimidazol-2-yl)carbamate methyl[5-(1-hydroxy-3-oxo-2-{2-[(trifluoromethyl)oxy]phenyl}-2,3-dihydro-1H-isoindol-1-yl)-1H-benzimidazol-2-yl]carbamate methyl{5-[2-(2,3-difluorophenyl)-1-hydroxy-3-oxo-2,3-dihydro-1H-isoindol-1-yl]-1H-benzimidazol-2-yl}carbamate cyclohexyl{5-[1-hydroxy-3-oxo-2-(phenylmethyl)-2,3-dihydro-1H-isoindol-1-yl]-1H-benzimidazol-2-yl}carbamate tetrahydrofuran-2-ylmethyl{5-[1-hydroxy-3-oxo-2-(phenylmethyl)-2,3-dihydro-1H-isoindol-1-yl]-1H-benzimidazol-2-yl}carbamate cyclopropylmethyl{5-[1-hydroxy-3-oxo-2-(phenylmethyl)-2,3-dihydro-1H-isoindol-1-yl]-1H-benzimidazol-2-yl}carbamate N-{5-[1-hydroxy-3-oxo-2-(phenylmethyl)-2,3-dihydro-1H-isoindol-1-yl]-1H-benzimidazol-2-yl}morpholine-4-carboxamide methyl{5-[2-(cyclopentylmethyl)-1-hydroxy-3-oxo-2,3-dihydro-1H-isoindol-1-yl]-1H-benzimidazol-2-yl}carbamate methyl{5-[2-(2,3-dimethylphenyl)-1-hydroxy-3-oxo-2,3-dihydro-1H-isoindol-1-yl]-1H-benzimidazol-2-yl}carbamate methyl{5-[2-(2,3-dihydro-1H-inden-1-yl)-1-hydroxy-3-oxo-2,3-dihydro-1H-isoindol-1-yl]-1H-benzimidazol-2-yl}carbamate methyl(2S)-cyclohexyl[1-hydroxy-1-(2-{[(methyloxy)carbonyl]amino}-1H-benzimidazol-5-yl)-3-oxo-1,3-dihydro-2H-isoindol-2-yl]ethanoate methyl{5-[2-(2,6-difluorophenyl)-1-hydroxy-3-oxo-2,3-dihydro-1H-isoindol-1-yl]-1H-benzimidazol-2-yl}carbamate methyl{5-[2-(3-chloro-4-fluorophenyl)-1-hydroxy-3-oxo-2,3-dihydro-1H-isoindol-1-yl]-1H-benzimidazol-2-yl}carbamate but-3-en-1-yl{5-[1-hydroxy-3-oxo-2-(phenylmethyl)-2,3-dihydro-1H-isoindol-1-yl]-1H-benzimidazol-2-yl}carbamate 2,2,2-trifluoroethyl{5-[1-hydroxy-3-oxo-2-(phenylmethyl)-2,3-dihydro-1H-isoindol-1-yl]-1H-benzimidazol-2-yl}carbamate methyl{5-[2-(5-chloro-2-fluorophenyl)-1-hydroxy-3-oxo-2,3-dihydro-1H-isoindol-1-yl]-1H-benzimidazol-2-yl}carbamate methyl(5-{2-[1-(5-chloro-2-methylphenyl)ethyl]-1-hydroxy-3-oxo-2,3-dihydro-1H-isoindol-1-yl}-1H-benzimidazol-2-yl)carbamate methyl(5-{1-hydroxy-3-oxo-2-[(1 S)-1-phenylpropyl]-2,3-dihydro-1H-isoindol-1-yl}-1H-benzimidazol-2-yl)carbamate methyl(5-{2-[1-(3-chloro-2-methylphenyl)ethyl]-1-hydroxy-3-oxo-2,3-dihydro-1H-isoindol-1-yl}-1H-benzimidazol-2-yl)carbamate methyl(5-{1-hydroxy-2-[1-(5-methyl-2-thienyl)ethyl]-3-oxo-2,3-dihydro-1H-isoindol-1-yl}-1H-benzimidazol-2-yl)carbamate methyl(5-{2-[1-(5-chloro-2-thienyl)ethyl]-1-hydroxy-3-oxo-2,3-dihydro-1H-isoindol-1-yl}-1H-benzimidazol-2-yl)carbamate methyl{5-[1-hydroxy-2-(3-iodophenyl)-3-oxo-2,3-dihydro-1H-isoindol-1-yl]-1H-benzimidazol-2-yl}carbamate methyl(5-{1-hydroxy-2-[3-(1-methylethyl)phenyl]-3-oxo-2,3-dihydro-1H-isoindol-1-yl}-1H-benzimidazol-2-yl)carbamate methyl{5-[2-(furan-2-ylmethyl)-1-hydroxy-3-oxo-2,3-dihydro-1H-isoindol-1-yl]-1H-benzimidazol-2-yl}carbamate methyl{5-[1-hydroxy-3-oxo-2-(3-thienylmethyl)-2,3-dihydro-1H-isoindol-1-yl]-1H-benzimidazol-2-yl}carbamate methyl{5-[2-(cyclobutylmethyl)-1-hydroxy-3-oxo-2,3-dihydro-1H-isoindol-1-yl]-1H-benzimidazol-2-yl}carbamate 3,3,3-trifluoro-2-hydroxy-N-{5-[1-hydroxy-3-oxo-2-(phenylmethyl)-2,3-dihydro-1H-isoindol-1-yl]-1H-benzimidazol-2-yl}-2-(trifluoromethyl)propanamide methyl(5-{1-hydroxy-2-[1-(4-methyl-2-thienyl)ethyl]-3-oxo-2,3-dihydro-1H-isoindol-1-yl}-1H-benzimidazol-2-yl)carbamate methyl(5-{2-[1-(4-bromo-2-thienyl)ethyl]-1-hydroxy-3-oxo-2,3-dihydro-1H-isoindol-1-yl}-1H-benzimidazol-2-yl)carbamate methyl{5-[1-hydroxy-2-(3-{[2-(methyloxy)ethyl]oxy}phenyl)-3-oxo-2,3-dihydro-1H-isoindol-1-yl]-1H-benzimidazol-2-yl}carbamate tetrahydrofuran-3-ylmethyl{5-[1-hydroxy-3-oxo-2-(phenylmethyl)-2,3-dihydro-1H-isoindol-1-yl]-1H-benzimidazol-2-yl}carbamate N-{5-[1-hydroxy-3-oxo-2-(phenylmethyl)-2,3-dihydro-1H-isoindol-1-yl]-1H-benzimidazol-2-yl}piperidine-1-carboxamide methyl{5-[2-(3-bromo-4-fluorophenyl)-1-hydroxy-3-oxo-2,3-dihydro-1H-isoindol-1-yl]-1H-benzimidazol-2-yl}carbamate 2,3-dihydroxypropyl{5-[1-hydroxy-3-oxo-2-(phenylmethyl)-2,3-dihydro-1H-isoindol-1-yl]-1H-benzimidazol-2-yl}carbamate methyl{5-[1-hydroxy-3-oxo-2-(tetrahydrofuran-2-ylmethyl)-2,3-dihydro-1H-isoindol-1-yl]-1H-benzimidazol-2-yl}carbamate methyl(5-{2-[3-(aminocarbonyl)phenyl]-1-hydroxy-3-oxo-2,3-dihydro-1H-isoindol-1-yl}-1H-benzimidazol-2-yl)carbamate 4,4,4-trifluoro-3-hydroxy-N-{5-[1-hydroxy-3-oxo-2-(phenylmethyl)-2,3-dihydro-1H-isoindol-1-yl]-1H-benzimidazol-2-yl}-3-(trifluoromethyl)butanamide methyl(5-{1-hydroxy-2-[3-(methylsulfonyl)phenyl]-3-oxo-2,3-dihydro-1H-isoindol-1-yl}-1H-benzimidazol-2-yl)carbamate methyl(5-{1-hydroxy-3-oxo-2-[3-(phenyloxy)phenyl]-2,3-dihydro-1H-isoindol-1-yl}-1H-benzimidazol-2-yl)carbamate methyl[5-(1-hydroxy-3-oxo-2-{3-[(phenylmethyl)oxy]phenyl}-2,3-dihydro-1H-isoindol-1-yl)-1H-benzimidazol-2-yl]carbamate methyl[5-(2-biphenyl-3-yl-1-hydroxy-3-oxo-2,3-dihydro-1H-isoindol-1-yl)-1H-benzimidazol-2-yl]carbamate 2,2-dimethyl-3-[(phenylmethyl)oxy]propyl{5-[1-hydroxy-3-oxo-2-(phenylmethyl)-2,3-dihydro-1H-isoindol-1-yl]-1H-benzimidazol-2-yl}carbamate methyl{5-[2-(3-chloro-2-fluorophenyl)-1-hydroxy-3-oxo-2,3-dihydro-1H-isoindol-1-yl]-1H-benzimidazol-2-yl}carbamate methyl{5-[2-(3-cyanophenyl)-1-hydroxy-3-oxo-2,3-dihydro-1H-isoindol-1-yl]-1H-benzimidazol-2-yl}carbamate methyl{5-[2-(3-ethynyl-4-fluorophenyl)-1-hydroxy-3-oxo-2,3-dihydro-1H-isoindol-1-yl]-1H-benzimidazol-2-yl}carbamate methyl{5-[2-(4-fluoro-3-methylphenyl)-1-hydroxy-3-oxo-2,3-dihydro-1H-isoindol-1-yl]-1H-benzimidazol-2-yl}carbamate methyl{6-[2-(3,4-dichloro-2-fluorophenyl)-1-hydroxy-3-oxo-2,3-dihydro-1H-isoindol-1-yl]-1H-benzimidazol-2-yl}carbamate

[(4S)-2,2-dimethyl-1,3-dioxolan-4-yl]methyl{5-[1-hydroxy-3-oxo-2-(phenylmethyl)-2,3-dihydro-1H-isoindol-1-yl]-1H-benzimidazol-2-yl}carbamate methyl{5-[2-(5-bromo-2-fluorophenyl)-1-hydroxy-3-oxo-2,3-dihydro-1H-isoindol-1-yl]-1H-benzimidazol-2-yl}carbamate methyl(5-{2-[3-(acetylamino)phenyl]-1-hydroxy-3-oxo-2,3-dihydro-1H-isoindol-1-yl}-1H-benzimidazol-2-yl)carbamate methyl(5-{1-hydroxy-3-oxo-2-[3-(phenylmethyl)phenyl]-2,3-dihydro-1H-isoindol-1-yl}-1H-benzimidazol-2-yl)carbamate methyl(5-{2-[1-(4-chloro-2-thienyl)ethyl]-1-hydroxy-3-oxo-2,3-dihydro-1H-isoindol-1-yl}-1H-benzimidazol-2-yl)carbamate methyl(5-{1-hydroxy-3-oxo-2-[3-(phenylcarbonyl)phenyl]-2,3-dihydro-1H-isoindol-1-yl}-1H-benzimidazol-2-yl)carbamate methyl[5-(2-{3-[(dimethylamino)methyl]phenyl}-1-hydroxy-3-oxo-2,3-dihydro-1H-isoindol-1-yl)-1H-benzimidazol-2-yl]carbamate methyl(5-{2-[3-(aminosulfonyl)phenyl]-1-hydroxy-3-oxo-2,3-dihydro-1H-isoindol-1-yl}-1H-benzimidazol-2-yl)carbamate methyl{5-[2-(3-acetylphenyl)-1-hydroxy-3-oxo-2,3-dihydro-1H-isoindol-1-yl]-1H-benzimidazol-2-yl}carbamate methyl{5-[2-(3-ethyl-4-fluorophenyl)-1-hydroxy-3-oxo-2,3-dihydro-1H-isoindol-1-yl]-1H-benzimidazol-2-yl}carbamate methyl{5-[2-(3-chloro-5-fluorophenyl)-1-hydroxy-3-oxo-2,3-dihydro-1H-isoindol-1-yl]-1H-benzimidazol-2-yl}carbamate N-{6-[1-hydroxy-3-oxo-2-(phenylmethyl)-2,3-dihydro-1H-isoindol-1-yl]-1H-benzimidazol-2-yl}-2-methylpropanamide methyl(5-{2-[1-(3-chloro-2-thienyl)ethyl]-1-hydroxy-3-oxo-2,3-dihydro-1H-isoindol-1-yl}-1H-benzimidazol-2-yl)carbamate methyl[5-(1-hydroxy-3-oxo-2-pyridin-3-yl-2,3-dihydro-1H-isoindol-1-yl)-1H-benzimidazol-2-yl]carbamate methyl(5-{1-hydroxy-3-oxo-2-[3-(phenylamino)phenyl]-2,3-dihydro-1H-isoindol-1-yl}-1H-benzimidazol-2-yl)carbamate methyl{5-[2-(5-bromo-2,4-difluorophenyl)-1-hydroxy-3-oxo-2,3-dihydro-1H-isoindol-1-yl]-1H-benzimidazol-2-yl}carbamate methyl{5-[2-(5-chloro-2,4-difluorophenyl)-1-hydroxy-3-oxo-2,3-dihydro-1H-isoindol-1-yl]-1H-benzimidazol-2-yl}carbamate methyl{5-[2-(3,5-dichloro-4-fluorophenyl)-1-hydroxy-3-oxo-2,3-dihydro-1H-isoindol-1-yl]-1H-benzimidazol-2-yl}carbamate 2,2-dimethyl-3-(methyloxy)propyl{5-[1-hydroxy-3-oxo-2-(phenylmethyl)-2,3-dihydro-1H-isoindol-1-yl]-1H-benzimidazol-2-yl}carbamate 3-hydroxy-2,2-dimethylpropyl{5-[1-hydroxy-3-oxo-2-(phenylmethyl)-2,3-dihydro-1H-isoindol-1-yl]-1H-benzimidazol-2-yl}carbamate methyl(5-{2-[1-(5-bromo-2-thienyl)ethyl]-1-hydroxy-3-oxo-2,3-dihydro-1H-isoindol-1-yl}-1H-benzimidazol-2-yl)carbamate methyl{5-[2-(4,5-dichloro-2-fluorophenyl)-1-hydroxy-3-oxo-2,3-dihydro-1H-isoindol-1-yl]-1H-benzimidazol-2-yl}carbamate methyl{5-[2-(3-bromo-2-fluorophenyl)-1-hydroxy-3-oxo-2,3-dihydro-1H-isoindol-1-yl]-1H-benzimidazol-2-yl}carbamate methyl{5-[2-(3-chloro-2,4-difluorophenyl)-1-hydroxy-3-oxo-2,3-dihydro-1H-isoindol-1-yl]-1H-benzimidazol-2-yl}carbamate N-{6-[1-hydroxy-3-oxo-2-(phenylmethyl)-2,3-dihydro-1H-isoindol-1-yl]-1H-benzimidazol-2-yl}pent-4-ynamide methyl(6-{1-methyl-3-oxo-2-[3-(trifluoromethyl)phenyl]-2,3-dihydro-1H-isoindol-1-yl}-1H-benzimidazol-2-yl)carbamate methyl[5-(1-hydroxy-3-oxo-2-{3-[(1,1,2,2-tetrafluoroethyl)oxy]phenyl}-2,3-dihydro-1H-isoindol-1-yl)-1H-benzimidazol-2-yl]carbamate methyl{5-[1-hydroxy-3-oxo-2-(3-piperidin-4-ylphenyl)-2,3-dihydro-1H-isoindol-1-yl]-1H-benzimidazol-2-yl}carbamate methyl{5-[2-(3-ethenylphenyl)-1-hydroxy-3-oxo-2,3-dihydro-1H-isoindol-1-yl]-1H-benzimidazol-2-yl}carbamate methyl(5-{2-[3-(dimethylamino)phenyl]-1-hydroxy-3-oxo-2,3-dihydro-1H-isoindol-1-yl}-1H-benzimidazol-2-yl)carbamate 2,2-difluoro-N-{6-[1-hydroxy-3-oxo-2-(phenylmethyl)-2,3-dihydro-1H-isoindol-1-yl]-1H-benzimidazol-2-yl}cyclopropanecarboxamide N-ethyl-N'-{6-[2-(4-fluorophenyl)-1-hydroxy-3-oxo-2,3-dihydro-1H-isoindol-1-yl]-1H-benzimidazol-2-yl}urea methyl{5-[2-(3-aminophenyl)-1-hydroxy-3-oxo-2,3-dihydro-1H-isoindol-1-yl]-1H-benzimidazol-2-yl}carbamate N-{5-[1-hydroxy-3-oxo-2-(phenylmethyl)-2,3-dihydro-1H-isoindol-1-yl]-1H-benzimidazol-2-yl}-4-[(phenylmethyl)oxy]butanamide N-{5-[1-hydroxy-3-oxo-2-(phenylmethyl)-2,3-dihydro-1H-isoindol-1-yl]-1H-benzimidazol-2-yl}-4-piperidin-1-ylbutanamide N-{5-[1-hydroxy-3-oxo-2-(phenylmethyl)-2,3-dihydro-1H-isoindol-1-yl]-1H-benzimidazol-2-yl}-4-(4-methylpiperazin-1-yl)butanamide N-{6-[2-(4-fluorophenyl)-1-hydroxy-3-oxo-2,3-dihydro-1H-isoindol-1-yl]-1H-benzimidazol-2-yl}butanamide methyl{6-[2-(3-bromophenyl)-5,6-dichloro-1-hydroxy-3-oxo-2,3-dihydro-1H-isoindol-1-yl]-1H-benzimidazol-2-yl}carbamate methyl[5-(1-hydroxy-2-{3-[methyl(phenyl)amino]phenyl}-3-oxo-2,3-dihydro-1H-isoindol-1-yl)-1H-benzimidazol-2-yl]carbamate methyl{5-[1-hydroxy-3-oxo-2-(phenylsulfonyl)-2,3-dihydro-1H-isoindol-1-yl]-1H-benzimidazol-2-yl}carbamate methyl{5-[(2-{[(phenylamino)carbonyl]amino}phenyl)carbonyl]-1H-benzimidazol-2-yl}carbamate methyl(5-{[2-({[(phenylmethyl)oxy]carbonyl}amino)phenyl]carbonyl}-1H-benzimidazol-2-yl)carbamate methyl[5-({2-[(2-phenylhydrazino)carbonyl]phenyl}carbonyl)-1H-benzimidazol-2-yl]carbamate methyl{5-(2-{[(phenyloxy)amino]carbonyl}phenyl)carbonyl]-1H-benzimidazol-2-yl}carbamate but-2-yn-1-yl{5-[2-(4-fluorophenyl)-1-hydroxy-3-oxo-2,3-dihydro-1H-isoindol-1-yl]-1H-benzimidazol-2-yl}carbamate N-{5-[1-hydroxy-3-oxo-2-(phenylmethyl)-2,3-dihydro-1H-isoindol-1-yl]-1H-benzimidazol-2-yl}-3-piperidin-1-ylpropanamide N-{6-[2-(4-fluorophenyl)-1-hydroxy-3-oxo-2,3-dihydro-1H-isoindol-1-yl]-1H-benzimidazol-2-yl}propanamide N-(4-fluorophenyl)-2-{[2-(pent-4-ynoylamino)-1H-benzimidazol-6-yl]carbonyl}benzamide 4-(diethylamino)-N-{5-[1-hydroxy-3-oxo-2-(phenylmethyl)-2,3-dihydro-1H-isoindol-1-yl]-1H-benzimidazol-2-yl}butanamide N-{5-[1-hydroxy-3-oxo-2-(phenylmethyl)-2,3-dihydro-1H-isoindol-1-yl]-1H-benzimidazol-2-yl}-4-pyrrolidin-1-ylbutanamide 3-piperidin-1-ylpropyl{6-[2-(4-fluorophenyl)-1-hydroxy-3-oxo-2,3-dihydro-1H-isoindol-1-yl]-1H-benzimidazol-2-yl}carbamate 3-(4-methylpiperazin-1-yl)propyl{6-[2-(4-fluorophenyl)-1-hydroxy-3-oxo-2,3-dihydro-1H-isoindol-1-yl]-1H-benzimidazol-2-yl}carbamate methyl{5-[2-(3-bromophenyl)-3-oxo-2,3-dihydro-1H-isoindol-1-yl]-1H-benzimidazol-2-yl}carbamate
methyl{5-[2-(3-ethynyl-2-fluorophenyl)-1-hydroxy-3-oxo-2,3-dihydro-1H-isoindol-1-yl]-1H-benzimidazol-2-yl}carbamate
2-piperidin-1-ylethyl{5-[2-(4-fluorophenyl)-1-hydroxy-3-oxo-2,3-dihydro-1H-isoindol-1-yl]-1H-benzimidazol-2-yl}carbamate
methyl{5-[2-(3-chloro-2-methylphenyl)-1-hydroxy-3-oxo-2,3-dihydro-1H-isoindol--yl]-1H-benzimidazol-2-yl}carbamate
methyl{5-[2-(5-chloro-2-methylphenyl)-1-hydroxy-3-oxo-2,3-dihydro-1H-isoindol-1-yl]-1H-benzimidazol-2-yl}carbamate
N-{6-[1-hydroxy-3-oxo-2-(phenylmethyl)-2,3-dihydro-1H-isoindol-1-yl]-1H-benzimidazol-2-yl}-2,2-dimethyl-3-piperidin-1-ylpropanamide
N-{5-[2-(4-fluorophenyl)-1-hydroxy-3-oxo-2,3-dihydro-1H-isoindol-1-yl]-1H-benzimidazol-2-yl}-4-piperidin-1-ylbutanamide
N-{5-[2-(3-chloro-2-fluorophenyl)-1-hydroxy-3-oxo-2,3-dihydro-1H-isoindol-1-yl]-1H-benzimidazol-2-yl}-4-piperidin-1-ylbutanamide
methyl[6-({2-[(phenylcarbonyl)amino]phenyl}carbonyl)-1H-benzimidazol-2-yl]carbamate
methyl{5-[1-hydroxy-2-(3-morpholin-4-ylphenyl)-3-oxo-2,3-dihydro-1H-isoindol-1-yl]-1H-benzimidazol-2-yl}carbamate
2-(dimethylamino)ethyl{6-[2-(3-chloro-2-fluorophenyl)-1-hydroxy-3-oxo-2,3-dihydro-1H-isoindol-1-yl]-1H-benzimidazol-2-yl}carbamate
2-(diethylamino)ethyl{5-[2-(3-chloro-2-fluorophenyl)-1-hydroxy-3-oxo-2,3-dihydro-1H-isoindol-1-yl]-1H-benzimidazol-2-yl}carbamate
2-piperidin-1-ylethyl{5-[2-(3-chloro-2-fluorophenyl)-1-hydroxy-3-oxo-2,3-dihydro-1H-isoindol-1-yl]-1H-benzimidazol-2-yl}carbamate
3-piperidin-1-ylpropyl{6-[2-(3-chloro-2-fluorophenyl)-1-hydroxy-3-oxo-2,3-dihydro-1H-isoindol-1-yl]-1H-benzimidazol-2-yl}carbamate
2-piperidin-1-ylethyl{6-[2-(3-bromophenyl)-3-oxo-2,3-dihydro-1H-isoindol-1-yl]-1H-benzimidazol-2-yl}carbamate
methyl{6-[2-(3-bromophenyl)-4,7-difluoro-1-hydroxy-3-oxo-2,3-dihydro-1H-isoindol-1-yl]-1H-benzimidazol-2-yl}carbamate
2-[methyl(phenylmethyl)amino]ethyl{5-[2-(3-chloro-2-fluorophenyl)-1-hydroxy-3-oxo-2,3-dihydro-1H-isoindol-1-yl]-1H-benzimidazol-2-yl}carbamate
methyl{5-[1-hydroxy-3-oxo-2-(3-pyrrolidin-1-ylphenyl)-2,3-dihydro-1H-isoindol-1-yl]-1H-benzimidazol-2-yl}carbamate
methyl{5-[2-(5-chloro-2,3-difluorophenyl)-1-hydroxy-3-oxo-2,3-dihydro-1H-isoindol-1-yl]-1H-benzimidazol-2-yl}carbamate
methyl{5-[1-hydroxy-3-oxo-2-(pyrrolidin-2-ylmethyl)-2,3-dihydro-1H-isoindol-1-yl]-1H-benzimidazol-2-yl}carbamate
methyl{5-[1-hydroxy-3-oxo-2-(pyrrolidin-3-ylmethyl)-2,3-dihydro-1H-isoindol-1-yl]-1H-benzimidazol-2-yl}carbamate
(1-methylpiperidin-2-yl)methyl{6-[2-(3-chloro-2-fluorophenyl)-1-hydroxy-3-oxo-2,3-dihydro-1H-isoindol-1-yl]-1H-benzimidazol-2-yl}carbamate
[(2S)-1-methylpyrrolidin-2-yl]methyl{6-[2-(3-chloro-2-fluorophenyl)-1-hydroxy-3-oxo-2,3-dihydro-1H-isoindol-1-yl]-1H-benzimidazol-2-yl}carbamate
octahydro-2H-quinolizin-1-ylmethyl{6-[2-(3-chloro-2-fluorophenyl)-1-hydroxy-3-oxo-2,3-dihydro-1H-isoindol-1-yl]-1H-benzimidazol-2-yl}carbamate
methyl{5-[2-(5-bromo-2-methylphenyl)-1-hydroxy-3-oxo-2,3-dihydro-1H-isoindol-1-yl]-1H-benzimidazol-2-yl}carbamate
5-[2-(3-chloro-2-fluorophenyl)-1-hydroxy-3-oxo-2,3-dihydro-1H-isoindol-1-yl]-1,3-dihydro-2H-benzimidazol-2-one
methyl{5-[2-(3-bromo-2,5-difluorophenyl)-1-hydroxy-3-oxo-2,3-dihydro-1H-isoindol-1-yl]-1H-benzimidazol-2-yl}carbamate
2-morpholin-4-ylethyl{6-[2-(3-chloro-2-fluorophenyl)-1-hydroxy-3-oxo-2,3dihydro-1H-isoindol-1-yl]-1H-benzimidazol-2-yl}carbamate
(1-methylpiperidin-3-yl)methyl{6-[2-(3-chloro-2-fluorophenyl)-1-hydroxy-3-oxo-2,3-dihydro-1H-isoindol-1-yl]-1H-benzimidazol-2-yl}carbamate
methyl(5-{2-[5-chloro-2-(methyloxy)phenyl]-1-hydroxy-3-oxo-2,3-dihydro-1H-isoindol-1-yl}-1H-benzimidazol-2-yl)carbamate
methyl[5-(2-{3-[cyclohexyl(methyl)amino]phenyl}-1-hydroxy-3-oxo-2,3-dihydro-1H-isoindol-1-yl)-1H-benzimidazol-2-yl]carbamate
8-azabicyclo[3.2.1]oct-3-ylmethyl{6-[2-(3-chloro-2-fluorophenyl)-1-hydroxy-3-oxo-2,3-dihydro-1H-isoindol-1-yl]-1H-benzimidazol-2-yl}carbamate
methyl{6-[1-(3-bromophenyl)-5-oxopyrrolidin-2-yl]-1H-benzimidazol-2-yl}carbamate
(1-methylpiperidin-4-yl)methyl{5-[1-hydroxy-3-oxo-2-(phenylmethyl)-2,3-dihydro-1H-isoindol-1-yl]-1H-benzimidazol-2-yl}carbamate
1,1-dimethylethyl4-({[({5-[1-hydroxy-3-oxo-2-(phenylmethyl)-2,3-dihydro-1H-isoindol-1-yl]-1H-benzimidazol-2-yl}amino)carbonyl]oxy}methyl)piperidine-1-carboxylate
(1-methylpiperidin-4-yl)methyl{5-[2-(3-chloro-2-fluorophenyl)-1-hydroxy-3-oxo-2,3-dihydro-1H-isoindol-1-yl]-1H-benzimidazol-2-yl}carbamate
2-(1-methylpiperidin-4-yl)ethyl{5-[2-(3-chloro-2-fluorophenyl)-1-hydroxy-3-oxo-2,3-dihydro-1H-isoindol-1-yl]-1H-benzimidazol-2-yl}carbamate
methyl({6-[2-(3-chloro-2-fluorophenyl)-1-hydroxy-3-oxo-2,3-dihydro-1H-isoindol-1-yl]-1H-benzimidazol-2-yl}amino)(oxo)acetate
N-(5-{1-hydroxy-3-oxo-2-[3-(phenyloxy)phenyl]-2,3-dihydro-1H-isoindol-1-yl}-1H-benzimidazol-2-yl)-4-piperidin-1-ylbutanamide
methyl{6-[2-(3-bromophenyl)-1-methyl-3-oxo-2,3-dihydro-1H-isoindol-1-yl]-1H-benzimidazol-2-yl}carbamate
4-(diethylamino)but-2-yn-1-yl{6-[2-(3-chloro-2-fluorophenyl)-1-hydroxy-3-oxo-2,3-dihydro-1H-isoindol-1-yl]-1H-benzimidazol-2-yl}carbamate
methyl{5-[2-(3-chloro-2,6-difluorophenyl)-1-hydroxy-3-oxo-2,3-dihydro-1H-isoindol-1-yl]-1H-benzimidazol-2-yl}carbamate
2-(2-oxopyrrolidin-1-yl)ethyl{6-[2-(3-chloro-2-fluorophenyl)-1-hydroxy-3-oxo-2,3-dihydro-1H-isoindol-1-yl]-1H-benzimidazol-2-yl}carbamate
2-(2,5-dioxopyrrolidin-1-yl)ethyl{6-[2-(3-chloro-2-fluorophenyl)-1-hydroxy-3-oxo-2,3-dihydro-1H-isoindol-1-yl]-1H-benzimidazol-2-yl}carbamate
2,2,3,3-tetrafluorocyclobutyl{5-[2-(3-chloro-2-fluorophenyl)-1-hydroxy-3-oxo-2,3-dihydro-1H-isoindol-1-yl]-1H-benzimidazol-2-yl}carbamate 1-acetyl-N-{5-[2-(3-chloro-2-fluorophenyl)-1-hydroxy-3-oxo-2,3-dihydro-1H-isoindol-1-yl]-1H-benzimidazol-2-yl}piperidine-4-carboxamide
N-{5-[2-(3-chloro-2-fluorophenyl)-1-hydroxy-3-oxo-2,3-dihydro-1H-isoindol-1-yl]-1H-benzimidazol-2-yl}cyclobutanecarboxamide
methyl[5-(2-{3-[ethyl(phenyl)amino]phenyl}-1-hydroxy-3-oxo-2,3-dihydro-1H-isoindol-1-yl)-1H-benzimidazol-2-yl]carbamate
N-{6-[2-(3-chloro-2-fluorophenyl)-1-hydroxy-3-oxo-2,3-dihydro-1H-isoindol-1-yl]-1H-benzimidazol-2-yl}-2,2-difluorocyclopropanecarboxamide
cyclobutyl{6-[2-(3-chloro-2-fluorophenyl)-1-hydroxy-3-oxo-2,3-dihydro-1H-isoindol-1-yl]-1H-benzimidazol-2-yl}carbamate
2,2-difluoroethyl{6-[2-(3-chloro-2-fluorophenyl)-1-hydroxy-3-oxo-2,3-dihydro-1H-isoindol-1-yl]-1H-benzimidazol-2-yl}carbamate
2-(3-chloro-2-fluorophenyl)-3-hydroxy-3-[2-(pyridin-2-ylamino)-1H-benzimidazol-5-yl]-2,3-dihydro-1H-isoindol-1-one
1-methylethyl{6-[2-(3-chloro-2-fluorophenyl)-1-hydroxy-3-oxo-2,3-dihydro-1H-isoindol-1-yl]-1H-benzimidazol-2-yl}carbamate
cyclopropylmethyl{6-[2-(3-chloro-2-fluorophenyl)-1-hydroxy-3-oxo-2,3-dihydro-1H-isoindol-1-yl]-1H-benzimidazol-2-yl}carbamate
N-{5-[2-(3-chloro-2-fluorophenyl)-1-hydroxy-3-oxo-2,3-dihydro-1H-isoindol-1-yl]-1H-benzimidazol-2-yl}cyclopropanecarboxamide
2-(methyloxy)ethyl{5-[2-(3-chloro-2-fluorophenyl)-1-hydroxy-3-oxo-2,3-dihydro-1H-isoindol-1-yl]-1H-benzimidazol-2-yl}carbamate
tetrahydrofuran-2-ylmethyl{6-[2-(3-chloro-2-fluorophenyl)-1-hydroxy-3-oxo-2,3-dihydro-1H-isoindol-1-yl]-1H-benzimidazol-2-yl}carbamate
N-{5-[2-(3-chloro-2-fluorophenyl)-1-hydroxy-3-oxo-2,3-dihydro-1H-isoindol-1-yl]-1H-benzimidazol-2-yl}-2-(2-thienyl)acetamide
methyl{6-[2-(3-chloro-2-fluorophenyl)-4,7-difluoro-1-hydroxy-3-oxo-2,3-dihydro-1H-isoindol-1-yl]-1H-benzimidazol-2-yl}carbamate
ethyl{6-[2-(3-chloro-2-fluorophenyl)-1-hydroxy-3-oxo-2,3-dihydro-1H-isoindol-1-yl]-1H-benzimidazol-2-yl}carbamate
2-fluoroethyl{6-[2-(3-chloro-2-fluorophenyl)-1-hydroxy-3-oxo-2,3-dihydro-1H-isoindol-1-yl]-1H-benzimidazol-2-yl}carbamate
methyl(5-{1-hydroxy-3-oxo-2-[2-(phenyloxy)phenyl]-2,3-dihydro-1H-isoindol-1-yl}-1H-benzimidazol-2-yl)carbamate
N'-{5-[2-(3-chloro-2-fluorophenyl)-1-hydroxy-3-oxo-2,3-dihydro-1H-isoindol-1-yl]-1H-benzimidazol-2-yl}-N,N-diethylpentanediamide
cyclobutylmethyl{6-[2-(3-chloro-2-fluorophenyl)-1-hydroxy-3-oxo-2,3-dihydro-1H-isoindol-1-yl]-1H-benzimidazol-2-yl}carbamate
2,2,2-trifluoroethyl{6-[2-(3-chloro-2-fluorophenyl)-1-hydroxy-3-oxo-2,3-dihydro-1H-isoindol-1-yl]-1H-benzimidazol-2-yl}carbamate
methyl(5-{2-[3-(1,1-dimethylethyl)phenyl]-1-hydroxy-3-oxo-2,3-dihydro-1H-isoindol-1-yl}-1H-benzimidazol-2-yl)carbamate
methyl{6-[2-(3-chloro-2-fluorophenyl)-7-fluoro-1-hydroxy-3-oxo-2,3-dihydro-1H-isoindol-1-yl]-1H-benzimidazol-2-yl}carbamate
2-(3-chloro-2-fluorophenyl)-3-hydroxy-3-[2-(phenylamino)-1H-benzimidazol-5-yl]-2,3-dihydro-1H-isoindol-1-one
methyl{6-[4,7-dichloro-2-(3-chloro-2-fluorophenyl)-1-hydroxy-3-oxo-2,3-dihydro-1H-isoindol-1-yl]-1H-benzimidazol-2-yl}carbamate
phenylmethyl2-[(2-{[(ethyloxy)carbonyl]amino}-1,3-benzoxazol-5-yl)carbonyl]benzoate
methyl{5-[2-(5-chloro-3-ethynyl-2-methylphenyl)-1-hydroxy-3-oxo-2,3-dihydro-1H-isoindol-1-yl]-1H-benzimidazol-2-yl}carbamate
methyl{5-[2-(5-ethynyl-2,4-difluorophenyl)-1-hydroxy-3-oxo-2,3-dihydro-1H-isoindol-1-yl]-1H-benzimidazol-2-yl}carbamate
methyl{5-[2-(3-ethynyl-2,4-difluorophenyl)-1-hydroxy-3-oxo-2,3-dihydro-1H-isoindol-1-yl]-1H-benzimidazol-2-yl}carbamate
2-(3-chloro-2-fluorophenyl)-3-hydroxy-3-[2-(pyrimidin-2-ylamino)-1H-benzimidazol-5-yl]-2,3-dihydro-1H-isoindol-1-one
methyl{5-[2-(3-ethynyl-2-fluorophenyl)-4,7-difluoro-1-hydroxy-3-oxo-2,3-dihydro-1H-isoindol-1-yl]-1H-benzimidazol-2-yl}carbamate
2-(3-chloro-2-fluorophenyl)-3-hydroxy-3-[2-(1,3-thiazol-2-ylamino)-1H-benzimidazol-5-yl]-2,3-dihydro-1H-isoindol-1-one
ethyl{5-[2-(3-chloro-2-fluorophenyl)-1-hydroxy-3-oxo-2,3-dihydro-1H-isoindol-1-yl]-1,3-benzoxazol-2-yl}carbamate
methyl{5-[2-(5-chloro-3-iodo-2-methylphenyl)-1-hydroxy-3-oxo-2,3-dihydro-1H-isoindol-1-yl]-1H-benzimidazol-2-yl}carbamate
methyl{5-[2-(3-ethyl-2-fluorophenyl)-1-hydroxy-3-oxo-2,3-dihydro-1H-isoindol-1-yl]-1H-benzimidazol-2-yl}carbamate
methyl{5-[2-(5-ethynyl-2-methylphenyl)-1-hydroxy-3-oxo-2,3-dihydro-1H-isoindol-1-yl]-1H-benzimidazol-2-yl}carbamate
2-(3-chloro-2-fluorophenyl)-3-hydroxy-3-[2-(pyrazin-2-ylamino)-1H-benzimidazol-5-yl]-2,3-dihydro-1H-isoindol-1-one
methyl{5-[2-(2-fluoro-3-iodophenyl)-1-hydroxy-3-oxo-2,3-dihydro-1H-isoindol-1-yl]-1H-benzimidazol-2-yl}carbamate
methyl{6-[2-(5-ethynyl-2-fluorophenyl)-1-hydroxy-3-oxo-2,3-dihydro-1H-isoindol-1-yl]-1H-benzimidazol-2-yl}carbamate
2-(3-ethynyl-2-fluorophenyl)-3-hydroxy-3-[2-(pyrimidin-2-ylamino)-1H-benzimidazol-5-yl]-2,3-dihydro-1H-isoindol-1-one
methyl{5-[2-(2,5-dimethylphenyl)-1-hydroxy-3-oxo-2,3-dihydro-1H-isoindol-1-yl]-1H-benzimidazol-2-yl}carbamate
methyl{5-[2-(3-ethenyl-2-fluorophenyl)-1-hydroxy-3-oxo-2,3-dihydro-1H-isoindol-1-yl]-1H-benzimidazol-2-yl}carbamate
methyl(6-{2-[2-fluoro-3-(methyloxy)phenyl]-1-hydroxy-3-oxo-2,3-dihydro-1H-isoindol-1-yl}-1H-benzimidazol-2-yl)carbamate
methyl(5-{1-hydroxy-2-[2-methyl-5-(methyloxy)phenyl]-3-oxo-2,3-dihydro-1H-isoindol-1-yl}-1H-benzimidazol-2-yl)carbamate
methyl{5-[2-(3-ethynyl-2-fluorophenyl)-7-fluoro-1-hydroxy-3-oxo-2,3-dihydro-1H-isoindol-1-yl]-1H-benzimidazol-2-yl}carbamate methyl{5-[2-(2-fluoro-3-prop-1-yn-1-ylphenyl)-1-hydroxy-3-oxo-2,3-dihydro-1H-isoindol-1-yl]-1H-benzimidazol-2-yl}carbamate
methyl{5-[2-(5-chloro-2-methylphenyl)-7-fluoro-1-hydroxy-3-oxo-2,3-dihydro-1H-isoindol-1-yl]-1H-benzimidazol-2-yl}carbamate
methyl{5-[2-(3-ethynyl-2-methylphenyl)-1-hydroxy-3-oxo-2,3-dihydro-1H-isoindol-1-yl]-1H-benzimidazol-2-yl}carbamate
3-hydroxy-2-[3-(methyloxy)phenyl]-3-[2-(pyrimidin-2-ylamino)-1H-benzimidazol-6-yl]-2,3-dihydro-1H-isoindol-1-one
3-hydroxy-2-(3-methylphenyl)-3-[2-(pyrimidin-2-ylamino)-1H-benzimidazol-6-yl]-2,3-dihydro-1H-isoindol-1-one
2-(5-chloro-2-methylphenyl)-3-hydroxy-3-[2-(pyrimidin-2-ylamino)-1H-benzimidazol-6-yl]-2,3-dihydro-1H-isoindol-1-one
methyl{6-[2-(5-chloro-2-methylphenyl)-4,7-difluoro-1-hydroxy-3-oxo-2,3-dihydro-1H-isoindol-1-yl]-1H-benzimidazol-2-yl}carbamate
methyl{5-[2-(3-ethynyl-2-fluorophenyl)-3-oxo-2,3-dihydro-1H-isoindol-1-yl]-1H-benzimidazol-2-yl}carbamate
2-(3-chloro-2-fluorophenyl)-3-{2-[(6-chloropyridazin-3-yl)amino]-1H-benzimidazol-5-yl}-3-hydroxy-2,3-dihydro-1H-isoindol-1-one
2-(3-chloro-2-fluorophenyl)-4,7-difluoro-3-hydroxy-3-[2-(pyrimidin-2-ylamino)-1H-benzimidazol-5-yl]-2,3-dihydro-1H-isoindol-1-one
methyl{5-[2-(2-fluoro-5-methylphenyl)-1-hydroxy-3-oxo-2,3-dihydro-1H-isoindol-1-yl]-1H-benzimidazol-2-yl}carbamate
methyl(5-{2-[2-fluoro-5-(methyloxy)phenyl]-1-hydroxy-3-oxo-2,3-dihydro-1H-isoindol-1-yl}-1H-benzimidazol-2-yl)carbamate
methyl(5-{1-hydroxy-2-[5-methyl-2-(methyloxy)phenyl]-3-oxo-2,3-dihydro-1H-isoindol-1-yl}-1H-benzimidazol-2-yl)carbamate
methyl{5-[2-(3-ethynyl-5-methylphenyl)-1-hydroxy-3-oxo-2,3-dihydro-1H-isoindol-1-yl]-1H-benzimidazol-2-yl}carbamate
2-(3-chloro-2-fluorophenyl)-3-{2-[(5-chloropyrimidin-2-yl)amino]-1H-benzimidazol-5-yl}-3-hydroxy-2,3-dihydro-1H-isoindol-1-one
2-(3-chloro-2-fluorophenyl)-3-hydroxy-3-{2-[(4-methylpyrimidin-2-yl)amino]-1H-benzimidazol-5-yl}-2,3-dihydro-1H-isoindol-1-one
3-(2-{[4,6-bis(methyloxy)pyrimidin-2-yl]amino}-1H-benzimidazol-5-yl)-2-(3-chloro-2-fluorophenyl)-3-hydroxy-2,3-dihydro-1H-isoindol-1-one
2-(3-chloro-2-fluorophenyl)-3-hydroxy-3-(2-{[4-methyl-6-(methyloxy)pyrimidin-2-yl]amino}-1H-benzimidazol-5-yl)-2,3-dihydro-1H-isoindol-1-one
3-hydroxy-2-(3-methylphenyl)-3-[2-(pyrazin-2-ylamino)-1H-benzimidazol-6-yl]-2,3-dihydro-1H-isoindol-1-one
2-(5-chloro-2-methylphenyl)-3-hydroxy-3-[2-(pyrazin-2-ylamino)-1H-benzimidazol-6-yl]-2,3-dihydro-1H-isoindol-1-one
methyl{6-[2-(2-fluoro-3-methylphenyl)-1-hydroxy-3-oxo-2,3-dihydro-1H-isoindol-1-yl]-1H-benzimidazol-2-yl}carbamate
3-hydroxy-2-[3-(methyloxy)phenyl]-3-[2-(pyrazin-2-ylamino)-1H-benzimidazol-5-yl]-2,3-dihydro-1H-isoindol-1-one
methyl{6-[(2-{[(2-thienylmethyl)amino]carbonyl}phenyl)carbonyl]-1H-benzimidazol-2-yl}carbamate
methyl{6-[(2-{[(3-methylphenyl)amino]carbonyl}phenyl)carbonyl]-1H-benzimidazol-2-yl}carbamate
methyl{6-[(2-{[(3-bromophenyl)amino]carbonyl}phenyl)carbonyl]-1H-benzimidazol-2-yl}carbamate
methyl{6-[(2-{[(3-chlorophenyl)amino]carbonyl}phenyl)carbonyl]-1H-benzimidazol-2-yl}carbamate
methyl{6-[(2-{[(3-fluorophenyl)amino]carbonyl}phenyl)carbonyl]-1H-benzimidazol-2-yl}carbamate
methyl(6-{[2-({[3-(methyloxy)phenyl]amino}carbonyl)phenyl]carbonyl}-1H-benzimidazol-2-yl)carbamate
methyl(6-{[2-({[3-(trifluoromethyl)phenyl]amino}carbonyl)phenyl]carbonyl}-1H-benzimidazol-2-yl)carbamate
methyl{6-[(2-{[(3-ethylphenyl)amino]carbonyl}phenyl)carbonyl]-1H-benzimidazol-2-yl}carbamate
methyl{6-[(2-{[(3-ethynylphenyl)amino]carbonyl}phenyl)carbonyl]-1H-benzimidazol-2-yl}carbamate
methyl{6-[(2-{[(3-chloro-4-fluorophenyl)amino]carbonyl}phenyl)carbonyl]-1H-benzimidazol-2-yl}carbamate
methyl{6-[(2-{[(5-chloro-2-fluorophenyl)amino]carbonyl}phenyl)carbonyl]-1H-benzimidazol-2-yl}carbamate
methyl{6-[(2-{[(3-iodophenyl)amino]carbonyl}phenyl)carbonyl]-1H-benzimidazol-2-yl}carbamate
methyl(6-{[2-({[3-(1-methylethyl)phenyl]amino}carbonyl)phenyl]carbonyl}-1H-benzimidazol-2-yl)carbamate
methyl{6-[(2-{[(3-thienylmethyl)amino]carbonyl}phenyl)carbonyl]-1H-benzimidazol-2-yl}carbamate
methyl{6-[(2-{[(3-bromo-4-fluorophenyl)amino]carbonyl}phenyl)carbonyl]-1H-benzimidazol-2-yl}carbamate
methyl{6-[(2-{[(3-chloro-2-fluorophenyl)amino]carbonyl}phenyl)carbonyl]-1H-benzimidazol-2-yl}carbamate
methyl{6-[(2-{[(4-fluoro-3-methylphenyl)amino]carbonyl}phenyl)carbonyl]-1H-benzimidazol-2-yl}carbamate
methyl{6-[(2-{[(5-bromo-2-fluorophenyl)amino]carbonyl}phenyl)carbonyl]-1H-benzimidazol-2-yl}carbamate
methyl{6-[(2-{[(5-bromo-2,4-difluorophenyl)amino]carbonyl}phenyl)carbonyl]-1H-benzimidazol-2-yl}carbamate
methyl{6-[(2-{[(5-chloro-2,4-difluorophenyl)amino]carbonyl}phenyl)carbonyl]-1H-benzimidazol-2-yl}carbamate
methyl{6-[(2-{[(3-bromo-2-fluorophenyl)amino]carbonyl}phenyl)carbonyl]-1H-benzimidazol-2-yl}carbamate
methyl{6-[(2-{[(3-ethenylphenyl)amino]carbonyl}phenyl)carbonyl]-1H-benzimidazol-2-yl}carbamate
methyl{6-[(2-{[(3-ethynyl-2-fluorophenyl)amino]carbonyl}phenyl)carbonyl]-1H-benzimidazol-2-yl}carbamate
methyl{6-[(2-{[(5-chloro-2-methylphenyl)amino]carbonyl}phenyl)carbonyl]-1H-benzimidazol-2-yl}carbamate methyl{6-[(2-{[(5-bromo-2-methylphenyl)amino]carbonyl}phenyl)carbonyl]-1H-benzimidazol-2-yl}carbamate methyl{6-[(2-{[(2-fluoro-3-iodophenyl)amino]carbonyl}phenyl)carbonyl]-1H-benzimidazol-2-yl}carbamate methyl{6-[(2-{[(3-ethenyl-2-fluorophenyl)amino]carbonyl}phenyl)carbonyl]-1H-benzimidazol-2-yl}carbamate; or methyl{6-[(2-{[(2-fluoro-5-methylphenyl)amino]carbonyl}phenyl)carbonyl]-1H-benzimidazol-2-yl}carbamate;

or a pharmaceutically acceptable salt of any of the above compounds.

5. The method according to claim 3, wherein the compound is methyl{5-[2-(5-chloro-2-methylphenyl)-1-hydroxy-3-oxo-2,3-dihydro-1H-isoindol-1-yl]-1H-benzimidazol-2-yl}carbamate, or a pharmaceutically acceptable salt thereof.

6. The method according to claim 4, wherein the compound is methyl{5-[2-(5-chloro-2-methylphenyl)-1-hydroxy-3-oxo-2,3-dihydro-1H-isoindol-1-yl]-1H-benzimidazol-2-yl}carbamate, or a pharmaceutically acceptable salt thereof.

7. The method according to claim 6, wherein the disease is rheumatoid arthritis.

8. The method according to claim 6, wherein the disease is selected from the group consisting of atherosclerosis, myocardioinfarction, ischemia, stroke, and restenosis.

9. The method according to claim 6, wherein the disease is diabetic retinopathy.

10. The method of claim 1, wherein said solid tumor is a cancer.

11. The method of claim 10, wherein said cancer is selected from sarcomas, carcinomas, and lymphomas.

12. The method of claim 10, wherein said cancer is selected from the group consisting of lung cancers, gastrointestinal cancers, liver cancers, bone cancers, nervous system cancers, gynecological cancers, hematologic cancers, skin cancers, and adrenal cancers.

13. The method of claim 1, wherein said mammalian patient is human in a disease state characterized by abnormal cellular proliferation or invasion.

14. The method of claim 13, wherein said therapeutically effective amount is in the range of about 0.1 to about 1,000 mg per day.

15. The method of claim 13, wherein said therapeutically effective amount is in the range of about 0.01 to about 100 mg/Kg per day based on body weight of said mammalian patient.

16. The method of claim 2, wherein said mammalian patient is a human in a disease state characterized by abnormal cellular proliferation or invasion.

17. The method of claim 16, wherein said therapeutically effective amount is in the range of about 0.1 to about 1,000 mg per day.

18. The method of claim 16, wherein said therapeutically effective amount is in the range of about 0.01 to about 100 mg/Kg per day based on body weight of said mammalian patient.

* * * * *